US010059954B2

(12) United States Patent
Flasinski

(10) Patent No.: US 10,059,954 B2
(45) Date of Patent: Aug. 28, 2018

(54) PLANT REGULATORY ELEMENTS FROM A UBIQUITIN GENE FROM BOUTELOUA GRACILIS

(71) Applicant: Monsanto Technology LLC, St. Louis, MO (US)

(72) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 152 days.

(21) Appl. No.: 15/046,906

(22) Filed: Feb. 18, 2016

(65) Prior Publication Data

US 2016/0177325 A1 Jun. 23, 2016

Related U.S. Application Data

(62) Division of application No. 14/133,599, filed on Dec. 18, 2013, now Pat. No. 9,303,266.

(60) Provisional application No. 61/739,720, filed on Dec. 19, 2012.

(51) Int. Cl.
*C12N 15/82* (2006.01)

(52) U.S. Cl.
CPC .................................. *C12N 15/8216* (2013.01)

(58) Field of Classification Search
None
See application file for complete search history.

(56) References Cited

U.S. PATENT DOCUMENTS 5,510,474 A * 4/1996 Quail .................... C07K 14/415 435/320.1
6,054,574 A 4/2000 Quail et al.
6,635,806 B1 10/2003 Kriz et al.
7,371,848 B2 5/2008 Conner et al.
8,168,859 B2 5/2012 Abbitt
2007/0061917 A1 3/2007 McCutchen et al.
2007/0204367 A1* 8/2007 Flasinski ............ C12N 15/8216 800/278
2009/0138985 A1 5/2009 Martinell et al.
2010/0058495 A1 3/2010 Abbitt
2011/0023183 A1* 1/2011 Stewart ................ C07K 14/415 800/279
2012/0180158 A1 7/2012 Abbitt
2012/0198584 A1 8/2012 Nuccio
2012/0246763 A1* 9/2012 Flasinski .............. C07K 14/415 800/298
2015/0067926 A1* 3/2015 Kumar ............... C12N 15/8216 800/306
2016/0177326 A1 6/2016 Flasinski

FOREIGN PATENT DOCUMENTS

RU 2326167 6/2008
WO WO 1989/012059 A1 12/1989
WO WO 1998/044781 A1 10/1998
WO WO 2001/094394 A2 12/2001
WO WO 2005/098007 10/2005
WO WO 2009/149304 A2 10/2009
WO WO 2011/130894 10/2011
WO WO 2012/134921 10/2012
WO WO 2012/158535 A1 11/2012

OTHER PUBLICATIONS

Potenza et al., In Vitro Cell Dev Biol Plant 40:1-22 (2004).*
Saha et al., In Silico Biol 7(1):7-19 (2007).*
Wang & Oard, Plant Cell Rep 22:129-34 (2003).*
Joung & Kamo, Plant Cell Rep 25:1081-88 (2006).*
Rose, Curr Top Microbiol Immunol, 326:277-90 (2008).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Benfey et al., "The CaMV 35S enhancer contains at least two domains which can confer different developmental and tissue-specific expression patterns," *EMBO J.*, 8(8):2195-2202, 1989.
Callis et al., "Introns increase gene expression in cultured maize cells," *Genes & Dev.* 1:1183-1200, 1987.
Cho et al., "Regulation of root-hair initiation and expansin gene expression in *Arabidopsis," The Plant Cell*, 14:3237-3253, 2002.
Christensen et al., "Ubiquitin promoter-based vectors for high-level expression of selectable and/or screenable marker genes in monocotyledonous plants," *Transgenic Research* 5:213-218, 1996.
Christiansen etal., "Maize polyubiquitin genes: structure, thermal perturbation of expression and transcript splicing, and promoter activity following transfer to protoplasts by electroporation," *Plant Mol. Biol.* 18:675-689, 1992.
Dolferus et al., "Differential Interactions of Promoter Elements in Stress Responses of the *Arabidopsis Adh* Gene," *Plant Physiol.* 105:1075-1087, 1994.
Donald et al., "Mutation of either G box or I box sequences profoundly affects expression from the *Arabidopsis rbcS-1A* promoter," *EMBO J.* 9:1717-1726, 1990.
International Search Report and Written Opinion for International Application No. PCT/US2013/075813, dated Jun. 10, 2014.
Jeon et al., "Tissue-Preferential Expression of a Rice a-Tubulin Gene, OsTubA1, Mediated by the First Intron," *Plant Physiol.* 123:1005-1014, 2000.
Kim et al., "A 20 nucleotide upstream element is essential for the nopaline synthase (nos) promoter activity," *Plant Molecular Biology* 24:105-117, 1994.

(Continued)

*Primary Examiner* — Cathy Kingdon Worley
*Assistant Examiner* — Russell T Boggs
(74) *Attorney, Agent, or Firm* — Dentons US LLP; Carine M. Doyle, Esq.

(57) ABSTRACT

The invention provides novel recombinant DNA molecules and constructs useful for modulating gene expression in plants, plant cells, seeds, and progeny plants. Plant regulatory elements comprising sequences from a ubiquitin gene from *Bouteloua gracilis*, as well as variants and fragments thereof having gene-regulatory activity, are provided. The invention also provides transgenic plants, plant cells, plant parts, seeds, and progeny plants comprising the recombinant DNA molecules of the invention, along with methods of their use.

17 Claims, 9 Drawing Sheets

Specification includes a Sequence Listing.

(56) References Cited

OTHER PUBLICATIONS

Mascarenhas et al., "Intron-mediated enhancement of heterologous gene expression in maize," *Plant Mol. Biol* 15:913-920, 1990.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Mol. Biol.*, 38:655-662, 1998.
Potenza et al., "Invited Review: Targeting Transgene Expression in Research, Agricultural, and Environmental Applications: Promoters Used in Plant Transformation," In Vitro *Cell. Dev. Biol.-Plant* 40:1-22, 2004.
Vasil et al., "Increased Gene Expression by the First Intron of Maize Shrunken-1 Locus in Grass Species," *Plant Physiol.* 91:1575-1579, 1989.
Welsch et al., "Structural and functional characterization of the phytoene synthase promoter from *Arabidopsis thaliana,*" *Planta*, 216:523-534, 2003.
Partial Supplementary European Search Report regarding European Application No. 13866064, dated May 20, 2016.
USPTO: Non-Final Office Action regarding U.S. Appl. No. 15/046,914, dated Mar. 3, 2017.
Grefen et al., "A ubiquitin-10 promoter-based vector set for fluorescent protein tagging facilitates temporal stability and native protein distribution in transient and stable expression studies," *The Plant Journal* 64:355-365, 2010.
Joung et al., "Expression of a polyubiquitin promoter isolated from *Gladiolus,*" *Plant Cell Rep.* 25:1081-1088, 2006.
Kiran et al., "The TATA-Box Sequence in the Basal Promoter Contributes to Determining Light-Dependent Gene Expression in Plants," *Plant Physiology* 142:364-376, 2006.
Rose, "Intron-Mediated Regulation of Gene Expression," *Current Topics in Microbiology and Immunology* 326:277-290, 2008.
Saha et al., "In Silico Analysis of the Lateral Organ Junction (LOJ) Gene and Promoter of *Arabidopsis thaliana,*" *In Silico Biology* 7:7-19, 2007.
Wang et al., "Rice ubiquitin promoters: deletion analysis and potential usefulness in plant transformation systems," *Plant Cell Rep.* 22:129-134, 2003.
Response to Non-Final Office Action regarding U.S. Appl. No. 15/046,914, dated Jun. 5, 2017.
Office Action regarding Russian Application No. 2015129061, dated Oct. 23, 2017.
Office Action regarding Bolivian Application No. SP-0410-2013, dated Aug. 21, 2017.
USPTO: Final Office Action regarding U.S. Appl. No. 15/046,914, dated Sep. 6, 2017.
USPTO: Examiner's Interview Summary regarding U.S. Appl. No. 15/046,914, dated Nov. 3, 2017.
Response to Final Office Action regarding U.S. Appl. No. 15/046,914, dated Nov. 6, 2017.
USPTO: Notice of Allowance and Fee(s) Due regarding U.S. Appl. No. 15/046,914, dated Dec. 19, 2017.

* cited by examiner

P-AGRne.Ubq1-1:1:5
(SEQ ID NO: 2; 2005bp)

P-AGRne.Ubq1-1:1:4
(SEQ ID NO: 6; 999 bp)

P-AGRne.Ubq1-1:1:6
(SEQ ID NO: 8; 762 bp)

P-ARUdo.Ubq1-1:1:4
(SEQ ID NO: 10; 4114 bp)

P-ARUdo.Ubq1-1:1:5
(SEQ ID NO: 14; 2012 bp)

P-ARUdo.Ubq1-1:1:6
(SEQ ID NO: 17; 1000 bp)

P-ARUdo.Ubq1-1:1:8
(SEQ ID NO: 22; 755 bp)

▬▬▬▬▬▬▬▬▬▬▬▬▬▬ P-ARUdo.Ubq2-1:1:4
(SEQ ID NO: 24; 2033 bp)

▬▬▬▬▬▬▬▬▬▬▬ P-ARUdo.Ubq2-1:1:6
(SEQ ID NO: 28; 2004 bp)

▬▬▬▬ P-ARUdo.Ubq2-1:1:5
(SEQ ID NO: 31; 1001 bp)

▬▬ P-ARUdo.Ubq2-1:1:7
(SEQ ID NO: 33; 696 bp)

▬▬▬▬▬▬▬▬▬▬▬▬▬▬▬ P-BOUgr.Ubq1-1:1:2
(SEQ ID NO: 35; 2371 bp)

▬▬▬▬▬▬▬▬▬▬▬ P-BOUgr.Ubq1-1:1:3
(SEQ ID NO: 39; 1999 bp)

▬▬▬▬▬ P-BOUgr.Ubq1-1:1:5
(SEQ ID NO: 42; 1022 bp)

▬▬▬ P-BOUgr.Ubq1-1:1:6
(SEQ ID NO: 44; 760 bp)

P-MISsi.Ubq1-1:1:2
(SEQ ID NO: 63; 5359bp)

P-MISsi.Ubq1-1:1:11
(SEQ ID NO: 67; 2423bp)

P-MISsi.Ubq1-1:1:10
(SEQ ID NO: 71; 1447bp)

P-MISsi.Ubq1-1:1:13
(SEQ ID NO: 73; 899bp)

P-MISsi.Ubq1-1:1:14
(SEQ ID NO: 75; 691bp)

P-MISsi.Ubq1-1:1:9
(SEQ ID NO: 77; 506bp)

P-SCHsc.Ubq1-1:1:12
(SEQ ID NO: 79; 2831 bp)

P-SCHsc.Ubq1-1:1:11
(SEQ ID NO: 83; 2033 bp)

P-SCHsc.Ubq1-1:1:10
(SEQ ID NO: 85; 1046 bp)

P-SCHsc.Ubq1-1:1:14
(SEQ ID NO: 87; 547 bp)

P-SORnu.Ubq1-1:1:4
(SEQ ID NO: 89; 2218 bp)

P-SORnu.Ubq1-1:1:5
(SEQ ID NO: 93; 1964 bp)

P-SORnu.Ubq1-1:1:6
(SEQ ID NO: 96; 1023 bp)

P-SORnu.Ubq1-1:1:7
(SEQ ID NO: 98; 724 bp)

Expression Cassette Configuration 1

Promoter or chimeric promoter [A]  Leader [B]  Intron [C]  Coding Region [D]  3' UTR [E]

Expression Cassette Configuration 2

Promoter or chimeric promoter [F]  Leader [G]  Intron [H]  Leader [I]  Coding Region [J]  3' UTR [K]

Expression Cassette Configuration 3

Promoter or chimeric promoter [L]  Leader [M]  Coding Region [N]  Intron [O]  Coding Region [P]  3' UTR [Q]

SEQUENCE LISTING

<160> NUMBER OF SEQ ID NOS: 171

<210> SEQ ID NO 1
<211> LENGTH: 3143
<212> TYPE: DNA
<213> ORGANISM: Agrostis nebulosa

<400> SEQUENCE: 1
ggcctcttta cgtttggcac aatttaattg aatcccggca tggcatgtta gaccggagtg 60
agccggccct tttactggta tgacactccc tctgtcttga gtgtcgctgt gccagcttgt 120
acctctgtct atgttcacag cccgtgctgt gtacctagac cctccgtttg tccacattca 180
ttttaatctc tattgtatct tgtcaaaacc taaaagccta aaacgactct gataaaggga 240
cagaaagatt atacaagagc aagtgtataa tgaaataatg taagcgagct atatgaattg 300
tcacgtgtca tatttatgtt gagacgaaga agagaaaata aacaccatgc aaatttatgg 360
cgagtgatag atggccagat gggcacaagg cctcctattt cttaaatcgg attttgtaag 420
aacgaaaaaa gggacttata agagaatagg atagaccata tatcaatgat gtagtatgca 480
tcaagatcta actattatat gagtgaattg ataaatttat tctaggtgac atggccttaa 540
cgatgaacag tacatggtta aatcaataga acaatagcca actctagcag ctctaaaaaa 600
agatatatat tcgtcgaggc actattatgc aaccacatag tcaacttcaa caccgcttga 660
gtgcgttctc atgttttttt tttcttgcaa attacgcttt tctaaaataa aataatttgg 720
atcgtgcaat tatttcactt taggtgtgcg tgactacgtg agtaacattt ttgaatctca 780
gaaaggaaat aaaagtataa tactgctgcc tactttgagg attcggcttg ttatttaaaa 840
ccgtctttaa ggtcaaatgc tcaagattca ttcaacaatt gaaacgtctc acatgattaa 900
atcatgtata aggatgctaa ggtcttgctt gacaatgttt ttctaggaat ttcatctaac 960
tttttgagtg aaactatcaa ataataattt taaaacaatt ttataagaga agctccggag 1020
ataaaaggcc atctaatcta tgttagaaga gtgaagttta ctccctctgt cccaaaaata 1080
gaattctaag tatgaaatga ttttttttgtt atacaaaagg agtatatatc acaagattga 1140
tgtcagttat gcttagggca cgtacacgac gctggtgctt taggtagacg ttaatcgttg 1200
tttctgcatt ttattttatt ttgttgccac ggtgtacatt tgggtagacg tttgtcacag 1260
gcattgccac tcaaacaagc agccggcgct tggagctttt atagtttgaa aagtgacggt 1320
tttaaggatg ggtaagctga ttagtatatg taagtttagc tttttccatt gtaggttaag 1380
ccttaaggct cttacacaat tgtttcatta ttctcattct ttaagagccc atataagcgt 1440
tcatgaattg tacatatcct tagatttttt tttttgggta aagctcgagc ttctgtatct 1500
aaaagtagag aaatcagaaa aagattcatg ttttggtagt tttgatttct tgcctccata 1560
ataattttgg tttaccattt tttgtttgat tttagtttta gaagcgttta tagcaggatt 1620
taaaatccaa aactaccatt atcttcaagt gaccgtcagt gagccgttta acggcgtcga 1680
caagtccaac ggacaccaac cagtgaacca ccagcgtcga gccaagcgat gcaaacggaa 1740
cggccgagac gttgacacct ttggcgcggc acggcatgtc ggatctccct ctctggcccc 1800
ctctcgagag ttccagctcc acctccaccg gtggcggttt ccaagtccgt tccgttccgt 1860
tccgcctcct gcctgctcct ctcagacggc acgaaaccgt gacggcaccg gcagcacggg 1920
gggattcctt ttccactgct ccttcctttt cccttcctcg cccgccgcta taaatagcca 1980
gccccgtccc cagattcttt cccaacctca tctttgttcg gagcacccac acaacccgat 2040
ccccaattcc ctcgtctctc ctcgcgagcc tcgtcgaccc ccccttcaag gtacggcgat 2100
cgtcctccct ccctctctct ctctaccttc tcttctctag actagatcgg cgacccggtc 2160
catggttagg gcctgctagt tctgttcctg ttttttccat ggctgcgagg taaaatagat 2220
ctgatggcgt tatgatggtt aactcgtcat actcttgcga tctatggtcc ctttaggaca 2280
tcgatttaat ttcggatggt tcgagatcgg tgatccatgg ttagtaccct aggcagtggg 2340
gttagatccg tgctgttagg gttcgtagat ggattctgat tgctcagtaa ctgggaaacc 2400
tgggatggtt ctagctggga atcctgggat ggttctagct ggttcgcaga tgagatcgat 2460
ttcatggtct gctatatctt gtttcgttgc ctaggttccg tttaatctgt ccgtggtatg 2520
atgttagcct ttgataaggt tcgatcgtgc tagctacgtc ctgcgcagca tttaattgtc 2580
aggtcataat ttttagcatt cctgtttttg tttggtttgg ttttgtctgg ttgggctgta 2640
gatagtttca atctacctgt cggtttattt tattaaattt ggattggatc tgtatgtgtc 2700
acatatatct tcatgattaa tatggttgga attatctctt catcttttag atatatatgg 2760
ataggtatat atgttgctgt gggttttact ggtactttat tagatatatt catgcttaga 2820
tacatgaagc aacgtgctgt tacagtttaa taattcttgt ttatctaata aacaaataag 2880
gataggtata tatgttgctg atggttttac tgatacttta ttagatagta cttctttgac 2940
atgaaggaac atcctgcgac agcttaataa ttattcttca tctaataaaa agcttgcttt 3000
ttaattattt tgatatactt ggatgatgtc atgcagcagc tatgtgtgaa ttttcggccc 3060
tgtcttcata tgatgtttat ttgcttggga ctgtttcttt ggctgataac tcaccctgtt 3120
gtttggtgat ccttctgcag gtg 3143

<210> SEQ ID NO 2
<211> LENGTH: 2005
<212> TYPE: DNA
<213> ORGANISM: Agrostis nebulosa

<400> SEQUENCE: 2
ggcctcttta cgtttggcac aatttaattg aatcccggca tggcatgtta gaccggagtg 60
agccggccct tttactggta tgacactccc tctgtcttga gtgtcgctgt gccagcttgt 120
acctctgtct atgttcacag cccgtgctgt gtacctagac cctccgtttg tccacattca 180
ttttaatctc tattgtatct tgtcaaaacc taaaagccta aaacgactct gataaaggga 240
cagaaagatt atacaagagc aagtgtataa tgaaataatg taagcgagct atatgaattg 300
tcacgtgtca tatttatgtt gagacgaaga agagaaaata aacaccatgc aaatttatgg 360
cgagtgatag atggccagat gggcacaagg cctcctattt cttaaatcgg attttgtaag 420
aacgaaaaaa gggacttata agagaatagg atagaccata tatcaatgat gtagtatgca 480
tcaagatcta actattatat gagtgaattg ataaatttat tctaggtgac atggccttaa 540
cgatgaacag tacatggtta aatcaataga acaatagcca actctagcag ctctaaaaaa 600
agatatatat tcgtcgaggc actattatgc aaccacatag tcaacttcaa caccgcttga 660
gtgcgttctc atgttttttt tttcttgcaa attacgcttt tctaaaataa aataatttgg 720
atcgtgcaat tatttcactt taggtgtgcg tgactacgtg agtaacattt ttgaatctca 780
gaaaggaaat aaaagtataa tactgctgcc tactttgagg attcggcttg ttatttaaaa 840
ccgtctttaa ggtcaaatgc tcaagattca ttcaacaatt gaaacgtctc acatgattaa 900
atcatgtata aggatgctaa ggtcttgctt gacaatgttt ttctaggaat ttcatctaac 960
tttttgagtg aaactatcaa ataataattt taaaacaatt ttataagaga agctccggag 1020

-continued

```
ataaaaggcc atctaatcta tgttagaaga gtgaagttta ctccctctgt cccaaaaata   1080

gaattctaag tatgaaatga tttttttgtt atacaaaagg agtatatatc acaagattga   1140

tgtcagttat gcttagggca cgtacacgac gctggtgctt taggtagacg ttaatcgttg   1200

tttctgcatt ttattttatt ttgttgccac ggtgtacatt tgggtagacg tttgtcacag   1260

gcattgccac tcaaacaagc agccggcgct tggagctttt atagtttgaa aagtgacggt   1320

tttaaggatg ggtaagctga ttagtatatg taagtttagc tttttccatt gtaggttaag   1380

ccttaaggct cttacacaat tgtttcatta ttctcattct ttaagagccc atataagcgt   1440

tcatgaattg tacatatcct tagatttttt tttttgggta aagctcgagc ttctgtatct   1500

aaaagtagag aaatcagaaa aagattcatg ttttggtagt tttgatttct tgcctccata   1560

ataattttgg tttaccattt tttgtttgat tttagtttta gaagcgttta tagcaggatt   1620

taaaatccaa aactaccatt atcttcaagt gaccgtcagt gagccgttta acggcgtcga   1680

caagtccaac ggacaccaac cagtgaacca ccagcgtcga gccaagcgat gcaaacggaa   1740

cggccgagac gttgacacct ttggcgcggc acggcatgtc ggatctccct ctctggcccc   1800

ctctcgagag ttccagctcc acctccaccg gtggcggttt ccaagtccgt tccgttccgt   1860

tccgcctcct gcctgctcct ctcagacggc acgaaaccgt gacggcaccg gcagcacggg   1920

gggattcctt ttccactgct ccttcctttt cccttcctcg cccgccgcta taaatagcca   1980

gccccgtccc cagattcttt cccaa                                           2005
```

<210> SEQ ID NO 3
<211> LENGTH: 85
<212> TYPE: DNA
<213> ORGANISM: Agrostis nebulosa

<400> SEQUENCE: 3

```
cctcatcttt gttcggagca cccacacaac ccgatcccca attccctcgt ctctcctcgc     60

gagcctcgtc gacccccccct tcaag                                           85
```

<210> SEQ ID NO 4
<211> LENGTH: 1053
<212> TYPE: DNA
<213> ORGANISM: Agrostis nebulosa

<400> SEQUENCE: 4

```
gtacggcgat cgtcctccct ccctctctct ctctaccttc tcttctctag actagatcgg     60

cgacccggtc catggttagg gcctgctagt tctgttcctg ttttttccat ggctgcgagg    120

taaaatagat ctgatggcgt tatgatggtt aactcgtcat actcttgcga tctatggtcc    180

ctttaggaca tcgatttaat ttcggatggt tcgagatcgg tgatccatgg ttagtaccct    240

aggcagtggg gttagatccg tgctgttagg gttcgtagat ggattctgat tgctcagtaa    300

ctgggaaacc tgggatggtt ctagctggga atcctgggat ggttctagct ggttcgcaga    360

tgagatcgat ttcatggtct gctatatctt gtttcgttgc ctaggttccg tttaatctgt    420

ccgtggtatg atgttagcct ttgataaggt tcgatcgtgc tagctacgtc ctgcgcagca    480

tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa tatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780
```

aacaaataag gataggtata tatgttgctg atggttttac tgatacttta ttagatagta 840
cttctttgac atgaaggaac atcctgcgac agcttaataa ttattcttca tctaataaaa 900
agcttgcttt ttaattattt tgatatactt ggatgatgtc atgcagcagc tatgtgtgaa 960
ttttcggccc tgtcttcata tgatgtttat ttgcttggga ctgtttcttt ggctgataac 1020
tcaccctgtt gtttggtgat ccttctgcag gtg 1053

<210> SEQ ID NO 5
<211> LENGTH: 2137
<212> TYPE: DNA
<213> ORGANISM: Agrostis nebulosa

<400> SEQUENCE: 5
gagaagctcc ggagataaaa ggccatctaa tctatgttag aagagtgaag tttactccct 60
ctgtcccaaa aatagaattc taagtatgaa atgatttttt tgttatacaa aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaag gatgggtaag ctgattagta tatgtaagtt tagctttttc 360
cattgtaggt taagccttaa ggctcttaca caattgtttc attattctca ttctttaaga 420
gcccatataa gcgttcatga attgtacata tccttagatt tttttttttg ggtaaagctc 480
gagcttctgt atctaaaagt agagaaatca gaaaaagatt catgttttgg tagttttgat 540
ttcttgcctc cataataatt ttggtttacc attttttgtt tgattttagt tttagaagcg 600
tttatagcag gatttaaaat ccaaaactac cattatcttc aagtgaccgt cagtgagccg 660
tttaacggcg tcgacaagtc caacggacac caaccagtga accaccagcg tcgagccaag 720
cgatgcaaac ggaacggccg agacgttgac acctttggcg cggcacggca tgtcggatct 780
ccctctctgg ccccctctcg agagttccag ctccacctcc accggtggcg gtttccaagt 840
ccgttccgtt ccgttccgcc tcctgcctgc tcctctcaga cggcacgaaa ccgtgacggc 900
accggcagca cggggggatt ccttttccac tgctccttcc ttttcccttc ctcgcccgcc 960
gctataaata gccagccccg tccccagatt ctttcccaac ctcatctttg ttcggagcac 1020
ccacacaacc cgatccccaa ttccctcgtc tctcctcgcg agcctcgtcg acccccccctt 1080 caaggtacgg cgatcgtcct ccctccctct ctctctctac cttctcttct ctagactaga 1140
tcggcgaccc ggtccatggt tagggcctgc tagttctgtt cctgtttttt ccatggctgc 1200
gaggtaaaat agatctgatg gcgttatgat ggttaactcg tcatactctt gcgatctatg 1260
gtccctttag gacatcgatt taatttcgga tggttcgaga tcggtgatcc atggttagta 1320
ccctaggcag tggggttaga tccgtgctgt tagggttcgt agatggattc tgattgctca 1380
gtaactggga aacctgggat ggttctagct gggaatcctg ggatggttct agctggttcg 1440
cagatgagat cgatttcatg gtctgctata tcttgtttcg ttgcctaggt tccgtttaat 1500
ctgtccgtgg tatgatgtta gcctttgata aggttcgatc gtgctagcta cgtcctgcgc 1560
agcatttaat tgtcaggtca taatttttag cattcctgtt tttgtttggt ttggttttgt 1620
ctggttgggc tgtagatagt ttcaatctac ctgtcggttt attttattaa atttggattg 1680
gatctgtatg tgtcacatat atcttcatga ttaatatggt tggaattatc tcttcatctt 1740
ttagatatat atggataggt atatatgttg ctgtgggttt tactggtact ttattagata 1800

-continued

```
tattcatgct tagatacatg aagcaacgtg ctgttacagt ttaataattc ttgtttatct   1860

aataaacaaa taaggatagg tatatatgtt gctgatggtt ttactgatac tttattagat   1920

agtacttctt tgacatgaag gaacatcctg cgacagctta ataattattc ttcatctaat   1980

aaaaagcttg ctttttaatt attttgatat acttggatga tgtcatgcag cagctatgtg   2040

tgaattttcg gccctgtctt catatgatgt ttatttgctt gggactgttt ctttggctga   2100

taactcaccc tgttgtttgg tgatccttct gcaggtg                            2137
```

<210> SEQ ID NO 6
<211> LENGTH: 999
<212> TYPE: DNA
<213> ORGANISM: Agrostis nebulosa

<400> SEQUENCE: 6

```
gagaagctcc ggagataaaa ggccatctaa tctatgttag aagagtgaag tttactccct     60

ctgtcccaaa aatagaattc taagtatgaa atgatttttt tgttatacaa aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaag gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatt tttttttttg ggtaaagctc    480

gagcttctgt atctaaaagt agagaaatca gaaaaagatt catgttttgg tagttttgat    540

ttcttgcctc cataataatt ttggtttacc attttttgtt tgattttagt tttagaagcg    600

tttatagcag gatttaaaat ccaaaactac cattatcttc aagtgaccgt cagtgagccg    660

tttaacggcg tcgacaagtc caacggacac caaccagtga accaccagcg tcgagccaag    720

cgatgcaaac ggaacggccg agacgttgac acctttggcg cggcacggca tgtcggatct    780

ccctctctgg ccccctctcg agagttccag ctccacctcc accggtggcg gtttccaagt    840

ccgttccgtt ccgttccgcc tcctgcctgc tcctctcaga cggcacgaaa ccgtgacggc    900

accggcagca cggggggatt ccttttccac tgctccttcc ttttcccttc ctcgcccgcc    960

gctataaata gccagccccg tccccagatt ctttcccaa                           999
```

<210> SEQ ID NO 7
<211> LENGTH: 1900
<212> TYPE: DNA
<213> ORGANISM: Agrostis nebulosa

<400> SEQUENCE: 7

```
gtagacgttt gtcacaggca ttgccactca aacaagcagc cggcgcttgg agcttttata     60

gtttgaaaag tgacggtttt aaggatgggt aagctgatta gtatatgtaa gtttagcttt    120

ttccattgta ggttaagcct taaggctctt acacaattgt ttcattattc tcattcttta    180

agagcccata taagcgttca tgaattgtac atatccttag attttttttt ttgggtaaag    240

ctcgagcttc tgtatctaaa agtagagaaa tcagaaaaag attcatgttt tggtagtttt    300

gatttcttgc ctccataata attttggttt accatttttt gtttgatttt agttttagaa    360

gcgtttatag caggatttaa aatccaaaac taccattatc ttcaagtgac cgtcagtgag    420

ccgtttaacg gcgtcgacaa gtccaacgga caccaaccag tgaaccacca gcgtcgagcc    480

aagcgatgca aacggaacgg ccgagacgtt gacacctttg gcgcggcacg gcatgtcgga    540
```

tctccctctc tggccccctc tcgagagttc cagctccacc tccaccggtg gcggtttcca 600
agtccgttcc gttccgttcc gcctcctgcc tgctcctctc agacggcacg aaaccgtgac 660
ggcaccggca gcacgggggg attccttttc cactgctcct tccttttccc ttcctcgccc 720
gccgctataa atagccagcc ccgtccccag attctttccc aacctcatct ttgttcggag 780
cacccacaca acccgatccc caattccctc gtctctcctc gcgagcctcg tcgacccccc 840
cttcaaggta cggcgatcgt cctccctccc tctctctctc taccttctct tctctagact 900
agatcggcga cccggtccat ggttagggcc tgctagttct gttcctgttt tttccatggc 960
tgcgaggtaa aatagatctg atggcgttat gatggttaac tcgtcatact cttgcgatct 1020
atggtccctt taggacatcg atttaatttc ggatggttcg agatcggtga tccatggtta 1080
gtaccctagg cagtggggtt agatccgtgc tgttagggtt cgtagatgga ttctgattgc 1140
tcagtaactg ggaaacctgg gatggttcta gctgggaatc ctgggatggt tctagctggt 1200
tcgcagatga gatcgatttc atggtctgct atatcttgtt tcgttgccta ggttccgttt 1260
aatctgtccg tggtatgatg ttagcctttg ataaggttcg atcgtgctag ctacgtcctg 1320
cgcagcattt aattgtcagg tcataatttt tagcattcct gtttttgttt ggtttggttt 1380
tgtctggttg ggctgtagat agtttcaatc tacctgtcgg tttattttat taaatttgga 1440
ttggatctgt atgtgtcaca tatatcttca tgattaatat ggttggaatt atctcttcat 1500
cttttagata tatatggata ggtatatatg ttgctgtggg ttttactggt actttattag 1560
atatattcat gcttagatac atgaagcaac gtgctgttac agtttaataa ttcttgttta 1620
tctaataaac aaataaggat aggtatatat gttgctgatg gttttactga tactttatta 1680
gatagtactt ctttgacatg aaggaacatc ctgcgacagc ttaataatta ttcttcatct 1740
aataaaaagc ttgcttttta attattttga tatacttgga tgatgtcatg cagcagctat 1800
gtgtgaattt tcggccctgt cttcatatga tgtttatttg cttgggactg tttctttggc 1860
tgataactca ccctgttgtt tggtgatcct tctgcaggtg 1900

<210> SEQ ID NO 8
<211> LENGTH: 762
<212> TYPE: DNA
<213> ORGANISM: Agrostis nebulosa

<400> SEQUENCE: 8
gtagacgttt gtcacaggca ttgccactca aacaagcagc cggcgcttgg agcttttata 60
gtttgaaaag tgacggtttt aaggatgggt aagctgatta gtatatgtaa gtttagcttt 120
ttccattgta ggttaagcct taaggctctt acacaattgt ttcattattc tcattcttta 180
agagcccata taagcgttca tgaattgtac atatccttag attttttttt ttgggtaaag 240
ctcgagcttc tgtatctaaa agtagagaaa tcagaaaaag attcatgttt tggtagtttt 300
gatttcttgc ctccataata attttggttt accatttttt gtttgatttt agttttagaa 360
gcgtttatag caggatttaa aatccaaaac taccattatc ttcaagtgac cgtcagtgag 420
ccgtttaacg gcgtcgacaa gtccaacgga caccaaccag tgaaccacca gcgtcgagcc 480
aagcgatgca aacggaacgg ccgagacgtt gacacctttg gcgcggcacg gcatgtcgga 540
tctccctctc tggccccctc tcgagagttc cagctccacc tccaccggtg gcggtttcca 600
agtccgttcc gttccgttcc gcctcctgcc tgctcctctc agacggcacg aaaccgtgac 660
ggcaccggca gcacgggggg attccttttc cactgctcct tccttttccc ttcctcgccc 720
gccgctataa atagccagcc ccgtccccag attctttccc aa 762

<210> SEQ ID NO 9
<211> LENGTH: 5068
<212> TYPE: DNA
<213> ORGANISM: Arundo donax

<400> SEQUENCE: 9
ggcctcttta cgtttggcac aatttgatcg aatccaacac ggcaagttaa catttgaaga 60
ttgaaccggg cactaatgca agtctacaac taagaactac aagaaagcat gttccttgag 120
gtacttggat gcaacctcac aattatcaaa ttaattaaca actacagtta gaattttaga 180
tcacaagaat atcacgaact gtggatacta cttcaagggc tattcttttc tgaatgttgc 240
agttggttgt tttaaacata ttacaaacta ggtgtttaaa tgccaaaaag ttcatggaaa 300
aagattaagc taatattcca tccgtccaca aaatttaaat gctaggaatc attatatttg 360
tggatagaag gagtagttag taagacctac acttaattac acattggtca ttcctggagg 420
aataatcccc catagcaagt tgttttgagt ttgactaccc aaacttgcat aaatttttttc 480 ttaaaaaaag ggggagcttc accattccat caagatggcg aggctaaatg aaacgcacga 540
tgggcaaaac ggactaacgt acaaacaaca aggcaatgaa agatagggtt ttgataaata 600
tcaaatatac aaagtcaacc aaagaaaaaa gagatcccaa tggctaacct ttggatccgt 660
gtcgcaattt gtgctttagg acatacaagg tggatttctt ctttggcaaa ctctataata 720
attgggtgac ggtggcctca cggcagcctc aaagagtcgg tagcaacttt tagatctttt 780
gagctgaaac tcaattatgt agtagaatga tatttagata gatagatcga aatttggggg 840
tgtgaaaaca aagaggttct caatattgat agcaactcca acgaatggat atggaaaata 900
catgattttt tattcgagta gaaaaaggag gggaacggaa caaatctagc aatagtagcc 960
accaaagatg aggaccctgg atttcggatc caatagtggt aaggaagaaa gggccggact 1020
atccagaata aggtgaattg gtcaaggaag cggaagtctc cataaagaaa ttgtgggctc 1080
acttgatgtg agaaagaaga ccgaccaaga agcgggtttt gggggacaga ggagattggt 1140
gccaggttgc agtggcatgt atgtggggga agaggcaatg acaacggccg agagaggaga 1200
agggaatgag gtaagtattt gaagtgaaga ggtgcccata taggttaaaa aatgagctgt 1260
ggatttaaat caaaggtgtc agcgacacag gcacggaagt accctaagtt acctatgtgg 1320
gtcgcatatc acgctaagtt ccttcaccgt acaaggtgaa agtaacactg gcaatgtgcc 1380
ccagctgcaa ggcttgtcta tcaatgtggc cctacaaggc tcctggctac cccaggagct 1440
caaaacacgt ggcacatggt ggtacttcgc ccgacctcta tgctcaccgt gcacccggcc 1500
ccgaggtcaa tggctcctga gcacccgact gcatgactgg acccctgagt acccgacccc 1560
cgggacaagc tcccgtggac cttccccggg gatcaggctc acgagtactc gacctcacgt 1620
caatggctct cccgagtacc caaccttgtg tcgatagctc actaaggatc atgtgctaat 1680
ccttagcatc tcggattttg agtactaggc cattatttgc atgccatcct cttggatcta 1740
tgcggatttt caaggacctt acctaagcat caacatgcac aaacacaaac ccttcgtgaa 1800
gccatcccca actactcggg tggcaggacc ctcgacacgt gcgatgcgag ctcggacaga 1860
gctgacaaga acctcccgac ggcgcattaa atgccctggc aagggcgccc cgcctcgtcg 1920
agctctggac ttcatcaagt cacatcaaca gcaggcaggc gctccttccg cagacttcat 1980
catgagggaa tccgttaccc tctatttaca tagtgcagcg gggaatgtgg agatcaaatc 2040
tctccaatga tgtcactgtg tagcatgtat tagcacgcca acaccctgtc gcttaccacg 2100

-continued

```
aggatcagcc atgcaagcaa gagatgttgg tcgggcctcg gtggcaactg aggctatagt   2160
gacctatgac gagcaggcca tagataggcc cactggcaag cccaagaatc gctagacggg   2220
ctagatctgg acacttgtcc gcaccaagca ctaccgttgc aactgcaacc tctatatgta   2280
actatagatt cacatgttgc gacatctttg cccaatacgt attgtaccct agacagctca   2340
ccctatcttt ttcttttttt tcctctttct tcttcctcct ccttgcatgg agacgtagaa   2400
ggactcctcc cttgtgacta ttaaaggaag gacttagggc tgtgctaggg gagagaactt   2460
ttggacttgg gagagctctg cactgaacat cttcctctcc acgcttgtaa tattttccac   2520
aacaaagaat tccataaagc cggatgtagg gctattatcc ctctcgggag gcctgaacca   2580
gggtaaaaca ccactcttct caccagcgtt cgccgcatta gtctagacta gcatcttttg   2640
accctatatc gaaccatcta gggactttac gtcccctgcc tgcagtttcc cggtgacaga   2700
atgactatga tttttcgtcg attttataaa agtgaaaaca accggttgat atctatgcgc   2760
actattttcc tacatatatt tctaacttct tgcttagcca tgtcggttaa gagcaagtgg   2820
agagcactct catttcgtag aacaagtgat gaatgccgac ctgcatcatc ttacttagac   2880
ttgatcatca agtggaatcc ccattcatct taataatctc atattgagtg ccaatgcaac   2940
attgttataa tcctcttcat atgctaattc ttcaaagcta acgtagttaa atgaaggcaa   3000
aatatgcaac ttcgtcctct aagtttgctc aaaggctcat tttaccctt  taactatcaa   3060
accgattact ttcgtccctg aactttcatg tttggtccaa tttaatccct gggctgatgt   3120
atccgtccac ggtggtgtgt ccaatcagtg aataatctag ttagtgaagc cagaagtcca   3180
tagtgcccct tgctctgtca ccatatatcc agttcaaccg caccaatttg ccatctcgaa   3240
ctggttcatg ttttattcag gttggtaaat gaattttgcc aattcaatgt agttagatat   3300
ttccatgtca ttttagtaca tttaccaatt ttttatattc tggctagaaa aggagaatgg   3360
tgacgtcttt cggaagatca agatcaatta tcaagtatca gcaacagcac ctgaaggttg   3420
gagtgcatta gttgtcattg agaataatgc tagctattca ttgcactggc attagagaca   3480
gagagggcga gccagtttga catggcaaat tagcacagtc aaactggata cgtggtgacg   3540
gagggagggg cactatgaat ttttggtgac ggagggaggg gcactatgaa tttttggctt   3600
tgctgacggg acacgccact atggatgaaa ttggacaaaa tacgaatatt caaggatgaa   3660
agtggtcggt ttgatagttc agggatgaaa tgtgtctttg ggcaaacttt gaggacgaag   3720
ttgcctattt tgcattaaac gaatatattt atataccca  aaaaaaagaa tacacatctc   3780
cactccgagc cggcatgtgg ggtcccact  agtcagccac tgtatggcgc cgactagctc   3840
aacggccacg aaccagccaa ccaccagcgc aacctaaacg gcgtaaacgt tgacggcatc   3900
tctctctcgc cccgtctcga agcttccgca ccgctcgctg gtcgctgccc ggcgccgctc   3960
gtgctggact ctttccgtgg cggcttccgc gaaattgcgt ggtggagagg agagacggaa   4020
ccgtcacggc actggattcc ttccccaccc ggcttggccg gcccctcctc gcctccataa   4080
ataggcaccc cgtcctcgcc tcctctcccc acctcatctc ctcctttccc gtgaaccgtg   4140
aacacaaccc gacccagatc ccctcttgcg agcttcgtcg atccctcctc cgcgtcaagg   4200
tacggagctt ctcctccccc ttcttctcta gatcggcgtg ttatgttgtt tccgtggttg   4260
cttggttgga tgaatcgaat gattcttagg gcctaggagg ctggttagat ctgttgcgtt   4320
ctgtttcgta gatggatttt ggtgtaagat caggtcggtt ccgctgttta acttgtgatg   4380
ctagtgtgat tttgggaggg atttgagttg ttaatctggg agttgttggg aggttctcgt   4440
```

```
aggcggattg tagatgaagt cgcccgcacg atttgcgtgg cttgttgggt agctagggtt   4500

agatctgctc ggatttttca ttgttactta ttgagagata atgtagctaa cctttacttg   4560

ttcatctatg tatctcgtat tcgtattcat ctggttcgat ggtgctagat agatgcgcct   4620

gatttgtccg atcgaattgg gtagcatccg cggcttgttt ggtagtgttc tgattgattt   4680

gtcgctctag atctgagtgg aataatatta catctcaaca tgttactaga aacttggttt   4740

atagctccgg atttacatgt ttattcttat gtaaggtttt aaatgaaaga tttatgctac   4800

tgctgctcgt tgatccttta gcatccacct gaggaacatg catgcatctg ttacttcttt   4860

tgatatatgc ttagatagtt gttagtatat actgctgttg ttcgatgatc cttcaggatg   4920

aacatgcatg atcatgttac ttgtttttat atgcttctgc tgttcgttga ttctttagta   4980

ctacctacct gatcatcttg catgtttcct gcttgttaga gattaattga ttaggcttac   5040

cttgttgcct ggtgattctt ccttgcag                                       5068
```

<210> SEQ ID NO 10
<211> LENGTH: 4114
<212> TYPE: DNA
<213> ORGANISM: Arundo donax

<400> SEQUENCE: 10

```
ggcctcttta cgtttggcac aatttgatcg aatccaacac ggcaagttaa catttgaaga     60

ttgaaccggg cactaatgca agtctacaac taagaactac aagaaagcat gttccttgag    120

gtacttggat gcaacctcac aattatcaaa ttaattaaca actacagtta gaattttaga    180

tcacaagaat atcacgaact gtggatacta cttcaagggc tattcttttc tgaatgttgc    240

agttggttgt tttaaacata ttacaaacta ggtgtttaaa tgccaaaaag ttcatggaaa    300

aagattaagc taatattcca tccgtccaca aaatttaaat gctaggaatc attatatttg    360

tggatagaag gagtagttag taagacctac acttaattac acattggtca ttcctggagg    420

aataatcccc catagcaagt tgttttgagt ttgactaccc aaacttgcat aaattttttc    480

ttaaaaaaag ggggagcttc accattccat caagatggcg aggctaaatg aaacgcacga    540

tgggcaaaac ggactaacgt acaaacaaca aggcaatgaa agatagggtt ttgataaata    600

tcaaatatac aaagtcaacc aaagaaaaaa gagatcccaa tggctaacct ttggatccgt    660

gtcgcaattt gtgctttagg acatacaagg tggatttctt ctttggcaaa ctctataata    720

attgggtgac ggtggcctca cggcagcctc aaagagtcgg tagcaacttt tagatctttt    780

gagctgaaac tcaattatgt agtagaatga tatttagata gatagatcga aatttggggg    840

tgtgaaaaca aagaggttct caatattgat agcaactcca acgaatggat atggaaaata    900

catgattttt tattcgagta gaaaaaggag gggaacggaa caaatctagc aatagtagcc    960

accaaagatg aggaccctgg atttcggatc caatagtggt aaggaagaaa gggccggact   1020

atccagaata aggtgaattg gtcaaggaag cggaagtctc cataaagaaa ttgtgggctc   1080

acttgatgtg agaaagaaga ccgaccaaga agcgggtttt gggggacaga ggagattggt   1140

gccaggttgc agtggcatgt atgtggggga agaggcaatg acaacggccg agagaggaga   1200

agggaatgag gtaagtattt gaagtgaaga ggtgcccata taggttaaaa aatgagctgt   1260

ggatttaaat caaaggtgtc agcgacacag gcacggaagt accctaagtt acctatgtgg   1320

gtcgcatatc acgctaagtt ccttcaccgt acaaggtgaa agtaacactg gcaatgtgcc   1380

ccagctgcaa ggcttgtcta tcaatgtggc cctacaaggc tcctggctac cccaggagct   1440

caaaacacgt ggcacatggt ggtacttcgc ccgacctcta tgctcaccgt gcacccggcc   1500
```

-continued ccgaggtcaa tggctcctga gcacccgact gcatgactgg acccctgagt acccgacccc 1560
cgggacaagc tcccgtggac cttccccggg gatcaggctc acgagtactc gacctcacgt 1620
caatggctct cccgagtacc caaccttgtg tcgatagctc actaaggatc atgtgctaat 1680
ccttagcatc tcggattttg agtactaggc cattatttgc atgccatcct cttggatcta 1740
tgcggatttt caaggacctt acctaagcat caacatgcac aaacacaaac ccttcgtgaa 1800
gccatcccca actactcggg tggcaggacc ctcgacacgt gcgatgcgag ctcggacaga 1860
gctgacaaga acctcccgac ggcgcattaa atgccctggc aagggcgccc cgcctcgtcg 1920
agctctggac ttcatcaagt cacatcaaca gcaggcaggc gctccttccg cagacttcat 1980
catgagggaa tccgttaccc tctatttaca tagtgcagcg gggaatgtgg agatcaaatc 2040
tctccaatga tgtcactgtg tagcatgtat tagcacgcca acaccctgtc gcttaccacg 2100
aggatcagcc atgcaagcaa gagatgttgg tcgggcctcg gtggcaactg aggctatagt 2160
gacctatgac gagcaggcca tagataggcc cactggcaag cccaagaatc gctagacggg 2220
ctagatctgg acacttgtcc gcaccaagca ctaccgttgc aactgcaacc tctatatgta 2280
actatagatt cacatgttgc gacatctttg cccaatacgt attgtaccct agacagctca 2340
ccctatcttt ttcttttttt tcctctttct tcttcctcct ccttgcatgg agacgtagaa 2400
ggactcctcc cttgtgacta ttaaaggaag gacttagggc tgtgctaggg gagagaactt 2460
ttggacttgg gagagctctg cactgaacat cttcctctcc acgcttgtaa tattttccac 2520
aacaaagaat tccataaagc cggatgtagg gctattatcc ctctcgggag gcctgaacca 2580
gggtaaaaca ccactcttct caccagcgtt cgccgcatta gtctagacta gcatcttttg 2640
accctatatc gaaccatcta gggactttac gtcccctgcc tgcagtttcc cggtgacaga 2700
atgactatga tttttcgtcg attttataaa agtgaaaaca accggttgat atctatgcgc 2760
actattttcc tacatatatt tctaacttct tgcttagcca tgtcggttaa gagcaagtgg 2820
agagcactct catttcgtag aacaagtgat gaatgccgac ctgcatcatc ttacttagac 2880
ttgatcatca agtggaatcc ccattcatct taataatctc atattgagtg ccaatgcaac 2940
attgttataa tcctcttcat atgctaattc ttcaaagcta acgtagttaa atgaaggcaa 3000
aatatgcaac ttcgtcctct aagtttgctc aaaggctcat ttttaccctt taactatcaa 3060
accgattact ttcgtccctg aactttcatg tttggtccaa tttaatccct gggctgatgt 3120
atccgtccac ggtggtgtgt ccaatcagtg aataatctag ttagtgaagc cagaagtcca 3180
tagtgcccct tgctctgtca ccatatatcc agttcaaccg caccaatttg ccatctcgaa 3240
ctggttcatg ttttattcag gttggtaaat gaattttgcc aattcaatgt agttagatat 3300
ttccatgtca ttttagtaca tttaccaatt ttttatattc tggctagaaa aggagaatgg 3360
tgacgtcttt cggaagatca agatcaatta tcaagtatca gcaacagcac ctgaaggttg 3420
gagtgcatta gttgtcattg agaataatgc tagctattca ttgcactggc attagagaca 3480
gagagggcga gccagtttga catggcaaat tagcacagtc aaactggata cgtggtgacg 3540
gagggagggg cactatgaat ttttggtgac ggagggaggg gcactatgaa tttttggctt 3600
tgctgacggg acacgccact atggatgaaa ttggacaaaa tacgaatatt caaggatgaa 3660
agtggtcggt ttgatagttc agggatgaaa tgtgtctttg ggcaaacttt gaggacgaag 3720
ttgcctattt tgcattaaac gaatatattt atatacccca aaaaaaagaa tacacatctc 3780
cactccgagc cggcatgtgg ggtccccact agtcagccac tgtatggcgc cgactagctc 3840
aacggccacg aaccagccaa ccaccagcgc aacctaaacg gcgtaaacgt tgacggcatc 3900
tctctctcgc cccgtctcga agcttccgca ccgctcgctg gtcgctgccc ggcgccgctc 3960
gtgctggact ctttccgtgg cggcttccgc gaaattgcgt ggtggagagg agagacggaa 4020
ccgtcacggc actggattcc ttccccaccc ggcttggccg gcccctcctc gcctccataa 4080
ataggcaccc cgtcctcgcc tcctctcccc acct 4114

<210> SEQ ID NO 11
<211> LENGTH: 85
<212> TYPE: DNA
<213> ORGANISM: Arundo donax

<400> SEQUENCE: 11
catctcctcc tttcccgtga accgtgaaca caacccgacc cagatcccct cttgcgagct 60
tcgtcgatcc ctcctccgcg tcaag 85

<210> SEQ ID NO 12
<211> LENGTH: 869
<212> TYPE: DNA
<213> ORGANISM: Arundo donax

<400> SEQUENCE: 12
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatctcgta ttcgtattca tctggttcga tggtgctaga tagatgcgcc 420
tgatttgtcc gatcgaattg ggtagcatcc gcggcttgtt tggtagtgtt ctgattgatt 480
tgtcgctcta gatctgagtg gaataatatt acatctcaac atgttactag aaacttggtt 540
tatagctccg gatttacatg tttattctta tgtaaggttt taaatgaaag atttatgcta 600
ctgctgctcg ttgatccttt agcatccacc tgaggaacat gcatgcatct gttacttctt 660
ttgatatatg cttagatagt tgttagtata tactgctgtt gttcgatgat ccttcaggat 720
gaacatgcat gatcatgtta cttgttttta tatgcttctg ctgttcgttg attctttagt 780
actacctacc tgatcatctt gcatgtttcc tgcttgttag agattaattg attaggctta 840
ccttgttgcc tggtgattct tccttgcag 869

<210> SEQ ID NO 13
<211> LENGTH: 2969
<212> TYPE: DNA
<213> ORGANISM: Arundo donax

<400> SEQUENCE: 13
gatcagccat gcaagcaaga gatgttggtc gggcctcggt ggcaactgag gctatagtga 60
cctatgacga gcaggccata gataggccca ctggcaagcc caagaatcgc tagacgggct 120
agatctggac acttgtccgc accaagcact accgttgcaa ctgcaacctc tatatgtaac 180
tatagattca catgttgcga catctttgcc caatacgtat tgtaccctag acagctcacc 240
ctatcttttt cttttttttc ctctttcttc ttcctcctcc ttgcatggag acgtagaagg 300
actcctccct tgtgactatt aaaggaagga cttagggctg tgctagggga gagaactttt 360

-continued

```
ggacttggga gagctctgca ctgaacatct tcctctccac gcttgtaata ttttccacaa    420
caaagaattc cataaagccg gatgtagggc tattatccct ctcgggaggc ctgaaccagg    480
gtaaaacacc actcttctca ccagcgttcg ccgcattagt ctagactagc atcttttgac    540
cctatatcga accatctagg gactttacgt cccctgcctg cagtttcccg gtgacagaat    600
gactatgatt tttcgtcgat tttataaaag tgaaaacaac cggttgatat ctatgcgcac    660
tattttccta catatatttc taacttcttg cttagccatg tcggttaaga gcaagtggag    720
agcactctca tttcgtagaa caagtgatga atgccgacct gcatcatctt acttagactt    780
gatcatcaag tggaatcccc attcatctta ataatctcat attgagtgcc aatgcaacat    840
tgttataatc ctcttcatat gctaattctt caaagctaac gtagttaaat gaaggcaaaa    900
tatgcaactt cgtcctctaa gtttgctcaa aggctcattt ttacccttta actatcaaac    960
cgattacttt cgtccctgaa ctttcatgtt tggtccaatt taatccctgg gctgatgtat   1020
ccgtccacgg tggtgtgtcc aatcagtgaa taatctagtt agtgaagcca gaagtccata   1080
gtgccccttg ctctgtcacc atatatccag ttcaaccgca ccaatttgcc atctcgaact   1140
ggttcatgtt ttattcaggt tggtaaatga attttgccaa ttcaatgtag ttagatattt   1200
ccatgtcatt ttagtacatt taccaatttt ttatattctg gctagaaaag gagaatggtg   1260
acgtctttcg gaagatcaag atcaattatc aagtatcagc aacagcacct gaaggttgga   1320
gtgcattagt tgtcattgag aataatgcta gctattcatt gcactggcat tagagacaga   1380
gagggcgagc cagtttgaca tggcaaatta gcacagtcaa actggatacg tggtgacgga   1440
gggaggggca ctatgaattt ttggtgacgg agggaggggc actatgaatt tttggctttg   1500
ctgacgggac acgccactat ggatgaaatt ggacaaaata cgaatattca aggatgaaag   1560
tggtcggttt gatagttcag ggatgaaatg tgtctttggg caaactttga ggacgaagtt   1620
gcctattttg cattaaacga atatatttat ataccccaaa aaaaagaata cacatctcca   1680
ctccgagccg gcatgtgggg tccccactag tcagccactg tatggcgccg actagctcaa   1740
cggccacgaa ccagccaacc accagcgcaa cctaaacggc gtaaacgttg acggcatctc   1800
tctctcgccc cgtctcgaag cttccgcacc gctcgctggt cgctgcccgg cgccgctcgt   1860
gctggactct ttccgtggcg gcttccgcga aattgcgtgg tggagaggag agacggaacc   1920
gtcacggcac tggattcctt ccccacccgg cttggccggc ccctcctcgc ctccataaat   1980
aggcaccccg tcctcgcctc ctctccccac ctcatctcct cctttcccgt gaaccgtgaa   2040
cacaacccga cccagatccc ctcttgcgag cttcgtcgat ccctcctccg cgtcaaggta   2100
cggagcttct cctccccctt cttctctaga tcggcgtgtt atgttgtttc cgtggttgct   2160
tggttggatg aatcgaatga ttcttagggc ctaggaggct ggttagatct gttgcgttct   2220
gtttcgtaga tggattttgg tgtaagatca ggtcggttcc gctgtttaac ttgtgatgct   2280
agtgtgattt ttgggaggat ttgagttgtt aatctgggag ttgttgggag gttctcgtag   2340
gcggattgta gatgaagtcg cccgcacgat ttgcgtggct tgttgggtag ctagggttag   2400
atctgctcgg atttttcatt gttacttatt gagagataat gtagctaacc tttacttgtt   2460
catctatgta tctcgtattc gtattcatct ggttcgatgg tgctagatag atgcgcctga   2520
tttgtccgat cgaattgggt agcatccgcg gcttgtttgg tagtgttctg attgatttgt   2580
cgctctagat ctgagtggaa taatattaca tctcaacatg ttactagaaa cttggtttat   2640
agctccggat ttacatgttt attcttatgt aaggttttaa atgaaagatt tatgctactg   2700
```

```
ctgctcgttg atcctttagc atccacctga ggaacatgca tgcatctgtt acttcttttg   2760

atatatgctt agatagttgt tagtatatac tgctgttgtt cgatgatcct tcaggatgaa   2820

catgcatgat catgttactt gtttttatat gcttctgctg ttcgttgatt ctttagtact   2880

acctacctga tcatcttgca tgtttcctgc ttgttagaga ttaattgatt aggcttacct   2940

tgttgcctgg tgattcttcc ttgcaggtg                                     2969
```

<210> SEQ ID NO 14
<211> LENGTH: 2012
<212> TYPE: DNA
<213> ORGANISM: Arundo donax

<400> SEQUENCE: 14

```
gatcagccat gcaagcaaga gatgttggtc gggcctcggt ggcaactgag gctatagtga     60

cctatgacga gcaggccata gataggccca ctggcaagcc caagaatcgc tagacgggct    120

agatctggac acttgtccgc accaagcact accgttgcaa ctgcaacctc tatatgtaac    180

tatagattca catgttgcga catctttgcc caatacgtat tgtaccctag acagctcacc    240

ctatcttttt cttttttttc ctctttcttc ttcctcctcc ttgcatggag acgtagaagg    300

actcctccct tgtgactatt aaaggaagga cttagggctg tgctagggga gagaactttt    360

ggacttggga gagctctgca ctgaacatct tcctctccac gcttgtaata ttttccacaa    420

caaagaattc cataaagccg gatgtagggc tattatccct ctcgggaggc ctgaaccagg    480

gtaaaacacc actcttctca ccagcgttcg ccgcattagt ctagactagc atcttttgac    540

cctatatcga accatctagg gactttacgt cccctgcctg cagtttcccg gtgacagaat    600

gactatgatt tttcgtcgat tttataaaag tgaaaacaac cggttgatat ctatgcgcac    660

tattttccta catatatttc taacttcttg cttagccatg tcggttaaga gcaagtggag    720

agcactctca tttcgtagaa caagtgatga atgccgacct gcatcatctt acttagactt    780

gatcatcaag tggaatcccc attcatctta ataatctcat attgagtgcc aatgcaacat    840

tgttataatc ctcttcatat gctaattctt caaagctaac gtagttaaat gaaggcaaaa    900

tatgcaactt cgtcctctaa gtttgctcaa aggctcattt ttaccctttta actatcaaac    960

cgattacttt cgtccctgaa ctttcatgtt tggtccaatt taatccctgg gctgatgtat   1020

ccgtccacgg tggtgtgtcc aatcagtgaa taatctagtt agtgaagcca gaagtccata   1080

gtgccccttg ctctgtcacc atatatccag ttcaaccgca ccaatttgcc atctcgaact   1140

ggttcatgtt ttattcaggt tggtaaatga attttgccaa ttcaatgtag ttagatattt   1200

ccatgtcatt ttagtacatt taccaatttt ttatattctg gctagaaaag gagaatggtg   1260

acgtctttcg gaagatcaag atcaattatc aagtatcagc aacagcacct gaaggttgga   1320

gtgcattagt tgtcattgag aataatgcta gctattcatt gcactggcat tagagacaga   1380

gagggcgagc cagtttgaca tggcaaatta gcacagtcaa actggatacg tggtgacgga   1440

gggaggggca ctatgaattt ttggtgacgg agggaggggc actatgaatt tttggctttg   1500

ctgacgggac acgccactat ggatgaaatt ggacaaaata cgaatattca aggatgaaag   1560

tggtcggttt gatagttcag ggatgaaatg tgtctttggg caaactttga ggacgaagtt   1620

gcctattttg cattaaacga atatatttat ataccccaaa aaaaagaata cacatctcca   1680

ctccgagccg gcatgtgggg tccccactag tcagccactg tatggcgccg actagctcaa   1740

cggccacgaa ccagccaacc accagcgcaa cctaaacggc gtaaacgttg acggcatctc   1800

tctctcgccc cgtctcgaag cttccgcacc gctcgctggt cgctgcccgg cgccgctcgt   1860
```

gctggactct ttccgtggcg gcttccgcga aattgcgtgg tggagaggag agacggaacc 1920
gtcacggcac tggattcctt ccccacccgg cttggccggc cctcctcgc ctccataaat 1980 aggcaccccg tcctcgcctc ctctccccac ct 2012

<210> SEQ ID NO 15
<211> LENGTH: 872
<212> TYPE: DNA
<213> ORGANISM: Arundo donax

<400> SEQUENCE: 15
gtacggagct tctcctcccc cttcttctct agatcggcgt gttatgttgt ttccgtggtt 60
gcttggttgg atgaatcgaa tgattcttag ggcctaggag gctggttaga tctgttgcgt 120
tctgtttcgt agatggattt tggtgtaaga tcaggtcggt tccgctgttt aacttgtgat 180
gctagtgtga tttttgggag gatttgagtt gttaatctgg gagttgttgg gaggttctcg 240
taggcggatt gtagatgaag tcgcccgcac gatttgcgtg gcttgttggg tagctagggt 300
tagatctgct cggatttttc attgttactt attgagagat aatgtagcta acctttactt 360
gttcatctat gtatctcgta ttcgtattca tctggttcga tggtgctaga tagatgcgcc 420
tgatttgtcc gatcgaattg ggtagcatcc gcggcttgtt tggtagtgtt ctgattgatt 480
tgtcgctcta gatctgagtg gaataatatt acatctcaac atgttactag aaacttggtt 540
tatagctccg gatttacatg tttattctta tgtaaggttt taaatgaaag atttatgcta 600
ctgctgctcg ttgatccttt agcatccacc tgaggaacat gcatgcatct gttacttctt 660
ttgatatatg cttagatagt tgttagtata tactgctgtt gttcgatgat ccttcaggat 720
gaacatgcat gatcatgtta cttgttttta tatgcttctg ctgttcgttg attctttagt 780
actacctacc tgatcatctt gcatgtttcc tgcttgttag agattaattg attaggctta 840
ccttgttgcc tggtgattct tccttgcagg tg 872

<210> SEQ ID NO 16
<211> LENGTH: 1954
<212> TYPE: DNA
<213> ORGANISM: Arundo donax

<400> SEQUENCE: 16
tgatgtatcc gtccacggtg gtgtgtccaa tcagtgaata atctagttag tgaagccaga 60
agtccatagt gccccttgct ctgtcaccat atatccagtt caaccgcacc aatttgccat 120
ctcgaactgg ttcatgtttt attcaggttg gtaaatgaat tttgccaatt caatgtagtt 180
agatatttcc atgtcatttt agtacattta ccaatttttt atattctggc tagaaaagga 240
gaatggtgac gtctttcgga agatcaagat caattatcaa gtatcagcaa cagcacctga 300
aggttggagt gcattagttg tcattgagaa taatgctagc tattcattgc actggcatta 360
gagacagaga gggcgagcca gtttgacatg gcaaattagc acagtcaaac tggatacgtg 420
gtgacggagg gaggggcact atgaattttt ggtgacggag ggaggggcac tatgaatttt 480
tggctttgct gacgggacac gccactatgg atgaaattgg acaaaatacg aatattcaag 540
gatgaaagtg gtcggtttga tagttcaggg atgaaatgtg tctttgggca aactttgagg 600
acgaagttgc ctattttgca ttaaacgaat atatttatat accccaaaaa aaagaataca 660
catctccact ccgagccggc atgtggggtc cccactagtc agccactgta tggcgccgac 720
tagctcaacg gccacgaacc agccaaccac cagcgcaacc taaacggcgt aaacgttgac 780

```
ggcatctctc tctcgccccg tctcgaagct tccgcaccgc tcgctggtcg ctgcccggcg    840

ccgctcgtgc tggactcttt ccgtggcggc ttccgcgaaa ttgcgtggtg gagaggagag    900

acggaaccgt cacggcactg gattccttcc ccacccggct tggccggccc ctcctcgcct    960

ccataaatag gcaccccgtc ctcgcctcct ctccccacct catctcctcc tttcccgtga   1020

accgtgaaca caacccgacc cagatcccct cttgcgagct tcgtcgatcc ctcctccgcg   1080

tcaaggtacg gagcttctcc tccccttct tctctagatc ggcgtgttat gttgtttccg   1140

tggttgcttg gttggatgaa tcgaatgatt cttagggcct aggaggctgg ttagatctgt   1200

tgcgttctgt ttcgtagatg gattttggtg taagatcagg tcggttccgc tgtttaactt   1260

gtgatgctag tgtgattttt gggaggattt gagttgttaa tctgggagtt gttgggaggt   1320

tctcgtaggc ggattgtaga tgaagtcgcc cgcacgattt gcgtggcttg ttgggtagct   1380

agggttagat ctgctcggat ttttcattgt tacttattga gagataatgt agctaacctt   1440

tacttgttca tctatgtatc tcgtattcgt attcatctgg ttcgatggtg ctagatagat   1500

gcgcctgatt tgtccgatcg aattgggtag catccgcggc ttgtttggta gtgttctgat   1560

tgatttgtcg ctctagatct gagtggaata atattacatc tcaacatgtt actagaaact   1620

tggtttatag ctccggattt acatgtttat tcttatgtaa ggttttaaat gaaagattta   1680

tgctactgct gctcgttgat cctttagcat ccacctgagg aacatgcatg catctgttac   1740

ttcttttgat atatgcttag atagttgtta gtatatactg ctgttgttcg atgatccttc   1800

aggatgaaca tgcatgatca tgttacttgt ttttatatgc ttctgctgtt cgttgattct   1860

ttagtactac ctacctgatc atcttgcatg tttcctgctt gttagagatt aattgattag   1920

gcttaccttg ttgcctggtg attcttcctt gcag                               1954
```

<210> SEQ ID NO 17
<211> LENGTH: 1000
<212> TYPE: DNA
<213> ORGANISM: Arundo donax

<400> SEQUENCE: 17

```
tgatgtatcc gtccacggtg gtgtgtccaa tcagtgaata atctagttag tgaagccaga     60

agtccatagt gccccttgct ctgtcaccat atatccagtt caaccgcacc aatttgccat    120

ctcgaactgg ttcatgtttt attcaggttg gtaaatgaat tttgccaatt caatgtagtt    180

agatatttcc atgtcatttt agtacattta ccaatttttt atattctggc tagaaaagga    240

gaatggtgac gtctttcgga agatcaagat caattatcaa gtatcagcaa cagcacctga    300

aggttggagt gcattagttg tcattgagaa taatgctagc tattcattgc actggcatta    360

gagacagaga gggcgagcca gtttgacatg gcaaattagc acagtcaaac tggatacgtg    420

gtgacggagg gaggggcact atgaattttt ggtgacggag ggaggggcac tatgaatttt    480

tggctttgct gacgggacac gccactatgg atgaaattgg acaaaatacg aatattcaag    540

gatgaaagtg gtcggtttga tagttcaggg atgaaatgtg tctttgggca aactttgagg    600

acgaagttgc ctattttgca ttaaacgaat atatttatat accccaaaaa aaagaataca    660

catctccact ccgagccggc atgtggggtc cccactagtc agccactgta tggcgccgac    720

tagctcaacg gccacgaacc agccaaccac cagcgcaacc taaacggcgt aaacgttgac    780

ggcatctctc tctcgccccg tctcgaagct tccgcaccgc tcgctggtcg ctgcccggcg    840

ccgctcgtgc tggactcttt ccgtggcggc ttccgcgaaa ttgcgtggtg gagaggagag    900

acggaaccgt cacggcactg gattccttcc ccacccggct tggccggccc ctcctcgcct    960
```

```
ccataaatag gcaccccgtc ctcgcctcct ctccccacct                    1000


<210> SEQ ID NO 18
<211> LENGTH: 1957
<212> TYPE: DNA
<213> ORGANISM: Arundo donax

<400> SEQUENCE: 18

tgatgtatcc gtccacggtg gtgtgtccaa tcagtgaata atctagttag tgaagccaga      60

agtccatagt gccccttgct ctgtcaccat atatccagtt caaccgcacc aatttgccat     120

ctcgaactgg ttcatgtttt attcaggttg gtaaatgaat tttgccaatt caatgtagtt     180

agatatttcc atgtcatttt agtacattta ccaatttttt atattctggc tagaaaagga     240

gaatggtgac gtctttcgga agatcaagat caattatcaa gtatcagcaa cagcacctga     300

aggttggagt gcattagttg tcattgagaa taatgctagc tattcattgc actggcatta     360

gagacagaga gggcgagcca gtttgacatg gcaaattagc acagtcaaac tggatacgtg     420

gtgacggagg gaggggcact atgaattttt ggtgacggag ggaggggcac tatgaatttt     480

tggctttgct gacgggacac gccactatgg atgaaattgg acaaaatacg aatattcaag     540

gatgaaagtg gtcggtttga tagttcaggg atgaaatgtg tctttgggca aactttgagg     600

acgaagttgc ctattttgca ttaaacgaat atatttatat accccaaaaa aaagaataca     660

catctccact ccgagccggc atgtggggtc cccactagtc agccactgta tggcgccgac     720

tagctcaacg gccacgaacc agccaaccac cagcgcaacc taaacggcgt aaacgttgac     780

ggcatctctc tctcgccccg tctcgaagct tccgcaccgc tcgctggtcg ctgcccggcg     840

ccgctcgtgc tggactcttt ccgtggcggc ttccgcgaaa ttgcgtggtg gagaggagag     900

acggaaccgt cacggcactg gattccttcc ccacccggct tggccggccc ctcctcgcct     960

ccataaatag gcaccccgtc ctcgcctcct ctccccacct catctcctcc tttcccgtga    1020

accgtgaaca caacccgacc cagatcccct cttgcgagct tcgtcgatcc ctcctccgcg    1080

tcaaggtacg gagcttctcc tccccccttct tctctagatc ggcgtgttat gttgtttccg    1140

tggttgcttg gttggatgaa tcgaatgatt cttagggcct aggaggctgg ttagatctgt    1200

tgcgttctgt ttcgtagatg gattttggtg taagatcagg tcggttccgc tgtttaactt    1260

gtgatgctag tgtgattttt gggaggattt gagttgttaa tctgggagtt gttgggaggt    1320

tctcgtaggc ggattgtaga tgaagtcgcc cgcacgattt gcgtggcttg ttgggtagct    1380

agggttagat ctgctcggat ttttcattgt tacttattga gagataatgt agctaacctt    1440

tacttgttca tctatgtatc tcgtattcgt attcatctgg ttcgatggtg ctagatagat    1500

gcgcctgatt tgtccgatcg aattgggtag catccgcggc ttgtttggta gtgttctgat    1560

tgatttgtcg ctctagatct gagtggaata atattacatc tcaacatgtt actagaaact    1620

tggtttatag ctccggattt acatgtttat tcttatgtaa ggttttaaat gaaagattta    1680

tgctactgct gctcgttgat cctttagcat ccacctgagg aacatgcatg catctgttac    1740

ttcttttgat atatgcttag atagttgtta gtatatactg ctgttgttcg atgatccttc    1800

aggatgaaca tgcatgatca tgttacttgt ttttatatgc ttctgctgtt cgttgattct    1860

ttagtactac ctacctgatc atcttgcatg tttcctgctt gttagagatt aattgattag    1920

gcttaccttg ttgcctggtg attcttcctt gcaggtg                             1957


<210> SEQ ID NO 19
```

<211> LENGTH: 1957
<212> TYPE: DNA
<213> ORGANISM: Arundo donax

<400> SEQUENCE: 19

```
tgatgtatcc gtccacggtg gtgtgtccaa tcagtgaata atctagttag tgaagccaga     60
agtccatagt gccccttgct ctgtcaccat atatccagtt caaccgcacc aatttgccat    120
ctcgaactgg ttcatgtttt attcaggttg gtaaatgaat tttgccaatt caatgtagtt    180
agatatttcc atgtcatttt agtacattta ccaatttttt atattctggc tagaaaagga    240
gaatggtgac gtctttcgga agatcaagat caattatcaa gtatcagcaa cagcacctga    300
aggttggagt gcattagttg tcattgagaa taatgctagc tattcattgc actggcatta    360
gagacagaga gggcgagcca gtttgacatg gcaaattagc acagtcaaac tggatacgtg    420
gtgacggagg gaggggcact atgaattttt ggtgacggag ggaggggcac tatgaatttt    480
tggctttgct gacgggacac gccactatgg atgaaattgg acaaaatacg aatattcaag    540
gatgaaagtg gtcggtttga tagttcaggg atgaaatgtg tctttgggca aactttgagg    600
acgaagttgc ctattttgca ttaaacgaat atatttatat accccaaaaa aaagaataca    660
catctccact ccgagccggc atgtggggtc cccactagtc agccactgta tggcgccgac    720
tagctcaacg gccacgaacc agccaaccac cagcgcaacc taaacggcgt aaacgttgac    780
ggcatctctc tctcgccccg tctcgaagct tccgcaccgc tcgctggtcg ctgcccggcg    840
ccgctcgtgc tggactcttt ccgtggcggc ttccgcgaaa ttgcgtggtg gagaggagag    900
acggaaccgt cacggcactg gattccttcc ccacccggct tggccggccc ctcctcgcct    960
ccataaatag gcaccccgtc ctcgcctcct ctccccacct catctcctcc tttcccgtga   1020
accgtgaaca caacccgacc cagatcccct cttgcgagct tcgtcgatcc ctcctccgcg   1080
tcaaggtacg gagcttctcc tccccctttct tctctagatc ggcgtgttat gttgtttccg   1140
tggttgcttg gttggatgaa tcgaatgatt cttagggcct aggaggctgg ttagatctgt   1200
tgcgttctgt ttcgtagatg gattttggtg taagatcagg tcggttccgc tgtttaactt   1260
gtgatgctag tgtgattttt gggaggattt gagttgttaa tctgggagtt gttgggaggt   1320
tctcgtaggc ggattgtaga tgaagtcgcc cgcacgattt gcgtggcttg ttgggtagct   1380
agggttagat ctgctcggat ttttcattgt tacttattga gagataatgt agctaacctt   1440
tacttgttca tctatgtata tcgtattcgt attcatctgg ttcgatggtg ctagatagat   1500
gcgcctgatt tgtccgatcg aattgggtag catccgcggc ttgtttggta gtgttctgat   1560
tgatttgtcg ctctagatct gagtggaata atattacatc tcaacatgtt actagaaact   1620
tggtttatag ctccggattt acatgtttat tcttatgtaa ggttttaaat gaaagattta   1680
tgctactgct gctcgttgat cctttagcat ccacctgagg aacatgcatg catctgttac   1740
ttcttttgat atatgcttag atagttgtta gtatatactg ctgttgttcg atgatccttc   1800
aggatgaaca tgcatgatca tgttacttgt ttttatatgc ttctgctgtt cgttgattct   1860
ttagtactac ctacctgatc atcttgcatg tttcctgctt gttagagatt aattgattag   1920
gcttaccttg ttgcctggtg attcttcctt gcaggtg                             1957
```

<210> SEQ ID NO 20
<211> LENGTH: 872
<212> TYPE: DNA
<213> ORGANISM: Arundo donax

<400> SEQUENCE: 20

```
gtacggagct tctcctcccc cttcttctct agatcggcgt gttatgttgt ttccgtggtt     60
gcttggttgg atgaatcgaa tgattcttag ggcctaggag gctggttaga tctgttgcgt    120
tctgtttcgt agatggattt tggtgtaaga tcaggtcggt tccgctgttt aacttgtgat    180
gctagtgtga tttttgggag gatttgagtt gttaatctgg gagttgttgg gaggttctcg    240
taggcggatt gtagatgaag tcgcccgcac gatttgcgtg gcttgttggg tagctagggt    300
tagatctgct cggatttttc attgttactt attgagagat aatgtagcta acctttactt    360
gttcatctat gtatatcgta ttcgtattca tctggttcga tggtgctaga tagatgcgcc    420
tgatttgtcc gatcgaattg ggtagcatcc gcggcttgtt tggtagtgtt ctgattgatt    480
tgtcgctcta gatctgagtg gaataatatt acatctcaac atgttactag aaacttggtt    540
tatagctccg gatttacatg tttattctta tgtaaggttt taaatgaaag atttatgcta    600
ctgctgctcg ttgatccttt agcatccacc tgaggaacat gcatgcatct gttacttctt    660
ttgatatatg cttagatagt tgttagtata tactgctgtt gttcgatgat ccttcaggat    720
gaacatgcat gatcatgtta cttgttttta tatgcttctg ctgttcgttg attctttagt    780
actacctacc tgatcatctt gcatgtttcc tgcttgttag agattaattg attaggctta    840
ccttgttgcc tggtgattct tccttgcagg tg                                  872
```

<210> SEQ ID NO 21
<211> LENGTH: 1712
<212> TYPE: DNA
<213> ORGANISM: Arundo donax

<400> SEQUENCE: 21

```
gtgacgtctt tcggaagatc aagatcaatt atcaagtatc agcaacagca cctgaaggtt     60
ggagtgcatt agttgtcatt gagaataatg ctagctattc attgcactgg cattagagac    120
agagagggcg agccagtttg acatggcaaa ttagcacagt caaactggat acgtggtgac    180
ggagggaggg gcactatgaa tttttggtga cggagggagg ggcactatga atttttggct    240
ttgctgacgg gacacgccac tatggatgaa attggacaaa atacgaatat tcaaggatga    300
aagtggtcgg tttgatagtt cagggatgaa atgtgtcttt gggcaaactt tgaggacgaa    360
gttgcctatt ttgcattaaa cgaatatatt tatataccccc aaaaaaaaga atacacatct    420
ccactccgag ccggcatgtg gggtccccac tagtcagcca ctgtatggcg ccgactagct    480
caacggccac gaaccagcca accaccagcg caacctaaac ggcgtaaacg ttgacggcat    540
ctctctctcg ccccgtctcg aagcttccgc accgctcgct ggtcgctgcc cggcgccgct    600
cgtgctggac tctttccgtg gcggcttccg cgaaattgcg tggtggagag gagagacgga    660
accgtcacgg cactggattc cttccccacc cggcttggcc ggcccctcct cgcctccata    720
aataggcacc ccgtcctcgc ctcctctccc cacctcatct cctcctttcc cgtgaaccgt    780
gaacacaacc cgacccagat cccctcttgc gagcttcgtc gatccctcct ccgcgtcaag    840
gtacggagct tctcctcccc cttcttctct agatcggcgt gttatgttgt ttccgtggtt    900
gcttggttgg atgaatcgaa tgattcttag ggcctaggag gctggttaga tctgttgcgt    960
tctgtttcgt agatggattt tggtgtaaga tcaggtcggt tccgctgttt aacttgtgat   1020
gctagtgtga tttttgggag gatttgagtt gttaatctgg gagttgttgg gaggttctcg   1080
taggcggatt gtagatgaag tcgcccgcac gatttgcgtg gcttgttggg tagctagggt   1140
tagatctgct cggatttttc attgttactt attgagagat aatgtagcta acctttactt   1200
```

-continued

```
gttcatctat gtatctcgta ttcgtattca tctggttcga tggtgctaga tagatgcgcc   1260

tgatttgtcc gatcgaattg ggtagcatcc gcggcttgtt tggtagtgtt ctgattgatt   1320

tgtcgctcta gatctgagtg gaataatatt acatctcaac atgttactag aaacttggtt   1380

tatagctccg gatttacatg tttattctta tgtaaggttt taaatgaaag atttatgcta   1440

ctgctgctcg ttgatccttt agcatccacc tgaggaacat gcatgcatct gttacttctt   1500

ttgatatatg cttagatagt tgttagtata tactgctgtt gttcgatgat ccttcaggat   1560

gaacatgcat gatcatgtta cttgttttta tatgcttctg ctgttcgttg attctttagt   1620

actacctacc tgatcatctt gcatgtttcc tgcttgttag agattaattg attaggctta   1680

ccttgttgcc tggtgattct tccttgcagg tg                                 1712
```

<210> SEQ ID NO 22
<211> LENGTH: 755
<212> TYPE: DNA
<213> ORGANISM: Arundo donax

<400> SEQUENCE: 22

```
gtgacgtctt tcggaagatc aagatcaatt atcaagtatc agcaacagca cctgaaggtt     60

ggagtgcatt agttgtcatt gagaataatg ctagctattc attgcactgg cattagagac    120

agagagggcg agccagtttg acatggcaaa ttagcacagt caaactggat acgtggtgac    180

ggagggaggg gcactatgaa tttttggtga cggagggagg ggcactatga atttttggct    240

ttgctgacgg gacacgccac tatggatgaa attggacaaa atacgaatat tcaaggatga    300

aagtggtcgg tttgatagtt cagggatgaa atgtgtcttt gggcaaactt tgaggacgaa    360

gttgcctatt ttgcattaaa cgaatatatt tatataccca aaaaaaaaga atacacatct    420

ccactccgag ccggcatgtg gggtccccac tagtcagcca ctgtatggcg ccgactagct    480

caacggccac gaaccagcca accaccagcg caacctaaac ggcgtaaacg ttgacggcat    540

ctctctctcg ccccgtctcg aagcttccgc accgctcgct ggtcgctgcc cggcgccgct    600

cgtgctggac tctttccgtg gcggcttccg cgaaattgcg tggtggagag gagagacgga    660

accgtcacgg cactggattc cttccccacc cggcttggcc ggcccctcct cgcctccata    720

aataggcacc ccgtcctcgc ctcctctccc cacct                               755
```

<210> SEQ ID NO 23
<211> LENGTH: 3276
<212> TYPE: DNA
<213> ORGANISM: Arundo donax

<400> SEQUENCE: 23

```
ggcctcttta cgtttggcac aatttgatcg aatccaacac ggcaagttag cctttgaagc     60

ttgaaccggg cactaatgca agtatataat aactgagaac tacaagaaag catattcctt    120

gaggtactta tgcaacctta caattatcaa attaattaac aactagcagt tagaatttta    180

tatcacaaga atatcatgaa ccgtggatac tacttcttaa agggctattc tttttctgaa    240

tgtcgcagtt ggttatttta accatattac aaactagggg tttaaatccc aaaaagttca    300

cggaaaggga ttaagcaagt agttagcaag actcacactt atgaccgtta gccaaattac    360

acattggtca ttccaggagg agtaatcccc catagctagt tgttttgagt ttgactaccc    420

aaacttgcat aatcgttttc ctagaggggg ggggggggtt caccattcca tcaagatgag    480

gcaaagctaa atgaaacaca cgagaggcaa aacggactga cgtgatagag tttttaataa    540

atatcaaata tgtagagtca accaaagaaa aaagatatcc caatggctaa actttggatc    600
```

-continued

```
tatgtcgtaa ttcgtgtttt aggacataca aggcgaattc cttctacggc aaactctaga    660
atagctgggc gacaatggcc tcacgatagc ctcaaagagt tggtagcaac tttgagatct    720
tttgatccga aactcaatta tgtagtacaa tgatatttag atagattgat tgaaagttgg    780
gggtgggggc gaaagcgaag gggatctcaa tattaataca tctatagtga atggatatag    840
aaaacacagg atttccaatt caagtagaaa taggaggaac ggaacagatc tagcaatagt    900
agccaccaaa gacgaggagg attctagatt gcaaatccaa ggtgaaagga agaaatgttg    960
aactatccag aataaggcgg attggccaag gaggcggaag tctctagaaa gaagtcattt   1020
ggctctgagg gctcacttga tgcgagaagg aagactgact gaggaatgga ttttggtgga   1080
ccgaggaaat tggtgctggg ttgcagaggc atgtatgtgg gaaaagaggc agtggcaacg   1140
atcgagagag gagaagggaa tgaggtaagt atttgaagtg aagaggagcc catataggtg   1200
aaaaataaaa ataatccatc gtggattcaa ataatcaaag ggctatgacc tttcatcaat   1260
tttagaaaag tgaaaacaac cggtttaaca cctatatgca ccattttcct acatagattt   1320
ttaacttctt acttaaccat gttgactaag agcaagtgga gagcactctc atttcataga   1380
acaagtgatg aatgccaacc tgcattatta tcttaattag actttgatca tcaagtggaa   1440
tcccatttat cttaataatc ttggcaacat tgttataatg ctacttcata tgctaattct   1500
tcaaagctaa catcgttaaa cgaatacata tctcctgtat tctaagaccc tatttagaat   1560
acagaaattt tacagaaatc agttcaattc tcgtagaatt gggaaagaaa tcctccgttc   1620
caaacgtgac ctaagccggc atggcacgac cccactcgtc aggcactgta tgtaaacgtc   1680
agcaactccg tggcaagtaa cgtcgagagg aggagcgggc ctaacggcgc cgactagctc   1740
aacggccacc aaccagccaa ccaccagcgc aaccgaaacg gcgcaaacgt tgacgtcatc   1800
tctctctctc tcgcgccccg cgtcccgaag cttccgcacc actcgctggt cgctgctagc   1860
tgggccccac cggccggccc cgttcgtgct ggactcttct tcctcgaaat tgcgtggtgg   1920
agagggagag ggggcacctc gagacggaac cgtcacggca cgggattcct tccccacccg   1980
gcccctcctc gtctccataa ataggcgccc cctcctcgcg tcctctcccc cgtctcatct   2040
cctcctgttc cgtgaaccgt gaacgcaacc cgacccccag atctctctcg cgagcatcgt   2100
cgatccctcc tccgcgtcaa ggtacggatc ttctccttcc tccccccttcc cctctgggtc   2160
ggcgtgtcgt gttgtttctc tagttgcttg gctggatgga tcgagtggtt cttagggctt   2220
agatggctgg ttagatctgt tgcgttctgt ttcgtagatg gatttttggt gtagatctgg   2280
taggttatgc tggttaactg gtgatgctcc tgcgattttt gggggatctg agttgttaat   2340
ctggtagttg tatggggttc tcgtagccgg attgtagatg aaatcgtccg cgcggtttgc   2400
gtggctcgtt ggttagctag ggttagatct gctcggattt ttcattgttc ctgattcaga   2460
gatgtagtta acctttactt gttcatcttt gtatctcgta ttcgtacctg catgtatgat   2520
ctgtttcgat ggtgctagat aggtgcgcct gatttgtccg atcgaatctg gtagcatgcg   2580
ctgtttgttt ggtagtgttc tgattgattt gtcgctctag atctgagtag aataggatta   2640
tttctcaaca tgatattaga agcttggttt atagctccgg attagcatgt atgttacatg   2700
tttattctta tgtaaggttt taaacggaag atatatgcta ctgctgctca ttgattcttt   2760
atcatccacc tgagtccatg catgcttctg ttacttcttt tgatatgtgc ttagatagct   2820
gttgatatgt actgctgctg ttagatgatc cttcaggatg aacatgcatg attctgttac   2880
ttgttttggt atgcttagat aaatcaagat acgcttctgc tgttcgttga ttctttagta   2940
```

```
ctacctacct gatcagctta gatagatcaa gatatgcttc tgctgttcgt tgattcttta   3000
gtaataccta cctgatcagc ttagatagat caagatacgc ttctgctgtt cgttgattct   3060
ctagtactac ctacctgata aacatgcatg ttttctgctt gttaaaggtt gattgcttag   3120
gctcatcttt ttcttttcgt tgattctcta gtactaccta cctgataaac atgcatgttt   3180
tctgcttgtt aaagattgat tgcttagtct catctttttc tttctctttt gtctaccgcc   3240
aggcctaacc ttgttgctgg tgactctttc ttgcag                              3276
```

<210> SEQ ID NO 24
<211> LENGTH: 2033
<212> TYPE: DNA
<213> ORGANISM: Arundo donax

<400> SEQUENCE: 24

```
ggcctcttta cgtttggcac aatttgatcg aatccaacac ggcaagttag cctttgaagc     60
ttgaaccggg cactaatgca agtatataat aactgagaac tacaagaaag catattcctt    120
gaggtactta tgcaacctta caattatcaa attaattaac aactagcagt tagaatttta    180
tatcacaaga atatcatgaa ccgtggatac tacttcttaa agggctattc tttttctgaa    240
tgtcgcagtt ggttatttta accatattac aaactagggg tttaaatccc aaaaagttca    300
cggaaaggga ttaagcaagt agttagcaag actcacactt atgaccgtta gccaaattac    360
acattggtca ttccaggagg agtaatcccc catagctagt tgttttgagt ttgactaccc    420
aaacttgcat aatcgttttc ctagaggggg gggggggtt caccattcca tcaagatgag    480
gcaaagctaa atgaaacaca cgagaggcaa aacggactga cgtgatagag tttttaataa    540
atatcaaata tgtagagtca accaaagaaa aaagatatcc caatggctaa actttggatc    600
tatgtcgtaa ttcgtgtttt aggacataca aggcgaattc cttctacggc aaactctaga    660
atagctgggc gacaatggcc tcacgatagc ctcaaagagt tggtagcaac tttgagatct    720
tttgatccga aactcaatta tgtagtacaa tgatatttag atagattgat tgaaagttgg    780
gggtgggggc gaaagcgaag gggatctcaa tattaataca tctatagtga atggatatag    840
aaaacacagg atttccaatt caagtagaaa taggaggaac ggaacagatc tagcaatagt    900
agccaccaaa gacgaggagg attctagatt gcaaatccaa ggtgaaagga agaaatgttg    960
aactatccag aataaggcgg attggccaag gaggcggaag tctctagaaa gaagtcattt   1020
ggctctgagg gctcacttga tgcgagaagg aagactgact gaggaatgga ttttggtgga   1080
ccgaggaaat tggtgctggg ttgcagaggc atgtatgtgg gaaaagaggc agtggcaacg   1140
atcgagagag gagaagggaa tgaggtaagt atttgaagtg aagaggagcc catataggtg   1200
aaaaataaaa ataatccatc gtggattcaa ataatcaaag ggctatgacc tttcatcaat   1260
tttagaaaag tgaaaacaac cggtttaaca cctatatgca ccatttttcct acatagattt   1320
ttaacttctt acttaaccat gttgactaag agcaagtgga gagcactctc atttcataga   1380
acaagtgatg aatgccaacc tgcattatta tcttaattag actttgatca tcaagtggaa   1440
tcccatttat cttaataatc ttggcaacat tgttataatg ctacttcata tgctaattct   1500
tcaaagctaa catcgttaaa cgaatacata tctcctgtat tctaagaccc tatttagaat   1560
acagaaattt tacagaaatc agttcaattc tcgtagaatt gggaaagaaa tcctccgttc   1620
caaacgtgac ctaagccggc atggcacgac cccactcgtc aggcactgta tgtaaacgtc   1680
agcaactccg tggcaagtaa cgtcgagagg aggagcgggc ctaacggcgc cgactagctc   1740
aacggccacc aaccagccaa ccaccagcgc aaccgaaacg gcgcaaacgt tgacgtcatc   1800
```

```
tctctctctc tcgcgccccg cgtcccgaag cttccgcacc actcgctggt cgctgctagc   1860

tgggccccac cggccggccc cgttcgtgct ggactcttct tcctcgaaat tgcgtggtgg   1920

agagggagag ggggcacctc gagacggaac cgtcacggca cgggattcct tccccacccg   1980

gcccctcctc gtctccataa ataggcgccc cctcctcgcg tcctctcccc cgt          2033
```

<210> SEQ ID NO 25
<211> LENGTH: 88
<212> TYPE: DNA
<213> ORGANISM: Arundo donax

<400> SEQUENCE: 25

```
ctcatctcct cctgttccgt gaaccgtgaa cgcaacccga cccccagatc tctctcgcga     60

gcatcgtcga tccctcctcc gcgtcaag                                        88
```

<210> SEQ ID NO 26
<211> LENGTH: 1155
<212> TYPE: DNA
<213> ORGANISM: Arundo donax

<400> SEQUENCE: 26

```
gtacggatct tctccttcct ccccccttccc ctctgggtcg gcgtgtcgtg ttgtttctct     60

agttgcttgg ctggatggat cgagtggttc ttagggctta gatggctggt tagatctgtt    120

gcgttctgtt tcgtagatgg atttttggtg tagatctggt aggttatgct ggttaactgg    180

tgatgctcct gcgatttttg ggggatctga gttgttaatc tggtagttgt atggggttct    240

cgtagccgga ttgtagatga aatcgtccgc gcggtttgcg tggctcgttg gttagctagg    300

gttagatctg ctcggatttt tcattgttcc tgattcagag atgtagttaa cctttacttg    360

ttcatctttg tatctcgtat tcgtacctgc atgtatgatc tgtttcgatg gtgctagata    420

ggtgcgcctg atttgtccga tcgaatctgg tagcatgcgc tgtttgtttg gtagtgttct    480

gattgatttg tcgctctaga tctgagtaga ataggattat ttctcaacat gatattagaa    540

gcttggttta tagctccgga ttagcatgta tgttacatgt ttattcttat gtaaggtttt    600

aaacggaaga tatatgctac tgctgctcat tgattcttta tcatccacct gagtccatgc    660

atgcttctgt tacttctttt gatatgtgct tagatagctg ttgatatgta ctgctgctgt    720

tagatgatcc ttcaggatga acatgcatga ttctgttact tgttttggta tgcttagata    780

aatcaagata cgcttctgct gttcgttgat tctttagtac tacctacctg atcagcttag    840

atagatcaag atatgcttct gctgttcgtt gattctttag taatacctac ctgatcagct    900

tagatagatc aagatacgct tctgctgttc gttgattctc tagtactacc tacctgataa    960

acatgcatgt tttctgcttg ttaaaggttg attgcttagg ctcatctttt tcttttcgtt   1020

gattctctag tactacctac ctgataaaca tgcatgtttt ctgcttgtta aagattgatt   1080

gcttagtctc atctttttct ttctcttttg tctaccgcca ggcctaacct tgttgctggt   1140

gactctttct tgcag                                                    1155
```

<210> SEQ ID NO 27
<211> LENGTH: 3250
<212> TYPE: DNA
<213> ORGANISM: Arundo donax

<400> SEQUENCE: 27

```
gaatccaaca cggcaagtta gcctttgaag cttgaaccgg gcactaatgc aagtatataa     60
```

-continued

```
taactgagaa ctacaagaaa gcatattcct tgaggtactt atgcaacctt acaattatca    120
aattaattaa caactagcag ttagaatttt atatcacaag aatatcatga accgtggata    180
ctacttctta aagggctatt ctttttctga atgtcgcagt tggttatttt aaccatatta    240
caaactaggg gtttaaatcc caaaaagttc acggaaaggg attaagcaag tagttagcaa    300
gactcacact tatgaccgtt agccaaatta cacattggtc attccaggag gagtaatccc    360
ccatagctag ttgttttgag tttgactacc caaacttgca taatcgtttt cctagagggg    420
gggggggggt tcaccattcc atcaagatga ggcaaagcta aatgaaacac acgagaggca    480
aaacggactg acgtgataga gtttttaata aatatcaaat atgtagagtc aaccaaagaa    540
aaaagatatc ccaatggcta aactttggat ctatgtcgta attcgtgttt taggacatac    600
aaggcgaatt ccttctacgg caaactctag aatagctggg cgacaatggc ctcacgatag    660
cctcaaagag ttggtagcaa ctttgagatc ttttgatccg aaactcaatt atgtagtaca    720
atgatattta gatagattga ttgaaagttg ggggtggggg cgaaagcgaa ggggatctca    780
atattaatac atctatagtg aatggatata gaaaacacag gatttccaat tcaagtagaa    840
ataggaggaa cggaacagat ctagcaatag tagccaccaa agacgaggag gattctagat    900
tgcaaatcca aggtgaaagg aagaaatgtt gaactatcca gaataaggcg gattggccaa    960
ggaggcggaa gtctctagaa agaagtcatt tggctctgag ggctcacttg atgcgagaag   1020
gaagactgac tgaggaatgg attttggtgg accgaggaaa ttggtgctgg gttgcagagg   1080
catgtatgtg ggaaaagagg cagtggcaac gatcgagaga ggagaaggga atgaggtaag   1140
tatttgaagt gaagaggagc ccatataggt gaaaaataaa aataatccat cgtggattca   1200
aataatcaaa gggctatgac ctttcatcaa ttttagaaaa gtgaaaacaa ccggtttaac   1260
acctatatgc accattttcc tacatagatt tttaacttct tacttaacca tgttgactaa   1320
gagcaagtgg agagcactct catttcatag aacaagtgat gaatgccaac ctgcattatt   1380
atcttaatta gactttgatc atcaagtgga atcccattta tcttaataat cttggcaaca   1440
ttgttataat gctacttcat atgctaattc ttcaaagcta acatcgttaa acgaatacat   1500
atctcctgta ttctaagacc ctatttagaa tacagaaatt ttacagaaat cagttcaatt   1560
ctcgtagaat tgggaaagaa atcctccgtt ccaaacgtga cctaagccgg catggcacga   1620
ccccactcgt caggcactgt atgtaaacgt cagcaactcc gtggcaagta acgtcgagag   1680
gaggagcggg cctaacggcg ccgactagct caacggccac caaccagcca accaccagcg   1740
caaccgaaac ggcgcaaacg ttgacgtcat ctctctctct ctcgcgcccc gcgtcccgaa   1800
gcttccgcac cactcgctgg tcgctgctag ctgggcccca ccggccggcc ccgttcgtgc   1860
tggactcttc ttcctcgaaa ttgcgtggtg gagagggaga gggggcacct cgagacggaa   1920
ccgtcacggc acgggattcc ttccccaccc ggcccctcct cgtctccata aataggcgcc   1980
ccctcctcgc gtcctctccc ccgtctcatc tcctcctgtt ccgtgaaccg tgaacgcaac   2040
ccgaccccca gatctctctc gcgagcatcg tcgatccctc ctccgcgtca aggtacggat   2100
cttctccttc ctccccctto ccctctgggt cggcgtgtcg tgttgtttct ctagttgctt   2160
ggctggatgg atcgagtggt tcttagggct tagatggctg gttagatctg ttgcgttctg   2220
tttcgtagat ggatttttgg tgtagatctg gtaggttatg ctggttaact ggtgatgctc   2280
ctgcgatttt tgggggatct gagttgttaa tctggtagtt gtatggggtt ctcgtagccg   2340
gattgtagat gaaatcgtcc gcgcggtttg cgtggctcgt tggttagcta gggttagatc   2400
tgctcggatt tttcattgtt cctgattcag agatgtagtt aacctttact tgttcatctt   2460
```

tgtatctcgt attcgtacct gcatgtatga tctgtttcga tggtgctaga taggtgcgcc 2520
tgatttgtcc gatcgaatct ggtagcatgc gctgtttgtt tggtagtgtt ctgattgatt 2580
tgtcgctcta gatctgagta gaataggatt atttctcaac atgatattag aagcttggtt 2640
tatagctccg gattagcatg tatgttacat gtttattctt atgtaaggtt ttaaacggaa 2700
gatatatgct actgctgctc attgattctt tatcatccac ctgagtccat gcatgcttct 2760
gttacttctt ttgatatgtg cttagatagc tgttgatatg tactgctgct gttagatgat 2820
ccttcaggat gaacatgcat gattctgtta cttgttttgg tatgcttaga taaatcaaga 2880
tacgcttctg ctgttcgttg attctttagt actacctacc tgatcagctt agatagatca 2940
agatatgctt ctgctgttcg ttgattcttt agtaatacct acctgatcag cttagataga 3000
tcaagatacg cttctgctgt tcgttgattc tctagtacta cctacctgat aaacatgcat 3060
gttttctgct tgttaaaggt tgattgctta ggctcatctt tttcttttcg ttgattctct 3120
agtactacct acctgataaa catgcatgtt ttctgcttgt taaagattga ttgcttagtc 3180
tcatcttttt ctttctcttt tgtctaccgc caggcctaac cttgttgctg gtgactcttt 3240
cttgcaggtg 3250

<210> SEQ ID NO 28
<211> LENGTH: 2004
<212> TYPE: DNA
<213> ORGANISM: Arundo donax

<400> SEQUENCE: 28
gaatccaaca cggcaagtta gcctttgaag cttgaaccgg gcactaatgc aagtatataa 60
taactgagaa ctacaagaaa gcatattcct tgaggtactt atgcaacctt acaattatca 120
aattaattaa caactagcag ttagaatttt atatcacaag aatatcatga accgtggata 180
ctacttctta aagggctatt ctttttctga atgtcgcagt tggttatttt aaccatatta 240
caaactaggg gtttaaatcc caaaaagttc acggaaaggg attaagcaag tagttagcaa 300
gactcacact tatgaccgtt agccaaatta cacattggtc attccaggag gagtaatccc 360
ccatagctag ttgttttgag tttgactacc caaacttgca taatcgtttt cctagagggg 420
gggggggggt tcaccattcc atcaagatga ggcaaagcta aatgaaacac acgagaggca 480
aaacggactg acgtgataga gtttttaata aatatcaaat atgtagagtc aaccaaagaa 540
aaaagatatc ccaatggcta aactttggat ctatgtcgta attcgtgttt taggacatac 600
aaggcgaatt ccttctacgg caaactctag aatagctggg cgacaatggc ctcacgatag 660
cctcaaagag ttggtagcaa ctttgagatc ttttgatccg aaactcaatt atgtagtaca 720
atgatattta gatagattga ttgaaagttg ggggtggggg cgaaagcgaa ggggatctca 780
atattaatac atctatagtg aatggatata gaaaacacag gatttccaat tcaagtagaa 840
ataggaggaa cggaacagat ctagcaatag tagccaccaa agacgaggag gattctagat 900
tgcaaatcca aggtgaaagg aagaaatgtt gaactatcca gaataaggcg gattggccaa 960
ggaggcggaa gtctctagaa agaagtcatt tggctctgag ggctcacttg atgcgagaag 1020
gaagactgac tgaggaatgg attttggtgg accgaggaaa ttggtgctgg gttgcagagg 1080
catgtatgtg ggaaaagagg cagtggcaac gatcgagaga ggagaaggga atgaggtaag 1140
tatttgaagt gaagaggagc ccatataggt gaaaaataaa aataatccat cgtggattca 1200
aataatcaaa gggctatgac ctttcatcaa ttttagaaaa gtgaaaacaa ccggtttaac 1260

-continued

```
acctatatgc accattttcc tacatagatt tttaacttct tacttaacca tgttgactaa   1320

gagcaagtgg agagcactct catttcatag aacaagtgat gaatgccaac ctgcattatt   1380

atcttaatta gactttgatc atcaagtgga atcccattta tcttaataat cttggcaaca   1440

ttgttataat gctacttcat atgctaattc ttcaaagcta acatcgttaa acgaatacat   1500

atctcctgta ttctaagacc ctatttagaa tacagaaatt ttacagaaat cagttcaatt   1560

ctcgtagaat tgggaaagaa atcctccgtt ccaaacgtga cctaagccgg catggcacga   1620

ccccactcgt caggcactgt atgtaaacgt cagcaactcc gtggcaagta acgtcgagag   1680

gaggagcggg cctaacggcg ccgactagct caacggccac caaccagcca accaccagcg   1740

caaccgaaac ggcgcaaacg ttgacgtcat ctctctctct ctcgcgcccc gcgtcccgaa   1800

gcttccgcac cactcgctgg tcgctgctag ctgggcccca ccggccggcc ccgttcgtgc   1860

tggactcttc ttcctcgaaa ttgcgtggtg gagagggaga gggggcacct cgagacggaa   1920

ccgtcacggc acgggattcc ttccccaccc ggcccctcct cgtctccata aataggcgcc   1980

ccctcctcgc gtcctctccc ccgt                                          2004
```

<210> SEQ ID NO 29
<211> LENGTH: 1158
<212> TYPE: DNA
<213> ORGANISM: Arundo donax

<400> SEQUENCE: 29

```
gtacggatct tctccttcct ccccccttccc ctctgggtcg gcgtgtcgtg ttgtttctct     60

agttgcttgg ctggatggat cgagtggttc ttagggctta gatggctggt tagatctgtt    120

gcgttctgtt tcgtagatgg atttttggtg tagatctggt aggttatgct ggttaactgg    180

tgatgctcct gcgatttttg ggggatctga gttgttaatc tggtagttgt atggggttct    240

cgtagccgga ttgtagatga aatcgtccgc gcggtttgcg tggctcgttg gttagctagg    300

gttagatctg ctcggatttt tcattgttcc tgattcagag atgtagttaa cctttacttg    360

ttcatctttg tatctcgtat tcgtacctgc atgtatgatc tgtttcgatg gtgctagata    420

ggtgcgcctg atttgtccga tcgaatctgg tagcatgcgc tgtttgtttg gtagtgttct    480

gattgatttg tcgctctaga tctgagtaga ataggattat ttctcaacat gatattagaa    540

gcttggttta tagctccgga ttagcatgta tgttacatgt ttattcttat gtaaggtttt    600

aaacggaaga tatatgctac tgctgctcat tgattcttta tcatccacct gagtccatgc    660

atgcttctgt tacttctttt gatatgtgct tagatagctg ttgatatgta ctgctgctgt    720

tagatgatcc ttcaggatga acatgcatga ttctgttact tgttttggta tgcttagata    780

aatcaagata cgcttctgct gttcgttgat tctttagtac tacctacctg atcagcttag    840

atagatcaag atatgcttct gctgttcgtt gattctttag taatacctac ctgatcagct    900

tagatagatc aagatacgct tctgctgttc gttgattctc tagtactacc tacctgataa    960

acatgcatgt tttctgcttg ttaaaggttg attgcttagg ctcatctttt tcttttcgtt   1020

gattctctag tactacctac ctgataaaca tgcatgtttt ctgcttgtta aagattgatt   1080

gcttagtctc atctttttct ttctcttttg tctaccgcca ggcctaacct tgttgctggt   1140

gactctttct tgcaggtg                                                 1158
```

<210> SEQ ID NO 30
<211> LENGTH: 2247
<212> TYPE: DNA
<213> ORGANISM: Arundo donax

<400> SEQUENCE: 30

```
tcacttgatg cgagaaggaa gactgactga ggaatggatt ttggtggacc gaggaaattg     60
gtgctgggtt gcagaggcat gtatgtggga aaagaggcag tggcaacgat cgagagagga    120
gaagggaatg aggtaagtat ttgaagtgaa gaggagccca tataggtgaa aaataaaaat    180
aatccatcgt ggattcaaat aatcaaaggg ctatgacctt tcatcaattt tagaaaagtg    240
aaaacaaccg gtttaacacc tatatgcacc attttcctac atagattttt aacttcttac    300
ttaaccatgt tgactaagag caagtggaga gcactctcat ttcatagaac aagtgatgaa    360
tgccaacctg cattattatc ttaattagac tttgatcatc aagtggaatc ccatttatct    420
taataatctt ggcaacattg ttataatgct acttcatatg ctaattcttc aaagctaaca    480
tcgttaaacg aatacatatc tcctgtattc taagacccta tttagaatac agaaatttta    540
cagaaatcag ttcaattctc gtagaattgg gaaagaaatc ctccgttcca aacgtgacct    600
aagccggcat ggcacgaccc cactcgtcag gcactgtatg taaacgtcag caactccgtg    660
gcaagtaacg tcgagaggag gagcgggcct aacggcgccg actagctcaa cggccaccaa    720
ccagccaacc accagcgcaa ccgaaacggc gcaaacgttg acgtcatctc tctctctctc    780
gcgccccgcg tcccgaagct tccgcaccac tcgctggtcg ctgctagctg ggccccaccg    840
gccggccccg ttcgtgctgg actcttcttc ctcgaaattg cgtggtggag agggagaggg    900
ggcacctcga gacggaaccg tcacggcacg ggattccttc cccacccggc ccctcctcgt    960
ctccataaat aggcgccccc tcctcgcgtc ctctccccg tctcatctcc tcctgttccg   1020
tgaaccgtga acgcaacccg acccccagat ctctctcgcg agcatcgtcg atccctcctc   1080
cgcgtcaagg tacggatctt ctccttcctc cccctccccc tctgggtcgg cgtgtcgtgt   1140
tgtttctcta gttgcttggc tggatggatc gagtggttct tagggcttag atggctggtt   1200
agatctgttg cgttctgttt cgtagatgga tttttggtgt agatctggta ggttatgctg   1260
gttaactggt gatgctcctg cgatttttgg gggatctgag ttgttaatct ggtagttgta   1320
tggggttctc gtagccggat tgtagatgaa atcgtccgcg cggtttgcgt ggctcgttgg   1380
ttagctaggg ttagatctgc tcggattttt cattgttcct gattcagaga tgtagttaac   1440
ctttacttgt tcatctttgt atctcgtatt cgtacctgca tgtatgatct gtttcgatgg   1500
tgctagatag gtgcgcctga tttgtccgat cgaatctggt agcatgcgct gtttgtttgg   1560
tagtgttctg attgatttgt cgctctagat ctgagtagaa taggattatt tctcaacatg   1620
atattagaag cttggtttat agctccggat tagcatgtat gttacatgtt tattcttatg   1680
taaggtttta aacggaagat atatgctact gctgctcatt gattctttat catccacctg   1740
agtccatgca tgcttctgtt acttcttttg atatgtgctt agatagctgt tgatatgtac   1800
tgctgctgtt agatgatcct tcaggatgaa catgcatgat tctgttactt gttttggtat   1860
gcttagataa atcaagatac gcttctgctg ttcgttgatt ctttagtact acctacctga   1920
tcagcttaga tagatcaaga tatgcttctg ctgttcgttg attctttagt aatacctacc   1980
tgatcagctt agatagatca agatacgctt ctgctgttcg ttgattctct agtactacct   2040
acctgataaa catgcatgtt ttctgcttgt taaaggttga ttgcttaggc tcatcttttt   2100
cttttcgttg attctctagt actacctacc tgataaacat gcatgttttc tgcttgttaa   2160
agattgattg cttagtctca tctttttctt tctcttttgt ctaccgccag gcctaacctt   2220
gttgctggtg actctttctt gcaggtg                                      2247
```

<210> SEQ ID NO 31
<211> LENGTH: 1001
<212> TYPE: DNA
<213> ORGANISM: Arundo donax

<400> SEQUENCE: 31

```
tcacttgatg cgagaaggaa gactgactga ggaatggatt ttggtggacc gaggaaattg     60
gtgctgggtt gcagaggcat gtatgtggga aaagaggcag tggcaacgat cgagagagga    120
gaagggaatg aggtaagtat ttgaagtgaa gaggagccca tataggtgaa aaataaaaat    180
aatccatcgt ggattcaaat aatcaaaggg ctatgacctt tcatcaattt tagaaaagtg    240
aaaacaaccg gtttaacacc tatatgcacc attttcctac atagattttt aacttcttac    300
ttaaccatgt tgactaagag caagtggaga gcactctcat ttcatagaac aagtgatgaa    360
tgccaacctg cattattatc ttaattagac tttgatcatc aagtggaatc ccatttatct    420
taataatctt ggcaacattg ttataatgct acttcatatg ctaattcttc aaagctaaca    480
tcgttaaacg aatacatatc tcctgtattc taagacccta tttagaatac agaaatttta    540
cagaaatcag ttcaattctc gtagaattgg gaaagaaatc ctccgttcca aacgtgacct    600
aagccggcat ggcacgaccc cactcgtcag gcactgtatg taaacgtcag caactccgtg    660
gcaagtaacg tcgagaggag gagcgggcct aacggcgccg actagctcaa cggccaccaa    720
ccagccaacc accagcgcaa ccgaaacggc gcaaacgttg acgtcatctc tctctctctc    780
gcgccccgcg tcccgaagct tccgcaccac tcgctggtcg ctgctagctg ggccccaccg    840
gccggccccg ttcgtgctgg actcttcttc ctcgaaattg cgtggtggag agggagaggg    900
ggcacctcga gacggaaccg tcacggcacg ggattccttc cccacccggc ccctcctcgt    960
ctccataaat aggcgccccc tcctcgcgtc ctctccccg t                        1001
```

<210> SEQ ID NO 32
<211> LENGTH: 1942
<212> TYPE: DNA
<213> ORGANISM: Arundo donax

<400> SEQUENCE: 32

```
catgttgact aagagcaagt ggagagcact ctcatttcat agaacaagtg atgaatgcca     60
acctgcatta ttatcttaat tagactttga tcatcaagtg gaatcccatt tatcttaata    120
atcttggcaa cattgttata atgctacttc atatgctaat tcttcaaagc taacatcgtt    180
aaacgaatac atatctcctg tattctaaga ccctatttag aatacagaaa ttttacagaa    240
atcagttcaa ttctcgtaga attgggaaag aaatcctccg ttccaaacgt gacctaagcc    300
ggcatggcac gaccccactc gtcaggcact gtatgtaaac gtcagcaact ccgtggcaag    360
taacgtcgag aggaggagcg ggcctaacgg cgccgactag ctcaacggcc accaaccagc    420
caaccaccag cgcaaccgaa acggcgcaaa cgttgacgtc atctctctct ctctcgcgcc    480
ccgcgtcccg aagcttccgc accactcgct ggtcgctgct agctgggccc caccggccgg    540
ccccgttcgt gctggactct tcttcctcga aattgcgtgg tggagaggga gagggggcac    600
ctcgagacgg aaccgtcacg gcacgggatt ccttccccac ccggcccctc ctcgtctcca    660
taaataggcg ccccctcctc gcgtcctctc cccgtctca tctcctcctg ttccgtgaac    720
cgtgaacgca acccgacccc cagatctctc tcgcgagcat cgtcgatccc tcctccgcgt    780
caaggtacgg atcttctcct tcctccccct tcccctctgg gtcggcgtgt cgtgttgttt    840
ctctagttgc ttggctggat ggatcgagtg gttcttaggg cttagatggc tggttagatc    900
```

tgttgcgttc tgtttcgtag atggattttt ggtgtagatc tggtaggtta tgctggttaa 960
ctggtgatgc tcctgcgatt tttgggggat ctgagttgtt aatctggtag ttgtatgggg 1020
ttctcgtagc cggattgtag atgaaatcgt ccgcgcggtt tgcgtggctc gttggttagc 1080
tagggttaga tctgctcgga tttttcattg ttcctgattc agagatgtag ttaaccttta 1140
cttgttcatc tttgtatctc gtattcgtac ctgcatgtat gatctgtttc gatggtgcta 1200
gataggtgcg cctgatttgt ccgatcgaat ctggtagcat gcgctgtttg tttggtagtg 1260
ttctgattga tttgtcgctc tagatctgag tagaatagga ttatttctca acatgatatt 1320
agaagcttgg tttatagctc cggattagca tgtatgttac atgtttattc ttatgtaagg 1380
ttttaaacgg aagatatatg ctactgctgc tcattgattc tttatcatcc acctgagtcc 1440
atgcatgctt ctgttacttc ttttgatatg tgcttagata gctgttgata tgtactgctg 1500
ctgttagatg atccttcagg atgaacatgc atgattctgt tacttgtttt ggtatgctta 1560
gataaatcaa gatacgcttc tgctgttcgt tgattcttta gtactaccta cctgatcagc 1620
ttagatagat caagatatgc ttctgctgtt cgttgattct ttagtaatac ctacctgatc 1680
agcttagata gatcaagata cgcttctgct gttcgttgat tctctagtac tacctacctg 1740
ataaacatgc atgttttctg cttgttaaag gttgattgct taggctcatc tttttctttt 1800
cgttgattct ctagtactac ctacctgata aacatgcatg ttttctgctt gttaaagatt 1860
gattgcttag tctcatcttt ttctttctct tttgtctacc gccaggccta accttgttgc 1920
tggtgactct ttcttgcagg tg 1942

<210> SEQ ID NO 33
<211> LENGTH: 696
<212> TYPE: DNA
<213> ORGANISM: Arundo donax

<400> SEQUENCE: 33
catgttgact aagagcaagt ggagagcact ctcatttcat agaacaagtg atgaatgcca 60
acctgcatta ttatcttaat tagactttga tcatcaagtg gaatcccatt tatcttaata 120
atcttggcaa cattgttata atgctacttc atatgctaat tcttcaaagc taacatcgtt 180
aaacgaatac atatctcctg tattctaaga ccctatttag aatacagaaa ttttacagaa 240
atcagttcaa ttctcgtaga attgggaaag aaatcctccg ttccaaacgt gacctaagcc 300
ggcatggcac gaccccactc gtcaggcact gtatgtaaac gtcagcaact ccgtggcaag 360
taacgtcgag aggaggagcg ggcctaacgg cgccgactag ctcaacggcc accaaccagc 420
caaccaccag cgcaaccgaa acggcgcaaa cgttgacgtc atctctctct ctctcgcgcc 480
ccgcgtcccg aagcttccgc accactcgct ggtcgctgct agctgggccc caccggccgg 540
ccccgttcgt gctggactct tcttcctcga aattgcgtgg tggagaggga gagggggcac 600
ctcgagacgg aaccgtcacg gcacgggatt ccttccccac ccggcccctc ctcgtctcca 660
taaataggcg ccccctcctc gcgtcctctc ccccgt 696

<210> SEQ ID NO 34
<211> LENGTH: 3511
<212> TYPE: DNA
<213> ORGANISM: Bouteloua gracilis

<400> SEQUENCE: 34
gtggccagct tttgttctag ttcaacggtc ccggccttcc gtgcacctaa tactacactg 60

-continued

```
attaatctat tgcagctaac ctcaaaagaa atacacttgc agttgtctgt cccaatcaag    120
ccactagcag actctcatgt cattgatgga ggaaattaaa ttcagtcttt gacgtggatg    180
caacaactgc acagtatacc atgcatctta attagccgtt gtgtcaaagt ttgttttgct    240
gacgttttga gaaaaccaac tttgaccaac aggagatgag cgtcttgcgt ttggcacagt    300
gtaatggaat ccggcacggc aagttagact ctgtagtgtt agcggtctct ttacgtttgg    360
cacaatttaa ttgaatcccg gcatggcatg ttagaccgga gtgagccggc ccttttactg    420
gtatgacact ccctctgtct tgagtgtcgc tgtgccagct tgtacctctg tctatgttca    480
cagcccgtgc tgtgtaccta gaccctccgt ttgtccacat tcattttaat ctctattgta    540
tcttgtcaaa acctaaaagc ctaaaacgac tctgataaag ggacagaaag attatacaag    600
agcaagtgta taatgaaata atgtaagcga gctatatgaa ttgtcacgtg tcatatttat    660
gttgagacga agaagagaaa ataaacacca tgcaaattta tggcgagtga tagatggcca    720
gatgggcaca aggcctccta tttcttaaat cggattttgt aagaacgaaa aaagggactt    780
ataagagaat aggatagacc atatatcaat gatgtagtat gcatcaagat ctaactatta    840
tatgagtgaa ttgataaatt tattctaggt gacatggcct taacgatgaa cagtacgtgg    900
ttaaatcaat agaacaatag ccaactctag cggctctaaa aaaagatata tattcgtcga    960
ggcactatta tgcaaccaca tagtcaactt caacgccgct tgagtgcgtt ctcatgtttt   1020
tttttcttg caaattacgc ttttctaaaa taaaataatt tggatcgtgc aattatttca   1080
ctttaggtgt gcgtgactac gtgagtaaca attttgaatc tcagaaagga aataaaagta   1140
taatactgct acctactttg aggattcagc ttgttactta aaaccgtctt taaggtcaaa   1200
tgctcaagat tcattcaaca attgaaacgt ctcacatgat taaaccatgt ataaggatgc   1260
taaggtcttg cttgacaatg tttttctagg aatttcatct aactttttga gtgaaactat   1320
caaataataa ttttaaaaca attttataag agaagctccg gagataaaag ggcatctaat   1380
ctatgttaga agagtgaagt ttactccctc tgtcccaaaa atagaattct aagtatgaaa   1440
tgattttttt gttatacgaa aggagtatat atcacaagat tgatgtcagt tatgcttagg   1500
gcacgtacac gacgctggtg ctttaggtag acgttaatcg ttgtttctgc attttatttt   1560
attttgttgc cacggtgtac atttgggtag acgtttgtca caggcattgc cactcaaaca   1620
agcagccggc gcttggagct tttatagttt gaaaagtgac ggttttaatg atgggtaagc   1680
tgattagtat atgtaagttt agctttttcc attgtaggtt aagccttaag gctcttacac   1740
aattgtttca ttattctcat tctttaagag cccatataag cgttcatgaa ttgtacatat   1800
ccttagatgt tttttttttt gggtaaagct cgagcttctc tatctaaaag tagagaaatc   1860
agaaaaagat tcatgttttg gtagttttga tttcttgcct ccataataat tttggtttac   1920
catttttgt ttgattttag ttttagaagc gtttatagca ggatttaaaa tccaaaacta   1980
ccattatctt caagtgaccg tcagtgagcc gtttaacggc gtcgacaagt ccaacggaca   2040
ccaaccagtg aaccaccagc gtcgagccaa gcgatgcaaa cggaacggcc gagacgttga   2100
cacctttggc gcggcacggc atgtcggatc tccctctctg gccagagagt tccagctcca   2160
cctccacctc cacctccacc ggtggcggtt tccaagtccg ttccgttccg ttccgttccg   2220
ttccgttccg cctcctgcct gctcctctca gacggcacga aaccgtgacg gcaccggcag   2280
cacgggggga ttcctttcc actgctcctt cctcttccct tcctcgcccg ccgctataaa   2340
tagccagccc cgtccccaga ttctttccca acctcatctt tgttcggagc acgcacacaa   2400
cccgatcccc aattccctcg tctctcctcg cgagcctcgt cgaccccccc cttcaaggta   2460
```

```
cggcgatcat cctccctccc tccctctctc taccttctct tctctagact agatcggcga   2520
cccggtccat ggttagggcc tgctagttct gttcctgttt tttccatggc tgcgaggtaa   2580
aatagatctg atggcgttat gatggttaac tcgtcatact cttgcgatct atggtccctt   2640
taggacatcg atttaatttc ggatggttcg agatcggtga tccatggtta gtaccctagg   2700
cagtggggtt agatccgtgc tgttagggtt cgtagatgga ttctgattgc tcagtaactg   2760
ggaaacctgg gatggttcta gctgggaatc ctgggatggt tctagctggt tcgcagatga   2820
gatcgatttc atggtctgct atatcttgtt tcgttgccta ggttccgttt aatctgtccg   2880
tggtatgatg ttagcctttg ataaggttcg atcgtgctag ctacgtcctg cgcagcattt   2940
aattgtcagg tcataatttt tagcattcct gtttttgttt ggtttggttt tgtctggttg   3000
ggctgtagat agtttcaatc tacctgtcgg tttattttat taaatttgga ttggatctgt   3060
atgtgtcaca tatatcttca tgattaagat ggttggaatt atctcttcat cttttagata   3120
tatatggata ggtatatatg ttgctgtggg ttttactggt actttattag atatattcat   3180
gcttagatac atgaagcaac gtgctgttac agtttaataa ttcttgttta tctaataaac   3240
aaataaggat aggtatatgt tgctgatggt tttactgata ctttattaga tagtactttg   3300
acatgaagga acatcctgcg acagcttaat aattattctt catctaataa aaagcttgct   3360
ttttaattat tttaattatt ttgatatact tggatgatgt catgcagcag ctatgtgtga   3420
attttcggcc ctgtcttcat atgatgttta tttgcttggg actgtttctt tggctgataa   3480
cttaccctgt tgtttggtga tccttctgca g                                  3511
```

<210> SEQ ID NO 35
<211> LENGTH: 2371
<212> TYPE: DNA
<213> ORGANISM: Bouteloua gracilis

<400> SEQUENCE: 35

```
gtggccagct tttgttctag ttcaacggtc ccggccttcc gtgcacctaa tactacactg     60
attaatctat tgcagctaac ctcaaaagaa atacacttgc agttgtctgt cccaatcaag    120
ccactagcag actctcatgt cattgatgga ggaaattaaa ttcagtcttt gacgtggatg    180
caacaactgc acagtatacc atgcatctta attagccgtt gtgtcaaagt ttgttttgct    240
gacgttttga gaaaaccaac tttgaccaac aggagatgag cgtcttgcgt ttggcacagt    300
gtaatggaat ccggcacggc aagttagact ctgtagtgtt agcggtctct ttacgtttgg    360
cacaatttaa ttgaatcccg gcatggcatg ttagaccgga gtgagccggc ccttttactg    420
gtatgacact ccctctgtct tgagtgtcgc tgtgccagct tgtacctctg tctatgttca    480
cagcccgtgc tgtgtaccta gaccctccgt ttgtccacat tcattttaat ctctattgta    540
tcttgtcaaa acctaaaagc ctaaaacgac tctgataaag ggacagaaag attatacaag    600
agcaagtgta taatgaaata atgtaagcga gctatatgaa ttgtcacgtg tcatatttat    660
gttgagacga agaagagaaa ataaacacca tgcaaattta tggcgagtga tagatggcca    720
gatgggcaca aggcctccta tttcttaaat cggattttgt aagaacgaaa aaagggactt    780
ataagagaat aggatagacc atatatcaat gatgtagtat gcatcaagat ctaactatta    840
tatgagtgaa ttgataaatt tattctaggt gacatggcct taacgatgaa cagtacgtgg    900
ttaaatcaat agaacaatag ccaactctag cggctctaaa aaaagatata tattcgtcga    960
ggcactatta tgcaaccaca tagtcaactt caacgccgct tgagtgcgtt ctcatgtttt   1020
```

```
tttttcttg caaattacgc ttttctaaaa taaaataatt tggatcgtgc aattatttca   1080
ctttaggtgt gcgtgactac gtgagtaaca attttgaatc tcagaaagga aataaaagta   1140
taatactgct acctactttg aggattcagc ttgttactta aaaccgtctt taaggtcaaa   1200
tgctcaagat tcattcaaca attgaaacgt ctcacatgat taaaccatgt ataaggatgc   1260
taaggtcttg cttgacaatg tttttctagg aatttcatct aactttttga gtgaaactat   1320
caaataataa ttttaaaaca attttataag agaagctccg gagataaaag ggcatctaat   1380
ctatgttaga agagtgaagt ttactccctc tgtcccaaaa atagaattct aagtatgaaa   1440
tgattttttt gttatacgaa aggagtatat atcacaagat tgatgtcagt tatgcttagg   1500
gcacgtacac gacgctggtg ctttaggtag acgttaatcg ttgtttctgc attttatttt   1560
attttgttgc cacggtgtac atttgggtag acgtttgtca caggcattgc cactcaaaca   1620
agcagccggc gcttggagct tttatagttt gaaaagtgac ggttttaatg atgggtaagc   1680
tgattagtat atgtaagttt agctttttcc attgtaggtt aagccttaag gctcttacac   1740
aattgtttca ttattctcat tctttaagag cccatataag cgttcatgaa ttgtacatat   1800
ccttagatgt tttttttttt gggtaaagct cgagcttctc tatctaaaag tagagaaatc   1860
agaaaaagat tcatgttttg gtagttttga tttcttgcct ccataataat tttggtttac   1920
catttttgt ttgattttag ttttagaagc gtttatagca ggatttaaaa tccaaaacta   1980
ccattatctt caagtgaccg tcagtgagcc gtttaacggc gtcgacaagt ccaacggaca   2040
ccaaccagtg aaccaccagc gtcgagccaa gcgatgcaaa cggaacggcc gagacgttga   2100
cacctttggc gcggcacggc atgtcggatc tccctctctg gccagagagt tccagctcca   2160
cctccacctc cacctccacc ggtggcggtt tccaagtccg ttccgttccg ttccgttccg   2220
ttccgttccg cctcctgcct gctcctctca gacggcacga aaccgtgacg gcaccggcag   2280
cacgggggga ttccttttcc actgctcctt cctcttccct tcctcgcccg ccgctataaa   2340
tagccagccc cgtccccaga ttctttccca a                                  2371
```

<210> SEQ ID NO 36
<211> LENGTH: 86
<212> TYPE: DNA
<213> ORGANISM: Bouteloua gracilis

<400> SEQUENCE: 36

```
cctcatcttt gttcggagca cgcacacaac ccgatcccca attccctcgt ctctcctcgc     60
gagcctcgtc gacccccccc ttcaag                                           86
```

<210> SEQ ID NO 37
<211> LENGTH: 1054
<212> TYPE: DNA
<213> ORGANISM: Bouteloua gracilis

<400> SEQUENCE: 37

```
gtacggcgat catcctccct ccctccctct ctctaccttc tcttctctag actagatcgg     60
cgacccggtc catggttagg gcctgctagt tctgttcctg ttttttccat ggctgcgagg    120
taaaatagat ctgatggcgt tatgatggtt aactcgtcat actcttgcga tctatggtcc    180
ctttaggaca tcgatttaat ttcggatggt tcgagatcgg tgatccatgg ttagtaccct    240
aggcagtggg gttagatccg tgctgttagg gttcgtagat ggattctgat tgctcagtaa    300
ctgggaaacc tgggatggtt ctagctggga atcctgggat ggttctagct ggttcgcaga    360
tgagatcgat ttcatggtct gctatatctt gtttcgttgc ctaggttccg tttaatctgt    420
```

```
ccgtggtatg atgttagcct ttgataaggt tcgatcgtgc tagctacgtc ctgcgcagca    480

tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa gatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780

aacaaataag gataggtata tgttgctgat ggttttactg atactttatt agatagtact    840

ttgacatgaa ggaacatcct gcgacagctt aataattatt cttcatctaa taaaaagctt    900

gctttttaat tattttaatt attttgatat acttggatga tgtcatgcag cagctatgtg    960

tgaattttcg gccctgtctt catatgatgt ttatttgctt gggactgttt ctttggctga   1020

taacttaccc tgttgtttgg tgatccttct gcag                               1054
```

<210> SEQ ID NO 38
<211> LENGTH: 3142
<212> TYPE: DNA
<213> ORGANISM: Bouteloua gracilis

<400> SEQUENCE: 38

```
gaatcccggc atggcatgtt agaccggagt gagccggccc ttttactggt atgacactcc     60

ctctgtcttg agtgtcgctg tgccagcttg tacctctgtc tatgttcaca gcccgtgctg    120

tgtacctaga ccctccgttt gtccacattc attttaatct ctattgtatc ttgtcaaaac    180

ctaaaagcct aaaacgactc tgataaaggg acagaaagat tatacaagag caagtgtata    240

atgaaataat gtaagcgagc tatatgaatt gtcacgtgtc atatttatgt tgagacgaag    300

aagagaaaat aaacaccatg caaatttatg gcgagtgata gatggccaga tgggcacaag    360

gcctcctatt tcttaaatcg gattttgtaa gaacgaaaaa agggacttat aagagaatag    420

gatagaccat atatcaatga tgtagtatgc atcaagatct aactattata tgagtgaatt    480

gataaattta ttctaggtga catggcctta acgatgaaca gtacgtggtt aaatcaatag    540

aacaatagcc aactctagcg gctctaaaaa aagatatata ttcgtcgagg cactattatg    600

caaccacata gtcaacttca acgccgcttg agtgcgttct catgtttttt ttttcttgca    660

aattacgctt ttctaaaata aaataatttg gatcgtgcaa ttatttcact ttaggtgtgc    720

gtgactacgt gagtaacaat tttgaatctc agaaaggaaa taaaagtata atactgctac    780

ctactttgag gattcagctt gttacttaaa accgtcttta aggtcaaatg ctcaagattc    840

attcaacaat tgaaacgtct cacatgatta aaccatgtat aaggatgcta aggtcttgct    900

tgacaatgtt tttctaggaa tttcatctaa ctttttgagt gaaactatca aataataatt    960

ttaaaacaat tttataagag aagctccgga gataaaaggg catctaatct atgttagaag   1020

agtgaagttt actccctctg tcccaaaaat agaattctaa gtatgaaatg atttttttgt   1080

tatacgaaag gagtatatat cacaagattg atgtcagtta tgcttagggc acgtacacga   1140

cgctggtgct ttaggtagac gttaatcgtt gtttctgcat tttattttat tttgttgcca   1200

cggtgtacat ttgggtagac gtttgtcaca ggcattgcca ctcaaacaag cagccggcgc   1260

ttggagcttt tatagtttga aaagtgacgg ttttaatgat gggtaagctg attagtatat   1320

gtaagtttag ctttttccat tgtaggttaa gccttaaggc tcttacacaa ttgtttcatt   1380

attctcattc tttaagagcc catataagcg ttcatgaatt gtacatatcc ttagatgttt   1440
```

```
ttttttttgg gtaaagctcg agcttctcta tctaaaagta gagaaatcag aaaaagattc   1500
atgttttggt agttttgatt tcttgcctcc ataataattt tggtttacca ttttttgttt   1560
gattttagtt ttagaagcgt ttatagcagg atttaaaatc caaaactacc attatcttca   1620
agtgaccgtc agtgagccgt ttaacggcgt cgacaagtcc aacggacacc aaccagtgaa   1680
ccaccagcgt cgagccaagc gatgcaaacg gaacggccga gacgttgaca cctttggcgc   1740
ggcacggcat gtcggatctc cctctctggc cagagagttc cagctccacc tccacctcca   1800
cctccaccgg tggcggtttc caagtccgtt ccgttccgtt ccgttccgtt ccgttccgcc   1860
tcctgcctgc tcctctcaga cggcacgaaa ccgtgacggc accggcagca cggggggatt   1920
ccttttccac tgctccttcc tcttcccttc ctcgcccgcc gctataaata gccagccccg   1980
tccccagatt ctttcccaac ctcatctttg ttcggagcac gcacacaacc cgatccccaa   2040
ttccctcgtc tctcctcgcg agcctcgtcg acccccccct tcaaggtacg gcgatcatcc   2100
tccctccctc cctctctcta ccttctcttc tctagactag atcggcgacc cggtccatgg   2160
ttagggcctg ctagttctgt tcctgttttt tccatggctg cgaggtaaaa tagatctgat   2220
ggcgttatga tggttaactc gtcatactct tgcgatctat ggtcccttta ggacatcgat   2280
ttaatttcgg atggttcgag atcggtgatc catggttagt accctaggca gtggggttag   2340
atccgtgctg ttagggttcg tagatggatt ctgattgctc agtaactggg aaacctggga   2400
tggttctagc tgggaatcct gggatggttc tagctggttc gcagatgaga tcgatttcat   2460
ggtctgctat atcttgtttc gttgcctagg ttccgtttaa tctgtccgtg gtatgatgtt   2520
agcctttgat aaggttcgat cgtgctagct acgtcctgcg cagcatttaa ttgtcaggtc   2580
ataattttta gcattcctgt ttttgtttgg tttggttttg tctggttggg ctgtagatag   2640
tttcaatcta cctgtcggtt tattttatta aatttggatt ggatctgtat gtgtcacata   2700
tatcttcatg attaagatgg ttggaattat ctcttcatct tttagatata tatggatagg   2760
tatatatgtt gctgtgggtt ttactggtac tttattagat atattcatgc ttagatacat   2820
gaagcaacgt gctgttacag tttaataatt cttgtttatc taataaacaa ataaggatag   2880
gtatatgttg ctgatggttt tactgatact ttattagata gtactttgac atgaaggaac   2940
atcctgcgac agcttaataa ttattcttca tctaataaaa agcttgcttt ttaattattt   3000
taattatttt gatatacttg gatgatgtca tgcagcagct atgtgtgaat tttcggccct   3060
gtcttcatat gatgtttatt tgcttgggac tgtttctttg gctgataact taccctgttg   3120
tttggtgatc cttctgcagg tg                                            3142
```

<210> SEQ ID NO 39
<211> LENGTH: 1999
<212> TYPE: DNA
<213> ORGANISM: Bouteloua gracilis

<400> SEQUENCE: 39

```
gaatcccggc atggcatgtt agaccggagt gagccggccc ttttactggt atgacactcc     60
ctctgtcttg agtgtcgctg tgccagcttg tacctctgtc tatgttcaca gcccgtgctg    120
tgtacctaga ccctccgttt gtccacattc attttaatct ctattgtatc ttgtcaaaac    180
ctaaaagcct aaaacgactc tgataaaggg acagaaagat tatacaagag caagtgtata    240
atgaaataat gtaagcgagc tatatgaatt gtcacgtgtc atatttatgt tgagacgaag    300
aagagaaaat aaacaccatg caaatttatg gcgagtgata gatggccaga tgggcacaag    360
gcctcctatt tcttaaatcg gattttgtaa gaacgaaaaa agggacttat aagagaatag    420
```

```
gatagaccat atatcaatga tgtagtatgc atcaagatct aactattata tgagtgaatt    480
gataaattta ttctaggtga catggcctta acgatgaaca gtacgtggtt aaatcaatag    540
aacaatagcc aactctagcg gctctaaaaa aagatatata ttcgtcgagg cactattatg    600
caaccacata gtcaacttca acgccgcttg agtgcgttct catgtttttt ttttcttgca    660
aattacgctt ttctaaaata aaataatttg gatcgtgcaa ttatttcact ttaggtgtgc    720
gtgactacgt gagtaacaat tttgaatctc agaaaggaaa taaaagtata atactgctac    780
ctactttgag gattcagctt gttacttaaa accgtcttta aggtcaaatg ctcaagattc    840
attcaacaat tgaaacgtct cacatgatta aaccatgtat aaggatgcta aggtcttgct    900
tgacaatgtt tttctaggaa tttcatctaa ctttttgagt gaaactatca aataataatt    960
ttaaaacaat tttataagag aagctccgga gataaaaggg catctaatct atgttagaag   1020
agtgaagttt actccctctg tcccaaaaat agaattctaa gtatgaaatg atttttttgt   1080
tatacgaaag gagtatatat cacaagattg atgtcagtta tgcttagggc acgtacacga   1140
cgctggtgct ttaggtagac gttaatcgtt gtttctgcat tttattttat tttgttgcca   1200
cggtgtacat ttgggtagac gtttgtcaca ggcattgcca ctcaaacaag cagccggcgc   1260
ttggagcttt tatagtttga aaagtgacgg ttttaatgat gggtaagctg attagtatat   1320
gtaagtttag ctttttccat tgtaggttaa gccttaaggc tcttacacaa ttgtttcatt   1380
attctcattc tttaagagcc catataagcg ttcatgaatt gtacatatcc ttagatgttt   1440
tttttttggg gtaaagctcg agcttctcta tctaaaagta gagaaatcag aaaaagattc   1500
atgttttggt agttttgatt tcttgcctcc ataataattt tggtttacca ttttttgttt   1560
gattttagtt ttagaagcgt ttatagcagg atttaaaatc caaaactacc attatcttca   1620
agtgaccgtc agtgagccgt ttaacggcgt cgacaagtcc aacggacacc aaccagtgaa   1680
ccaccagcgt cgagccaagc gatgcaaacg gaacggccga gacgttgaca cctttggcgc   1740
ggcacggcat gtcggatctc cctctctggc cagagagttc cagctccacc tccacctcca   1800
cctccaccgg tggcggtttc caagtccgtt ccgttccgtt ccgttccgtt ccgttccgcc   1860
tcctgcctgc tcctctcaga cggcacgaaa ccgtgacggc accggcagca cggggggatt   1920
ccttttccac tgctccttcc tcttcccttc ctcgcccgcc gctataaata gccagccccg   1980
tccccagatt ctttcccaa                                                1999
```

<210> SEQ ID NO 40
<211> LENGTH: 1057
<212> TYPE: DNA
<213> ORGANISM: Bouteloua gracilis

<400> SEQUENCE: 40

```
gtacggcgat catcctccct ccctccctct ctctaccttc tcttctctag actagatcgg     60
cgacccggtc catggttagg gcctgctagt tctgttcctg ttttttccat ggctgcgagg    120
taaaatagat ctgatggcgt tatgatggtt aactcgtcat actcttgcga tctatggtcc    180
ctttaggaca tcgatttaat ttcggatggt tcgagatcgg tgatccatgg ttagtaccct    240
aggcagtggg gttagatccg tgctgttagg gttcgtagat ggattctgat tgctcagtaa    300
ctgggaaacc tgggatggtt ctagctggga atcctgggat ggttctagct ggttcgcaga    360
tgagatcgat ttcatggtct gctatatctt gtttcgttgc ctaggttccg tttaatctgt    420
ccgtggtatg atgttagcct ttgataaggt tcgatcgtgc tagctacgtc ctgcgcagca    480
```

```
tttaattgtc aggtcataat ttttagcatt cctgtttttg tttggtttgg ttttgtctgg    540

ttgggctgta gatagtttca atctacctgt cggtttattt tattaaattt ggattggatc    600

tgtatgtgtc acatatatct tcatgattaa gatggttgga attatctctt catcttttag    660

atatatatgg ataggtatat atgttgctgt gggttttact ggtactttat tagatatatt    720

catgcttaga tacatgaagc aacgtgctgt tacagtttaa taattcttgt ttatctaata    780

aacaaataag gataggtata tgttgctgat ggttttactg atactttatt agatagtact    840

ttgacatgaa ggaacatcct gcgacagctt aataattatt cttcatctaa taaaaagctt    900

gctttttaat tattttaatt attttgatat acttggatga tgtcatgcag cagctatgtg    960

tgaattttcg gccctgtctt catatgatgt ttatttgctt gggactgttt ctttggctga   1020

taacttaccc tgttgtttgg tgatccttct gcaggtg                            1057


<210> SEQ ID NO 41
<211> LENGTH: 2165
<212> TYPE: DNA
<213> ORGANISM: Bouteloua gracilis

<400> SEQUENCE: 41

gagaagctcc ggagataaaa gggcatctaa tctatgttag aagagtgaag tttactccct     60

ctgtcccaaa aatagaattc taagtatgaa atgatttttt tgttatacga aaggagtata    120

tatcacaaga ttgatgtcag ttatgcttag ggcacgtaca cgacgctggt gctttaggta    180

gacgttaatc gttgtttctg cattttattt tattttgttg ccacggtgta catttgggta    240

gacgtttgtc acaggcattg ccactcaaac aagcagccgg cgcttggagc ttttatagtt    300

tgaaaagtga cggttttaat gatgggtaag ctgattagta tatgtaagtt tagctttttc    360

cattgtaggt taagccttaa ggctcttaca caattgtttc attattctca ttctttaaga    420

gcccatataa gcgttcatga attgtacata tccttagatg tttttttttt tgggtaaagc    480

tcgagcttct ctatctaaaa gtagagaaat cagaaaaaga ttcatgtttt ggtagttttg    540

atttcttgcc tccataataa ttttggttta ccatttttg tttgatttta gttttagaag     600

cgtttatagc aggatttaaa atccaaaact accattatct tcaagtgacc gtcagtgagc    660

cgtttaacgg cgtcgacaag tccaacggac accaaccagt gaaccaccag cgtcgagcca    720

agcgatgcaa acggaacggc cgagacgttg acacctttgg cgcggcacgg catgtcggat    780

ctccctctct ggccagagag ttccagctcc acctccacct ccacctccac cggtggcggt    840

ttccaagtcc gttccgttcc gttccgttcc gttccgttcc gcctcctgcc tgctcctctc    900

agacggcacg aaaccgtgac ggcaccggca gcacgggggg attccttttc cactgctcct    960

tcctcttccc ttcctcgccc gccgctataa atagccagcc ccgtccccag attctttccc   1020

aacctcatct ttgttcggag cacgcacaca acccgatccc caattccctc gtctctcctc   1080

gcgagcctcg tcgacccccc ccttcaaggt acggcgatca tcctccctcc ctccctctct   1140

ctaccttctc ttctctagac tagatcggcg acccggtcca tggttagggc ctgctagttc   1200

tgttcctgtt ttttccatgg ctgcgaggta aaatagatct gatggcgtta tgatggttaa   1260

ctcgtcatac tcttgcgatc tatggtccct ttaggacatc gatttaattt cggatggttc   1320

gagatcggtg atccatggtt agtaccctag gcagtggggt tagatccgtg ctgttagggt   1380

tcgtagatgg attctgattg ctcagtaact gggaaacctg ggatggttct agctgggaat   1440

cctgggatgg ttctagctgg ttcgcagatg agatcgattt catggtctgc tatatcttgt   1500

ttcgttgcct aggttccgtt taatctgtcc gtggtatgat gttagccttt gataaggttc   1560
```

gatcgtgcta gctacgtcct gcgcagcatt taattgtcag gtcataattt ttagcattcc 1620
tgtttttgtt tggtttggtt ttgtctggtt gggctgtaga tagtttcaat ctacctgtcg 1680
gtttatttta ttaaatttgg attggatctg tatgtgtcac atatatcttc atgattaaga 1740
tggttggaat tatctcttca tcttttagat atatatggat aggtatatat gttgctgtgg 1800
gttttactgg tactttatta gatatattca tgcttagata catgaagcaa cgtgctgtta 1860
cagtttaata attcttgttt atctaataaa caaataagga taggtatatg ttgctgatgg 1920
ttttactgat actttattag atagtacttt gacatgaagg aacatcctgc gacagcttaa 1980
taattattct tcatctaata aaaagcttgc tttttaatta ttttaattat tttgatatac 2040
ttggatgatg tcatgcagca gctatgtgtg aattttcggc cctgtcttca tatgatgttt 2100
atttgcttgg gactgtttct ttggctgata acttaccctg ttgtttggtg atccttctgc 2160
aggtg 2165

<210> SEQ ID NO 42
<211> LENGTH: 1022
<212> TYPE: DNA
<213> ORGANISM: Bouteloua gracilis

<400> SEQUENCE: 42
gagaagctcc ggagataaaa gggcatctaa tctatgttag aagagtgaag tttactccct 60
ctgtcccaaa aatagaattc taagtatgaa atgatttttt tgttatacga aaggagtata 120
tatcacaaga ttgatgtcag ttatgcttag ggcacgtaca cgacgctggt gctttaggta 180
gacgttaatc gttgtttctg cattttattt tattttgttg ccacggtgta catttgggta 240
gacgtttgtc acaggcattg ccactcaaac aagcagccgg cgcttggagc ttttatagtt 300
tgaaaagtga cggttttaat gatgggtaag ctgattagta tatgtaagtt tagctttttc 360
cattgtaggt taagccttaa ggctcttaca caattgtttc attattctca ttctttaaga 420
gcccatataa gcgttcatga attgtacata tccttagatg tttttttttt tgggtaaagc 480
tcgagcttct ctatctaaaa gtagagaaat cagaaaaaga ttcatgtttt ggtagttttg 540
atttcttgcc tccataataa ttttggttta ccattttttg tttgatttta gttttagaag 600
cgtttatagc aggatttaaa atccaaaact accattatct tcaagtgacc gtcagtgagc 660
cgtttaacgg cgtcgacaag tccaacggac accaaccagt gaaccaccag cgtcgagcca 720
agcgatgcaa acggaacggc cgagacgttg acacctttgg cgcggcacgg catgtcggat 780
ctccctctct ggccagagag ttccagctcc acctccacct ccacctccac cggtggcggt 840
ttccaagtcc gttccgttcc gttccgttcc gttccgttcc gcctcctgcc tgctcctctc 900
agacggcacg aaaccgtgac ggcaccggca gcacgggggg attccttttc cactgctcct 960
tcctcttccc ttcctcgccc gccgctataa atagccagcc ccgtccccag attctttccc 1020
aa 1022

<210> SEQ ID NO 43
<211> LENGTH: 1903
<212> TYPE: DNA
<213> ORGANISM: Bouteloua gracilis

<400> SEQUENCE: 43
actcaaacaa gcagccggcg cttggagctt ttatagtttg aaaagtgacg gttttaatga 60
tgggtaagct gattagtata tgtaagttta gctttttcca ttgtaggtta agccttaagg 120

-continued

```
ctcttacaca attgtttcat tattctcatt ctttaagagc ccatataagc gttcatgaat    180
tgtacatatc cttagatgtt tttttttttg ggtaaagctc gagcttctct atctaaaagt    240
agagaaatca gaaaaagatt catgttttgg tagttttgat ttcttgcctc cataataatt    300
ttggtttacc attttttgtt tgattttagt tttagaagcg tttatagcag gatttaaaat    360
ccaaaactac cattatcttc aagtgaccgt cagtgagccg tttaacggcg tcgacaagtc    420
caacggacac caaccagtga accaccagcg tcgagccaag cgatgcaaac ggaacggccg    480
agacgttgac acctttggcg cggcacggca tgtcggatct ccctctctgg ccagagagtt    540
ccagctccac ctccacctcc acctccaccg gtggcggttt ccaagtccgt tccgttccgt    600
tccgttccgt tccgttccgc ctcctgcctg ctcctctcag acggcacgaa accgtgacgg    660
caccggcagc acggggggat tccttttcca ctgctccttc ctcttccctt cctcgcccgc    720
cgctataaat agccagcccc gtccccagat tctttcccaa cctcatcttt gttcggagca    780
cgcacacaac ccgatcccca attccctcgt ctctcctcgc gagcctcgtc gacccccccc    840
ttcaaggtac ggcgatcatc ctccctccct ccctctctct accttctctt ctctagacta    900
gatcggcgac ccggtccatg gttagggcct gctagttctg ttcctgtttt ttccatggct    960
gcgaggtaaa atagatctga tggcgttatg atggttaact cgtcatactc ttgcgatcta   1020
tggtcccttt aggacatcga tttaatttcg gatggttcga gatcggtgat ccatggttag   1080
taccctaggc agtggggtta gatccgtgct gttagggttc gtagatggat tctgattgct   1140
cagtaactgg gaaacctggg atggttctag ctgggaatcc tgggatggtt ctagctggtt   1200
cgcagatgag atcgatttca tggtctgcta tatcttgttt cgttgcctag gttccgttta   1260
atctgtccgt ggtatgatgt tagcctttga taaggttcga tcgtgctagc tacgtcctgc   1320
gcagcattta attgtcaggt cataattttt agcattcctg tttttgtttg gtttggtttt   1380
gtctggttgg gctgtagata gtttcaatct acctgtcggt ttattttatt aaatttggat   1440
tggatctgta tgtgtcacat atatcttcat gattaagatg gttggaatta tctcttcatc   1500
ttttagatat atatggatag gtatatatgt tgctgtgggt tttactggta ctttattaga   1560
tatattcatg cttagataca tgaagcaacg tgctgttaca gtttaataat tcttgtttat   1620
ctaataaaca aataaggata ggtatatgtt gctgatggtt ttactgatac tttattagat   1680
agtactttga catgaaggaa catcctgcga cagcttaata attattcttc atctaataaa   1740
aagcttgctt tttaattatt ttaattattt tgatatactt ggatgatgtc atgcagcagc   1800
tatgtgtgaa ttttcggccc tgtcttcata tgatgtttat ttgcttggga ctgtttcttt   1860
ggctgataac ttaccctgtt gtttggtgat ccttctgcag gtg                     1903
```

<210> SEQ ID NO 44
<211> LENGTH: 760
<212> TYPE: DNA
<213> ORGANISM: Bouteloua gracilis

<400> SEQUENCE: 44

```
actcaaacaa gcagccggcg cttggagctt ttatagtttg aaaagtgacg gttttaatga     60
tgggtaagct gattagtata tgtaagttta gctttttcca ttgtaggtta agccttaagg    120
ctcttacaca attgtttcat tattctcatt ctttaagagc ccatataagc gttcatgaat    180
tgtacatatc cttagatgtt tttttttttg ggtaaagctc gagcttctct atctaaaagt    240
agagaaatca gaaaaagatt catgttttgg tagttttgat ttcttgcctc cataataatt    300
ttggtttacc attttttgtt tgattttagt tttagaagcg tttatagcag gatttaaaat    360
```

-continued ccaaaactac cattatcttc aagtgaccgt cagtgagccg tttaacggcg tcgacaagtc 420
caacggacac caaccagtga accaccagcg tcgagccaag cgatgcaaac ggaacggccg 480
agacgttgac acctttggcg cggcacggca tgtcggatct ccctctctgg ccagagagtt 540
ccagctccac ctccacctcc acctccaccg gtggcggttt ccaagtccgt tccgttccgt 600
tccgttccgt tccgttccgc ctcctgcctg ctcctctcag acggcacgaa accgtgacgg 660
caccggcagc acggggggat tccttttcca ctgctccttc ctcttccctt cctcgcccgc 720
cgctataaat agccagcccc gtccccagat tctttcccaa 760

<210> SEQ ID NO 45
<211> LENGTH: 3234
<212> TYPE: DNA
<213> ORGANISM: Bouteloua gracilis
<400> SEQUENCE: 45
ggcctcttta cgtttggcac aacttagttg aatccggctt ccggcaaact atatggcaag 60
ttagacccaa gtgtgagccg gccaccgcaa gttattgtga cattatacgt aggaagcaag 120
tgtataataa gaatatgaga taatgtaagc agctatatga attatcacgt catatttatg 180
ttaagatgaa gaggagagaa taaacggtac gtaaatttat agcgagtgat agacgggcac 240
gaggcctcct agctatttcc ataaatcgga ttttgtaaga acaaaaaaga ggacttatta 300
taagagaatg tggtaagtaa gcatactccc tccgtttcaa attataagtt gttttaactt 360
tttttttata tctattttac tatacattag atataataat gtgtctagat acataataaa 420
atggatgaac aaaaaagtca aagtgactta caatttggaa cggagggagt aagttcaagc 480
catcaaggca cttctatgca accacatagt caacttgaat gccgcttgag tgccttctca 540
agtttttttt ttcttgcaaa aattgtttct ttttttttaa aaaagtataa tttggatcgt 600
gcaaatttct ctctaggtgt gtgtgtgact gtgtgagtaa caatttctct agttgtgcgt 660
gactgctgct tactttggag attacaatat atttctaaaa tgcttcgatt acttatttat 720
aaaccgtctc taaggccaat tgctcaagat tcattcaaca attgaaacgt ctcacatgat 780
taaatcatat aaagtttcta agtcttgttt gacaagattt ttttagattt tcatctaaat 840
tggatgaaac tatcaaacac taattttaaa aaatataaga gaagctccgg agataaaagg 900
tcgtctatgt tattataaga gtaaagtcgt ctattctctt cgtcccaaca tatataattc 960
taagcatgaa ttgctttctt tttggacaaa aggagtatgc cacaacacaa gaatgatgtc 1020
accgtcatgc ttagatcctt ttatggtaaa gcttcacctt ctataatcta acaatagaga 1080
aatcggggaa aaatcatgtt ttggttgttt ttatttctaa cctccacaat aactttggtt 1140
taccattttt tgtttgattt tagttttaga gaagcgttta taacaggacc taaaatcttt 1200
ttttgagtac acagtacaac gcagacgctc atacacgcac gcacaatgtc ctctatgaac 1260
acacgtaagg aaaccctaca ccttgagcac cttcgaagga ctgagccggc aaatctagag 1320
attctcgaag tcactattgg cacctcgtta tcaacgagaa cgtcgcttac cacttaaagc 1380
ataacaccga gaaatcccgt aacaaatcca gtaaaatacg agcacccgta ccaagttgaa 1440
tatttgaacc cgagtgggta gattccaccg caaaggacct aaccagatca tttcgcaaac 1500
aggaactaaa atcggtagag agcccagaca aaaacctttt ctaagagcaa ctccagtgaa 1560
agcccctact ttaggtataa aatgcaacac tagtggagct tctaaataaa cttctatttt 1620
tcatgccctc ctaaaattta ctcctaaaac cctagctata ggagcctcct atccatcctc 1680

-continued tattttattc cactagaatt gattataaat ttagcctctt aaattttata agttgggagt 1740
cgagggtaac tagagttgct ctaaacggac cttatcttca agtgacctca gtgagcccgt 1800
ttaacggcgt cgacaagtct aatctaacgg acaccaacca gagaaccacc gccagcgccg 1860
agccaagcga cgttgacatc ttggcgcggc acggcatctc cctggcgtct ggtcccctcc 1920
cgagacttcc gctccacctc ccaccggtgg cggtttccga gtccgttccg cctcctctca 1980
cacggcacga aaccttgacg gcaccggcag cacgggggat tccgttccca cggctccttc 2040
cctttccctt cctcgcccgc tgctataaat agccagcccc atccccagct tcttccccaa 2100
cctcatcttc tcgtgttgtt cggcccaacc cgatcgatcc ccaattccct cgtcgtctct 2160
cgtcgcgagc ctcgtcgatc cccgcttcaa ggtacagcga tcgatcgatc atcctcgctc 2220
tctctacctt ctctctctta gggcgtgctg gttctgttcc tgtttttcca tggctgcgag 2280
gtacaataga ttggcgattc atggttaggg cctgctagtt ctgttcctgt tttttttttt 2340
tccatggctg cgaggcacaa tagatctgat ggcgttatga tggttaactt gtcatactct 2400
tgcgatctat ggtcccttta ggagtttagg acatcgattt aatttcggat agttcgagat 2460
ctgtgatcca tggttagtac cctaggcagt ggggttagat ccgtgctgtt atggttcgta 2520
gatggattct gattgctcag taactgggaa tcctgggatg gttctagctg gttcgcagat 2580
aagatcgatt tcatgatatg ctatatcttg tttggttgcc gtggttccgt taaatctgtc 2640
tgttatgatc ttagtctttg ataaggttcg gtcgtgctag ctacgtcctg tgcagcactt 2700
aattgtcagg tcataatttt tagcatgcct ttttttttatt ggtttggttt tgtctgactg 2760
ggctgtagat agtttcaatc tttgtctgac tgggctgtag atagtttcaa tcttcctgtc 2820
tgtttatttt attaaatttg gatctgtatg tgtgtcatat atcttcatct tttagatata 2880
tcgataggta tatatgttgc tgtcgttttt tactgttcct ttatgagata tattcatgct 2940
tagatacatg aaacaacgtg ctgttacagt ttaatagttc ttgtttatct aataaacaaa 3000
taaggatagg tgctgcagtt agttttactg gtactttttt tgacatgaac ctacggctta 3060
ataattagtc ttcatcaaat aaaaagcata ttttttaatt atttcgatat acttgaatga 3120
tgtcatatgc agcatctgtg tgaatttttg gccctgtctt catatgatgt ttatttgctt 3180
gggactgttt ctttggctga taactcaccc tgttgtttgg tgatccttct gcag 3234

<210> SEQ ID NO 46
<211> LENGTH: 2100
<212> TYPE: DNA
<213> ORGANISM: Bouteloua gracilis
<400> SEQUENCE: 46
ggcctcttta cgtttggcac aacttagttg aatccggctt ccggcaaact atatggcaag 60
ttagacccaa gtgtgagccg gccaccgcaa gttattgtga cattatacgt aggaagcaag 120
tgtataataa gaatatgaga taatgtaagc agctatatga attatcacgt catatttatg 180
ttaagatgaa gaggagagaa taaacggtac gtaaatttat agcgagtgat agacgggcac 240
gaggcctcct agctatttcc ataaatcgga ttttgtaaga acaaaaaaga ggacttatta 300
taagagaatg tggtaagtaa gcatactccc tccgtttcaa attataagtt gttttaactt 360
tttttttata tctattttac tatacattag atataataat gtgtctagat acataataaa 420
atggatgaac aaaaaagtca aagtgactta caatttggaa cggagggagt aagttcaagc 480
catcaaggca cttctatgca accacatagt caacttgaat gccgcttgag tgccttctca 540
agtttttttt ttcttgcaaa aattgtttct ttttttttaa aaaagtataa tttggatcgt 600
gcaaatttct ctctaggtgt gtgtgtgact gtgtgagtaa caatttctct agttgtgcgt 660
gactgctgct tactttggag attacaatat atttctaaaa tgcttcgatt acttatttat 720
aaaccgtctc taaggccaat tgctcaagat tcattcaaca attgaaacgt ctcacatgat 780
taaatcatat aaagtttcta agtcttgttt gacaagattt ttttagattt tcatctaaat 840
tggatgaaac tatcaaacac taattttaaa aaatataaga gaagctccgg agataaaagg 900
tcgtctatgt tattataaga gtaaagtcgt ctattctctt cgtcccaaca tatataattc 960
taagcatgaa ttgctttctt tttggacaaa aggagtatgc cacaacacaa gaatgatgtc 1020
accgtcatgc ttagatcctt ttatggtaaa gcttcacctt ctataatcta acaatagaga 1080
aatcggggaa aaatcatgtt ttggttgttt ttatttctaa cctccacaat aactttggtt 1140
taccattttt tgtttgattt tagttttaga gaagcgttta taacaggacc taaaatcttt 1200
ttttgagtac acagtacaac gcagacgctc atacacgcac gcacaatgtc ctctatgaac 1260
acacgtaagg aaaccctaca ccttgagcac cttcgaagga ctgagccggc aaatctagag 1320
attctcgaag tcactattgg cacctcgtta tcaacgagaa cgtcgcttac cacttaaagc 1380
ataacaccga gaaatcccgt aacaaatcca gtaaaatacg agcacccgta ccaagttgaa 1440
tatttgaacc cgagtgggta gattccaccg caaaggacct aaccagatca tttcgcaaac 1500
aggaactaaa atcggtagag agcccagaca aaaacctttt ctaagagcaa ctccagtgaa 1560
agcccctact ttaggtataa aatgcaacac tagtggagct tctaaataaa cttctatttt 1620
tcatgccctc ctaaaattta ctcctaaaac cctagctata ggagcctcct atccatcctc 1680
tattttattc cactagaatt gattataaat ttagcctctt aaattttata agttgggagt 1740
cgagggtaac tagagttgct ctaaacggac cttatcttca agtgacctca gtgagcccgt 1800
ttaacggcgt cgacaagtct aatctaacgg acaccaacca gagaaccacc gccagcgccg 1860
agccaagcga cgttgacatc ttggcgcggc acggcatctc cctggcgtct ggtcccctcc 1920
cgagacttcc gctccacctc ccaccggtgg cggtttccga gtccgttccg cctcctctca 1980
cacggcacga aaccttgacg gcaccggcag cacgggggat tccgttccca cggctccttc 2040
cctttccctt cctcgcccgc tgctataaat agccagcccc atccccagct tcttccccaa 2100

<210> SEQ ID NO 47
<211> LENGTH: 91
<212> TYPE: DNA
<213> ORGANISM: Bouteloua gracilis

<400> SEQUENCE: 47
cctcatcttc tcgtgttgtt cggcccaacc cgatcgatcc ccaattccct cgtcgtctct 60
cgtcgcgagc ctcgtcgatc cccgcttcaa g 91

<210> SEQ ID NO 48
<211> LENGTH: 1043
<212> TYPE: DNA
<213> ORGANISM: Bouteloua gracilis

<400> SEQUENCE: 48
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt ttttttttt ccatggctgc gaggcacaat agatctgatg 180
gcgttatgat ggttaacttg tcatactctt gcgatctatg gtccctttag gagtttagga 240

-continued

```
catcgattta atttcggata gttcgagatc tgtgatccat ggttagtacc ctaggcagtg    300
gggttagatc cgtgctgtta tggttcgtag atggattctg attgctcagt aactgggaat    360
cctgggatgg ttctagctgg ttcgcagata agatcgattt catgatatgc tatatcttgt    420
ttggttgccg tggttccgtt aaatctgtct gttatgatct tagtctttga taaggttcgg    480
tcgtgctagc tacgtcctgt gcagcactta attgtcaggt cataattttt agcatgcctt    540 tttttattg gtttggtttt gtctgactgg gctgtagata gtttcaatct ttgtctgact     600
gggctgtaga tagtttcaat cttcctgtct gtttatttta ttaaatttgg atctgtatgt    660
gtgtcatata tcttcatctt ttagatatat cgataggtat atatgttgct gtcgtttttt    720
actgttcctt tatgagatat attcatgctt agatacatga aacaacgtgc tgttacagtt    780
taatagttct tgtttatcta ataaacaaat aaggataggt gctgcagtta gttttactgg    840
tacttttttt gacatgaacc tacggcttaa taattagtct tcatcaaata aaaagcatat    900
tttttaatta tttcgatata cttgaatgat gtcatatgca gcatctgtgt gaatttttgg    960
ccctgtcttc atatgatgtt tatttgcttg ggactgtttc tttggctgat aactcaccct   1020
gttgtttggt gatccttctg cag                                           1043
```

```
<210> SEQ ID NO 49
<211> LENGTH: 3176
<212> TYPE: DNA
<213> ORGANISM: Bouteloua gracilis

<400> SEQUENCE: 49
aagttagacc caagtgtgag ccggccaccg caagttattg tgacattata cgtaggaagc     60
aagtgtataa taagaatatg agataatgta agcagctata tgaattatca cgtcatattt    120
atgttaagat gaagaggaga gaataaacgg tacgtaaatt tatagcgagt gatagacggg    180
cacgaggcct cctagctatt tccataaatc ggattttgta agaacaaaaa agaggactta    240
ttataagaga atgtggtaag taagcatact ccctccgttt caaattataa gttgttttaa    300
cttttttttt atatctattt tactatacat tagatataat aatgtgtcta gatacataat    360
aaaatggatg aacaaaaaag tcaaagtgac ttacaatttg gaacggaggg agtaagttca    420
agccatcaag gcacttctat gcaaccacat agtcaacttg aatgccgctt gagtgccttc    480
tcaagttttt tttttcttgc aaaaattgtt tctttttttt taaaaaagta taatttggat    540
cgtgcaaatt tctctctagg tgtgtgtgtg actgtgtgag taacaatttc tctagttgtg    600
cgtgactgct gcttactttg gagattacaa tatatttcta aaatgcttcg attacttatt    660
tataaaccgt ctctaaggcc aattgctcaa gattcattca acaattgaaa cgtctcacat    720
gattaaatca tataaagttt ctaagtcttg tttgacaaga tttttttaga ttttcatcta    780
aattggatga aactatcaaa cactaatttt aaaaaaatata agagaagctc cggagataaa   840
aggtcgtcta tgttattata agagtaaagt cgtctattct cttcgtccca acatatataa    900
ttctaagcat gaattgcttt ctttttggac aaaaggagta tgccacaaca caagaatgat    960
gtcaccgtca tgcttagatc cttttatggt aaagcttcac cttctataat ctaacaatag   1020
agaaatcggg gaaaaatcat gttttggttg tttttatttc taacctccac aataactttg   1080
gtttaccatt ttttgtttga ttttagtttt agagaagcgt ttataacagg acctaaaatc   1140
tttttttgag tacacagtac aacgcagacg ctcatacacg cacgcacaat gtcctctatg   1200
aacacacgta aggaaaccct acaccttgag caccttcgaa ggactgagcc ggcaaatcta   1260
gagattctcg aagtcactat tggcacctcg ttatcaacga gaacgtcgct taccacttaa   1320
```

agcataacac cgagaaatcc cgtaacaaat ccagtaaaat acgagcaccc gtaccaagtt 1380
gaatatttga acccgagtgg gtagattcca ccgcaaagga cctaaccaga tcatttcgca 1440
aacaggaact aaaatcggta gagagcccag acaaaaacct tttctaagag caactccagt 1500
gaaagcccct actttaggta taaaatgcaa cactagtgga gcttctaaat aaacttctat 1560
ttttcatgcc ctcctaaaat ttactcctaa aaccctagct ataggagcct cctatccatc 1620
ctctatttta ttccactaga attgattata aatttagcct cttaaatttt ataagttggg 1680
agtcgagggt aactagagtt gctctaaacg gaccttatct tcaagtgacc tcagtgagcc 1740
cgtttaacgg cgtcgacaag tctaatctaa cggacaccaa ccagagaacc accgccagcg 1800
ccgagccaag cgacgttgac atcttggcgc ggcacggcat ctccctggcg tctggtcccc 1860
tcccgagact tccgctccac ctcccaccgg tggcggtttc cgagtccgtt ccgcctcctc 1920
tcacacggca cgaaaccttg acggcaccgg cagcacgggg gattccgttc ccacggctcc 1980
ttccctttcc cttcctcgcc cgctgctata aatagccagc cccatcccca gcttcttccc 2040
caacctcatc ttctcgtgtt gttcggccca acccgatcga tccccaattc cctcgtcgtc 2100
tctcgtcgcg agcctcgtcg atccccgctt caaggtacag cgatcgatcg atcatcctcg 2160
ctctctctac cttctctctc ttagggcgtg ctggttctgt tcctgttttt ccatggctgc 2220
gaggtacaat agattggcga ttcatggtta gggcctgcta gttctgttcc tgtttttttt 2280
ttttccatgg ctgcgaggca caatagatct gatggcgtta tgatggttaa cttgtcatac 2340
tcttgcgatc tatggtccct ttaggagttt aggacatcga tttaatttcg gatagttcga 2400
gatctgtgat ccatggttag taccctaggc agtggggtta gatccgtgct gttatggttc 2460
gtagatggat tctgattgct cagtaactgg gaatcctggg atggttctag ctggttcgca 2520
gataagatcg atttcatgat atgctatatc ttgtttggtt gccgtggttc cgttaaatct 2580
gtctgttatg atcttagtct tgataaggtt cggtcgtgct agctacgtcc tgtgcagcac 2640
ttaattgtca ggtcataatt tttagcatgc cttttttta ttggtttggt tttgtctgac 2700
tgggctgtag atagtttcaa tctttgtctg actgggctgt agatagtttc aatcttcctg 2760
tctgtttatt ttattaaatt tggatctgta tgtgtgtcat atatcttcat cttttagata 2820
tatcgatagg tatatatgtt gctgtcgttt tttactgttc ctttatgaga tatattcatg 2880
cttagataca tgaaacaacg tgctgttaca gtttaatagt tcttgtttat ctaataaaca 2940
aataaggata ggtgctgcag ttagttttac tggtactttt tttgacatga acctacggct 3000
taataattag tcttcatcaa ataaaaagca tattttttaa ttatttcgat atacttgaat 3060
gatgtcatat gcagcatctg tgtgaatttt tggccctgtc ttcatatgat gtttatttgc 3120
ttgggactgt ttctttggct gataactcac cctgttgttt ggtgatcctt ctgcag 3176

<210> SEQ ID NO 50
<211> LENGTH: 2043
<212> TYPE: DNA
<213> ORGANISM: Bouteloua gracilis

<400> SEQUENCE: 50
aagttagacc caagtgtgag ccggccaccg caagttattg tgacattata cgtaggaagc 60
aagtgtataa taagaatatg agataatgta agcagctata tgaattatca cgtcatattt 120
atgttaagat gaagaggaga gaataaacgg tacgtaaatt tatagcgagt gatagacggg 180
cacgaggcct cctagctatt tccataaatc ggattttgta agaacaaaaa agaggactta 240

```
ttataagaga atgtggtaag taagcatact ccctccgttt caaattataa gttgttttaa    300

cttttttttt atatctattt tactatacat tagatataat aatgtgtcta gatacataat    360

aaaatggatg aacaaaaaag tcaaagtgac ttacaatttg gaacggaggg agtaagttca    420

agccatcaag gcacttctat gcaaccacat agtcaacttg aatgccgctt gagtgccttc    480

tcaagttttt tttttcttgc aaaaattgtt tctttttttt taaaaaagta taatttggat    540

cgtgcaaatt tctctctagg tgtgtgtgtg actgtgtgag taacaatttc tctagttgtg    600

cgtgactgct gcttactttg gagattacaa tatatttcta aaatgcttcg attacttatt    660

tataaaccgt ctctaaggcc aattgctcaa gattcattca acaattgaaa cgtctcacat    720

gattaaatca tataaagttt ctaagtcttg tttgacaaga ttttttttaga ttttcatcta    780

aattggatga aactatcaaa cactaatttt aaaaaatata agagaagctc cggagataaa    840

aggtcgtcta tgttattata agagtaaagt cgtctattct cttcgtccca acatatataa    900

ttctaagcat gaattgcttt ctttttggac aaaaggagta tgccacaaca caagaatgat    960

gtcaccgtca tgcttagatc cttttatggt aaagcttcac cttctataat ctaacaatag   1020

agaaatcggg gaaaaatcat gttttggttg tttttatttc taacctccac aataactttg   1080

gtttaccatt ttttgtttga ttttagtttt agagaagcgt ttataacagg acctaaaatc   1140

tttttttgag tacacagtac aacgcagacg ctcatacacg cacgcacaat gtcctctatg   1200

aacacacgta aggaaaccct acaccttgag caccttcgaa ggactgagcc ggcaaatcta   1260

gagattctcg aagtcactat tggcacctcg ttatcaacga gaacgtcgct taccacttaa   1320

agcataacac cgagaaatcc cgtaacaaat ccagtaaaat acgagcaccc gtaccaagtt   1380

gaatatttga acccgagtgg gtagattcca ccgcaaagga cctaaccaga tcatttcgca   1440

aacaggaact aaaatcggta gagagcccag acaaaaacct tttctaagag caactccagt   1500

gaaagcccct actttaggta taaaatgcaa cactagtgga gcttctaaat aaacttctat   1560

ttttcatgcc ctcctaaaat ttactcctaa aaccctagct ataggagcct cctatccatc   1620

ctctatttta ttccactaga attgattata aatttagcct cttaaatttt ataagttggg   1680

agtcgagggt aactagagtt gctctaaacg gaccttatct tcaagtgacc tcagtgagcc   1740

cgtttaacgg cgtcgacaag tctaatctaa cggacaccaa ccagagaacc accgccagcg   1800

ccgagccaag cgacgttgac atcttggcgc ggcacggcat ctccctggcg tctggtcccc   1860

tcccgagact tccgctccac ctcccaccgg tggcggtttc cgagtccgtt ccgcctcctc   1920

tcacacggca cgaaaccttg acggcaccgg cagcacgggg gattccgttc ccacggctcc   1980

ttccctttcc cttcctcgcc cgctgctata aatagccagc cccatcccca gcttcttccc   2040

caa                                                                 2043
```

<210> SEQ ID NO 51
<211> LENGTH: 1042
<212> TYPE: DNA
<213> ORGANISM: Bouteloua gracilis

<400> SEQUENCE: 51

```
gtacagcgat cgatcgatca tcctcgctct ctctaccttc tctctcttag ggcgtgctgg     60

ttctgttcct gtttttccat ggctgcgagg tacaatagat tggcgattca tggttagggc    120

ctgctagttc tgttcctgtt tttttttttt ccatggctgc gaggcacaat agatctgatg    180

gcgttatgat ggttaacttg tcatactctt gcgatctatg gtccctttag gagtttagga    240

catcgattta atttcggata gttcgagatc tgtgatccat ggttagtacc ctaggcagtg    300
```

```
gggttagatc cgtgctgtta tggttcgtag atggattctg attgctcagt aactgggaat    360
cctgggatgg ttctagctgg ttcgcagata agatcgattt catgatatgc tatatcttgt    420
ttggttgccg tggttccgtt aaatctgtct gttatgatct tagtcttgat aaggttcggt    480
cgtgctagct acgtcctgtg cagcacttaa ttgtcaggtc ataattttta gcatgccttt    540
tttttattgg tttggttttg tctgactggg ctgtagatag tttcaatctt tgtctgactg    600
ggctgtagat agtttcaatc ttcctgtctg tttattttat taaatttgga tctgtatgtg    660
tgtcatatat cttcatcttt tagatatatc gataggtata tatgttgctg tcgtttttta    720
ctgttccttt atgagatata ttcatgctta gatacatgaa acaacgtgct gttacagttt    780
aatagttctt gtttatctaa taaacaaata aggataggtg ctgcagttag ttttactggt    840
actttttttg acatgaacct acggcttaat aattagtctt catcaaataa aaagcatatt    900
ttttaattat ttcgatatac ttgaatgatg tcatatgcag catctgtgtg aatttttggc    960
cctgtcttca tatgatgttt atttgcttgg gactgtttct ttggctgata actcaccctg   1020
ttgtttggtg atccttctgc ag                                            1042
```

```
<210> SEQ ID NO 52
<211> LENGTH: 3139
<212> TYPE: DNA
<213> ORGANISM: Bouteloua gracilis

<400> SEQUENCE: 52
```

```
gacattatac gtaggaagca agtgtataat aagaatatga gataatgtaa gcagctatat     60
gaattatcac gtcatattta tgttaagatg aagaggagag aataaacggt acgtaaattt    120
atagcgagtg atagacgggc acgaggcctc ctagctattt ccataaatcg gattttgtaa    180
gaacaaaaaa gaggacttat tataagagaa tgtggtaagt aagcatactc cctccgtttc    240
aaattataag ttgttttaac ttttttttta tatctatttt actatacatt agatataata    300
atgtgtctag atacataata aaatggatga acaaaaaagt caaagtgact tacaatttgg    360
aacggaggga gtaagttcaa gccatcaagg cacttctatg caaccacata gtcaacttga    420
atgccgcttg agtgccttct caagtttttt ttttcttgca aaaattgttt cttttttttt    480
aaaaaagtat aatttggatc gtgcaaattt ctctctaggt gtgtgtgtga ctgtgtgagt    540
aacaatttct ctagttgtgc gtgactgctg cttactttgg agattacaat atatttctaa    600
aatgcttcga ttacttattt ataaaccgtc tctaaggcca attgctcaag attcattcaa    660
caattgaaac gtctcacatg attaaatcat ataaagtttc taagtcttgt ttgacaagat    720
ttttttagat tttcatctaa attggatgaa actatcaaac actaatttta aaaaatataa    780
gagaagctcc ggagataaaa ggtcgtctat gttattataa gagtaaagtc gtctattctc    840
ttcgtcccaa catatataat tctaagcatg aattgctttc tttttggaca aaaggagtat    900
gccacaacac aagaatgatg tcaccgtcat gcttagatcc ttttatggta aagcttcacc    960
ttctataatc taacaataga gaaatcgggg aaaaatcatg ttttggttgt ttttatttct   1020
aacctccaca ataactttgg tttaccattt tttgtttgat tttagtttta gagaagcgtt   1080
tataacagga cctaaaatct ttttttgagt acacagtaca acgcagacgc tcatacacgc   1140
acgcacaatg tcctctatga acacacgtaa ggaaacccta caccttgagc accttcgaag   1200
gactgagccg gcaaatctag agattctcga agtcactatt ggcacctcgt tatcaacgag   1260
aacgtcgctt accacttaaa gcataacacc gagaaatccc gtaacaaatc cagtaaaata   1320
```

-continued

```
cgagcacccg taccaagttg aatatttgaa cccgagtggg tagattccac cgcaaaggac   1380
ctaaccagat catttcgcaa acaggaacta aaatcggtag agagcccaga caaaaacctt   1440
ttctaagagc aactccagtg aaagccccta ctttaggtat aaaatgcaac actagtggag   1500
cttctaaata aacttctatt tttcatgccc tcctaaaatt tactcctaaa accctagcta   1560
taggagcctc ctatccatcc tctattttat tccactagaa ttgattataa atttagcctc   1620
ttaaatttta taagttggga gtcgagggta actagagttg ctctaaacgg accttatctt   1680
caagtgacct cagtgagccc gtttaacggc gtcgacaagt ctaatctaac ggacaccaac   1740
cagagaacca ccgccagcgc cgagccaagc gacgttgaca tcttggcgcg gcacggcatc   1800
tccctggcgt ctggtcccct cccgagactt ccgctccacc tcccaccggt ggcggtttcc   1860
gagtccgttc cgcctcctct cacacggcac gaaaccttga cggcaccggc agcacggggg   1920
attccgttcc cacggctcct tccctttccc ttcctcgccc gctgctataa atagccagcc   1980
ccatccccag cttcttcccc aacctcatct tctcgtgttg ttcggcccaa cccgatcgat   2040
ccccaattcc ctcgtcgtct ctcgtcgcga gcctcgtcga tccccgcttc aaggtacagc   2100
gatcgatcga tcatcctcgc tctctctacc ttctctctct tagggcgtgc tggttctgtt   2160
cctgtttttc catggctgcg aggtacaata gattggcgat tcatggttag ggcctgctag   2220
ttctgttcct gttttttttt tttccatggc tgcgaggcac aatagatctg atggcgttat   2280
gatggttaac ttgtcatact cttgcgatct atggtccctt taggagttta ggacatcgat   2340
ttaatttcgg atagttcgag atctgtgatc catggttagt accctaggca gtggggttag   2400
atccgtgctg ttatggttcg tagatggatt ctgattgctc agtaactggg aatcctggga   2460
tggttctagc tggttcgcag ataagatcga tttcatgata tgctatatct tgtttggttg   2520
ccgtggttcc gttaaatctg tctgttatga tcttagtctt tgataaggtt cggtcgtgct   2580
agctacgtcc tgtgcagcac ttaattgtca ggtcataatt tttagcatgc cttttttta    2640
ttggtttggt tttgtctgac tgggctgtag atagtttcaa tctttgtctg actgggctgt   2700
agatagtttc aatcttcctg tctgtttatt ttattaaatt tggatctgta tgtgtgtcat   2760
atatcttcat cttttagata tatcgatagg tatatatgtt gctgtcgttt tttactgttc   2820
ctttatgaga tatattcatg cttagataca tgaaacaacg tgctgttaca gtttaatagt   2880
tcttgtttat ctaataaaca aataaggata ggtgctgcag ttagttttac tggtactttt   2940
tttgacatga acctacggct taataattag tcttcatcaa ataaaaagca tattttttaa   3000
ttatttcgat atacttgaat gatgtcatat gcagcatctg tgtgaatttt tggccctgtc   3060
ttcatatgat gtttatttgc ttgggactgt ttctttggct gataactcac cctgttgttt   3120
ggtgatcctt ctgcaggtg                                                 3139
```

<210> SEQ ID NO 53
<211> LENGTH: 2002
<212> TYPE: DNA
<213> ORGANISM: Bouteloua gracilis

<400> SEQUENCE: 53

```
gacattatac gtaggaagca agtgtataat aagaatatga gataatgtaa gcagctatat     60
gaattatcac gtcatattta tgttaagatg aagaggagag aataaacggt acgtaaattt    120
atagcgagtg atagacgggc acgaggcctc ctagctattt ccataaatcg gattttgtaa    180
gaacaaaaaa gaggacttat tataagagaa tgtggtaagt aagcatactc cctccgtttc    240
aaattataag ttgttttaac ttttttttta tatctatttt actatacatt agatataata    300
```

```
atgtgtctag atacataata aaatggatga acaaaaaagt caaagtgact tacaatttgg    360
aacggaggga gtaagttcaa gccatcaagg cacttctatg caaccacata gtcaacttga    420
atgccgcttg agtgccttct caagtttttt ttttcttgca aaaattgttt cttttttttt    480
aaaaaagtat aatttggatc gtgcaaattt ctctctaggt gtgtgtgtga ctgtgtgagt    540
aacaatttct ctagttgtgc gtgactgctg cttactttgg agattacaat atatttctaa    600
aatgcttcga ttacttattt ataaaccgtc tctaaggcca attgctcaag attcattcaa    660
caattgaaac gtctcacatg attaaatcat ataaagtttc taagtcttgt ttgacaagat    720
tttttagat tttcatctaa attggatgaa actatcaaac actaatttta aaaaatataa    780
gagaagctcc ggagataaaa ggtcgtctat gttattataa gagtaaagtc gtctattctc    840
ttcgtcccaa catatataat tctaagcatg aattgctttc tttttggaca aaaggagtat    900
gccacaacac aagaatgatg tcaccgtcat gcttagatcc ttttatggta aagcttcacc    960
ttctataatc taacaataga gaaatcgggg aaaaatcatg ttttggttgt ttttatttct   1020
aacctccaca ataactttgg tttaccattt tttgtttgat tttagtttta gagaagcgtt   1080
tataacagga cctaaaatct ttttttgagt acacagtaca acgcagacgc tcatacacgc   1140
acgcacaatg tcctctatga acacacgtaa ggaaacccta caccttgagc accttcgaag   1200
gactgagccg gcaaatctag agattctcga agtcactatt ggcacctcgt tatcaacgag   1260
aacgtcgctt accacttaaa gcataacacc gagaaatccc gtaacaaatc cagtaaaata   1320
cgagcacccg taccaagttg aatatttgaa cccgagtggg tagattccac cgcaaaggac   1380
ctaaccagat catttcgcaa acaggaacta aaatcggtag agagcccaga caaaaacctt   1440
ttctaagagc aactccagtg aaagccccta ctttaggtat aaaatgcaac actagtggag   1500
cttctaaata aacttctatt tttcatgccc tcctaaaatt tactcctaaa accctagcta   1560
taggagcctc ctatccatcc tctattttat tccactagaa ttgattataa atttagcctc   1620
ttaaatttta taagttggga gtcgagggta actagagttg ctctaaacgg accttatctt   1680
caagtgacct cagtgagccc gtttaacggc gtcgacaagt ctaatctaac ggacaccaac   1740
cagagaacca ccgccagcgc cgagccaagc gacgttgaca tcttggcgcg gcacggcatc   1800
tccctggcgt ctggtcccct cccgagactt ccgctccacc tcccaccggt ggcggtttcc   1860
gagtccgttc cgcctcctct cacacggcac gaaaccttga cggcaccggc agcacggggg   1920
attccgttcc cacggctcct tccctttccc ttcctcgccc gctgctataa atagccagcc   1980
ccatccccag cttcttcccc aa                                             2002
```

<210> SEQ ID NO 54
<211> LENGTH: 1046
<212> TYPE: DNA
<213> ORGANISM: Bouteloua gracilis

<400> SEQUENCE: 54

```
gtacagcgat cgatcgatca tcctcgctct ctctaccttc tctctcttag ggcgtgctgg     60
ttctgttcct gtttttccat ggctgcgagg tacaatagat tggcgattca tggttagggc    120
ctgctagttc tgttcctgtt tttttttttt ccatggctgc gaggcacaat agatctgatg    180
gcgttatgat ggttaacttg tcatactctt gcgatctatg gtccctttag gagtttagga    240
catcgattta atttcggata gttcgagatc tgtgatccat ggttagtacc ctaggcagtg    300
gggttagatc cgtgctgtta tggttcgtag atggattctg attgctcagt aactgggaat    360
```

```
cctgggatgg ttctagctgg ttcgcagata agatcgattt catgatatgc tatatcttgt    420
ttggttgccg tggttccgtt aaatctgtct gttatgatct tagtctttga taaggttcgg    480
tcgtgctagc tacgtcctgt gcagcactta attgtcaggt cataattttt agcatgcctt    540 tttttattg gtttggtttt gtctgactgg gctgtagata gtttcaatct ttgtctgact    600
gggctgtaga tagtttcaat cttcctgtct gtttatttta ttaaatttgg atctgtatgt    660
gtgtcatata tcttcatctt ttagatatat cgataggtat atatgttgct gtcgtttttt    720
actgttcctt tatgagatat attcatgctt agatacatga aacaacgtgc tgttacagtt    780
taatagttct tgtttatcta ataaacaaat aaggataggt gctgcagtta gttttactgg    840
tacttttttt gacatgaacc tacggcttaa taattagtct tcatcaaata aaaagcatat    900
tttttaatta tttcgatata cttgaatgat gtcatatgca gcatctgtgt gaatttttgg    960
ccctgtcttc atatgatgtt tatttgcttg ggactgtttc tttggctgat aactcaccct   1020
gttgtttggt gatccttctg caggtg                                        1046
```

<210> SEQ ID NO 55
<211> LENGTH: 2160
<212> TYPE: DNA
<213> ORGANISM: Bouteloua gracilis

<400> SEQUENCE: 55

```
gagaaatcgg ggaaaaatca tgttttggtt gtttttattt ctaacctcca caataacttt     60
ggtttaccat tttttgtttg attttagttt tagagaagcg tttataacag gacctaaaat    120
ctttttttga gtacacagta caacgcagac gctcatacac gcacgcacaa tgtcctctat    180
gaacacacgt aaggaaaccc tacaccttga gcaccttcga aggactgagc cggcaaatct    240
agagattctc gaagtcacta ttggcacctc gttatcaacg agaacgtcgc ttaccactta    300
aagcataaca ccgagaaatc ccgtaacaaa tccagtaaaa tacgagcacc cgtaccaagt    360
tgaatatttg aacccgagtg ggtagattcc accgcaaagg acctaaccag atcatttcgc    420
aaacaggaac taaaatcggt agagagccca gacaaaaacc ttttctaaga gcaactccag    480
tgaaagcccc tactttaggt ataaaatgca acactagtgg agcttctaaa taaacttcta    540
tttttcatgc cctcctaaaa tttactccta aaaccctagc tataggagcc tcctatccat    600
cctctatttt attccactag aattgattat aaatttagcc tcttaaattt tataagttgg    660
gagtcgaggg taactagagt tgctctaaac ggaccttatc ttcaagtgac ctcagtgagc    720
ccgtttaacg gcgtcgacaa gtctaatcta acggacacca accagagaac caccgccagc    780
gccgagccaa gcgacgttga catcttggcg cggcacggca tctccctggc gtctggtccc    840
ctcccgagac ttccgctcca cctcccaccg gtggcggttt ccgagtccgt tccgcctcct    900
ctcacacggc acgaaacctt gacggcaccg gcagcacggg ggattccgtt cccacggctc    960
cttccctttc ccttcctcgc ccgctgctat aaatagccag ccccatcccc agcttcttcc   1020
ccaacctcat cttctcgtgt tgttcggccc aacccgatcg atccccaatt ccctcgtcgt   1080
ctctcgtcgc gagcctcgtc gatccccgct tcaaggtaca gcgatcgatc gatcatcctc   1140
gctctctcta ccttctctct cttagggcgt gctggttctg ttcctgtttt tccatggctg   1200
cgaggtacaa tagattggcg attcatggtt agggcctgct agttctgttc ctgttttttt   1260
ttttccatgg ctgcgaggca caatagatct gatggcgtta tgatggttaa cttgtcatac   1320
tcttgcgatc tatggtccct ttaggagttt aggacatcga tttaatttcg gatagttcga   1380
gatctgtgat ccatggttag taccctaggc agtggggtta gatccgtgct gttatggttc   1440
```

gtagatggat tctgattgct cagtaactgg gaatcctggg atggttctag ctggttcgca 1500
gataagatcg atttcatgat atgctatatc ttgtttggtt gccgtggttc cgttaaatct 1560
gtctgttatg atcttagtct ttgataaggt tcggtcgtgc tagctacgtc ctgtgcagca 1620
cttaattgtc aggtcataat ttttagcatg cctttttttt attggtttgg ttttgtctga 1680
ctgggctgta gatagtttca atctttgtct gactgggctg tagatagttt caatcttcct 1740
gtctgtttat tttattaaat ttggatctgt atgtgtgtca tatatcttca tcttttagat 1800
atatcgatag gtatatatgt tgctgtcgtt ttttactgtt cctttatgag atatattcat 1860
gcttagatac atgaaacaac gtgctgttac agtttaatag ttcttgttta tctaataaac 1920
aaataaggat aggtgctgca gttagtttta ctggtacttt ttttgacatg aacctacggc 1980
ttaataatta gtcttcatca aataaaaagc atatttttta attatttcga tatacttgaa 2040
tgatgtcata tgcagcatct gtgtgaattt ttggccctgt cttcatatga tgtttatttg 2100
cttgggactg tttctttggc tgataactca ccctgttgtt tggtgatcct tctgcaggtg 2160

<210> SEQ ID NO 56
<211> LENGTH: 1024
<212> TYPE: DNA
<213> ORGANISM: Bouteloua gracilis

<400> SEQUENCE: 56
gagaaatcgg ggaaaaatca tgttttggtt gtttttattt ctaacctcca caataacttt 60
ggtttaccat tttttgtttg attttagttt tagagaagcg tttataacag gacctaaaat 120 cttttttga gtacacagta caacgcagac gctcatacac gcacgcacaa tgtcctctat 180
gaacacacgt aaggaaaccc tacaccttga gcaccttcga aggactgagc cggcaaatct 240
agagattctc gaagtcacta ttggcacctc gttatcaacg agaacgtcgc ttaccactta 300
aagcataaca ccgagaaatc ccgtaacaaa tccagtaaaa tacgagcacc cgtaccaagt 360
tgaatatttg aacccgagtg ggtagattcc accgcaaagg acctaaccag atcatttcgc 420
aaacaggaac taaaatcggt agagagccca gacaaaaacc ttttctaaga gcaactccag 480
tgaaagcccc tactttaggt ataaaatgca acactagtgg agcttctaaa taaacttcta 540
tttttcatgc cctcctaaaa tttactccta aaaccctagc tataggagcc tcctatccat 600
cctctatttt attccactag aattgattat aaatttagcc tcttaaattt tataagttgg 660
gagtcgaggg taactagagt tgctctaaac ggaccttatc ttcaagtgac ctcagtgagc 720
ccgtttaacg gcgtcgacaa gtctaatcta acggacacca accagagaac caccgccagc 780
gccgagccaa gcgacgttga catcttggcg cggcacggca tctccctggc gtctggtccc 840
ctcccgagac ttccgctcca cctcccaccg gtggcggttt ccgagtccgt tccgcctcct 900
ctcacacggc acgaaacctt gacggcaccg gcagcacggg ggattccgtt cccacggctc 960
cttccctttc ccttcctcgc ccgctgctat aaatagccag ccccatcccc agcttcttcc 1020
ccaa 1024

<210> SEQ ID NO 57
<211> LENGTH: 1045
<212> TYPE: DNA
<213> ORGANISM: Bouteloua gracilis

<400> SEQUENCE: 57
gtacagcgat cgatcgatca tcctcgctct ctctaccttc tctctcttag ggcgtgctgg 60

```
ttctgttcct gtttttccat ggctgcgagg tacaatagat tggcgattca tggttagggc    120
ctgctagttc tgttcctgtt ttttttttc catggctgcg aggcacaata gatctgatgg    180
cgttatgatg gttaacttgt catactcttg cgatctatgg tccctttagg agtttaggac    240
atcgatttaa tttcggatag ttcgagatct gtgatccatg gttagtaccc taggcagtgg    300
ggttagatcc gtgctgttat ggttcgtaga tggattctga ttgctcagta actgggaatc    360
ctgggatggt tctagctggt tcgcagataa gatcgatttc atgatatgct atatcttgtt    420
tggttgccgt ggttccgtta aatctgtctg ttatgatctt agtctttgat aaggttcggt    480
cgtgctagct acgtcctgtg cagcacttaa ttgtcaggtc ataattttta gcatgccttt    540
tttttattgg tttggttttg tctgactggg ctgtagatag tttcaatctt tgtctgactg    600
ggctgtagat agtttcaatc ttcctgtctg tttattttat taaatttgga tctgtatgtg    660
tgtcatatat cttcatcttt tagatatatc gataggtata tatgttgctg tcgtttttta    720
ctgttccttt atgagatata ttcatgctta gatacatgaa acaacgtgct gttacagttt    780
aatagttctt gtttatctaa taaacaaata aggataggtg ctgcagttag ttttactggt    840
actttttttg acatgaacct acggcttaat aattagtctt catcaaataa aaagcatatt    900
ttttaattat ttcgatatac ttgaatgatg tcatatgcag catctgtgtg aatttttggc    960
cctgtcttca tatgatgttt atttgcttgg gactgtttct ttggctgata actcaccctg   1020
ttgtttggtg atccttctgc aggtg                                         1045

<210> SEQ ID NO 58
<211> LENGTH: 2160
<212> TYPE: DNA
<213> ORGANISM: Bouteloua gracilis

<400> SEQUENCE: 58

gagaaatcgg ggaaaaatca tgttttggtt gtttttattt ctaacctcca caataacttt     60
ggtttaccat tttttgtttg attttagttt tagagaagcg tttataacag gacctaaaat    120
cttttttttga gtacacagta caacgcagac gctcatacac gcacgcacaa tgtcctctat    180
gaacacacgt aaggaaaccc tacaccttga gcaccttcga aggactgagc cggcaaatct    240
agagattctc gaagtcacta ttggcacctc gttatcaacg agaacgtcgc ttaccactta    300
aagcataaca ccgagaaatc ccgtaacaaa tccagtaaaa tacgagcacc cgtaccaagt    360
tgaatatttg aacccgagtg ggtagattcc accgcaaagg acctaaccag atcatttcgc    420
aaacaggaac taaaatcggt agagagccca gacaaaaacc ttttctaaga gcaactccag    480
tgaaagcccc tactttaggt ataaaatgca acactagtgg agcttctaaa taaacttcta    540
tttttcatgc cctcctaaaa tttactccta aaaccctagc tataggagcc tcctatccat    600
cctctatttt attccactag aattgattat aaatttagcc tcttaaattt tataagttgg    660
gagtcgaggg taactagagt tgctctaaac ggaccttatc ttcaagtgac ctcagtgagc    720
ccgtttaacg gcgtcgacaa gtctaatcta acggacacca accagagaac caccgccagc    780
gccgagccaa gcgacgttga catcttggcg cggcacggca tctccctggc gtctggtccc    840
ctcccgagac ttccgctcca cctcccaccg gtggcggttt ccgagtccgt tccgcctcct    900
ctcacacggc acgaaacctt gacggcaccg gcagcacggg ggattccgtt cccacggctc    960
cttccctttc ccttcctcgc ccgctgctat aaatagccag ccccatcccc agcttcttcc   1020
ccaacctcat cttctcgtgt tgttcggccc aacccgatcg atccccaatt ccctcgtcgt   1080
ctctcgtcgc gagcctcgtc gatccccgct tcaaggtaca gcgatcgatc gatcatcctc   1140
```

gctctctcta ccttctctct cttagggcgt gctggttctg ttcctgtttt tccatggctg 1200
cgaggtacaa tagattggcg attcatggtt agggcctgct agttctgttc ctgttttttt 1260
tttttccatg gctgcgaggc acaatagatc tgatggcgtt atgatggtta acttgtcata 1320
ctcttgcgat ctatggtccc tttaggagtt taggacatcg atttaatttc ggatagttcg 1380
agatctgtga tccatggtta gtaccctagg cagtggggtt agatccgtgc tgttatggtt 1440
cgtagatgga ttctgattgc tcagtaactg ggaatcctgg gatggttcta gctggttcgc 1500
agataagatc gatttcatga tatgctatat cttgtttggt tgccgtggtt ccgttaaatc 1560
tgtctgttat gatcttagtc ttgataaggt tcggtcgtgc tagctacgtc ctgtgcagca 1620
cttaattgtc aggtcataat tttagcatg cctttttttt attggtttgg ttttgtctga 1680
ctgggctgta gatagtttca atctttgtct gactgggctg tagatagttt caatcttcct 1740
gtctgtttat tttattaaat ttggatctgt atgtgtgtca tatatcttca tcttttagat 1800
atatcgatag gtatatatgt tgctgtcgtt ttttactgtt cctttatgag atatattcat 1860
gcttagatac atgaaacaac gtgctgttac agtttaatag ttcttgttta tctaataaac 1920
aaataaggat aggtgctgca gttagtttta ctggtacttt ttttgacatg aacctacggc 1980
ttaataatta gtcttcatca aataaaaagc atatttttta attatttcga tatacttgaa 2040
tgatgtcata tgcagcatct gtgtgaattt ttggccctgt cttcatatga tgtttatttg 2100
cttgggactg tttctttggc tgataactca ccctgttgtt tggtgatcct tctgcaggtg 2160

<210> SEQ ID NO 59
<211> LENGTH: 1045
<212> TYPE: DNA
<213> ORGANISM: Bouteloua gracilis

<400> SEQUENCE: 59
gtacagcgat cgatcgatca tcctcgctct ctctaccttc tctctcttag ggcgtgctgg 60
ttctgttcct gtttttccat ggctgcgagg tacaatagat tggcgattca tggttagggc 120
ctgctagttc tgttcctgtt tttttttt ccatggctgc gaggcacaat agatctgatg 180
gcgttatgat ggttaacttg tcatactctt gcgatctatg gtccctttag gagtttagga 240
catcgattta atttcggata gttcgagatc tgtgatccat ggttagtacc ctaggcagtg 300
gggttagatc cgtgctgtta tggttcgtag atggattctg attgctcagt aactgggaat 360
cctgggatgg ttctagctgg ttcgcagata agatcgattt catgatatgc tatatcttgt 420
ttggttgccg tggttccgtt aaatctgtct gttatgatct tagtcttgat aaggttcggt 480
cgtgctagct acgtcctgtg cagcacttaa ttgtcaggtc ataattttta gcatgccttt 540
tttttattgg tttggttttg tctgactggg ctgtagatag tttcaatctt tgtctgactg 600
ggctgtagat agtttcaatc ttcctgtctg tttattttat taaatttgga tctgtatgtg 660
tgtcatatat cttcatcttt tagatatatc gataggtata tatgttgctg tcgtttttta 720
ctgttccttt atgagatata ttcatgctta gatacatgaa acaacgtgct gttacagttt 780
aatagttctt gtttatctaa taaacaaata aggataggtg ctgcagttag ttttactggt 840
actttttttg acatgaacct acggcttaat aattagtctt catcaaataa aaagcatatt 900
ttttaattat ttcgatatac ttgaatgatg tcatatgcag catctgtgtg aatttttggc 960
cctgtcttca tatgatgttt atttgcttgg gactgtttct ttggctgata actcaccctg 1020
ttgtttggtg atccttctgc aggtg 1045

<210> SEQ ID NO 60
<211> LENGTH: 1885
<212> TYPE: DNA
<213> ORGANISM: Bouteloua gracilis

<400> SEQUENCE: 60
caacgagaac gtcgcttacc acttaaagca taacaccgag aaatcccgta acaaatccag 60
taaaatacga gcacccgtac caagttgaat atttgaaccc gagtgggtag attccaccgc 120
aaaggaccta accagatcat ttcgcaaaca ggaactaaaa tcggtagaga gcccagacaa 180 aaacctttc taagagcaac tccagtgaaa gcccctactt taggtataaa atgcaacact 240
agtggagctt ctaaataaac ttctattttt catgccctcc taaaatttac tcctaaaacc 300
ctagctatag gagcctccta tccatcctct attttattcc actagaattg attataaatt 360
tagcctctta aattttataa gttgggagtc gagggtaact agagttgctc taaacggacc 420
ttatcttcaa gtgacctcag tgagcccgtt taacggcgtc gacaagtcta atctaacgga 480
caccaaccag agaaccaccg ccagcgccga gccaagcgac gttgacatct tggcgcggca 540
cggcatctcc ctggcgtctg gtcccctccc gagacttccg ctccacctcc caccggtggc 600
ggtttccgag tccgttccgc ctcctctcac acggcacgaa accttgacgg caccggcagc 660
acgggggatt ccgttcccac ggctccttcc ctttcccttc ctcgcccgct gctataaata 720
gccagcccca tccccagctt cttccccaac ctcatcttct cgtgttgttc ggcccaaccc 780
gatcgatccc caattccctc gtcgtctctc gtcgcgagcc tcgtcgatcc ccgcttcaag 840
gtacagcgat cgatcgatca tcctcgctct ctctaccttc tctctcttag ggcgtgctgg 900
ttctgttcct gtttttccat ggctgcgagg tacaatagat tggcgattca tggttagggc 960
ctgctagttc tgttcctgtt ttttttttt ccatggctgc gaggcacaat agatctgatg 1020
gcgttatgat ggttaacttg tcatactctt gcgatctatg gtccctttag gagtttagga 1080
catcgattta atttcggata gttcgagatc tgtgatccat ggttagtacc ctaggcagtg 1140
gggttagatc cgtgctgtta tggttcgtag atggattctg attgctcagt aactgggaat 1200
cctgggatgg ttctagctgg ttcgcagata agatcgattt catgatatgc tatatcttgt 1260
ttggttgccg tggttccgtt aaatctgtct gttatgatct tagtcttgat aaggttcggt 1320
cgtgctagct acgtcctgtg cagcacttaa ttgtcaggtc ataattttta gcatgccttt 1380
tttttattgg tttggttttg tctgactggg ctgtagatag tttcaatctt tgtctgactg 1440
ggctgtagat agtttcaatc ttcctgtctg tttattttat taaatttgga tctgtatgtg 1500
tgtcatatat cttcatcttt tagatatatc gataggtata tatgttgctg tcgtttttta 1560
ctgttccttt atgagatata ttcatgctta gatacatgaa acaacgtgct gttacagttt 1620
aatagttctt gtttatctaa taaacaaata aggataggtg ctgcagttag ttttactggt 1680 acttttttg acatgaacct acggcttaat aattagtctt catcaaataa aaagcatatt 1740
ttttaattat ttcgatatac ttgaatgatg tcatatgcag catctgtgtg aatttttggc 1800
cctgtcttca tatgatgttt atttgcttgg gactgtttct ttggctgata actcaccctg 1860
ttgtttggtg atccttctgc aggtg 1885

<210> SEQ ID NO 61
<211> LENGTH: 749
<212> TYPE: DNA
<213> ORGANISM: Bouteloua gracilis

<400> SEQUENCE: 61

-continued caacgagaac gtcgcttacc acttaaagca taacaccgag aaatcccgta acaaatccag 60
taaaatacga gcacccgtac caagttgaat atttgaaccc gagtgggtag attccaccgc 120
aaaggaccta accagatcat ttcgcaaaca ggaactaaaa tcggtagaga gcccagacaa 180
aaaccttttc taagagcaac tccagtgaaa gcccctactt taggtataaa atgcaacact 240
agtggagctt ctaaataaac ttctattttt catgccctcc taaaatttac tcctaaaacc 300
ctagctatag gagcctccta tccatcctct attttattcc actagaattg attataaatt 360
tagcctctta aattttataa gttgggagtc gagggtaact agagttgctc taaacggacc 420
ttatcttcaa gtgacctcag tgagcccgtt taacggcgtc gacaagtcta atctaacgga 480
caccaaccag agaaccaccg ccagcgccga gccaagcgac gttgacatct tggcgcggca 540
cggcatctcc ctggcgtctg gtcccctccc gagacttccg ctccacctcc caccggtggc 600
ggtttccgag tccgttccgc ctcctctcac acggcacgaa accttgacgg caccggcagc 660
acgggggatt ccgttcccac ggctccttcc ctttcccttc ctcgcccgct gctataaata 720
gccagcccca tccccagctt cttccccaa 749

<210> SEQ ID NO 62
<211> LENGTH: 6813
<212> TYPE: DNA
<213> ORGANISM: Miscanthus sinesis

<400> SEQUENCE: 62
agcagactcg cattatcgat gggggaaatg aaattcagcg tttgacgtgg atgcaacaac 60
tgcactgcac aggatatctt agccgttgtg tcgaagtttg ctttgctaac gttttgagaa 120
aaccagcttt gaccaacacg agacgagcgc cttacgtttg gcacaatgta atgtagcccg 180
gcacggcaag ttagactagt atattgtgtt agccggcctc tttacgtttg gcacagttta 240
attgaatccg gcatggcaag ttagactgga gtgtgagccg gtcattgcaa agttattatg 300
acatatatat aagagcacaa gtgtataata agataatgta agcaaggcag caagctatat 360
gaattgtcac gttatattta tgttgagatg ttgagatgaa gaagagaaaa taaacagcct 420
ataaattcat agcgagtgat agacgggcac aaggcctcct atttcttaaa ccgaattttg 480
taagaacaaa aaaaaggact tataggagaa tgggatagac catatatcaa cgggaaaggt 540
acacgttgct cgagtgtttt aggcgttctg ctcactcgat cctgtagctg tccgatctgc 600
ggcgtcaaca cggcgcgcaa caagcggtgg cgggcccctc ggtagccgcg gtcggaccgg 660
acgatggcct atggcgaccc gcggcctggg cgtggcctgt gcgtgcatgc gccataggtc 720
ccggtgcatg gtgcaggcgg caggtgcatg tgcatggagt aggctttggt gctggtgcag 780
gctttggtca ggtgcaggag gggtaggttg cgcaggtgag aggtgaggtg catgctgacc 840
cgtcacatca ccttactcct agcccctaag tcttgcatgt atgcagattt attcttttag 900
cagcgacaga ttcagcagcg agagaccggc taccgtagca ttttcatttt tatttgataa 960
ttagtattta attatggact aattaggttc aaaatattcg tctcgcgatt tccaaccaaa 1020
ctgtgcaatt agttttttc gtctacattt aatgctctat acacgtatca caagattcaa 1080
cgtgatggct actgtagcac tttttgaaaa aactttttgc aactaaacaa ggcctgaggt 1140
atcgtttaaa tttaggtaca aaaaatataa gggtgtcaca tcgaatgtta cacgagatat 1200
catatgtgag tgttcggata gtaataataa aataaattac acaagtcctt agtaatccac 1260
gagacgaatt tattgagtct aattaatcag tcattagcac atggtgcatt catgcatctg 1320

-continued

```
catattattt tgtgttgctt ggttgaaagt tggatttcaa attgagttga atttgcattt   1380
tgaaattgct ttggaaaaat tagaaaaaaa gaaaaaaaat gaatttccct ccctcctttc   1440
tcatttccct gctttcggcc cctctgtgta gaactattcg agttctcagg tcgagtgctc   1500
gaatcatcta gcttctcttt tttgaggaga gccagagagc cagattcaga atagccagcc   1560
tcctttttag gagagagctc atcccctttt atagttgaag gcagcgacga agccagcggg   1620
gggctacccg tgctccagcc tccctacggc catgatttac atggaacccg ggcttagctc   1680
gggctaccgc catgaggagg aagaagaaga taaggagggg ctagaggaag aagaagagga   1740
agctagccct ggcttcgtcg attcctggct tcgtcgctgg ttgaagggga tgggctctta   1800
caagtcagag aaagagagag aatgtatacg tgtgctatct agtcttgttg cccacgctgt   1860
caggtacgag acggttgtcg gcgcccacaa tactgtttat gtccagatgc atgtggcagg   1920
ctctaccgtg ttcgcctgtt atggcaaatg tcggcgcata caatactatt tgggttctga   1980
cacgcctgaa aggttgcata gtgcctatct ggcatggcct ggtggcaccg tccggcatgt   2040
gcgcaggata tgccagggta cggtccttgg tattacggtt tgacttgagc gccttacctt   2100
atctgctccg cctgatcccc gggctcttac cgagcgggcg tccccggtcg gtcgttccca   2160
gtcggccccg actgtgtcgg tcggggaaga gctgcaagca gaggtccggc gtatccccga   2220
tcgaaaaagg aagtcggagt cagactatgt ctccacctta gccaggcctt ccggtcgggg   2280
atcggatcat tctcccggcc tgtcattagg tatctgggtc ggcccgagag gtgtgcgttg   2340
tcgctacgct gtctgctggg ccgagtttct gttgggaagc gggtccattg gggaccccgg   2400
gtttatgaac ccgacacgtg gtcactatgc tgcatactcc ctatacagcc gctgaccagt   2460
acgctggttc accgcgtcgc ccgcgcggga cggaatggga tgtcacgacc cgctgaacgc   2520
cggggcatgg catcagcggc gaacaggcac ccggcgtgga gctgtccgtg tcaccatcta   2580
cagtgttgac gggacccgca taaaaggaga aaaaaggccc gacggtcctg gaagccttcc   2640
tctccttagc tcttctccct ctttctctct gtgtaacctg ctcttcccct tcgtctataa   2700
aaagggaagt aggacgtccc aggaagagaa gggcggttca ccactctaca tggctataga   2760
cataaaaaca cacgccttgg gagcacactc acatcagaga cttgggacct atccctctct   2820
cgctcgtttg taacccctac tacaaacttt tagtgctagt aacacgagca gcagcgacga   2880
actagacgta aggactttct gcccgaacca gtataaacat cgtgtcatct aagcacacca   2940
tacgagccag acgcgcaata ctagaaattt actagtcggt aactcgaaac accgacatct   3000
agctaatctt tttgttttat ttggtttccc tttgaaatct tctaatttag ctttcataga   3060
aataatctag gtattttta ttttatatgt tctatctgtt tgcattaatt ttgatcattt   3120
gatctgaatg ctgtggtcac gagaatcgag tgtttcatgg ccttaaaaca ctcgattatg   3180
ccatctgacc cgttttcaac cattctagtg tttctgagct atatcaatgg tgcagcatgt   3240
tagtatacat atctaactat tactccgtat atgagtgagt tgttaaattt attccaggtg   3300
aaatggcatt aacgatagcc aataggcggc taaattaata gccatactct aacagctcta   3360
aaaaacatat attcatcgag gcacctttat gcaaccacat agtcaacttc aacgtcgctt   3420
gcgtgcgttc tcaagttttc tttcttgcaa attacatttt ttttaaaaaa aagtataatt   3480
tgtatcgtgc gattttttct ctctaggtgt gcgtgactgt gggagtaaca attttgaatc   3540
tcaagaagga aataaaagaa taatactgct gcctactttg aggatttcag tatttttctc   3600
taaaatgttt tggtgtgata tctaaaccgt ctttaaagcc aattgctcaa gattcattca   3660
acaattgaaa cgtctcacat gactaaatga tataaggttg ctaaggtctt tcttgataag   3720
```

-continued

```
cttttttatg aatttcatct aaattttcga gtgaaactat taaatactaa ggttgctaag   3780
tgtcattctc gctcgagaag tctaacgctt taaactttaa ccaaatatat acaagaaaat   3840
attaatattt atagtacata attagtatca ttagatagat cgttgaatct attttcataa   3900
caaacttatt tgaagaaaca aatgttgttc atatatttct atatacgaat accatagcga   3960
cacttatttt agaatgtagg gagtactccc tttgtgccgc tttgagtgtc gctttggcag   4020
ctagtaccta tgtccacctt cacagcttgt gcctagtacc tagactcttt ctctgtccac   4080
attcatttaa tctctgttgt accttgttcg gagataaaac gactctgata aagggacgag   4140
gaagtagtat gttagaggag tgaagtctac tccctttgcc gcaaaaaggt aatcctaagt   4200
gtgaattgta ttcttttttg accaaaggaa tatacaacaa gaatgatgtc atcatcatgc   4260
ttcgatcctt ttttttggta aagcttgagc ttctgtaaaa atagagaaat catgggaaaa   4320
atcacgtttt ggtggttttg atttctagcc tccacaataa ctttggtttt actatttttt   4380
gtttgatttt agtttcagaa gtccactttt gtacgtgctc gtagagccta aacaaaaggc   4440
tttccaaaac gaccttatct tcgagtgttg taaaaaaaat gagcccgttt aacggcgtcg   4500
acaagtctaa cggacaccaa ccagcgaacc accagcgccg agccaagcga agcagactgc   4560
agacggcacg gccgagacgt tgacaccttg gcgcggcaac ggcatctctc tggccccctc   4620
tcgagagttc cgctccacct ccgcatccac ctccacctcc acctccaccg gtggcggttt   4680
ccaagtccgt cccgttccgc cacctgctcc tctcacacgg cacgaaaccg tcacggcacc   4740
ggcagcacag cacgggggat tcctttccca ccgctccgtc cctttctctt cctcgcccgc   4800
ccgttataaa tagccagccc catccctcgt ctctcgtgtt gttcggagcg cacacacaac   4860
ccgatcccca atcaatcgat ccccgcttca aggtacggcg atcctcctcc ctctctctct   4920
accttctctt ctctacacta gatcggcggt ccatggttag ggcctgctag ttccgttcct   4980
gtttttccat ggctgcgagg tacaatagat ctgatggcgt tatgatggtt aacttgtcat   5040
gcttttgcga tttatagtcc ctttagatag ttcgagatcg gtgatccatg gttagtaccc   5100
taggctgtgg agtcgggtta gatccgcgct gttagggttc gtatatggag gcgagctgtt   5160
ctgattgtta acttgctggg aatcctggga tggttctagc tgttccgcag atgagatcga   5220
tttcatgatc tgctgtatct atccgtggta tgatgttagc ctttgatatg gttcgatcgt   5280
gctagctacg tcctgtgcac ttaattgtca ggtcataatt tttactatac tttttttttg   5340
gtttggtttg gtttcgtctg atttggctgt cgttctagat cagagtagaa actgtttcaa   5400
actacctgtt ggatttatta aggtagcgtt tggttcctgg tatcgaatca tacacgcacc   5460
agtgcatctt ggatagccag ctggggccca cctgtccaac cgtttggttg ccggatcgaa   5520
cgagtccatt caagaccgaa ccatgcagag caatcgaata ttctcttgtg acgctgtatc   5580
atccagttcg gcaaaaaaca ccgaatgccg ccatacagga caccgtactg agcgtctgca   5640
actctgcatc ccgctcactg ctcacatctc cgcttgccgc ctcacccatc cgactcagac   5700
cagagccaca cggattactg ctgctggtgt gtgtattaac aaaagatcca tttgaccgga   5760
gcacatgcag cttggatgga aaaaatttat tatattcgtc agtgctgcat atgtactcat   5820
acttgcatga tggttttatt tattcgacct catcagtcct ggcactatgg aaagtcattg   5880
tagtatagat tttttaatat aatataaatc attggtgact tatcttgctt aattttattt   5940
tcttattatg aaatatcgtt gcattcataa tagcaaattt gtgcaaatat atagaatcta   6000
cgtgaaattc ttggttggac caatacaaca aacccctcaa acattctctt gtactgaacc   6060
```

```
ataccattcc gtacaaccat ccaaacaaaa atcatgtatc atcatgtaca tgtaaccaaa   6120
caattaacac gcaccatcct attcagactt gtctcatcca taatctatcc atccaggatg   6180
atccatccca ttcatctata tacacccaat caaacgctac ctaaaatttg gatctgtatg   6240
tgtcacatat atcttaataa gatggatgga aatatctctt tatcttttag atatggatag   6300
gtatatatgt tgctgtgggt ttgttagtta tatatatacg tgcttacata cgtgaagaaa   6360
cctgctgcta cagtttaata attcttgttc atctcaacaa ataacgatag gcgtatatgt   6420
tgctgtgttt tttactggta ctttgttaga tatatacatg cttacataca tgaagaacac   6480
atgctacagt tcaaaaattc ttgttcatct cataaacaaa aaggaggtgt atatgttgct   6540
gtgggtttta ctggtacttt attagatata tacatgctta catagatgaa gcaacatgct   6600
gctatggtgt ttaataatta ttgtttatct aataaacaaa catgcttttt aattatcttg   6660
atatgtttgg atgatggcat atgcagcagc tatgtgtgga ttttaaatac ccagcatcat   6720
gagcatgcat gaccctgcct tagtatgcag ttatttgctt gagactgttt cttttgttga   6780
tactcatcct ttagttcggt cactcttctg cag                               6813
```

```
<210> SEQ ID NO 63
<211> LENGTH: 5359
<212> TYPE: DNA
<213> ORGANISM: Miscanthus sinesis

<400> SEQUENCE: 63

agcagactcg cattatcgat gggggaaatg aaattcagcg tttgacgtgg atgcaacaac     60
tgcactgcac aggatatctt agccgttgtg tcgaagtttg ctttgctaac gttttgagaa    120
aaccagcttt gaccaacacg agacgagcgc cttacgtttg gcacaatgta atgtagcccg    180
gcacggcaag ttagactagt atattgtgtt agccggcctc tttacgtttg gcacagttta    240
attgaatccg gcatggcaag ttagactgga gtgtgagccg gtcattgcaa agttattatg    300
acatatatat aagagcacaa gtgtataata agataatgta agcaaggcag caagctatat    360
gaattgtcac gttatattta tgttgagatg ttgagatgaa gaagagaaaa taaacagcct    420
ataaattcat agcgagtgat agacgggcac aaggcctcct atttcttaaa ccgaattttg    480
taagaacaaa aaaaaggact tataggagaa tgggatagac catatatcaa cgggaaaggt    540
acacgttgct cgagtgtttt aggcgttctg ctcactcgat cctgtagctg tccgatctgc    600
ggcgtcaaca cggcgcgcaa caagcggtgg cgggcccctc ggtagccgcg gtcggaccgg    660
acgatggcct atggcgaccc gcggcctggg cgtggcctgt gcgtgcatgc gccataggtc    720
ccggtgcatg gtgcaggcgg caggtgcatg tgcatggagt aggctttggt gctggtgcag    780
gctttggtca ggtgcaggag gggtaggttg cgcaggtgag aggtgaggtg catgctgacc    840
cgtcacatca ccttactcct agcccctaag tcttgcatgt atgcagattt attcttttag    900
cagcgacaga ttcagcagcg agagaccggc taccgtagca ttttcatttt tatttgataa    960
ttagtattta attatggact aattaggttc aaaatattcg tctcgcgatt tccaaccaaa   1020
ctgtgcaatt agtttttttc gtctacattt aatgctctat acacgtatca caagattcaa   1080
cgtgatggct actgtagcac tttttgaaaa aactttttgc aactaaacaa ggcctgaggt   1140
atcgtttaaa tttaggtaca aaaaatataa gggtgtcaca tcgaatgtta cacgagatat   1200
catatgtgag tgttcggata gtaataataa aataaattac acaagtcctt agtaatccac   1260
gagacgaatt tattgagtct aattaatcag tcattagcac atggtgcatt catgcatctg   1320
catattattt tgtgttgctt ggttgaaagt tggatttcaa attgagttga atttgcattt   1380
```

tgaaattgct ttggaaaaat tagaaaaaaa gaaaaaaaat gaatttccct ccctcctttc 1440
tcatttccct gctttcggcc cctctgtgta gaactattcg agttctcagg tcgagtgctc 1500
gaatcatcta gcttctcttt tttgaggaga gccagagagc cagattcaga atagccagcc 1560
tcctttttag gagagagctc atcccctttt atagttgaag gcagcgacga agccagcggg 1620
gggctacccg tgctccagcc tccctacggc catgatttac atggaacccg ggcttagctc 1680
gggctaccgc catgaggagg aagaagaaga taaggagggg ctagaggaag aagaagagga 1740
agctagccct ggcttcgtcg attcctggct tcgtcgctgg ttgaagggga tgggctctta 1800
caagtcagag aaagagagag aatgtatacg tgtgctatct agtcttgttg cccacgctgt 1860
caggtacgag acggttgtcg gcgcccacaa tactgtttat gtccagatgc atgtggcagg 1920
ctctaccgtg ttcgcctgtt atggcaaatg tcggcgcata caatactatt tgggttctga 1980
cacgcctgaa aggttgcata gtgcctatct ggcatggcct ggtggcaccg tccggcatgt 2040
gcgcaggata tgccagggta cggtccttgg tattacggtt tgacttgagc gccttacctt 2100
atctgctccg cctgatcccc gggctcttac cgagcgggcg tccccggtcg gtcgttccca 2160
gtcggccccg actgtgtcgg tcggggaaga gctgcaagca gaggtccggc gtatccccga 2220
tcgaaaaagg aagtcggagt cagactatgt ctccacctta gccaggcctt ccggtcgggg 2280
atcggatcat tctcccggcc tgtcattagg tatctgggtc ggcccgagag gtgtgcgttg 2340
tcgctacgct gtctgctggg ccgagtttct gttgggaagc gggtccattg gggaccccgg 2400
gtttatgaac ccgacacgtg gtcactatgc tgcatactcc ctatacagcc gctgaccagt 2460
acgctggttc accgcgtcgc ccgcgcggga cggaatggga tgtcacgacc cgctgaacgc 2520
cggggcatgg catcagcggc gaacaggcac ccggcgtgga gctgtccgtg tcaccatcta 2580
cagtgttgac gggacccgca taaaaggaga aaaaaggccc gacggtcctg gaagccttcc 2640
tctccttagc tcttctccct ctttctctct gtgtaacctg ctcttcccct tcgtctataa 2700
aaagggaagt aggacgtccc aggaagagaa gggcggttca ccactctaca tggctataga 2760
cataaaaaca cacgccttgg gagcacactc acatcagaga cttgggacct atccctctct 2820
cgctcgtttg taacccctac tacaaacttt tagtgctagt aacacgagca gcagcgacga 2880
actagacgta aggactttct gcccgaacca gtataaacat cgtgtcatct aagcacacca 2940
tacgagccag acgcgcaata ctagaaattt actagtcggt aactcgaaac accgacatct 3000
agctaatctt tttgttttat ttggtttccc tttgaaatct tctaatttag ctttcataga 3060
aataatctag gtatttttta ttttatatgt tctatctgtt tgcattaatt ttgatcattt 3120
gatctgaatg ctgtggtcac gagaatcgag tgtttcatgg ccttaaaaca ctcgattatg 3180
ccatctgacc cgttttcaac cattctagtg tttctgagct atatcaatgg tgcagcatgt 3240
tagtatacat atctaactat tactccgtat atgagtgagt tgttaaattt attccaggtg 3300
aaatggcatt aacgatagcc aataggcggc taaattaata gccatactct aacagctcta 3360
aaaaacatat attcatcgag gcacctttat gcaaccacat agtcaacttc aacgtcgctt 3420
gcgtgcgttc tcaagttttc tttcttgcaa attacatttt ttttaaaaaa aagtataatt 3480
tgtatcgtgc gatttttttct ctctaggtgt gcgtgactgt gggagtaaca attttgaatc 3540
tcaagaagga aataaaagaa taatactgct gcctactttg aggatttcag tattttttctc 3600
taaaatgttt tggtgtgata tctaaaccgt ctttaaagcc aattgctcaa gattcattca 3660
acaattgaaa cgtctcacat gactaaatga tataaggttg ctaaggtctt tcttgataag 3720
cttttttatg aatttcatct aaattttcga gtgaaactat taaatactaa ggttgctaag 3780
tgtcattctc gctcgagaag tctaacgctt taaactttaa ccaaatatat acaagaaaat 3840
attaatattt atagtacata attagtatca ttagatagat cgttgaatct attttcataa 3900
caaacttatt tgaagaaaca aatgttgttc atatatttct atatacgaat accatagcga 3960
cacttatttt agaatgtagg gagtactccc tttgtgccgc tttgagtgtc gctttggcag 4020
ctagtaccta tgtccacctt cacagcttgt gcctagtacc tagactcttt ctctgtccac 4080
attcatttaa tctctgttgt accttgttcg gagataaaac gactctgata aagggacgag 4140
gaagtagtat gttagaggag tgaagtctac tccctttgcc gcaaaaaggt aatcctaagt 4200
gtgaattgta ttcttttttg accaaaggaa tatacaacaa gaatgatgtc atcatcatgc 4260
ttcgatcctt ttttttggta aagcttgagc ttctgtaaaa atagagaaat catgggaaaa 4320
atcacgtttt ggtggttttg atttctagcc tccacaataa ctttggtttt actatttttt 4380
gtttgatttt agtttcagaa gtccactttt gtacgtgctc gtagagccta aacaaaaggc 4440
tttccaaaac gaccttatct tcgagtgttg taaaaaaaat gagcccgttt aacggcgtcg 4500
acaagtctaa cggacaccaa ccagcgaacc accagcgccg agccaagcga agcagactgc 4560
agacggcacg gccgagacgt tgacaccttg gcgcggcaac ggcatctctc tggccccctc 4620
tcgagagttc cgctccacct ccgcatccac ctccacctcc acctccaccg gtggcggttt 4680
ccaagtccgt cccgttccgc cacctgctcc tctcacacgg cacgaaaccg tcacggcacc 4740
ggcagcacag cacgggggat tcctttccca ccgctccgtc cctttctctt cctcgcccgc 4800
ccgttataaa tagccagccc catccctcgt ctctcgtgtt gttcggagcg cacacacaac 4860
ccgatcccca atcaatcgat ccccgcttca aggtacggcg atcctcctcc ctctctctct 4920
accttctctt ctctacacta gatcggcggt ccatggttag ggcctgctag ttccgttcct 4980
gtttttccat ggctgcgagg tacaatagat ctgatggcgt tatgatggtt aacttgtcat 5040
gcttttgcga tttatagtcc ctttagatag ttcgagatcg gtgatccatg gttagtaccc 5100
taggctgtgg agtcgggtta gatccgcgct gttagggttc gtatatggag gcgagctgtt 5160
ctgattgtta acttgctggg aatcctggga tggttctagc tgttccgcag atgagatcga 5220
tttcatgatc tgctgtatct atccgtggta tgatgttagc ctttgatatg gttcgatcgt 5280
gctagctacg tcctgtgcac ttaattgtca ggtcataatt tttactatac ttttttttg 5340 gtttggtttg gtttcgtct 5359

<210> SEQ ID NO 64
<211> LENGTH: 63
<212> TYPE: DNA
<213> ORGANISM: Miscanthus sinesis

<400> SEQUENCE: 64
gatttggctg tcgttctaga tcagagtaga aactgtttca aactacctgt tggatttatt 60
aag 63

<210> SEQ ID NO 65
<211> LENGTH: 1391
<212> TYPE: DNA
<213> ORGANISM: Miscanthus sinesis

<400> SEQUENCE: 65
gtagcgtttg gttcctggta tcgaatcata cacgcaccag tgcatcttgg atagccagct 60
ggggcccacc tgtccaaccg tttggttgcc ggatcgaacg agtccattca agaccgaacc 120
atgcagagca atcgaatatt ctcttgtgac gctgtatcat ccagttcggc aaaaaacacc 180
gaatgccgcc atacaggaca ccgtactgag cgtctgcaac tctgcatccc gctcactgct 240
cacatctccg cttgccgcct cacccatccg actcagacca gagccacacg gattactgct 300
gctggtgtgt gtattaacaa aagatccatt tgaccggagc acatgcagct tggatggaaa 360
aaatttatta tattcgtcag tgctgcatat gtactcatac ttgcatgatg gttttattta 420
ttcgacctca tcagtcctgg cactatggaa agtcattgta gtatagattt tttaatataa 480
tataaatcat tggtgactta tcttgcttaa ttttattttc ttattatgaa atatcgttgc 540
attcataata gcaaatttgt gcaaatatat agaatctacg tgaaattctt ggttggacca 600
atacaacaaa cccctcaaac attctcttgt actgaaccat accattccgt acaaccatcc 660
aaacaaaaat catgtatcat catgtacatg taaccaaaca attaacacgc accatcctat 720
tcagacttgt ctcatccata atctatccat ccaggatgat ccatcccatt catctatata 780
cacccaatca aacgctacct aaaatttgga tctgtatgtg tcacatatat cttaataaga 840
tggatggaaa tatctcttta tcttttagat atggataggt atatatgttg ctgtgggttt 900
gttagttata tatatacgtg cttacatacg tgaagaaacc tgctgctaca gtttaataat 960
tcttgttcat ctcaacaaat aacgataggc gtatatgttg ctgtgttttt tactggtact 1020
ttgttagata tatacatgct tacatacatg aagaacacat gctacagttc aaaaattctt 1080
gttcatctca taaacaaaaa ggaggtgtat atgttgctgt gggttttact ggtactttat 1140
tagatatata catgcttaca tagatgaagc aacatgctgc tatggtgttt aataattatt 1200
gtttatctaa taaacaaaca tgctttttaa ttatcttgat atgtttggat gatggcatat 1260
gcagcagcta tgtgtggatt ttaaataccc agcatcatga gcatgcatga ccctgcctta 1320
gtatgcagtt atttgcttga gactgtttct tttgttgata ctcatccttt agttcggtca 1380
ctcttctgca g 1391

<210> SEQ ID NO 66
<211> LENGTH: 4402
<212> TYPE: DNA
<213> ORGANISM: Miscanthus sinesis

<400> SEQUENCE: 66
cacgtggtca ctatgctgca tactccctat acagccgctg accagtacgc tggttcaccg 60
cgtcgcccgc gcgggacgga atgggatgtc acgacccgct gaacgccggg gcatggcatc 120
agcggcgaac aggcacccgg cgtggagctg tccgtgtcac catctacagt gttgacggga 180
cccgcataaa aggagaaaaa aggcccgacg gtcctggaag ccttcctctc cttagctctt 240
ctccctcttt ctctctgtgt aacctgctct tcccccttcgt ctataaaaag ggaagtagga 300
cgtcccagga agagaagggc ggttcaccac tctacatggc tatagacata aaaacacacg 360
ccttgggagc acactcacat cagagacttg ggacctatcc ctctctcgct cgtttgtaac 420
ccctactaca aacttttagt gctagtaaca cgagcagcag cgacgaacta gacgtaagga 480
ctttctgccc gaaccagtat aaacatcgtg tcatctaagc acaccatacg agccagacgc 540
gcaatactag aaatttacta gtcggtaact cgaaacaccg acatctagct aatctttttg 600
ttttatttgg tttccctttg aaatcttcta atttagcttt catagaaata atctaggtat 660
tttttatttt atatgttcta tctgtttgca ttaattttga tcatttgatc tgaatgctgt 720
ggtcacgaga atcgagtgtt tcatggcctt aaaacactcg attatgccat ctgacccgtt 780

-continued

```
ttcaaccatt ctagtgtttc tgagctatat caatggtgca gcatgttagt atacatatct    840
aactattact ccgtatatga gtgagttgtt aaatttattc caggtgaaat ggcattaacg    900
atagccaata ggcggctaaa ttaatagcca tactctaaca gctctaaaaa acatatattc    960
atcgaggcac ctttatgcaa ccacatagtc aacttcaacg tcgcttgcgt gcgttctcaa   1020
gttttctttc ttgcaaatta catttttttt aaaaaaaagt ataatttgta tcgtgcgatt   1080
ttttctctct aggtgtgcgt gactgtggga gtaacaattt tgaatctcaa gaaggaaata   1140
aaagaataat actgctgcct actttgagga tttcagtatt tttctctaaa atgttttggt   1200
gtgatatcta aaccgtcttt aaagccaatt gctcaagatt cattcaacaa ttgaaacgtc   1260
tcacatgact aaatgatata aggttgctaa ggtctttctt gataagcttt tttatgaatt   1320
tcatctaaat tttcgagtga aactattaaa tactaaggtt gctaagtgtc attctcgctc   1380
gagaagtcta acgctttaaa ctttaaccaa atatatacaa gaaaatatta atatttatag   1440
tacataatta gtatcattag atagatcgtt gaatctattt tcataacaaa cttatttgaa   1500
gaaacaaatg ttgttcatat atttctatat acgaatacca tagcgacact tattttagaa   1560
tgtagggagt actccctttg tgccgctttg agtgtcgctt tggcagctag tacctatgtc   1620
caccttcaca gcttgtgcct agtacctaga ctctttctct gtccacattc atttaatctc   1680
tgttgtacct tgttcggaga taaaacgact ctgataaagg gacgaggaag tagtatgtta   1740
gaggagtgaa gtctactccc tttgccgcaa aaaggtaatc ctaagtgtga attgtattct   1800
tttttgacca aaggaatata caacaagaat gatgtcatca tcatgcttcg atcctttttt   1860
ttggtaaagc ttgagcttct gtaaaaatag agaaatcatg ggaaaaatca cgttttggtg   1920
gttttgattt ctagcctcca caataacttt ggttttacta tttttgtttt gattttagtt   1980
tcagaagtcc acttttgtac gtgctcgtag agcctaaaca aaaggctttc caaaacgacc   2040
ttatcttcga gtgttgtaaa aaaaaatgagc ccgtttaacg gcgtcgacaa gtctaacgga   2100
caccaaccag cgaaccacca gcgccgagcc aagcgaagca gactgcagac ggcacggccg   2160
agacgttgac accttggcgc ggcaacggca tctctctggc cccctctcga gagttccgct   2220
ccacctccgc atccacctcc acctccacct ccaccggtgg cggtttccaa gtccgtcccg   2280
ttccgccacc tgctcctctc acacggcacg aaaccgtcac ggcaccggca gcacagcacg   2340
ggggattcct ttcccaccgc tccgtccctt tctcttcctc gcccgcccgt tataaatagc   2400
cagccccatc cctcgtctct cgtgttgttc ggagcgcaca cacaacccga tccccaatca   2460
atcgatcccc gcttcaaggt acggcgatcc tcctccctct ctctctacct tctcttctct   2520
acactagatc ggcggtccat ggttagggcc tgctagttcc gttcctgttt ttccatggct   2580
gcgaggtaca atagatctga tggcgttatg atggttaact tgtcatgctt ttgcgattta   2640
tagtcccttt agatagttcg agatcggtga tccatggtta gtaccctagg ctgtggagtc   2700
gggttagatc cgcgctgtta gggttcgtat atggaggcga gctgttctga ttgttaactt   2760
gctgggaatc ctgggatggt tctagctgtt ccgcagatga gatcgatttc atgatctgct   2820
gtatctatcc gtggtatgat gttagccttt gatatggttc gatcgtgcta gctacgtcct   2880
gtgcacttaa ttgtcaggtc ataattttta ctatactttt tttttggttt ggtttggttt   2940
cgtctgattt ggctgtcgtt ctagatcaga gtagaaactg tttcaaacta cctgttggat   3000
ttattaaggt agcgtttggt tcctggtatc gaatcataca cgcaccagtg catcttggat   3060
agccagctgg ggcccacctg tccaaccgtt tggttgccgg atcgaacgag tccattcaag   3120
accgaaccat gcagagcaat cgaatattct cttgtgacgc tgtatcatcc agttcggcaa   3180
```

aaaacaccga atgccgccat acaggacacc gtactgagcg tctgcaactc tgcatcccgc 3240
tcactgctca catctccgct tgccgcctca cccatccgac tcagaccaga gccacacgga 3300
ttactgctgc tggtgtgtgt attaacaaaa gatccatttg accggagcac atgcagcttg 3360
gatggaaaaa atttattata ttcgtcagtg ctgcatatgt actcatactt gcatgatggt 3420
tttatttatt cgacctcatc agtcctggca ctatggaaag tcattgtagt atagattttt 3480
taatataata taaatcattg gtgacttatc ttgcttaatt ttattttctt attatgaaat 3540
atcgttgcat tcataatagc aaatttgtgc aaatatatag aatctacgtg aaattcttgg 3600
ttggaccaat acaacaaacc cctcaaacat tctcttgtac tgaaccatac cattccgtac 3660
aaccatccaa acaaaaatca tgtatcatca tgtacatgta accaaacaat taacacgcac 3720
catcctattc agacttgtct catccataat ctatccatcc aggatgatcc atcccattca 3780
tctatataca cccaatcaaa cgctacctaa aatttggatc tgtatgtgtc acatatatct 3840
taataagatg gatggaaata tctctttatc ttttagatat ggataggtat atatgttgct 3900
gtgggtttgt tagttatata tatacgtgct tacatacgtg aagaaacctg ctgctacagt 3960
ttaataattc ttgttcatct caacaaataa cgataggcgt atatgttgct gtgtttttta 4020
ctggtacttt gttagatata tacatgctta catacatgaa gaacacatgc tacagttcaa 4080
aaattcttgt tcatctcata aacaaaaagg aggtgtatat gttgctgtgg gttttactgg 4140
tactttatta gatatataca tgcttacata gatgaagcaa catgctgcta tggtgtttaa 4200
taattattgt ttatctaata aacaaacatg ctttttaatt atcttgatat gtttggatga 4260
tggcatatgc agcagctatg tgtggatttt aaatacccag catcatgagc atgcatgacc 4320
ctgccttagt atgcagttat ttgcttgaga ctgtttcttt tgttgatact catcctttag 4380
ttcggtcact cttctgcagg tg 4402

<210> SEQ ID NO 67
<211> LENGTH: 2423
<212> TYPE: DNA
<213> ORGANISM: Miscanthus sinesis

<400> SEQUENCE: 67
cacgtggtca ctatgctgca tactccctat acagccgctg accagtacgc tggttcaccg 60
cgtcgcccgc gcgggacgga atgggatgtc acgacccgct gaacgccggg gcatggcatc 120
agcggcgaac aggcacccgg cgtggagctg tccgtgtcac catctacagt gttgacggga 180
cccgcataaa aggagaaaaa aggcccgacg gtcctggaag ccttcctctc cttagctctt 240
ctccctcttt ctctctgtgt aacctgctct tccccttcgt ctataaaaag ggaagtagga 300
cgtcccagga agagaagggc ggttcaccac tctacatggc tatagacata aaaacacacg 360
ccttgggagc acactcacat cagagacttg ggacctatcc ctctctcgct cgtttgtaac 420
ccctactaca aacttttagt gctagtaaca cgagcagcag cgacgaacta gacgtaagga 480
ctttctgccc gaaccagtat aaacatcgtg tcatctaagc acaccatacg agccagacgc 540
gcaatactag aaatttacta gtcggtaact cgaaacaccg acatctagct aatctttttg 600
ttttatttgg tttccctttg aaatcttcta atttagcttt catagaaata atctaggtat 660
tttttatttt atatgttcta tctgtttgca ttaattttga tcatttgatc tgaatgctgt 720
ggtcacgaga atcgagtgtt tcatggcctt aaaacactcg attatgccat ctgacccgtt 780
ttcaaccatt ctagtgtttc tgagctatat caatggtgca gcatgttagt atacatatct 840

```
aactattact ccgtatatga gtgagttgtt aaatttattc caggtgaaat ggcattaacg    900
atagccaata ggcggctaaa ttaatagcca tactctaaca gctctaaaaa acatatattc    960
atcgaggcac ctttatgcaa ccacatagtc aacttcaacg tcgcttgcgt gcgttctcaa   1020
gttttctttc ttgcaaatta cattttttttt aaaaaaaagt ataatttgta tcgtgcgatt   1080
ttttctctct aggtgtgcgt gactgtggga gtaacaattt tgaatctcaa gaaggaaata   1140
aaagaataat actgctgcct actttgagga tttcagtatt tttctctaaa atgttttggt   1200
gtgatatcta aaccgtcttt aaagccaatt gctcaagatt cattcaacaa ttgaaacgtc   1260
tcacatgact aaatgatata aggttgctaa ggtctttctt gataagcttt tttatgaatt   1320
tcatctaaat tttcgagtga aactattaaa tactaaggtt gctaagtgtc attctcgctc   1380
gagaagtcta acgctttaaa ctttaaccaa atatatacaa gaaaatatta atatttatag   1440
tacataatta gtatcattag atagatcgtt gaatctattt tcataacaaa cttatttgaa   1500
gaaacaaatg ttgttcatat atttctatat acgaatacca tagcgacact tattttagaa   1560
tgtagggagt actccctttg tgccgctttg agtgtcgctt tggcagctag tacctatgtc   1620
caccttcaca gcttgtgcct agtacctaga ctctttctct gtccacattc atttaatctc   1680
tgttgtacct tgttcggaga taaaacgact ctgataaagg gacgaggaag tagtatgtta   1740
gaggagtgaa gtctactccc tttgccgcaa aaaggtaatc ctaagtgtga attgtattct   1800
tttttgacca aaggaatata caacaagaat gatgtcatca tcatgcttcg atcctttttt   1860
ttggtaaagc ttgagcttct gtaaaaatag agaaatcatg ggaaaaatca cgttttggtg   1920
gttttgattt ctagcctcca caataacttt ggttttacta ttttttgttt gattttagtt   1980
tcagaagtcc acttttgtac gtgctcgtag agcctaaaca aaaggctttc caaaacgacc   2040
ttatcttcga gtgttgtaaa aaaaatgagc ccgtttaacg gcgtcgacaa gtctaacgga   2100
caccaaccag cgaaccacca gcgccgagcc aagcgaagca gactgcagac ggcacggccg   2160
agacgttgac accttggcgc ggcaacggca tctctctggc cccctctcga gagttccgct   2220
ccacctccgc atccacctcc acctccacct ccaccggtgg cggtttccaa gtccgtcccg   2280
ttccgccacc tgctcctctc acacggcacg aaaccgtcac ggcaccggca gcacagcacg   2340
ggggattcct ttcccaccgc tccgtccctt tctcttcctc gcccgcccgt tataaatagc   2400
cagccccatc cctcgtctct cgt                                           2423
```

<210> SEQ ID NO 68
<211> LENGTH: 55
<212> TYPE: DNA
<213> ORGANISM: Miscanthus sinesis

<400> SEQUENCE: 68

```
gttgttcgga gcgcacacac aacccgatcc ccaatcaatc gatccccgct tcaag          55
```

<210> SEQ ID NO 69
<211> LENGTH: 1924
<212> TYPE: DNA
<213> ORGANISM: Miscanthus sinesis

<400> SEQUENCE: 69

```
gtacggcgat cctcctccct ctctctctac cttctcttct ctacactaga tcggcggtcc     60
atggttaggg cctgctagtt ccgttcctgt ttttccatgg ctgcgaggta caatagatct    120
gatggcgtta tgatggttaa cttgtcatgc ttttgcgatt tatagtccct ttagatagtt    180
cgagatcggt gatccatggt tagtacccta ggctgtggag tcgggttaga tccgcgctgt    240
```

tagggttcgt atatggaggc gagctgttct gattgttaac ttgctgggaa tcctgggatg 300
gttctagctg ttccgcagat gagatcgatt tcatgatctg ctgtatctat ccgtggtatg 360
atgttagcct ttgatatggt tcgatcgtgc tagctacgtc ctgtgcactt aattgtcagg 420
tcataatttt tactatactt tttttttggt ttggtttggt ttcgtctgat ttggctgtcg 480
ttctagatca gagtagaaac tgtttcaaac tacctgttgg atttattaag gtagcgtttg 540
gttcctggta tcgaatcata cacgcaccag tgcatcttgg atagccagct ggggcccacc 600
tgtccaaccg tttggttgcc ggatcgaacg agtccattca agaccgaacc atgcagagca 660
atcgaatatt ctcttgtgac gctgtatcat ccagttcggc aaaaaacacc gaatgccgcc 720
atacaggaca ccgtactgag cgtctgcaac tctgcatccc gctcactgct cacatctccg 780
cttgccgcct cacccatccg actcagacca gagccacacg gattactgct gctggtgtgt 840
gtattaacaa aagatccatt tgaccggagc acatgcagct tggatggaaa aaatttatta 900
tattcgtcag tgctgcatat gtactcatac ttgcatgatg gttttattta ttcgacctca 960
tcagtcctgg cactatggaa agtcattgta gtatagattt tttaatataa tataaatcat 1020
tggtgactta tcttgcttaa ttttattttc ttattatgaa atatcgttgc attcataata 1080
gcaaatttgt gcaaatatat agaatctacg tgaaattctt ggttggacca atacaacaaa 1140
cccctcaaac attctcttgt actgaaccat accattccgt acaaccatcc aaacaaaaat 1200
catgtatcat catgtacatg taaccaaaca attaacacgc accatcctat tcagacttgt 1260
ctcatccata atctatccat ccaggatgat ccatcccatt catctatata cacccaatca 1320
aacgctacct aaaatttgga tctgtatgtg tcacatatat cttaataaga tggatggaaa 1380
tatctcttta tcttttagat atggataggt atatatgttg ctgtgggttt gttagttata 1440
tatatacgtg cttacatacg tgaagaaacc tgctgctaca gtttaataat tcttgttcat 1500
ctcaacaaat aacgataggc gtatatgttg ctgtgttttt tactggtact ttgttagata 1560
tatacatgct tacatacatg aagaacacat gctacagttc aaaaattctt gttcatctca 1620
taaacaaaaa ggaggtgtat atgttgctgt gggttttact ggtactttat tagatatata 1680
catgcttaca tagatgaagc aacatgctgc tatggtgttt aataattatt gtttatctaa 1740
taaacaaaca tgctttttaa ttatcttgat atgtttggat gatggcatat gcagcagcta 1800
tgtgtggatt ttaaataccc agcatcatga gcatgcatga ccctgcctta gtatgcagtt 1860
atttgcttga gactgtttct tttgttgata ctcatccttt agttcggtca ctcttctgca 1920
ggtg 1924

<210> SEQ ID NO 70
<211> LENGTH: 3426
<212> TYPE: DNA
<213> ORGANISM: Miscanthus sinesis

<400> SEQUENCE: 70
gcaaccacat agtcaacttc aacgtcgctt gcgtgcgttc tcaagttttc tttcttgcaa 60
attacatttt ttttaaaaaa aagtataatt tgtatcgtgc gatttttttct ctctaggtgt 120 gcgtgactgt gggagtaaca attttgaatc tcaagaagga aataaaagaa taatactgct 180
gcctactttg aggatttcag tatttttctc taaaatgttt tggtgtgata tctaaaccgt 240
ctttaaagcc aattgctcaa gattcattca acaattgaaa cgtctcacat gactaaatga 300
tataaggttg ctaaggtctt tcttgataag cttttttatg aatttcatct aaattttcga 360
gtgaaactat taaatactaa ggttgctaag tgtcattctc gctcgagaag tctaacgctt 420
taaactttaa ccaaatatat acaagaaaat attaatattt atagtacata attagtatca 480
ttagatagat cgttgaatct attttcataa caaacttatt tgaagaaaca aatgttgttc 540
atatatttct atatacgaat accatagcga cacttatttt agaatgtagg gagtactccc 600
tttgtgccgc tttgagtgtc gctttggcag ctagtaccta tgtccacctt cacagcttgt 660
gcctagtacc tagactcttt ctctgtccac attcatttaa tctctgttgt accttgttcg 720
gagataaaac gactctgata aagggacgag gaagtagtat gttagaggag tgaagtctac 780
tccctttgcc gcaaaaaggt aatcctaagt gtgaattgta ttcttttttg accaaaggaa 840
tatacaacaa gaatgatgtc atcatcatgc ttcgatcctt ttttttggta aagcttgagc 900
ttctgtaaaa atagagaaat catgggaaaa atcacgtttt ggtggttttg atttctagcc 960
tccacaataa ctttggtttt actatttttt gtttgatttt agtttcagaa gtccactttt 1020
gtacgtgctc gtagagccta aacaaaaggc tttccaaaac gaccttatct tcgagtgttg 1080
taaaaaaaat gagcccgttt aacggcgtcg acaagtctaa cggacaccaa ccagcgaacc 1140
accagcgccg agccaagcga agcagactgc agacggcacg gccgagacgt tgacaccttg 1200
gcgcggcaac ggcatctctc tggccccctc tcgagagttc cgctccacct ccgcatccac 1260
ctccacctcc acctccaccg gtggcggttt ccaagtccgt cccgttccgc cacctgctcc 1320
tctcacacgg cacgaaaccg tcacggcacc ggcagcacag cacgggggat tcctttccca 1380
ccgctccgtc cctttctctt cctcgcccgc ccgttataaa tagccagccc catccctcgt 1440
ctctcgtgtt gttcggagcg cacacacaac ccgatcccca atcaatcgat ccccgcttca 1500
aggtacggcg atcctcctcc ctctctctct accttctctt ctctacacta gatcggcggt 1560
ccatggttag ggcctgctag ttccgttcct gtttttccat ggctgcgagg tacaatagat 1620
ctgatggcgt tatgatggtt aacttgtcat gcttttgcga tttatagtcc ctttagatag 1680
ttcgagatcg gtgatccatg gttagtaccc taggctgtgg agtcgggtta gatccgcgct 1740
gttagggttc gtatatggag gcgagctgtt ctgattgtta acttgctggg aatcctggga 1800
tggttctagc tgttccgcag atgagatcga tttcatgatc tgctgtatct atccgtggta 1860
tgatgttagc ctttgatatg gttcgatcgt gctagctacg tcctgtgcac ttaattgtca 1920
ggtcataatt tttactatac ttttttttttg gtttggtttg gtttcgtctg atttggctgt 1980
cgttctagat cagagtagaa actgtttcaa actacctgtt ggatttatta aggtagcgtt 2040
tggttcctgg tatcgaatca tacacgcacc agtgcatctt ggatagccag ctggggccca 2100
cctgtccaac cgtttggttg ccggatcgaa cgagtccatt caagaccgaa ccatgcagag 2160
caatcgaata ttctcttgtg acgctgtatc atccagttcg gcaaaaaaca ccgaatgccg 2220
ccatacagga caccgtactg agcgtctgca actctgcatc ccgctcactg ctcacatctc 2280
cgcttgccgc ctcacccatc cgactcagac cagagccaca cggattactg ctgctggtgt 2340
gtgtattaac aaaagatcca tttgaccgga gcacatgcag cttggatgga aaaaatttat 2400
tatattcgtc agtgctgcat atgtactcat acttgcatga tggttttatt tattcgacct 2460
catcagtcct ggcactatgg aaagtcattg tagtatagat tttttaatat aatataaatc 2520
attggtgact tatcttgctt aattttattt tcttattatg aaatatcgtt gcattcataa 2580
tagcaaattt gtgcaaatat atagaatcta cgtgaaattc ttggttggac caatacaaca 2640
aacccctcaa acattctctt gtactgaacc ataccattcc gtacaaccat ccaaacaaaa 2700
atcatgtatc atcatgtaca tgtaaccaaa caattaacac gcaccatcct attcagactt 2760
gtctcatcca taatctatcc atccaggatg atccatccca ttcatctata tacacccaat 2820
caaacgctac ctaaaatttg gatctgtatg tgtcacatat atcttaataa gatggatgga 2880
aatatctctt tatcttttag atatggatag gtatatatgt tgctgtgggt ttgttagtta 2940
tatatatacg tgcttacata cgtgaagaaa cctgctgcta cagtttaata attcttgttc 3000
atctcaacaa ataacgatag gcgtatatgt tgctgtgttt tttactggta ctttgttaga 3060
tatatacatg cttacataca tgaagaacac atgctacagt tcaaaaattc ttgttcatct 3120
cataaacaaa aaggaggtgt atatgttgct gtgggtttta ctggtacttt attagatata 3180
tacatgctta catagatgaa gcaacatgct gctatggtgt ttaataatta ttgtttatct 3240
aataaacaaa catgcttttt aattatcttg atatgtttgg atgatggcat atgcagcagc 3300
tatgtgtgga ttttaaatac ccagcatcat gagcatgcat gaccctgcct tagtatgcag 3360
ttatttgctt gagactgttt cttttgttga tactcatcct ttagttcggt cactcttctg 3420
caggtg 3426

<210> SEQ ID NO 71
<211> LENGTH: 1447
<212> TYPE: DNA
<213> ORGANISM: Miscanthus sinesis

<400> SEQUENCE: 71
gcaaccacat agtcaacttc aacgtcgctt gcgtgcgttc tcaagttttc tttcttgcaa 60
attacatttt ttttaaaaaa aagtataatt tgtatcgtgc gatttttttct ctctaggtgt 120 gcgtgactgt gggagtaaca attttgaatc tcaagaagga aataaaagaa taatactgct 180
gcctactttg aggatttcag tatttttctc taaaatgttt tggtgtgata tctaaaccgt 240
ctttaaagcc aattgctcaa gattcattca acaattgaaa cgtctcacat gactaaatga 300
tataaggttg ctaaggtctt tcttgataag cttttttatg aatttcatct aaattttcga 360
gtgaaactat taaatactaa ggttgctaag tgtcattctc gctcgagaag tctaacgctt 420
taaactttaa ccaaatatat acaagaaaat attaatattt atagtacata attagtatca 480
ttagatagat cgttgaatct attttcataa caaacttatt tgaagaaaca aatgttgttc 540
atatatttct atatacgaat accatagcga cacttatttt agaatgtagg gagtactccc 600
tttgtgccgc tttgagtgtc gctttggcag ctagtaccta tgtccacctt cacagcttgt 660
gcctagtacc tagactcttt ctctgtccac attcatttaa tctctgttgt accttgttcg 720
gagataaaac gactctgata aagggacgag gaagtagtat gttagaggag tgaagtctac 780
tccctttgcc gcaaaaaggt aatcctaagt gtgaattgta ttcttttttg accaaaggaa 840
tatacaacaa gaatgatgtc atcatcatgc ttcgatcctt ttttttggta aagcttgagc 900
ttctgtaaaa atagagaaat catgggaaaa atcacgtttt ggtggttttg atttctagcc 960
tccacaataa ctttggtttt actatttttt gtttgatttt agtttcagaa gtccactttt 1020
gtacgtgctc gtagagccta aacaaaaggc tttccaaaac gaccttatct tcgagtgttg 1080
taaaaaaaat gagcccgttt aacggcgtcg acaagtctaa cggacaccaa ccagcgaacc 1140
accagcgccg agccaagcga agcagactgc agacggcacg gccgagacgt tgacaccttg 1200
gcgcggcaac ggcatctctc tggccccctc tcgagagttc cgctccacct ccgcatccac 1260
ctccacctcc acctccaccg gtggcggttt ccaagtccgt cccgttccgc cacctgctcc 1320
tctcacacgg cacgaaaccg tcacggcacc ggcagcacag cacgggggat tcctttccca 1380
ccgctccgtc cctttctctt cctcgcccgc ccgttataaa tagccagccc catccctcgt 1440
ctctcgt 1447

<210> SEQ ID NO 72
<211> LENGTH: 2878
<212> TYPE: DNA
<213> ORGANISM: Miscanthus sinesis

<400> SEQUENCE: 72
ctatatacga ataccatagc gacacttatt ttagaatgta gggagtactc cctttgtgcc 60
gctttgagtg tcgctttggc agctagtacc tatgtccacc ttcacagctt gtgcctagta 120
cctagactct ttctctgtcc acattcattt aatctctgtt gtaccttgtt cggagataaa 180
acgactctga taaagggacg aggaagtagt atgttagagg agtgaagtct actccctttg 240
ccgcaaaaag gtaatcctaa gtgtgaattg tattcttttt tgaccaaagg aatatacaac 300
aagaatgatg tcatcatcat gcttcgatcc ttttttttgg taaagcttga gcttctgtaa 360
aaatagagaa atcatgggaa aaatcacgtt ttggtggttt tgatttctag cctccacaat 420
aactttggtt ttactatttt ttgtttgatt ttagtttcag aagtccactt ttgtacgtgc 480
tcgtagagcc taaacaaaag gctttccaaa acgaccttat cttcgagtgt tgtaaaaaaa 540
atgagcccgt ttaacggcgt cgacaagtct aacggacacc aaccagcgaa ccaccagcgc 600
cgagccaagc gaagcagact gcagacggca cggccgagac gttgacacct tggcgcggca 660
acggcatctc tctggccccc tctcgagagt tccgctccac ctccgcatcc acctccacct 720
ccacctccac cggtggcggt ttccaagtcc gtcccgttcc gccacctgct cctctcacac 780
ggcacgaaac cgtcacggca ccggcagcac agcacggggg attcctttcc caccgctccg 840
tccctttctc ttcctcgccc gcccgttata aatagccagc cccatccctc gtctctcgtg 900
ttgttcggag cgcacacaca acccgatccc caatcaatcg atccccgctt caaggtacgg 960
cgatcctcct ccctctctct ctaccttctc ttctctacac tagatcggcg gtccatggtt 1020
agggcctgct agttccgttc ctgtttttcc atggctgcga ggtacaatag atctgatggc 1080
gttatgatgg ttaacttgtc atgcttttgc gatttatagt ccctttagat agttcgagat 1140
cggtgatcca tggttagtac cctaggctgt ggagtcgggt tagatccgcg ctgttagggt 1200
tcgtatatgg aggcgagctg ttctgattgt taacttgctg ggaatcctgg gatggttcta 1260
gctgttccgc agatgagatc gatttcatga tctgctgtat ctatccgtgg tatgatgtta 1320
gcctttgata tggttcgatc gtgctagcta cgtcctgtgc acttaattgt caggtcataa 1380
tttttactat actttttttt tggtttggtt tggtttcgtc tgatttggct gtcgttctag 1440
atcagagtag aaactgtttc aaactacctg ttggatttat taaggtagcg tttggttcct 1500
ggtatcgaat catacacgca ccagtgcatc ttggatagcc agctggggcc cacctgtcca 1560
accgtttggt tgccggatcg aacgagtcca ttcaagaccg aaccatgcag agcaatcgaa 1620
tattctcttg tgacgctgta tcatccagtt cggcaaaaaa caccgaatgc cgccatacag 1680
gacaccgtac tgagcgtctg caactctgca tcccgctcac tgctcacatc tccgcttgcc 1740
gcctcaccca tccgactcag accagagcca cacggattac tgctgctggt gtgtgtatta 1800
acaaaagatc catttgaccg gagcacatgc agcttggatg gaaaaaattt attatattcg 1860
tcagtgctgc atatgtactc atacttgcat gatggtttta tttattcgac ctcatcagtc 1920
ctggcactat ggaaagtcat tgtagtatag attttttaat ataatataaa tcattggtga 1980
cttatcttgc ttaattttat tttcttatta tgaaatatcg ttgcattcat aatagcaaat 2040
ttgtgcaaat atatagaatc tacgtgaaat tcttggttgg accaatacaa caaacccctc 2100
aaacattctc ttgtactgaa ccataccatt ccgtacaacc atccaaacaa aaatcatgta 2160
tcatcatgta catgtaacca aacaattaac acgcaccatc ctattcagac ttgtctcatc 2220
cataatctat ccatccagga tgatccatcc cattcatcta tatacaccca atcaaacgct 2280
acctaaaatt tggatctgta tgtgtcacat atatcttaat aagatggatg gaaatatctc 2340
tttatctttt agatatggat aggtatatat gttgctgtgg gtttgttagt tatatatata 2400
cgtgcttaca tacgtgaaga aacctgctgc tacagtttaa taattcttgt tcatctcaac 2460
aaataacgat aggcgtatat gttgctgtgt tttttactgg tactttgtta gatatataca 2520
tgcttacata catgaagaac acatgctaca gttcaaaaat tcttgttcat ctcataaaca 2580
aaaaggaggt gtatatgttg ctgtgggttt tactggtact ttattagata tatacatgct 2640
tacatagatg aagcaacatg ctgctatggt gtttaataat tattgtttat ctaataaaca 2700
aacatgcttt ttaattatct tgatatgttt ggatgatggc atatgcagca gctatgtgtg 2760
gattttaaat acccagcatc atgagcatgc atgaccctgc cttagtatgc agttatttgc 2820
ttgagactgt ttcttttgtt gatactcatc ctttagttcg gtcactcttc tgcaggtg 2878

<210> SEQ ID NO 73
<211> LENGTH: 899
<212> TYPE: DNA
<213> ORGANISM: Miscanthus sinesis

<400> SEQUENCE: 73
ctatatacga ataccatagc gacacttatt ttagaatgta gggagtactc cctttgtgcc 60
gctttgagtg tcgctttggc agctagtacc tatgtccacc ttcacagctt gtgcctagta 120
cctagactct ttctctgtcc acattcattt aatctctgtt gtaccttgtt cggagataaa 180
acgactctga taaagggacg aggaagtagt atgttagagg agtgaagtct actccctttg 240
ccgcaaaaag gtaatcctaa gtgtgaattg tattcttttt tgaccaaagg aatatacaac 300
aagaatgatg tcatcatcat gcttcgatcc tttttttgg taaagcttga gcttctgtaa 360
aaatagagaa atcatgggaa aaatcacgtt ttggtggttt tgatttctag cctccacaat 420
aactttggtt ttactatttt ttgtttgatt ttagtttcag aagtccactt ttgtacgtgc 480
tcgtagagcc taaacaaaag gctttccaaa acgaccttat cttcgagtgt tgtaaaaaaa 540
atgagcccgt ttaacggcgt cgacaagtct aacggacacc aaccagcgaa ccaccagcgc 600
cgagccaagc gaagcagact gcagacggca cggccgagac gttgacacct tggcgcggca 660
acggcatctc tctggccccc tctcgagagt tccgctccac ctccgcatcc acctccacct 720
ccacctccac cggtggcggt ttccaagtcc gtcccgttcc gccacctgct cctctcacac 780
ggcacgaaac cgtcacggca ccggcagcac agcacggggg attcctttcc caccgctccg 840
tccctttctc ttcctcgccc gcccgttata aatagccagc cccatccctc gtctctcgt 899

<210> SEQ ID NO 74
<211> LENGTH: 2670
<212> TYPE: DNA
<213> ORGANISM: Miscanthus sinesis

<400> SEQUENCE: 74
gtatgttaga ggagtgaagt ctactccctt tgccgcaaaa aggtaatcct aagtgtgaat 60
tgtattcttt tttgaccaaa ggaatataca acaagaatga tgtcatcatc atgcttcgat 120

-continued

```
cctttttttt ggtaaagctt gagcttctgt aaaaatagag aaatcatggg aaaaatcacg    180
ttttggtggt tttgatttct agcctccaca ataactttgg ttttactatt ttttgtttga    240
ttttagtttc agaagtccac ttttgtacgt gctcgtagag cctaaacaaa aggctttcca    300
aaacgacctt atcttcgagt gttgtaaaaa aaatgagccc gtttaacggc gtcgacaagt    360
ctaacggaca ccaaccagcg aaccaccagc gccgagccaa gcgaagcaga ctgcagacgg    420
cacggccgag acgttgacac cttggcgcgg caacggcatc tctctggccc cctctcgaga    480
gttccgctcc acctccgcat ccacctccac ctccacctcc accggtggcg gtttccaagt    540
ccgtcccgtt ccgccacctg ctcctctcac acggcacgaa accgtcacgg caccggcagc    600
acagcacggg ggattccttt cccaccgctc cgtccctttc tcttcctcgc ccgcccgtta    660
taaatagcca gccccatccc tcgtctctcg tgttgttcgg agcgcacaca caacccgatc    720
cccaatcaat cgatccccgc ttcaaggtac ggcgatcctc ctccctctct ctctaccttc    780
tcttctctac actagatcgg cggtccatgg ttagggcctg ctagttccgt tcctgttttt    840
ccatggctgc gaggtacaat agatctgatg gcgttatgat ggttaacttg tcatgctttt    900
gcgatttata gtccctttag atagttcgag atcggtgatc catggttagt accctaggct    960
gtggagtcgg gttagatccg cgctgttagg gttcgtatat ggaggcgagc tgttctgatt   1020
gttaacttgc tgggaatcct gggatggttc tagctgttcc gcagatgaga tcgatttcat   1080
gatctgctgt atctatccgt ggtatgatgt tagcctttga tatggttcga tcgtgctagc   1140
tacgtcctgt gcacttaatt gtcaggtcat aatttttact atactttttt tttggtttgg   1200
tttggtttcg tctgatttgg ctgtcgttct agatcagagt agaaactgtt tcaaactacc   1260
tgttggattt attaaggtag cgtttggttc ctggtatcga atcatacacg caccagtgca   1320
tcttggatag ccagctgggg cccacctgtc caaccgtttg gttgccggat cgaacgagtc   1380
cattcaagac cgaaccatgc agagcaatcg aatattctct tgtgacgctg tatcatccag   1440
ttcggcaaaa aacaccgaat gccgccatac aggacaccgt actgagcgtc tgcaactctg   1500
catcccgctc actgctcaca tctccgcttg ccgcctcacc catccgactc agaccagagc   1560
cacacggatt actgctgctg gtgtgtgtat taacaaaaga tccatttgac cggagcacat   1620
gcagcttgga tggaaaaaat ttattatatt cgtcagtgct gcatatgtac tcatacttgc   1680
atgatggttt tatttattcg acctcatcag tcctggcact atggaaagtc attgtagtat   1740
agatttttta atataatata aatcattggt gacttatctt gcttaatttt attttcttat   1800
tatgaaatat cgttgcattc ataatagcaa atttgtgcaa atatatagaa tctacgtgaa   1860
attcttggtt ggaccaatac aacaaacccc tcaaacattc tcttgtactg aaccatacca   1920
ttccgtacaa ccatccaaac aaaaatcatg tatcatcatg tacatgtaac caaacaatta   1980
acacgcacca tcctattcag acttgtctca tccataatct atccatccag gatgatccat   2040
cccattcatc tatatacacc caatcaaacg ctacctaaaa tttggatctg tatgtgtcac   2100
atatatctta ataagatgga tggaaatatc tctttatctt ttagatatgg ataggtatat   2160
atgttgctgt gggtttgtta gttatatata tacgtgctta catacgtgaa gaaacctgct   2220
gctacagttt aataattctt gttcatctca acaaataacg ataggcgtat atgttgctgt   2280
gtttttttact ggtactttgt tagatatata catgcttaca tacatgaaga acacatgcta   2340
cagttcaaaa attcttgttc atctcataaa caaaaaggag gtgtatatgt tgctgtgggt   2400
tttactggta ctttattaga tatatacatg cttacataga tgaagcaaca tgctgctatg   2460
gtgtttaata attattgttt atctaataaa caaacatgct ttttaattat cttgatatgt   2520
```

ttggatgatg gcatatgcag cagctatgtg tggattttaa atacccagca tcatgagcat 2580
gcatgaccct gccttagtat gcagttattt gcttgagact gtttcttttg ttgatactca 2640
tcctttagtt cggtcactct tctgcaggtg 2670

<210> SEQ ID NO 75
<211> LENGTH: 691
<212> TYPE: DNA
<213> ORGANISM: Miscanthus sinesis

<400> SEQUENCE: 75
gtatgttaga ggagtgaagt ctactccctt tgccgcaaaa aggtaatcct aagtgtgaat 60
tgtattcttt tttgaccaaa ggaatataca acaagaatga tgtcatcatc atgcttcgat 120
cctttttttt ggtaaagctt gagcttctgt aaaaatagag aaatcatggg aaaaatcacg 180
ttttggtggt tttgatttct agcctccaca ataactttgg ttttactatt ttttgtttga 240
ttttagtttc agaagtccac ttttgtacgt gctcgtagag cctaaacaaa aggctttcca 300
aaacgacctt atcttcgagt gttgtaaaaa aaatgagccc gtttaacggc gtcgacaagt 360
ctaacggaca ccaaccagcg aaccaccagc gccgagccaa gcgaagcaga ctgcagacgg 420
cacggccgag acgttgacac cttggcgcgg caacggcatc tctctggccc cctctcgaga 480
gttccgctcc acctccgcat ccacctccac ctccacctcc accggtggcg gtttccaagt 540
ccgtcccgtt ccgccacctg ctcctctcac acggcacgaa accgtcacgg caccggcagc 600
acagcacggg ggattccttt cccaccgctc cgtccctttc tcttcctcgc ccgcccgtta 660
taaatagcca gccccatccc tcgtctctcg t 691

<210> SEQ ID NO 76
<211> LENGTH: 2485
<212> TYPE: DNA
<213> ORGANISM: Miscanthus sinesis

<400> SEQUENCE: 76
gtggttttga tttctagcct ccacaataac tttggtttta ctattttttg tttgatttta 60
gtttcagaag tccacttttg tacgtgctcg tagagcctaa acaaaaggct ttccaaaacg 120
accttatctt cgagtgttgt aaaaaaaatg agcccgttta acggcgtcga caagtctaac 180
ggacaccaac cagcgaacca ccagcgccga gccaagcgaa gcagactgca gacggcacgg 240
ccgagacgtt gacaccttgg cgcggcaacg gcatctctct ggccccctct cgagagttcc 300
gctccacctc cgcatccacc tccacctcca cctccaccgg tggcggtttc caagtccgtc 360
ccgttccgcc acctgctcct ctcacacggc acgaaaccgt cacggcaccg gcagcacagc 420
acgggggatt cctttcccac cgctccgtcc ctttctcttc ctcgcccgcc cgttataaat 480
agccagcccc atccctcgtc tctcgtgttg ttcggagcgc acacacaacc cgatccccaa 540
tcaatcgatc cccgcttcaa ggtacggcga tcctcctccc tctctctcta ccttctcttc 600
tctacactag atcggcggtc catggttagg gcctgctagt tccgttcctg tttttccatg 660
gctgcgaggt acaatagatc tgatggcgtt atgatggtta acttgtcatg cttttgcgat 720
ttatagtccc tttagatagt tcgagatcgg tgatccatgg ttagtaccct aggctgtgga 780
gtcgggttag atccgcgctg ttagggttcg tatatggagg cgagctgttc tgattgttaa 840
cttgctggga atcctgggat ggttctagct gttccgcaga tgagatcgat ttcatgatct 900
gctgtatcta tccgtggtat gatgttagcc tttgatatgg ttcgatcgtg ctagctacgt 960

```
cctgtgcact taattgtcag gtcataattt ttactatact tttttttgg tttggtttgg   1020
tttcgtctga tttggctgtc gttctagatc agagtagaaa ctgtttcaaa ctacctgttg   1080
gatttattaa ggtagcgttt ggttcctggt atcgaatcat acacgcacca gtgcatcttg   1140
gatagccagc tggggcccac ctgtccaacc gtttggttgc cggatcgaac gagtccattc   1200
aagaccgaac catgcagagc aatcgaatat tctcttgtga cgctgtatca tccagttcgg   1260
caaaaaacac cgaatgccgc catacaggac accgtactga gcgtctgcaa ctctgcatcc   1320
cgctcactgc tcacatctcc gcttgccgcc tcacccatcc gactcagacc agagccacac   1380
ggattactgc tgctggtgtg tgtattaaca aaagatccat ttgaccggag cacatgcagc   1440
ttggatggaa aaaatttatt atattcgtca gtgctgcata tgtactcata cttgcatgat   1500
ggttttattt attcgacctc atcagtcctg gcactatgga aagtcattgt agtatagatt   1560
ttttaatata atataaatca ttggtgactt atcttgctta attttatttt cttattatga   1620
aatatcgttg cattcataat agcaaatttg tgcaaatata tagaatctac gtgaaattct   1680
tggttggacc aatacaacaa acccctcaaa cattctcttg tactgaacca taccattccg   1740
tacaaccatc caaacaaaaa tcatgtatca tcatgtacat gtaaccaaac aattaacacg   1800
caccatccta ttcagacttg tctcatccat aatctatcca tccaggatga tccatcccat   1860
tcatctatat acacccaatc aaacgctacc taaaatttgg atctgtatgt gtcacatata   1920
tcttaataag atggatggaa atatctcttt atcttttaga tatggatagg tatatatgtt   1980
gctgtgggtt tgttagttat atatatacgt gcttacatac gtgaagaaac ctgctgctac   2040
agtttaataa ttcttgttca tctcaacaaa taacgatagg cgtatatgtt gctgtgtttt   2100
ttactggtac tttgttagat atatacatgc ttacatacat gaagaacaca tgctacagtt   2160
caaaaattct tgttcatctc ataaacaaaa aggaggtgta tatgttgctg tgggttttac   2220
tggtacttta ttagatatat acatgcttac atagatgaag caacatgctg ctatggtgtt   2280
taataattat tgtttatcta ataaacaaac atgcttttta attatcttga tatgtttgga   2340
tgatggcata tgcagcagct atgtgtggat tttaaatacc cagcatcatg agcatgcatg   2400
accctgcctt agtatgcagt tatttgcttg agactgtttc ttttgttgat actcatcctt   2460
tagttcggtc actcttctgc aggtg                                         2485
```

<210> SEQ ID NO 77
<211> LENGTH: 506
<212> TYPE: DNA
<213> ORGANISM: Miscanthus sinesis

<400> SEQUENCE: 77

```
gtggttttga tttctagcct ccacaataac tttggtttta ctatttttg tttgatttta     60
gtttcagaag tccacttttg tacgtgctcg tagagcctaa acaaaaggct ttccaaaacg   120
accttatctt cgagtgttgt aaaaaaaatg agcccgttta acggcgtcga caagtctaac   180
ggacaccaac cagcgaacca ccagcgccga gccaagcgaa gcagactgca gacggcacgg   240
ccgagacgtt gacaccttgg cgcggcaacg gcatctctct ggccccctct cgagagttcc   300
gctccacctc cgcatccacc tccacctcca cctccaccgg tggcggtttc caagtccgtc   360
ccgttccgcc acctgctcct ctcacacggc acgaaaccgt cacggcaccg gcagcacagc   420
acgggggatt cctttcccac cgctccgtcc ctttctcttc ctcgcccgcc cgttataaat   480
agccagcccc atccctcgtc tctcgt                                        506
```

-continued

<210> SEQ ID NO 78
<211> LENGTH: 4079
<212> TYPE: DNA
<213> ORGANISM: Schizachyium scoparium

<400> SEQUENCE: 78
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240
ctattatgca accacatagt caacttcaaa gccgcttgag tgcgttctaa aaaaaaaatt 300
tcttgtaaat tacgcttttc tcaaaaaaat tggatcatgc atttatttca ctctaggtgt 360
gcgtgactac gtgaataaca attttgaatc tcagcaagga aataaaagta taataccgct 420
gtctactttg aagatcacaa tatctttctc ttagaatgtt tctgtttgtt atttaaaacc 480
atcgttatta aggtcaaatg atcaagattc attcaacaat tgaaacttct cacatgatta 540
catcatatat aaggttgcta aggtcttgct tgacaaggta tctctagtaa catctagttt 600
ttttgagtga aataataaaa ttttaaagca atgttacaag agaagctctg gagataaaag 660
ttagaagggt gaagtttact ccctctatcc caaagatgta attctaagaa tgacttaaat 720
tttttataca aaaggagtat atatcacaag attgatgtca tcgttatgct taggccacgt 780
acacgacgct ggcgcttatg tggacgttaa tcggtaattc ttcattttat tttattttgt 840
tgtcaccgcg tacatttggg ttaggcgttt gttaaaggca ttgccactca aacaagcagc 900
cgcgtttgga gcttttatag tttgaaaagt gacggttgta aagatgagta agctgattat 960
tagtagagta aattataatt atcatacaac aactctcaaa gtgggtgcac gttagtccaa 1020
catcttataa tttatccaac tcaatacaac aactatatag gtgggtgcat gttggtccaa 1080
catcttctaa tttgtttaat ttgatacgag aacttgtctt attggtacat atatgatcca 1140
aagcattgta acaacgtgtt tatgtatact cttaatcatg gtcatcagaa gctaacacac 1200
acgctcatgc catccatatc attcaacttt tgaatcgttt actatacaat attatttcta 1260
aatttggctg taaagatggc attgatttca taaatatgaa aaataccaaa ttgcacattt 1320
tctttctata ttataatatt gttttcatct attttcaccc cgtaaccttt aatttggtca 1380
tttagggctc actaaaactg atatgtgggt tgtgcatcgc ataagaatca agaacccaga 1440
agtaattttc aatactaaga aacaacaaaa tttggttttt ttttgtttgg tttcgattat 1500
agccgaacta accaaattta agaaagcttt ttatatttgg ccacataaga aatgatatca 1560
tttaatattg taactgattc aagctgagta atagatgaga tgagtgtgtt aggatgtgta 1620
gcttccgatg atagagaatt agagtgtaca aagacgcatc gttacaatat ttggacctta 1680
tatgcaccaa tgtgtcaagt ctcgcttcaa attaactata ttaaaagatg ttggatcaac 1740
atgcactcac ttagatatca gtcgtattaa attgaacaaa ttacaagata ttggactatg 1800
cacccactca aatagttgtt atatagtgaa tacagtttac tcttagtagt atatgtaagt 1860
tcagcctttt ctattgtagg ttaagcctta attaaggctc ttacacaatt gtttcattat 1920
tcgcgttcga agcagcttct tcgtagattt tgcgagggaa ggctgcctcg gttttgcctt 1980
ccctagcact catgtgagag cctctggcaa taggtcttct cattttttatt cacattcttt 2040 aagagcccat ataagcgttc atgacttgta tatactctta gatctttttt tgtgggtaaa 2100
gctcaagcta atctaaaaat agagaaatca ggaacaaaga atcatgtttt ggtggttttg 2160
atttctagcc tccacaataa ttttagttta cctttttttg tttgatttta attttagaag 2220
ggtttatagc aggacttaaa atccaaaatg accattatct tcgagtaata acccgtttaa 2280
cggcgtcgac aagtctaacg gacaccaacc catgaaccac cagcgccgag ccaagaactg 2340
aaggtcgaga cgttgacacc tttggcgcga cacggcatgt tggcatctcc ctctctggcc 2400
ccctctcgag aattccgctc caccgcctca accggagacg gtttccaaag ttgtgcttag 2460
atgctcaaaa gttggtgaaa tcatttttat ttggcaattt gtgtccaact atagactaat 2520
taggctcaaa agatttgtct cgtaaagtac attcaaactg tgtaattagt tattttattt 2580
atctacattt aatactctat gaatgcgtca agagatttga tgtgacttta atgtgacgga 2640
caatctgaaa cttttacgca acttgcatat aaacagagcc caagtccgtt ccgttccgtt 2700
ccgcttcctc ctcccagacg gcacgaaacc gtgacggcac cggcagcacg gggattcctt 2760
tcccaccgct ccttcctttt cccttcatcg cccgcagcta taaatagcca cccccgtccg 2820
caacttcttt ccccaacctc atcttttgtt cggagcacgc acacaatccg atcgatcccc 2880
aatcccctcg tctctcctcg cgagcctcgt cgatccgcca ttcaaggtac ggcgatcatc 2940
ctccctccct ctctacctgc tcttctgtag atcggcgacc ccatccatgg ttagggcctg 3000
ctagttctgt tcctgttttt tttccatggc tgcgaggtag aatagatctg atggcgttat 3060
gatggttaat ttgtcatact cttgcggtct atgggtccct ttaggtcatc aatttaattt 3120
tgggtggttg agatcggtga tccatggtta gtaccctagt cagtggggtt ggatccgtgc 3180
tattagggtt cgtagatgga ttctgatggc tcagtaactg ggaatcctag gatggttcca 3240
tctggtttgc agatgagaac gatttcatca tctgctatat cttgtttcgt tgcgtaggtt 3300
ctgtttaaac taatccgtgg tatgatgtta gcctttgata aggttgattt catcatctgc 3360
tatatcttgt ttcgttgcgt aggttctgtt taaactaatc cgtggtatga tgttagcctt 3420
tgataaggtt tgattgtgct agctacgtcc tgtgcagcag ttaattgtca ggtcatacgt 3480
cataattttt agcatgtctg tttttgtttg atttcgttgt ctgattaggc tgtagatagt 3540
ttcgatctac ctgtcggttt attttattaa aatttggatc cgtatgtgtg tcacatatat 3600
cttcatgatt aagatggagt tatatgggta ggttatacat gtggctgtgg atcatgatta 3660
agatggattg aagtatctct ttatctttta gttaggatag attattatat atgttgctgt 3720
tgattttatt ggttctttat tatatatatt catgcttata tacataaaag caatgtgcta 3780
ttacagttta atagttcttg attatctaat aaacaaataa ggataggtat atttgttgct 3840
gttggtttta ctggtactct attagatagt actttgacat gaagcaacat cctgctatgg 3900
attaataatt attcttcgtc taataaaaag catggttttt aattattttg atttgatata 3960
cttggatgat gtcatatgca gcagctattt gtgaattttt cggccgtatc ttcatattgc 4020
ttgggactgt ttctttggtt gataactcac cctgttgttt ggtgatcctt ctgcaggtg 4079

<210> SEQ ID NO 79
<211> LENGTH: 2831
<212> TYPE: DNA
<213> ORGANISM: Schizachyium scoparium

<400> SEQUENCE: 79
ctctatgcct gtgtcattgt gccagcccct acctctgtca atgttcaaga tccaaataag 60
agaatgggat agaccatata ttaatggtgt agtatgcatc aagatctgaa tattatatga 120
gtgaattgat aaatttattc taggtgacat ggccttaacg atggccagta cgtggttaaa 180
tcaatgaatc aatagccata ctctaatagc tctaaaaaag gatatatatt tgtcgaggca 240

```
ctattatgca accacatagt caacttcaaa gccgcttgag tgcgttctaa aaaaaaaatt    300
tcttgtaaat tacgcttttc tcaaaaaaat tggatcatgc atttatttca ctctaggtgt    360
gcgtgactac gtgaataaca attttgaatc tcagcaagga aataaaagta taataccgct    420
gtctactttg aagatcacaa tatctttctc ttagaatgtt tctgtttgtt atttaaaacc    480
atcgttatta aggtcaaatg atcaagattc attcaacaat tgaaacttct cacatgatta    540
catcatatat aaggttgcta aggtcttgct tgacaaggta tctctagtaa catctagttt    600
ttttgagtga aataataaaa ttttaaagca atgttacaag agaagctctg gagataaaag    660
ttagaagggt gaagtttact ccctctatcc caaagatgta attctaagaa tgacttaaat    720
tttttataca aaaggagtat atatcacaag attgatgtca tcgttatgct taggccacgt    780
acacgacgct ggcgcttatg tggacgttaa tcggtaattc ttcattttat tttattttgt    840
tgtcaccgcg tacatttggg ttaggcgttt gttaaaggca ttgccactca aacaagcagc    900
cgcgtttgga gcttttatag tttgaaaagt gacggttgta aagatgagta agctgattat    960
tagtagagta aattataatt atcatacaac aactctcaaa gtgggtgcac gttagtccaa   1020
catcttataa tttatccaac tcaatacaac aactatatag gtgggtgcat gttggtccaa   1080
catcttctaa tttgtttaat ttgatacgag aacttgtctt attggtacat atatgatcca   1140
aagcattgta acaacgtgtt tatgtatact cttaatcatg gtcatcagaa gctaacacac   1200
acgctcatgc catccatatc attcaacttt tgaatcgttt actatacaat attatttcta   1260
aatttggctg taaagatggc attgatttca taaatatgaa aaataccaaa ttgcacattt   1320
tctttctata ttataatatt gttttcatct attttcaccc cgtaaccttt aatttggtca   1380
tttagggctc actaaaactg atatgtgggt tgtgcatcgc ataagaatca agaacccaga   1440
agtaattttc aatactaaga aacaacaaaa tttggttttt ttttgtttgg tttcgattat   1500
agccgaacta accaaattta agaaagcttt ttatatttgg ccacataaga aatgatatca   1560
tttaatattg taactgattc aagctgagta atagatgaga tgagtgtgtt aggatgtgta   1620
gcttccgatg atagagaatt agagtgtaca aagacgcatc gttacaatat ttggacctta   1680
tatgcaccaa tgtgtcaagt ctcgcttcaa attaactata ttaaaagatg ttggatcaac   1740
atgcactcac ttagatatca gtcgtattaa attgaacaaa ttacaagata ttggactatg   1800
cacccactca aatagttgtt atatagtgaa tacagtttac tcttagtagt atatgtaagt   1860
tcagcctttt ctattgtagg ttaagcctta attaaggctc ttacacaatt gtttcattat   1920
tcgcgttcga agcagcttct tcgtagattt tgcgagggaa ggctgcctcg gttttgcctt   1980
ccctagcact catgtgagag cctctggcaa taggtcttct catttttatt cacattcttt   2040
aagagcccat ataagcgttc atgacttgta tatactctta gatctttttt tgtgggtaaa   2100
gctcaagcta atctaaaaat agagaaatca ggaacaaaga atcatgtttt ggtggttttg   2160
atttctagcc tccacaataa ttttagttta cctttttttg tttgatttta attttagaag   2220
ggtttatagc aggacttaaa atccaaaatg accattatct tcgagtaata acccgtttaa   2280
cggcgtcgac aagtctaacg gacaccaacc catgaaccac cagcgccgag ccaagaactg   2340
aaggtcgaga cgttgacacc tttggcgcga cacggcatgt tggcatctcc ctctctggcc   2400
ccctctcgag aattccgctc caccgcctca accggagacg gtttccaaag ttgtgcttag   2460
atgctcaaaa gttggtgaaa tcatttttat ttggcaattt gtgtccaact atagactaat   2520
taggctcaaa agatttgtct cgtaaagtac attcaaactg tgtaattagt tattttattt   2580
```

atctacattt aatactctat gaatgcgtca agagatttga tgtgacttta atgtgacgga 2640
caatctgaaa cttttacgca acttgcatat aaacagagcc caagtccgtt ccgttccgtt 2700
ccgcttcctc ctcccagacg gcacgaaacc gtgacggcac cggcagcacg gggattcctt 2760
tcccaccgct ccttcctttt cccttcatcg cccgcagcta taaatagcca cccccgtccg 2820
caacttcttt c 2831

<210> SEQ ID NO 80
<211> LENGTH: 95
<212> TYPE: DNA
<213> ORGANISM: Schizachyium scoparium

<400> SEQUENCE: 80
cccaacctca tcttttgttc ggagcacgca cacaatccga tcgatcccca atcccctcgt 60
ctctcctcgc gagcctcgtc gatccgccat tcaag 95

<210> SEQ ID NO 81
<211> LENGTH: 1153
<212> TYPE: DNA
<213> ORGANISM: Schizachyium scoparium

<400> SEQUENCE: 81
gtacggcgat catcctccct ccctctctac ctgctcttct gtagatcggc gaccccatcc 60
atggttaggg cctgctagtt ctgttcctgt ttttttcca tggctgcgag gtagaataga 120
tctgatggcg ttatgatggt taatttgtca tactcttgcg gtctatgggt ccctttaggt 180
catcaattta attttgggtg gttgagatcg gtgatccatg gttagtaccc tagtcagtgg 240
ggttggatcc gtgctattag ggttcgtaga tggattctga tggctcagta actgggaatc 300
ctaggatggt tccatctggt ttgcagatga gaacgatttc atcatctgct atatcttgtt 360
tcgttgcgta ggttctgttt aaactaatcc gtggtatgat gttagccttt gataaggttg 420
atttcatcat ctgctatatc ttgtttcgtt gcgtaggttc tgtttaaact aatccgtggt 480
atgatgttag cctttgataa ggtttgattg tgctagctac gtcctgtgca gcagttaatt 540
gtcaggtcat acgtcataat ttttagcatg tctgtttttg tttgatttcg ttgtctgatt 600
aggctgtaga tagtttcgat ctacctgtcg gtttatttta ttaaaatttg gatccgtatg 660
tgtgtcacat atatcttcat gattaagatg gagttatatg ggtaggttat acatgtggct 720
gtggatcatg attaagatgg attgaagtat ctctttatct tttagttagg atagattatt 780
atatatgttg ctgttgattt tattggttct ttattatata tattcatgct tatatacata 840
aaagcaatgt gctattacag tttaatagtt cttgattatc taataaacaa ataaggatag 900
gtatatttgt tgctgttggt tttactggta ctctattaga tagtactttg acatgaagca 960
acatcctgct atggattaat aattattctt cgtctaataa aaagcatggt ttttaattat 1020
tttgatttga tatacttgga tgatgtcata tgcagcagct atttgtgaat ttttcggccg 1080
tatcttcata ttgcttggga ctgtttcttt ggttgataac tcaccctgtt gtttggtgat 1140
ccttctgcag gtg 1153

<210> SEQ ID NO 82
<211> LENGTH: 3281
<212> TYPE: DNA
<213> ORGANISM: Schizachyium scoparium

<400> SEQUENCE: 82
gtggacgtta atcggtaatt cttcatttta ttttattttg ttgtcaccgc gtacatttgg 60

-continued

```
gttaggcgtt tgttaaaggc attgccactc aaacaagcag ccgcgtttgg agcttttata    120
gtttgaaaag tgacggttgt aaagatgagt aagctgatta ttagtagagt aaattataat    180
tatcatacaa caactctcaa agtgggtgca cgttagtcca acatcttata atttatccaa    240
ctcaatacaa caactatata ggtgggtgca tgttggtcca acatcttcta atttgtttaa    300
tttgatacga gaacttgtct tattggtaca tatatgatcc aaagcattgt aacaacgtgt    360
ttatgtatac tcttaatcat ggtcatcaga agctaacaca cacgctcatg ccatccatat    420
cattcaactt ttgaatcgtt tactatacaa tattatttct aaatttggct gtaaagatgg    480
cattgatttc ataaatatga aaaataccaa attgcacatt ttctttctat attataatat    540
tgttttcatc tattttcacc ccgtaacctt taatttggtc atttagggct cactaaaact    600
gatatgtggg ttgtgcatcg cataagaatc aagaacccag aagtaatttt caatactaag    660
aaacaacaaa atttggtttt tttttgtttg gtttcgatta tagccgaact aaccaaattt    720
aagaaagctt tttatatttg gccacataag aaatgatatc atttaatatt gtaactgatt    780
caagctgagt aatagatgag atgagtgtgt taggatgtgt agcttccgat gatagagaat    840
tagagtgtac aaagacgcat cgttacaata tttggacctt atatgcacca atgtgtcaag    900
tctcgcttca aattaactat attaaaagat gttggatcaa catgcactca cttagatatc    960
agtcgtatta aattgaacaa attacaagat attggactat gcacccactc aaatagttgt   1020
tatatagtga atacagttta ctcttagtag tatatgtaag ttcagccttt tctattgtag   1080
gttaagcctt aattaaggct cttacacaat tgtttcatta ttcgcgttcg aagcagcttc   1140
ttcgtagatt ttgcgaggga aggctgcctc ggttttgcct tccctagcac tcatgtgaga   1200
gcctctggca ataggtcttc tcatttttat tcacattctt taagagccca tataagcgtt   1260
catgacttgt atatactctt agatcttttt tttgtgggta aagctcaagc taatctaaaa   1320
atagagaaat caggaacaaa gaatcatgtt ttggtggttt tgatttctag cctccacaat   1380
aattttagtt tacctttttt tgtttgattt taattttaga agggtttata gcaggactta   1440
aaatccaaaa tgaccattat cttcgagtaa taacccgttt aacggcgtcg acaagtctaa   1500
cggacaccaa cccatgaacc accagcgccg agccaagaac tgaaggtcga gacgttgaca   1560
cctttggcgc gacacggcat gttggcatct ccctctctgg ccccctctcg agaattccgc   1620
tccaccgcct caaccggaga cggtttccaa agttgtgctt agatgctcaa aagttggtga   1680
aatcattttt atttggcaat ttgtgtccaa ctatagacta attaggctca aaagatttgt   1740
ctcgtaaagt acattcaaac tgtgtaatta gttattttat ttatctacat ttaatactct   1800
atgaatgcgt caagagattt gatgtgactt taatgtgacg gacaatctga aacttttacg   1860
caacttgcat ataaacagag cccaagtccg ttccgttccg ttccgcttcc tcctcccaga   1920
cggcacgaaa ccgtgacggc accggcagca cggggattcc tttcccaccg ctccttcctt   1980
ttcccttcat cgcccgcagc tataaatagc cacccccgtc cgcaacttct ttccccaacc   2040
tcatcttttg ttcggagcac gcacacaatc cgatcgatcc ccaatcccct cgtctctcct   2100
cgcgagcctc gtcgatccgc cattcaaggt acggcgatca tcctccctcc ctctctacct   2160
gctcttctgt agatcggcga ccccatccat ggttagggcc tgctagttct gttcctgttt   2220
tttttccatg gctgcgaggt agaatagatc tgatggcgtt atgatggtta atttgtcata   2280
ctcttgcggt ctatgggtcc ctttaggtca tcaatttaat tttgggtggt tgagatcggt   2340
gatccatggt tagtacccta gtcagtgggg ttggatccgt gctattaggg ttcgtagatg   2400
```

```
gattctgatg gctcagtaac tgggaatcct aggatggttc catctggttt gcagatgaga   2460
acgatttcat catctgctat atcttgtttc gttgcgtagg ttctgtttaa actaatccgt   2520
ggtatgatgt tagcctttga taaggttgat ttcatcatct gctatatctt gtttcgttgc   2580
gtaggttctg tttaaactaa tccgtggtat gatgttagcc tttgataagg tttgattgtg   2640
ctagctacgt cctgtgcagc agttaattgt caggtcatac gtcataattt ttagcatgtc   2700
tgtttttgtt tgatttcgtt gtctgattag gctgtagata gtttcgatct acctgtcggt   2760
ttattttatt aaaatttgga tccgtatgtg tgtcacatat atcttcatga ttaagatgga   2820
gttatatggg taggttatac atgtggctgt ggatcatgat taagatggat tgaagtatct   2880
ctttatcttt tagttaggat agattattat atatgttgct gttgatttta ttggttcttt   2940
attatatata ttcatgctta tatacataaa agcaatgtgc tattacagtt taatagttct   3000
tgattatcta ataaacaaat aaggataggt atatttgttg ctgttggttt tactggtact   3060
ctattagata gtactttgac atgaagcaac atcctgctat ggattaataa ttattcttcg   3120
tctaataaaa agcatggttt ttaattattt tgatttgata tacttggatg atgtcatatg   3180
cagcagctat ttgtgaattt ttcggccgta tcttcatatt gcttgggact gtttctttgg   3240
ttgataactc accctgttgt ttggtgatcc ttctgcaggt g                        3281
```

<210> SEQ ID NO 83
<211> LENGTH: 2033
<212> TYPE: DNA
<213> ORGANISM: Schizachyium scoparium

<400> SEQUENCE: 83

```
gtggacgtta atcggtaatt cttcatttta ttttattttg ttgtcaccgc gtacatttgg     60
gttaggcgtt tgttaaaggc attgccactc aaacaagcag ccgcgtttgg agcttttata    120
gtttgaaaag tgacggttgt aaagatgagt aagctgatta ttagtagagt aaattataat    180
tatcatacaa caactctcaa agtgggtgca cgttagtcca acatcttata atttatccaa    240
ctcaatacaa caactatata ggtgggtgca tgttggtcca acatcttcta atttgtttaa    300
tttgatacga gaacttgtct tattggtaca tatatgatcc aaagcattgt aacaacgtgt    360
ttatgtatac tcttaatcat ggtcatcaga agctaacaca cacgctcatg ccatccatat    420
cattcaactt ttgaatcgtt tactatacaa tattatttct aaatttggct gtaaagatgg    480
cattgatttc ataaatatga aaaataccaa attgcacatt ttctttctat attataatat    540
tgttttcatc tattttcacc ccgtaacctt taatttggtc atttagggct cactaaaact    600
gatatgtggg ttgtgcatcg cataagaatc aagaacccag aagtaatttt caatactaag    660
aaacaacaaa atttggtttt tttttgtttg gtttcgatta tagccgaact aaccaaattt    720
aagaaagctt tttatatttg gccacataag aaatgatatc atttaatatt gtaactgatt    780
caagctgagt aatagatgag atgagtgtgt taggatgtgt agcttccgat gatagagaat    840
tagagtgtac aaagacgcat cgttacaata tttggacctt atatgcacca atgtgtcaag    900
tctcgcttca aattaactat attaaaagat gttggatcaa catgcactca cttagatatc    960
agtcgtatta aattgaacaa attacaagat attggactat gcacccactc aaatagttgt   1020
tatatagtga atacagttta ctcttagtag tatatgtaag ttcagccttt tctattgtag   1080
gttaagcctt aattaaggct cttacacaat tgtttcatta ttcgcgttcg aagcagcttc   1140
ttcgtagatt ttgcgaggga aggctgcctc ggttttgcct tccctagcac tcatgtgaga   1200
gcctctggca ataggtcttc tcatttttat tcacattctt taagagccca tataagcgtt   1260
```

-continued

```
catgacttgt atatactctt agatcttttt tttgtgggta aagctcaagc taatctaaaa   1320
atagagaaat caggaacaaa gaatcatgtt ttggtggttt tgatttctag cctccacaat   1380
aattttagtt taccttttt  tgtttgattt taattttaga agggtttata gcaggactta   1440
aaatccaaaa tgaccattat cttcgagtaa taacccgttt aacggcgtcg acaagtctaa   1500
cggacaccaa cccatgaacc accagcgccg agccaagaac tgaaggtcga gacgttgaca   1560
cctttggcgc gacacggcat gttggcatct ccctctctgg ccccctctcg agaattccgc   1620
tccaccgcct caaccggaga cggtttccaa agttgtgctt agatgctcaa aagttggtga   1680
aatcattttt atttggcaat ttgtgtccaa ctatagacta attaggctca aaagatttgt   1740
ctcgtaaagt acattcaaac tgtgtaatta gttattttat ttatctacat ttaatactct   1800
atgaatgcgt caagagattt gatgtgactt taatgtgacg gacaatctga aacttttacg   1860
caacttgcat ataaacagag cccaagtccg ttccgttccg ttccgcttcc tcctcccaga   1920
cggcacgaaa ccgtgacggc accggcagca cggggattcc tttcccaccg ctccttcctt   1980
ttcccttcat cgcccgcagc tataaatagc cacccccgtc cgcaacttct ttc          2033
```

<210> SEQ ID NO 84
<211> LENGTH: 2294
<212> TYPE: DNA
<213> ORGANISM: Schizachyium scoparium

<400> SEQUENCE: 84

```
gatattggac tatgcaccca ctcaaatagt tgttatatag tgaatacagt ttactcttag     60
tagtatatgt aagttcagcc ttttctattg taggttaagc cttaattaag gctcttacac    120
aattgtttca ttattcgcgt tcgaagcagc ttcttcgtag attttgcgag ggaaggctgc    180
ctcggttttg ccttccctag cactcatgtg agagcctctg gcaataggtc ttctcatttt    240
tattcacatt ctttaagagc ccatataagc gttcatgact tgtatatact cttagatctt    300
tttttgtgg  gtaaagctca agctaatcta aaaatagaga aatcaggaac aaagaatcat    360
gttttggtgg ttttgatttc tagcctccac aataatttta gtttaccttt ttttgtttga    420
ttttaatttt agaagggttt atagcaggac ttaaaatcca aaatgaccat tatcttcgag    480
taataacccg tttaacggcg tcgacaagtc taacggacac caacccatga accaccagcg    540
ccgagccaag aactgaaggt cgagacgttg acacctttgg cgcgacacgg catgttggca    600
tctccctctc tggccccctc tcgagaattc cgctccaccg cctcaaccgg agacggtttc    660
caaagttgtg cttagatgct caaaagttgg tgaaatcatt tttatttggc aatttgtgtc    720
caactataga ctaattaggc tcaaaagatt tgtctcgtaa agtacattca aactgtgtaa    780
ttagttattt tatttatcta catttaatac tctatgaatg cgtcaagaga tttgatgtga    840
ctttaatgtg acggacaatc tgaaactttt acgcaacttg catataaaca gagcccaagt    900
ccgttccgtt ccgttccgct tcctcctccc agacggcacg aaaccgtgac ggcaccggca    960
gcacggggat tcctttccca ccgctccttc cttttccctt catcgcccgc agctataaat   1020
agccaccccc gtccgcaact tctttcccca acctcatctt ttgttcggag cacgcacaca   1080
atccgatcga tccccaatcc cctcgtctct cctcgcgagc ctcgtcgatc cgccattcaa   1140
ggtacggcga tcatcctccc tccctctcta cctgctcttc tgtagatcgg cgaccccatc   1200
catggttagg gcctgctagt tctgttcctg ttttttttcc atggctgcga ggtagaatag   1260
atctgatggc gttatgatgg ttaatttgtc atactcttgc ggtctatggg tccctttagg   1320
```

-continued

```
tcatcaattt aattttgggt ggttgagatc ggtgatccat ggttagtacc ctagtcagtg   1380
gggttggatc cgtgctatta gggttcgtag atggattctg atggctcagt aactgggaat   1440
cctaggatgg ttccatctgg tttgcagatg agaacgattt catcatctgc tatatcttgt   1500
ttcgttgcgt aggttctgtt taaactaatc cgtggtatga tgttagcctt tgataaggtt   1560
gatttcatca tctgctatat cttgtttcgt tgcgtaggtt ctgtttaaac taatccgtgg   1620
tatgatgtta gcctttgata aggtttgatt gtgctagcta cgtcctgtgc agcagttaat   1680
tgtcaggtca tacgtcataa tttttagcat gtctgttttt gtttgatttc gttgtctgat   1740
taggctgtag atagtttcga tctacctgtc ggtttatttt attaaaattt ggatccgtat   1800
gtgtgtcaca tatatcttca tgattaagat ggagttatat gggtaggtta tacatgtggc   1860
tgtggatcat gattaagatg gattgaagta tctctttatc ttttagttag gatagattat   1920
tatatatgtt gctgttgatt ttattggttc tttattatat atattcatgc ttatatacat   1980
aaaagcaatg tgctattaca gtttaatagt tcttgattat ctaataaaca aataaggata   2040
ggtatatttg ttgctgttgg ttttactggt actctattag atagtacttt gacatgaagc   2100
aacatcctgc tatggattaa taattattct tcgtctaata aaaagcatgg tttttaatta   2160
ttttgatttg atatacttgg atgatgtcat atgcagcagc tatttgtgaa tttttcggcc   2220
gtatcttcat attgcttggg actgtttctt tggttgataa ctcaccctgt tgtttggtga   2280
tccttctgca ggtg                                                     2294
```

<210> SEQ ID NO 85
<211> LENGTH: 1046
<212> TYPE: DNA
<213> ORGANISM: Schizachyium scoparium

<400> SEQUENCE: 85

```
gatattggac tatgcaccca ctcaaatagt tgttatatag tgaatacagt ttactcttag     60
tagtatatgt aagttcagcc ttttctattg taggttaagc cttaattaag gctcttacac    120
aattgtttca ttattcgcgt tcgaagcagc ttcttcgtag attttgcgag ggaaggctgc    180
ctcggttttg ccttccctag cactcatgtg agagcctctg gcaataggtc ttctcatttt    240
tattcacatt ctttaagagc ccatataagc gttcatgact tgtatatact cttagatctt    300
ttttttgtgg gtaaagctca agctaatcta aaaatagaga aatcaggaac aaagaatcat    360
gttttggtgg ttttgatttc tagcctccac aataatttta gtttaccttt ttttgtttga    420
ttttaatttt agaagggttt atagcaggac ttaaaatcca aaatgaccat tatcttcgag    480
taataacccg tttaacggcg tcgacaagtc taacggacac caacccatga accaccagcg    540
ccgagccaag aactgaaggt cgagacgttg acacctttgg cgcgacacgg catgttggca    600
tctccctctc tggccccctc tcgagaattc cgctccaccg cctcaaccgg agacggtttc    660
caaagttgtg cttagatgct caaaagttgg tgaaatcatt tttatttggc aatttgtgtc    720
caactataga ctaattaggc tcaaaagatt tgtctcgtaa agtacattca aactgtgtaa    780
ttagttattt tatttatcta catttaatac tctatgaatg cgtcaagaga tttgatgtga    840
ctttaatgtg acggacaatc tgaaactttt acgcaacttg catataaaca gagcccaagt    900
ccgttccgtt ccgttccgct tcctcctccc agacggcacg aaaccgtgac ggcaccggca    960
gcacggggat tcctttccca ccgctccttc cttttccctt catcgcccgc agctataaat   1020
agccaccccc gtccgcaact tctttc                                        1046
```

<210> SEQ ID NO 86
<211> LENGTH: 1795
<212> TYPE: DNA
<213> ORGANISM: Schizachyium scoparium

<400> SEQUENCE: 86
gtcgacaagt ctaacggaca ccaacccatg aaccaccagc gccgagccaa gaactgaagg 60
tcgagacgtt gacacctttg gcgcgacacg gcatgttggc atctccctct ctggcccccct 120 ctcgagaatt ccgctccacc gcctcaaccg gagacggttt ccaaagttgt gcttagatgc 180
tcaaaagttg gtgaaatcat ttttatttgg caatttgtgt ccaactatag actaattagg 240
ctcaaaagat ttgtctcgta aagtacattc aaactgtgta attagttatt ttatttatct 300
acatttaata ctctatgaat gcgtcaagag atttgatgtg actttaatgt gacggacaat 360
ctgaaacttt tacgcaactt gcatataaac agagcccaag tccgttccgt tccgttccgc 420
ttcctcctcc cagacggcac gaaaccgtga cggcaccggc agcacgggga ttcctttccc 480
accgctcctt cctttccct tcatcgcccg cagctataaa tagccacccc cgtccgcaac 540
ttctttcccc aacctcatct tttgttcgga gcacgcacac aatccgatcg atccccaatc 600
ccctcgtctc tcctcgcgag cctcgtcgat ccgccattca aggtacggcg atcatcctcc 660
ctccctctct acctgctctt ctgtagatcg gcgaccccat ccatggttag ggcctgctag 720
ttctgttcct gttttttttc catggctgcg aggtagaata gatctgatgg cgttatgatg 780
gttaatttgt catactcttg cggtctatgg gtccctttag gtcatcaatt taattttggg 840
tggttgagat cggtgatcca tggttagtac cctagtcagt ggggttggat ccgtgctatt 900
agggttcgta gatggattct gatggctcag taactgggaa tcctaggatg gttccatctg 960
gtttgcagat gagaacgatt tcatcatctg ctatatcttg tttcgttgcg taggttctgt 1020
ttaaactaat ccgtggtatg atgttagcct ttgataaggt tgatttcatc atctgctata 1080
tcttgtttcg ttgcgtaggt tctgtttaaa ctaatccgtg gtatgatgtt agcctttgat 1140
aaggtttgat tgtgctagct acgtcctgtg cagcagttaa ttgtcaggtc atacgtcata 1200
atttttagca tgtctgtttt tgtttgattt cgttgtctga ttaggctgta gatagtttcg 1260
atctacctgt cggtttattt tattaaaatt tggatccgta tgtgtgtcac atatatcttc 1320
atgattaaga tggagttata tgggtaggtt atacatgtgg ctgtggatca tgattaagat 1380
ggattgaagt atctctttat cttttagtta ggatagatta ttatatatgt tgctgttgat 1440
tttattggtt ctttattata tatattcatg cttatataca taaaagcaat gtgctattac 1500
agtttaatag ttcttgatta tctaataaac aaataaggat aggtatattt gttgctgttg 1560
gttttactgg tactctatta gatagtactt tgacatgaag caacatcctg ctatggatta 1620
ataattattc ttcgtctaat aaaaagcatg gtttttaatt attttgattt gatatacttg 1680
gatgatgtca tatgcagcag ctatttgtga atttttcggc cgtatcttca tattgcttgg 1740
gactgtttct ttggttgata actcaccctg ttgtttggtg atccttctgc aggtg 1795

<210> SEQ ID NO 87
<211> LENGTH: 547
<212> TYPE: DNA
<213> ORGANISM: Schizachyium scoparium

<400> SEQUENCE: 87
gtcgacaagt ctaacggaca ccaacccatg aaccaccagc gccgagccaa gaactgaagg 60
tcgagacgtt gacacctttg gcgcgacacg gcatgttggc atctccctct ctggcccccct 120

-continued

```
ctcgagaatt ccgctccacc gcctcaaccg gagacggttt ccaaagttgt gcttagatgc    180

tcaaaagttg gtgaaatcat ttttatttgg caatttgtgt ccaactatag actaattagg    240

ctcaaaagat ttgtctcgta aagtacattc aaactgtgta attagttatt ttatttatct    300

acatttaata ctctatgaat gcgtcaagag atttgatgtg actttaatgt gacggacaat    360

ctgaaacttt tacgcaactt gcatataaac agagcccaag tccgttccgt tccgttccgc    420

ttcctcctcc cagacggcac gaaaccgtga cggcaccggc agcacgggga ttcctttccc    480

accgctcctt ccttttccct tcatcgcccg cagctataaa tagccacccc cgtccgcaac    540

ttctttc                                                              547
```

```
<210> SEQ ID NO 88
<211> LENGTH: 3357
<212> TYPE: DNA
<213> ORGANISM: Sorghastrum nutans

<400> SEQUENCE: 88
```

```
gtggccagct tttgttctag ttcaacggtc cgggccttcc gggaacctaa tgcactaatt     60

gattattatt aatctactat tgcagctaac ctcaaaagaa atgctctgca gttagttgtc    120

cgtcccaatc aatccaccag cagactcaca ttattgatgg aggaaattaa attcagcctt    180

tgacgtggat gcaacaactg cacaagatac catctacttt gcttaatttg ctgatgtttt    240

gagaaaatta aaccagcttt gaccaacaca tgagatgggc gccttacgtt tggcacaatg    300

taatgtagtc cggcacggca agttagactc tgtgtgtagt gttatattag ccggcctctt    360

taggtttggc acaatttaat tgaatccggc atggcaagtt agactgcagt gtgagccggt    420

caccgcaagt taggatataa tatacaagag caagtataca ataaagtgac attagcgtaa    480

agttatatga catatggaat ataagagaaa atacggagta tataataagg tgaactgtat    540

agcgatcaaa tttatgctaa gcgaagaaaa gagaagataa ataggttgaa aacttatagt    600

gagctttggc tcataatcta aataattatg agagagtggg atcgaccaca tattcatttt    660

gtagtacgta ctctctccgt tttttataag ttgctttgat ttttttttat atcaattttg    720

ctatacatct aaacataata ggaatatcaa gttcatgaag gtcgtgattt gcactaaata    780

tgttccctta ttagatagac gagttgttta gttttattgt agatgatata gcgcttgcat    840

atagcatgtg aaccggctaa attattagcc atacacgact ataaaaaatg acattccttt    900

gaggaacttt tatgcaacca aatagtcaac ttcaatgttg ctagagcggg ctttaagcca    960

aaagcagctg ctgctttgtt tccgagagaa gggacattct agttgatagc aaaacaaata   1020

cgtagcagtt gtagcgagtg tgtgagtaat aatttttctc tagtgtgtac gagtatgcga   1080

gtaataattt taaatctcta gaaggaagaa aaataatatt gctacctact ttgaggatat   1140

caataccttt ctctaaaatg ttttggtgaa gccatcttta aagctaattg ttcaagattc   1200

aaccattggg acgtctcaaa tgattagatc ctataatact cctacgtact aaattataag   1260

tcgttttgat tttattggta catacatttt gctatgtgtt tagatataat aatatgtcta   1320

gatacattgg atgaaccgaa aaaatcgaaa cgacttataa tttggatcga aaggagtatt   1380

tgctaaagtc cttttcgaag ttccggctct aaatttttgg ataaaatttt atgaaatact   1440

atcttaagaa gtaatttgac tagagaagct tgaagagtat aatctcttaa ttttgtgcta   1500

caggagtgaa gccaacgtcg tatttagatc tagatgctgt caggtagtga ggacggaggg   1560

agtattggat aaagtcattc caagatctta gaaaattaaa gtatattaag tttgattaaa   1620

tttatatgac aagtaataac attcatgatg ccaattaagt atcattagat tcttcatcaa   1680
```

ctatattttc atagtatact tatttaatgt tataaatttt tataattttt tttataattt 1740
tagctaaact cgagatcgat tcttataatt aaaaataaac tgaaaaaaaa tcacatgttc 1800
aagtgacagg aggagccagt ttaacggcgt cgacaagtct aacggacacc aaccagcgaa 1860
ccaccagcgc cgagccaatc ccaagcgaag ccgactgcag acggccgaga cgttgacacc 1920
tttggcgcgg catccatctc tccggccccc tcttgagagt tccgccccac cggcggcggt 1980
ttccaagtcc gttccgcccg ccttcgcggt tggacttgtt ccggtggcgc ctggcggatc 2040
gcgtggcgga gcggagacga cgaggtgagc cgtgggcgtt cctcctcctg ctcctctcac 2100
acggcacgga acggaaccgt gacggcaccg ggcagcacgg gcgggattcc ttccccacct 2160
ctccttcggt cctccctcca tcataaatag ccaccccccct cccaccttct ttccccacct 2220
cgtctcccct cgtgttattc ggagcacaga cacaccccga tccccaatcc tctcctcgcg 2280
agcctcgtcg atccccgctt caaggtacgg cgatcatcct ccctccctaa ctccaatccg 2340
tggttagggc ctgctagatc gtcctccctc cctacctgcg atccgtggtt cgcgcctgct 2400
agttctgttt cctgtttgtc gatggctgcg aggtataaata gatctgatgg cgtgcggtgt 2460
gacggttaaa ttcacatgct cttgcgattt atacgcgaat cgatctggga ttgctcgaga 2520
tcggtgatcc atggttagaa ccctaggcgg tggagtcggg ttaaatccgt gctgttaggg 2580
ttcgtaggtg gatgcgacct gttctggttg tttacttgtc agtatttagg aatcctacta 2640
ggatggttct agctggttcg cagatgagat cgatttcatg atctgctata tctttcgttg 2700
cctaagtttc gtttaatctg tccgtggtat gatgttagcc tttgatatgc ttcgatcgtg 2760
ctagctacct cctgtgcact aaattatcag ctcgtaattt ttagcatgcc cttttttttt 2820
tgggtattgt tcgattgagg tgtcgttcta gatcagagta ggaagactgt ttcaaactac 2880
ctgctggatt tattaaattt ggatctgtat gagtatcaca tatatctcca taatttagat 2940
ggatggaaat atcccttttt cttttagata ctgtttggta tagattttgc tgtgggtttt 3000
actggtactt agatactctt cgtttagata tggatatgtt tacatgcaga tacatgaagc 3060
aacatgctgc tacagtttaa tatggatagg tgtatatgtt gttgtgggtc ctttacttac 3120
atgcttagat acatgaagca acatgctgct acgtttaata attattgttt atctgatctg 3180
atttaaacaa acatgctttt taattgtcct gaaatgcttg gatgatggca tatgcagcag 3240
ctatgtgtgg attttaaata cccagcatga gcatgcatga ccctaactta gtatgctgtt 3300
tatttgcttg acttttcttt tgttgatact caccctttttg tttgttgact cttgcag 3357

<210> SEQ ID NO 89
<211> LENGTH: 2218
<212> TYPE: DNA
<213> ORGANISM: Sorghastrum nutans

<400> SEQUENCE: 89
gtggccagct tttgttctag ttcaacggtc cgggccttcc gggaacctaa tgcactaatt 60
gattattatt aatctactat tgcagctaac ctcaaaagaa atgctctgca gttagttgtc 120
cgtcccaatc aatccaccag cagactcaca ttattgatgg aggaaattaa attcagcctt 180
tgacgtggat gcaacaactg cacaagatac catctacttt gcttaatttg ctgatgtttt 240
gagaaaatta aaccagcttt gaccaacaca tgagatgggc gccttacgtt tggcacaatg 300
taatgtagtc cggcacggca agttagactc tgtgtgtagt gttatattag ccggcctctt 360
taggtttggc acaatttaat tgaatccggc atggcaagtt agactgcagt gtgagccggt 420

```
caccgcaagt taggatataa tatacaagag caagtataca ataaagtgac attagcgtaa    480

agttatatga catatggaat ataagagaaa atacggagta tataataagg tgaactgtat    540

agcgatcaaa tttatgctaa gcgaagaaaa gagaagataa ataggttgaa aacttatagt    600

gagctttggc tcataatcta aataattatg agagagtggg atcgaccaca tattcatttt    660

gtagtacgta ctctctccgt tttttataag ttgctttgat ttttttttat atcaattttg    720

ctatacatct aaacataata ggaatatcaa gttcatgaag gtcgtgattt gcactaaata    780

tgttccctta ttagatagac gagttgttta gttttattgt agatgatata gcgcttgcat    840

atagcatgtg aaccggctaa attattagcc atacacgact ataaaaaatg acattccttt    900

gaggaacttt tatgcaacca aatagtcaac ttcaatgttg ctagagcggg ctttaagcca    960

aaagcagctg ctgctttgtt tccgagagaa gggacattct agttgatagc aaaacaaata   1020

cgtagcagtt gtagcgagtg tgtgagtaat aatttttctc tagtgtgtac gagtatgcga   1080

gtaataattt taaatctcta gaaggaagaa aaataatatt gctacctact ttgaggatat   1140

caataccttt ctctaaaatg ttttggtgaa gccatcttta aagctaattg ttcaagattc   1200

aaccattggg acgtctcaaa tgattagatc ctataatact cctacgtact aaattataag   1260

tcgttttgat tttattggta catacatttt gctatgtgtt tagatataat aatatgtcta   1320

gatacattgg atgaaccgaa aaaatcgaaa cgacttataa tttggatcga aaggagtatt   1380

tgctaaagtc cttttcgaag ttccggctct aaatttttgg ataaaatttt atgaaatact   1440

atcttaagaa gtaatttgac tagagaagct tgaagagtat aatctcttaa ttttgtgcta   1500

caggagtgaa gccaacgtcg tatttagatc tagatgctgt caggtagtga ggacggaggg   1560

agtattggat aaagtcattc caagatctta gaaaattaaa gtatattaag tttgattaaa   1620

tttatatgac aagtaataac attcatgatg ccaattaagt atcattagat tcttcatcaa   1680

ctatattttc atagtatact tatttaatgt tataaatttt tataattttt tttataattt   1740

tagctaaact cgagatcgat tcttataatt aaaaataaac tgaaaaaaaa tcacatgttc   1800

aagtgacagg aggagccagt ttaacggcgt cgacaagtct aacggacacc aaccagcgaa   1860

ccaccagcgc cgagccaatc ccaagcgaag ccgactgcag acggccgaga cgttgacacc   1920

tttggcgcgg catccatctc tccggccccc tcttgagagt tccgccccac cggcggcggt   1980

ttccaagtcc gttccgcccg ccttcgcggt tggacttgtt ccggtggcgc ctggcggatc   2040

gcgtggcgga gcggagacga cgaggtgagc cgtgggcgtt cctcctcctg ctcctctcac   2100

acggcacgga acggaaccgt gacggcaccg ggcagcacgg gcgggattcc ttccccacct   2160

ctccttcggt cctccctcca tcataaatag ccaccccccct cccaccttct ttccccac    2218
```

<210> SEQ ID NO 90
<211> LENGTH: 86
<212> TYPE: DNA
<213> ORGANISM: Sorghastrum nutans

<400> SEQUENCE: 90

```
ctcgtctccc ctcgtgttat tcggagcaca gacacacccc gatccccaat cctctcctcg     60

cgagcctcgt cgatccccgc ttcaag                                          86
```

<210> SEQ ID NO 91
<211> LENGTH: 1053
<212> TYPE: DNA
<213> ORGANISM: Sorghastrum nutans

<400> SEQUENCE: 91

```
gtacggcgat catcctccct ccctaactcc aatccgtggt tagggcctgc tagatcgtcc      60
tccctcccta cctgcgatcc gtggttcgcg cctgctagtt ctgtttcctg tttgtcgatg     120
gctgcgaggt ataatagatc tgatggcgtg cggtgtgacg gttaaattca catgctcttg     180
cgatttatac gcgaatcgat ctgggattgc tcgagatcgg tgatccatgg ttagaaccct     240
aggcggtgga gtcgggttaa atccgtgctg ttagggttcg taggtggatg cgacctgttc     300
tggttgttta cttgtcagta tttaggaatc ctactaggat ggttctagct ggttcgcaga     360
tgagatcgat ttcatgatct gctatatctt tcgttgccta agtttcgttt aatctgtccg     420
tggtatgatg ttagcctttg atatgcttcg atcgtgctag ctacctcctg tgcactaaat     480
tatcagctcg taatttttag catgcccttt tttttttggg tattgttcga ttgaggtgtc     540
gttctagatc agagtaggaa gactgtttca aactacctgc tggatttatt aaatttggat     600
ctgtatgagt atcacatata tctccataat ttagatggat ggaaatatcc ctttttcttt     660
tagatactgt ttggtataga ttttgctgtg ggttttactg gtacttagat actcttcgtt     720
tagatatgga tatgtttaca tgcagataca tgaagcaaca tgctgctaca gtttaatatg     780
gataggtgta tatgttgttg tgggtccttt acttacatgc ttagatacat gaagcaacat     840
gctgctacgt ttaataatta ttgtttatct gatctgattt aaacaaacat gctttttaat     900
tgtcctgaaa tgcttggatg atggcatatg cagcagctat gtgtggattt taaataccca     960
gcatgagcat gcatgaccct aacttagtat gctgtttatt tgcttgactt ttcttttgtt    1020
gatactcacc cttttgtttg ttgactcttg cag                                 1053
```

<210> SEQ ID NO 92
<211> LENGTH: 3106
<212> TYPE: DNA
<213> ORGANISM: Sorghastrum nutans

<400> SEQUENCE: 92

```
agctttgacc aacacatgag atgggcgcct tacgtttggc acaatgtaat gtagtccggc      60
acggcaagtt agactctgtg tgtagtgtta tattagccgg cctctttagg tttggcacaa     120
tttaattgaa tccggcatgg caagttagac tgcagtgtga gccggtcacc gcaagttagg     180
atataatata caagagcaag tatacaataa agtgacatta gcgtaaagtt atatgacata     240
tggaatataa gagaaaatac ggagtatata ataaggtgaa ctgtatagcg atcaaattta     300
tgctaagcga agaaaagaga agataaatag gttgaaaact tatagtgagc tttggctcat     360
aatctaaata attatgagag agtgggatcg accacatatt cattttgtag tacgtactct     420
ctccgttttt tataagttgc tttgattttt ttttatatca attttgctat acatctaaac     480
ataataggaa tatcaagttc atgaaggtcg tgatttgcac taaatatgtt cccttattag     540
atagacgagt tgtttagttt tattgtagat gatatagcgc ttgcatatag catgtgaacc     600
ggctaaatta ttagccatac acgactataa aaaatgacat tcctttgagg aacttttatg     660
caaccaaata gtcaacttca atgttgctag agcgggcttt aagccaaaag cagctgctgc     720
tttgtttccg agagaaggga cattctagtt gatagcaaaa caaatacgta gcagttgtag     780
cgagtgtgtg agtaataatt tttctctagt gtgtacgagt atgcgagtaa taattttaaa     840
tctctagaag gaagaaaaat aatattgcta cctactttga ggatatcaat acctttctct     900
aaaatgtttt ggtgaagcca tctttaaagc taattgttca agattcaacc attgggacgt     960
ctcaaatgat tagatcctat aatactccta cgtactaaat tataagtcgt tttgatttta    1020
```

```
ttggtacata cattttgcta tgtgtttaga tataataata tgtctagata cattggatga   1080
accgaaaaaa tcgaaacgac ttataatttg gatcgaaagg agtatttgct aaagtccttt   1140
tcgaagttcc ggctctaaat ttttggataa aattttatga aatactatct taagaagtaa   1200
tttgactaga gaagcttgaa gagtataatc tcttaatttt gtgctacagg agtgaagcca   1260
acgtcgtatt tagatctaga tgctgtcagg tagtgaggac ggagggagta ttggataaag   1320
tcattccaag atcttagaaa attaaagtat attaagtttg attaaattta tatgacaagt   1380
aataacattc atgatgccaa ttaagtatca ttagattctt catcaactat attttcatag   1440
tatacttatt taatgttata aatttttata attttttta taattttagc taaactcgag   1500
atcgattctt ataattaaaa ataaactgaa aaaaaatcac atgttcaagt gacaggagga   1560
gccagtttaa cggcgtcgac aagtctaacg gacaccaacc agcgaaccac cagcgccgag   1620
ccaatcccaa gcgaagccga ctgcagacgg ccgagacgtt gacacctttg gcgcggcatc   1680
catctctccg gccccctctt gagagttccg ccccaccggc ggcggtttcc aagtccgttc   1740
cgcccgcctt cgcggttgga cttgttccgg tggcgcctgg cggatcgcgt ggcggagcgg   1800
agacgacgag gtgagccgtg ggcgttcctc ctcctgctcc tctcacacgg cacggaacgg   1860
aaccgtgacg gcaccgggca gcacgggcgg gattccttcc ccacctctcc ttcggtcctc   1920
cctccatcat aaatagccac ccccctccca ccttctttcc ccacctcgtc tcccctcgtg   1980
ttattcggag cacagacaca ccccgatccc caatcctctc ctcgcgagcc tcgtcgatcc   2040
ccgcttcaag gtacggcgat catcctccct ccctaactcc aatccgtggt tagggcctgc   2100
tagatcgtcc tccctcccta cctgcgatcc gtggttcgcg cctgctagtt ctgtttcctg   2160
tttgtcgatg gctgcgaggt ataatagatc tgatggcgtg cggtgtgacg gttaaattca   2220
catgctcttg cgatttatac gcgaatcgat ctgggattgc tcgagatcgg tgatccatgg   2280
ttagaaccct aggcggtgga gtcgggttaa atccgtgctg ttagggttcg taggtggatg   2340
cgacctgttc tggttgttta cttgtcagta tttaggaatc ctactaggat ggttctagct   2400
ggttcgcaga tgagatcgat ttcatgatct gctatatctt tcgttgccta agtttcgttt   2460
aatctgtccg tggtatgatg ttagcctttg atatgcttcg atcgtgctag ctacctcctg   2520
tgcactaaat tatcagctcg taatttttag catgcccttt tttttttggg tattgttcga   2580
ttgaggtgtc gttctagatc agagtaggaa gactgtttca aactacctgc tggatttatt   2640
aaatttggat ctgtatgagt atcacatata tctccataat ttagatggat ggaaatatcc   2700
ctttttcttt tagatactgt ttggtataga ttttgctgtg ggttttactg gtacttagat   2760
actcttcgtt tagatatgga tatgtttaca tgcagataca tgaagcaaca tgctgctaca   2820
gtttaatatg gataggtgta tatgttgttg tgggtccttt acttacatgc ttagatacat   2880
gaagcaacat gctgctacgt ttaataatta ttgtttatct gatctgattt aaacaaacat   2940
gctttttaat tgtcctgaaa tgcttggatg atggcatatg cagcagctat gtgtggattt   3000
taaataccca gcatgagcat gcatgaccct aacttagtat gctgtttatt tgcttgactt   3060
ttcttttgtt gatactcacc cttttgtttg ttgactcttg caggtg                  3106
```

<210> SEQ ID NO 93
<211> LENGTH: 1964
<212> TYPE: DNA
<213> ORGANISM: Sorghastrum nutans

<400> SEQUENCE: 93

```
agctttgacc aacacatgag atgggcgcct tacgtttggc acaatgtaat gtagtccggc     60
```

acggcaagtt agactctgtg tgtagtgtta tattagccgg cctctttagg tttggcacaa 120
tttaattgaa tccggcatgg caagttagac tgcagtgtga gccggtcacc gcaagttagg 180
atataatata caagagcaag tatacaataa agtgacatta gcgtaaagtt atatgacata 240
tggaatataa gagaaaatac ggagtatata ataaggtgaa ctgtatagcg atcaaattta 300
tgctaagcga agaaaagaga agataaatag gttgaaaact tatagtgagc tttggctcat 360
aatctaaata attatgagag agtgggatcg accacatatt cattttgtag tacgtactct 420
ctccgttttt tataagttgc tttgattttt ttttatatca attttgctat acatctaaac 480
ataataggaa tatcaagttc atgaaggtcg tgatttgcac taaatatgtt cccttattag 540
atagacgagt tgtttagttt tattgtagat gatatagcgc ttgcatatag catgtgaacc 600
ggctaaatta ttagccatac acgactataa aaaatgacat tcctttgagg aacttttatg 660
caaccaaata gtcaacttca atgttgctag agcgggcttt aagccaaaag cagctgctgc 720
tttgtttccg agagaaggga cattctagtt gatagcaaaa caaatacgta gcagttgtag 780
cgagtgtgtg agtaataatt tttctctagt gtgtacgagt atgcgagtaa taattttaaa 840
tctctagaag gaagaaaaat aatattgcta cctactttga ggatatcaat acctttctct 900
aaaatgtttt ggtgaagcca tctttaaagc taattgttca agattcaacc attgggacgt 960
ctcaaatgat tagatcctat aatactccta cgtactaaat tataagtcgt tttgatttta 1020
ttggtacata cattttgcta tgtgtttaga tataataata tgtctagata cattggatga 1080
accgaaaaaa tcgaaacgac ttataatttg gatcgaaagg agtatttgct aaagtccttt 1140
tcgaagttcc ggctctaaat ttttggataa aattttatga aatactatct taagaagtaa 1200
tttgactaga gaagcttgaa gagtataatc tcttaatttt gtgctacagg agtgaagcca 1260
acgtcgtatt tagatctaga tgctgtcagg tagtgaggac ggagggagta ttggataaag 1320
tcattccaag atcttagaaa attaaagtat attaagtttg attaaattta tatgacaagt 1380
aataacattc atgatgccaa ttaagtatca ttagattctt catcaactat attttcatag 1440
tatacttatt taatgttata aatttttata attttttta taattttagc taaactcgag 1500
atcgattctt ataattaaaa ataaactgaa aaaaaatcac atgttcaagt gacaggagga 1560
gccagtttaa cggcgtcgac aagtctaacg gacaccaacc agcgaaccac cagcgccgag 1620
ccaatcccaa gcgaagccga ctgcagacgg ccgagacgtt gacacctttg gcgcggcatc 1680
catctctccg gccccctctt gagagttccg ccccaccggc ggcggtttcc aagtccgttc 1740
cgcccgcctt cgcggttgga cttgttccgg tggcgcctgg cggatcgcgt ggcggagcgg 1800
agacgacgag gtgagccgtg ggcgttcctc ctcctgctcc tctcacacgg cacggaacgg 1860
aaccgtgacg gcaccgggca gcacgggcgg gattccttcc ccacctctcc ttcggtcctc 1920
cctccatcat aaatagccac ccccctccca ccttctttcc ccac 1964

<210> SEQ ID NO 94
<211> LENGTH: 1056
<212> TYPE: DNA
<213> ORGANISM: Sorghastrum nutans

<400> SEQUENCE: 94
gtacggcgat catcctccct ccctaactcc aatccgtggt tagggcctgc tagatcgtcc 60
tccctcccta cctgcgatcc gtggttcgcg cctgctagtt ctgtttcctg tttgtcgatg 120
gctgcgaggt ataatagatc tgatggcgtg cggtgtgacg gttaaattca catgctcttg 180

```
cgatttatac gcgaatcgat ctgggattgc tcgagatcgg tgatccatgg ttagaaccct    240

aggcggtgga gtcgggttaa atccgtgctg ttagggttcg taggtggatg cgacctgttc    300

tggttgttta cttgtcagta tttaggaatc ctactaggat ggttctagct ggttcgcaga    360

tgagatcgat ttcatgatct gctatatctt tcgttgccta agtttcgttt aatctgtccg    420

tggtatgatg ttagcctttg atatgcttcg atcgtgctag ctacctcctg tgcactaaat    480

tatcagctcg taatttttag catgcccttt tttttttggg tattgttcga ttgaggtgtc    540

gttctagatc agagtaggaa gactgtttca aactacctgc tggatttatt aaatttggat    600

ctgtatgagt atcacatata tctccataat ttagatggat ggaaatatcc ctttttcttt    660

tagatactgt ttggtataga ttttgctgtg ggttttactg gtacttagat actcttcgtt    720

tagatatgga tatgtttaca tgcagataca tgaagcaaca tgctgctaca gtttaatatg    780

gataggtgta tatgttgttg tgggtccttt acttacatgc ttagatacat gaagcaacat    840

gctgctacgt ttaataatta ttgtttatct gatctgattt aaacaaacat gctttttaat    900

tgtcctgaaa tgcttggatg atggcatatg cagcagctat gtgtggattt taaataccca    960

gcatgagcat gcatgaccct aacttagtat gctgtttatt tgcttgactt ttcttttgtt   1020

gatactcacc cttttgtttg ttgactcttg caggtg                              1056
```

<210> SEQ ID NO 95
<211> LENGTH: 2165
<212> TYPE: DNA
<213> ORGANISM: Sorghastrum nutans

<400> SEQUENCE: 95

```
gattcaacca ttgggacgtc tcaaatgatt agatcctata atactcctac gtactaaatt     60

ataagtcgtt ttgattttat tggtacatac attttgctat gtgtttagat ataataatat    120

gtctagatac attggatgaa ccgaaaaaat cgaaacgact tataatttgg atcgaaagga    180

gtatttgcta aagtcctttt cgaagttccg gctctaaatt tttggataaa attttatgaa    240

atactatctt aagaagtaat ttgactagag aagcttgaag agtataatct cttaattttg    300

tgctacagga gtgaagccaa cgtcgtattt agatctagat gctgtcaggt agtgaggacg    360

gagggagtat tggataaagt cattccaaga tcttagaaaa ttaaagtata ttaagtttga    420

ttaaatttat atgacaagta ataacattca tgatgccaat taagtatcat tagattcttc    480

atcaactata ttttcatagt atacttattt aatgttataa atttttataa ttttttttat    540

aattttagct aaactcgaga tcgattctta taattaaaaa taaactgaaa aaaaatcaca    600

tgttcaagtg acaggaggag ccagtttaac ggcgtcgaca agtctaacgg acaccaacca    660

gcgaaccacc agcgccgagc caatcccaag cgaagccgac tgcagacggc cgagacgttg    720

acacctttgg cgcggcatcc atctctccgg ccccctcttg agagttccgc cccaccggcg    780

gcggtttcca agtccgttcc gcccgccttc gcggttggac ttgttccggt ggcgcctggc    840

ggatcgcgtg gcggagcgga gacgacgagg tgagccgtgg gcgttcctcc tcctgctcct    900

ctcacacggc acggaacgga accgtgacgg caccgggcag cacgggcggg attccttccc    960

cacctctcct tcggtcctcc ctccatcata aatagccacc cccctcccac cttctttccc   1020

cacctcgtct cccctcgtgt tattcggagc acagacacac cccgatcccc aatcctctcc   1080

tcgcgagcct cgtcgatccc cgcttcaagg tacggcgatc atcctccctc cctaactcca   1140

atccgtggtt agggcctgct agatcgtcct ccctccctac ctgcgatccg tggttcgcgc   1200

ctgctagttc tgtttcctgt ttgtcgatgg ctgcgaggta taatagatct gatggcgtgc   1260
```

ggtgtgacgg ttaaattcac atgctcttgc gatttatacg cgaatcgatc tgggattgct 1320
cgagatcggt gatccatggt tagaacccta ggcggtggag tcgggttaaa tccgtgctgt 1380
tagggttcgt aggtggatgc gacctgttct ggttgtttac ttgtcagtat ttaggaatcc 1440
tactaggatg gttctagctg gttcgcagat gagatcgatt tcatgatctg ctatatcttt 1500
cgttgcctaa gtttcgttta atctgtccgt ggtatgatgt tagcctttga tatgcttcga 1560
tcgtgctagc tacctcctgt gcactaaatt atcagctcgt aatttttagc atgccctttt 1620 tttttgggt attgttcgat tgaggtgtcg ttctagatca gagtaggaag actgtttcaa 1680
actacctgct ggatttatta aatttggatc tgtatgagta tcacatatat ctccataatt 1740
tagatggatg gaaatatccc tttttctttt agatactgtt tggtatagat tttgctgtgg 1800
gttttactgg tacttagata ctcttcgttt agatatggat atgtttacat gcagatacat 1860
gaagcaacat gctgctacag tttaatatgg ataggtgtat atgttgttgt gggtccttta 1920
cttacatgct tagatacatg aagcaacatg ctgctacgtt taataattat tgtttatctg 1980
atctgattta aacaaacatg ctttttaatt gtcctgaaat gcttggatga tggcatatgc 2040
agcagctatg tgtggatttt aaatacccag catgagcatg catgacccta acttagtatg 2100
ctgtttattt gcttgacttt tcttttgttg atactcaccc ttttgtttgt tgactcttgc 2160
aggtg 2165

<210> SEQ ID NO 96
<211> LENGTH: 1023
<212> TYPE: DNA
<213> ORGANISM: Sorghastrum nutans

<400> SEQUENCE: 96
gattcaacca ttgggacgtc tcaaatgatt agatcctata atactcctac gtactaaatt 60
ataagtcgtt ttgattttat tggtacatac attttgctat gtgtttagat ataataatat 120
gtctagatac attggatgaa ccgaaaaaat cgaaacgact tataatttgg atcgaaagga 180
gtatttgcta aagtcctttt cgaagttccg gctctaaatt tttggataaa attttatgaa 240
atactatctt aagaagtaat ttgactagag aagcttgaag agtataatct cttaattttg 300
tgctacagga gtgaagccaa cgtcgtattt agatctagat gctgtcaggt agtgaggacg 360
gagggagtat tggataaagt cattccaaga tcttagaaaa ttaaagtata ttaagtttga 420
ttaaatttat atgacaagta ataacattca tgatgccaat taagtatcat tagattcttc 480
atcaactata ttttcatagt atacttattt aatgttataa atttttataa ttttttttat 540
aattttagct aaactcgaga tcgattctta taattaaaaa taaactgaaa aaaaatcaca 600
tgttcaagtg acaggaggag ccagtttaac ggcgtcgaca agtctaacgg acaccaacca 660
gcgaaccacc agcgccgagc caatcccaag cgaagccgac tgcagacggc cgagacgttg 720
acacctttgg cgcggcatcc atctctccgg ccccctcttg agagttccgc cccaccggcg 780
gcggtttcca agtccgttcc gcccgccttc gcggttggac ttgttccggt ggcgcctggc 840
ggatcgcgtg gcggagcgga gacgacgagg tgagccgtgg gcgttcctcc tcctgctcct 900
ctcacacggc acggaacgga accgtgacgg caccgggcag cacgggcggg attccttccc 960
cacctctcct tcggtcctcc ctccatcata aatagccacc cccctcccac cttctttccc 1020
cac 1023

<210> SEQ ID NO 97

<211> LENGTH: 1866
<212> TYPE: DNA
<213> ORGANISM: Sorghastrum nutans

<400> SEQUENCE: 97
gtgctacagg agtgaagcca acgtcgtatt tagatctaga tgctgtcagg tagtgaggac 60
ggagggagta ttggataaag tcattccaag atcttagaaa attaaagtat attaagtttg 120
attaaattta tatgacaagt aataacattc atgatgccaa ttaagtatca ttagattctt 180
catcaactat attttcatag tatacttatt taatgttata aatttttata atttttttta 240
taattttagc taaactcgag atcgattctt ataattaaaa ataaactgaa aaaaaatcac 300
atgttcaagt gacaggagga gccagtttaa cggcgtcgac aagtctaacg gacaccaacc 360
agcgaaccac cagcgccgag ccaatcccaa gcgaagccga ctgcagacgg ccgagacgtt 420
gacacctttg gcgcggcatc catctctccg gccccctctt gagagttccg ccccaccggc 480
ggcggtttcc aagtccgttc cgcccgcctt cgcggttgga cttgttccgg tggcgcctgg 540
cggatcgcgt ggcggagcgg agacgacgag gtgagccgtg ggcgttcctc ctcctgctcc 600
tctcacacgg cacggaacgg aaccgtgacg gcaccgggca gcacgggcgg gattccttcc 660
ccacctctcc ttcggtcctc cctccatcat aaatagccac ccccctccca ccttctttcc 720
ccacctcgtc tcccctcgtg ttattcggag cacagacaca ccccgatccc caatcctctc 780
ctcgcgagcc tcgtcgatcc ccgcttcaag gtacggcgat catcctccct ccctaactcc 840
aatccgtggt tagggcctgc tagatcgtcc tccctcccta cctgcgatcc gtggttcgcg 900
cctgctagtt ctgtttcctg tttgtcgatg gctgcgaggt ataatagatc tgatggcgtg 960
cggtgtgacg gttaaattca catgctcttg cgatttatac gcgaatcgat ctgggattgc 1020
tcgagatcgg tgatccatgg ttagaaccct aggcggtgga gtcgggttaa atccgtgctg 1080
ttagggttcg taggtggatg cgacctgttc tggttgttta cttgtcagta tttaggaatc 1140
ctactaggat ggttctagct ggttcgcaga tgagatcgat ttcatgatct gctatatctt 1200
tcgttgccta agtttcgttt aatctgtccg tggtatgatg ttagcctttg atatgcttcg 1260
atcgtgctag ctacctcctg tgcactaaat tatcagctcg taatttttag catgcccttt 1320
ttttttgggg tattgttcga ttgaggtgtc gttctagatc agagtaggaa gactgtttca 1380
aactacctgc tggatttatt aaatttggat ctgtatgagt atcacatata tctccataat 1440
ttagatggat ggaaatatcc ctttttcttt tagatactgt ttggtataga ttttgctgtg 1500
ggttttactg gtacttagat actcttcgtt tagatatgga tatgtttaca tgcagataca 1560
tgaagcaaca tgctgctaca gtttaatatg gataggtgta tatgttgttg tgggtccttt 1620
acttacatgc ttagatacat gaagcaacat gctgctacgt ttaataatta ttgtttatct 1680
gatctgattt aaacaaacat gctttttaat tgtcctgaaa tgcttggatg atggcatatg 1740
cagcagctat gtgtggattt taaataccca gcatgagcat gcatgaccct aacttagtat 1800
gctgtttatt tgcttgactt ttcttttgtt gatactcacc cttttgtttg ttgactcttg 1860
caggtg 1866

<210> SEQ ID NO 98
<211> LENGTH: 724
<212> TYPE: DNA
<213> ORGANISM: Sorghastrum nutans

<400> SEQUENCE: 98
gtgctacagg agtgaagcca acgtcgtatt tagatctaga tgctgtcagg tagtgaggac 60
ggagggagta ttggataaag tcattccaag atcttagaaa attaaagtat attaagtttg 120
attaaattta tatgacaagt aataacattc atgatgccaa ttaagtatca ttagattctt 180
catcaactat attttcatag tatacttatt taatgttata aatttttata attttttta 240 taattttagc taaactcgag atcgattctt ataattaaaa ataaactgaa aaaaaatcac 300
atgttcaagt gacaggagga gccagtttaa cggcgtcgac aagtctaacg gacaccaacc 360
agcgaaccac cagcgccgag ccaatcccaa gcgaagccga ctgcagacgg ccgagacgtt 420
gacacctttg gcgcggcatc catctctccg gccccctctt gagagttccg ccccaccggc 480
ggcggtttcc aagtccgttc cgcccgcctt cgcggttgga cttgttccgg tggcgcctgg 540
cggatcgcgt ggcggagcgg agacgacgag gtgagccgtg ggcgttcctc ctcctgctcc 600
tctcacacgg cacggaacgg aaccgtgacg gcaccgggca gcacgggcgg gattccttcc 660
ccacctctcc ttcggtcctc cctccatcat aaatagccac ccccctccca ccttctttcc 720
ccac 724

<210> SEQ ID NO 99
<211> LENGTH: 2625
<212> TYPE: DNA
<213> ORGANISM: Setaria italica

<400> SEQUENCE: 99
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220
gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac agggt 2625

<210> SEQ ID NO 100
<211> LENGTH: 1492
<212> TYPE: DNA
<213> ORGANISM: Setaria italica

<400> SEQUENCE: 100
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ccgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900

```
ggttaacgcc agaaacagtg tttggccagg gtatgaacat aacaaaaaat attcacacga    960

aagaatggaa gtatggagct gctactgtgt aaatgccaag caggaaactc acgcccgcta   1020

acatccaacg gccaacagct cgacgtgccg gtcagcagag catcggaaca ctggtgattg   1080

gtggagccgg cagtatgcgc cccagcacgg ccgaggtggt ggtggcccgt ggccctgctg   1140

tctgcgcggc tcgggacaac ttgaaactgg gccaccgcct cgtcgcaact cgcaacccgt   1200

tggcggaaga aaggaatggc tcgtaggggc ccgggtagaa tcgaagaatg ttgcgctggg   1260

cttcgattca cataacatgg gcctgaagct ctaaaacgac ggcccggtcg ccgcgcgatg   1320

gaaagagacc ggatcctcct cgtgaattct ggaaggccac acgagagcga cccaccaccg   1380

acgcggagga gtcgtgcgtg gtccaacacg gccggcgggc tgggctgcga ccttaaccag   1440

caaggcacgc cacgacccgc cccgccctcg aggcataaat accctcccat cc           1492
```

```
<210> SEQ ID NO 101
<211> LENGTH: 127
<212> TYPE: DNA
<213> ORGANISM: Setaria italica

<400> SEQUENCE: 101

cgttgccgca agactcagat cagattccga tccccagttc ttccccaatc accttgtggt     60

ctctcgtgtc gcggttccca gggacgcctc cggctcgtcg ctcgacagcg atctccgccc    120

cagcaag                                                              127
```

```
<210> SEQ ID NO 102
<211> LENGTH: 1006
<212> TYPE: DNA
<213> ORGANISM: Setaria italica

<400> SEQUENCE: 102

gtatagattc agttccttgc tccgatccca atctggttga gatgttgctc cgatgcgact     60

tgattatgtc atatatctgc ggtttgcacc gatctgaagc ctagggtttc tcgagcgacc    120

cagttatttg caatttgcga tttgctcgtt tgttgcgcag cgtagtttat gtttggagta    180

atcgaggatt tgtatgcggc gtcggcgcta cctgcttaat cacgccatgt gacgcggtta    240

cttgcagagg ctgggttctg ttatgtcgtg atctaagaat ctagattagg ctcagtcgtt    300

cttgctgtcg actagtttgt tttgatatcc atgtagtaca agttacttaa aatttaggtc    360

caatatattt tgcatgcttt tggcctgtta ttcttgccaa caagttgtcc tggtaaaaag    420

tagatgtgaa agtcacgtat tgggacaaat tgatggttta gtgctatagt tctatagttc    480

tgtgatacat ctatctgatt ttttttggtc tattggtgcc taacttatct gaaaatcatg    540

gaacatgagg ctagtttgat catggtttag ttcattgtga ttaataatgt atgatttagt    600

agctattttg gtgatcgtgt cattttattt gtgaatggaa tcattgtatg taaatgaagc    660

tagttcaggg gttacgatgt agctggcttt gtattctaaa ggctgctatt attcatccat    720

cgatttcacc tatatgtaat ccagagcttt tgatgtgaaa tttgtctgat ccttcactag    780

gaaggacaga acattgttaa tattttggca catctgtctt attctcatcc tttgtttgaa    840

catgttagcc tgttcaaaca gatactgttg taatgtccta gttatatagg tacatatgtg    900

ttctctattg agtttatgga cttttgtgtg tgaagttata tttcattttg ctcaaaactc    960

atgtttgcaa gctttctgac attattctat tgttctgaaa cagggt                  1006
```

```
<210> SEQ ID NO 103
```

<211> LENGTH: 2625
<212> TYPE: DNA
<213> ORGANISM: Setaria italica

<400> SEQUENCE: 103
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cccgttgccg 1500
caagactcag atcagattcc gatccccagt tcttccccaa tcaccttgtg gtctctcgtg 1560
tcgcggttcc cagggacgcc tccggctcgt cgctcgacag cgatctccgc cccagcaagg 1620
tatagattca gttccttgct ccgatcccaa tctggttgag atgttgctcc gatgcgactt 1680
gattatgtca tatatctgcg gtttgcaccg atctgaagcc tagggtttct cgagcgaccc 1740
agttatttgc aatttgcgat ttgctcgttt gttgcgcagc gtagtttatg tttggagtaa 1800
tcgaggattt gtatgcggcg tcggcgctac ctgcttaatc acgccatgtg acgcggttac 1860
ttgcagaggc tgggttctgt tatgtcgtga tctaagaatc tagattaggc tcagtcgttc 1920
ttgctgtcga ctagtttgtt ttgatatcca tgtagtacaa gttacttaaa atttaggtcc 1980
aatatatttt gcatgctttt ggcctgttat tcttgccaac aagttgtcct ggtaaaaagt 2040
agatgtgaaa gtcacgtatt gggacaaatt gatggtttag tgctatagtt ctatagttct 2100
gtgatacatc tatctgattt tttttggtct attggtgcct aacttatctg aaaatcatgg 2160
aacatgaggc tagtttgatc atggtttagt tcattgtgat taataatgta tgatttagta 2220
gctattttgg tgatcgtgtc attttatttg tgaatggaat cattgtatgt aaatgaagct 2280
agttcagggg ttacgatgta gctggctttg tattctaaag gctgctatta ttcatccatc 2340
gatttcacct atatgtaatc cagagctttt gatgtgaaat ttgtctgatc cttcactagg 2400
aaggacagaa cattgttaat attttggcac atctgtctta ttctcatcct ttgtttgaac 2460
atgttagcct gttcaaacag atactgttgt aatgtcctag ttatataggt acatatgtgt 2520
tctctattga gtttatggac ttttgtgtgt gaagttatat ttcattttgc tcaaaactca 2580
tgtttgcaag ctttctgaca ttattctatt gttctgaaac aggtg 2625

<210> SEQ ID NO 104
<211> LENGTH: 1492
<212> TYPE: DNA
<213> ORGANISM: Setaria italica

<400> SEQUENCE: 104
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacac gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag catcggaaca ctggtgattg 1080
gtggagccgg cagtatgcgc cccagcacgg ccgaggtggt ggtggcccgt ggccctgctg 1140
tctgcgcggc tcgggacaac ttgaaactgg gccaccgcct cgtcgcaact cgcaacccgt 1200
tggcggaaga aaggaatggc tcgtaggggc ccgggtagaa tcgaagaatg ttgcgctggg 1260
cttcgattca cataacatgg gcctgaagct ctaaaacgac ggcccggtcg ccgcgcgatg 1320
gaaagagacc ggatcctcct cgtgaattct ggaaggccac acgagagcga cccaccaccg 1380
acgcggagga gtcgtgcgtg gtccaacacg gccggcgggc tgggctgcga ccttaaccag 1440
caaggcacgc cacgacccgc cccgccctcg aggcataaat accctcccat cc 1492

<210> SEQ ID NO 105
<211> LENGTH: 1006
<212> TYPE: DNA
<213> ORGANISM: Setaria italica

<400> SEQUENCE: 105
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttatttg caatttgcga tttgctcgtt tgttgcgcag cgtagtttat gtttggagta 180
atcgaggatt tgtatgcggc gtcggcgcta cctgcttaat cacgccatgt gacgcggtta 240
cttgcagagg ctgggttctg ttatgtcgtg atctaagaat ctagattagg ctcagtcgtt 300
cttgctgtcg actagtttgt tttgatatcc atgtagtaca agttacttaa aatttaggtc 360
caatatattt tgcatgcttt tggcctgtta ttcttgccaa caagttgtcc tggtaaaaag 420
tagatgtgaa agtcacgtat tgggacaaat tgatggttta gtgctatagt tctatagttc 480
tgtgatacat ctatctgatt ttttttggtc tattggtgcc taacttatct gaaaatcatg 540
gaacatgagg ctagtttgat catggtttag ttcattgtga ttaataatgt atgatttagt 600
agctattttg gtgatcgtgt cattttattt gtgaatggaa tcattgtatg taaatgaagc 660
tagttcaggg gttacgatgt agctggcttt gtattctaaa ggctgctatt attcatccat 720
cgatttcacc tatatgtaat ccagagcttt tgatgtgaaa tttgtctgat ccttcactag 780
gaaggacaga acattgttaa tattttggca catctgtctt attctcatcc tttgtttgaa 840
catgttagcc tgttcaaaca gatactgttg taatgtccta gttatatagg tacatatgtg 900
ttctctattg agtttatgga cttttgtgtg tgaagttata tttcattttg ctcaaaactc 960
atgtttgcaa gctttctgac attattctat tgttctgaaa caggtg 1006

<210> SEQ ID NO 106
<211> LENGTH: 2167
<212> TYPE: DNA
<213> ORGANISM: Setaria italica

<400> SEQUENCE: 106
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960
gctgggctgc gaccttaacc agcaaggcac gccacgaccc gccccgccct cgaggcataa 1020
ataccctccc atcccgttgc cgcaagactc agatcagatt ccgatcccca gttcttcccc 1080
aatcaccttg tggtctctcg tgtcgcggtt cccagggacg cctccggctc gtcgctcgac 1140
agcgatctcc gccccagcaa ggtatagatt cagttccttg ctccgatccc aatctggttg 1200
agatgttgct ccgatgcgac ttgattatgt catatatctg cggtttgcac cgatctgaag 1260
cctagggttt ctcgagcgac ccagttattt gcaatttgcg atttgctcgt ttgttgcgca 1320
gcgtagttta tgtttggagt aatcgaggat ttgtatgcgg cgtcggcgct acctgcttaa 1380
tcacgccatg tgacgcggtt acttgcagag gctgggttct gttatgtcgt gatctaagaa 1440
tctagattag gctcagtcgt tcttgctgtc gactagtttg ttttgatatc catgtagtac 1500
aagttactta aaatttaggt ccaatatatt ttgcatgctt ttggcctgtt attcttgcca 1560
acaagttgtc ctggtaaaaa gtagatgtga aagtcacgta ttgggacaaa ttgatggttt 1620
agtgctatag ttctatagtt ctgtgataca tctatctgat ttttttggt ctattggtgc 1680 ctaacttatc tgaaaatcat ggaacatgag gctagtttga tcatggttta gttcattgtg 1740
attaataatg tatgatttag tagctatttt ggtgatcgtg tcattttatt tgtgaatgga 1800
atcattgtat gtaaatgaag ctagttcagg ggttacgatg tagctggctt tgtattctaa 1860
aggctgctat tattcatcca tcgatttcac ctatatgtaa tccagagctt ttgatgtgaa 1920
atttgtctga tccttcacta ggaaggacag aacattgtta atattttggc acatctgtct 1980
tattctcatc ctttgtttga acatgttagc ctgttcaaac agatactgtt gtaatgtcct 2040
agttatatag gtacatatgt gttctctatt gagtttatgg acttttgtgt gtgaagttat 2100
atttcatttt gctcaaaact catgtttgca agctttctga cattattcta ttgttctgaa 2160
acaggtg 2167

<210> SEQ ID NO 107
<211> LENGTH: 1034
<212> TYPE: DNA
<213> ORGANISM: Setaria italica

<400> SEQUENCE: 107
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac acgtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agcatcggaa cactggtgat tggtggagcc ggcagtatgc gccccagcac ggccgaggtg 660
gtggtggccc gtggccctgc tgtctgcgcg gctcgggaca acttgaaact gggccaccgc 720
ctcgtcgcaa ctcgcaaccc gttggcggaa gaaaggaatg gctcgtaggg gcccgggtag 780
aatcgaagaa tgttgcgctg ggcttcgatt cacataacat gggcctgaag ctctaaaacg 840
acggcccggt cgccgcgcga tggaaagaga ccggatcctc ctcgtgaatt ctggaaggcc 900
acacgagagc gacccaccac cgacgcggag gagtcgtgcg tggtccaaca cggccggcgg 960
gctgggctgc gaccttaacc agcaaggcac gccacgaccc gccccgccct cgaggcataa 1020
ataccctccc atcc 1034

<210> SEQ ID NO 108
<211> LENGTH: 1813
<212> TYPE: DNA
<213> ORGANISM: Setaria italica

<400> SEQUENCE: 108
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag gtg 1813

<210> SEQ ID NO 109
<211> LENGTH: 680
<212> TYPE: DNA
<213> ORGANISM: Setaria italica

<400> SEQUENCE: 109
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc 680

<210> SEQ ID NO 110
<211> LENGTH: 2634
<212> TYPE: DNA
<213> ORGANISM: Setaria viridis

<400> SEQUENCE: 110
actgccgcga cacgcctcac tggcgggagg gctccgagcg ctctctcccc ggcggccggc 60
ggagcagcga tctggattgg agagaataga ggaaagagag ggaaaaggag agagatagcg 120
caaagagctg aaaagataag gttgtgcggg ctgtggtgat tagaggacca ctaatccctc 180
catctcctaa tgacgcggtg cccaagacca gtgccgcggc acaccagcgt ctaagtgaac 240
ttccgctaac cttccggtca ttgcgcctga aagatgtcat gtggcgaggc ccccctctca 300
gtagattgcc aactgcctac cgtgccactc ttccatgcat gattgctccc gtctatcccg 360
tttctcacaa cagatagaca acagtaagca tcactaaagc aagcatgtgt agaaccttaa 420
aaaaaggctt atactaccag tatactatca accagcatgc cgtttttgaa gtatccagga 480
ttagaagctt ctactgcgct tttatattat agctgtggac ctgtggtaac ctttctcttt 540
tggcgcttgc ttaatctcgg ccgtgctggt ccatgcttag gcactaggca gagatagagc 600
cgggggtgaa tggggctaaa gctcagctgc tcgaggggcc gtgggctggt ttccactagc 660
ctacagctgt gccacgtgcg gccgcgcaag ccgaagcaag cacgctgagc cgttggacag 720
cttgtcataa tgccattacg tggattacag gtaactggcc ctgtaactac tcgttcggcc 780
atcatcaaac gacgacgtcc gctaggcgac gacacgggta atgcacgcag ccacccaggc 840
gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320

```
ggaaagagac cggatcctcc tcgtgaattc tggaaggcca cacgagagcg acccaccacc   1380
gacgcggagg agtcgtgcgt ggtccaacac ggccggcggg ctgggctgcg accttaacca   1440
gcaaggcacg ccacgacccg cctcgccctc gaggcataaa taccctccca tcccgttgcc   1500
gcaagactca gatcagattc cgatccccag ttcttcccca atcaccttgt ggtctctcgt   1560
gtcgcggttc ccagggacgc ctccggctcg tcgctcgaca gcgatctccg ccccagcaag   1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
cagttgtttg caatttgcga tttgctcgtt tgttgcgcat cgtagtttat gtttggagta   1800
atcgaggatt tgtatgcggc gtcggcgcta cctgcttaat cacgccatgt gacgcggtta   1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatatttg catgcttttg gcctgttatt cttgccaaca agttgtcctg   2040
gtaaaaagta gatgtgaaag tcacgtattg ggacaaattg atggttaagt gctatagttc   2100
tatagttctg tgatacatct atctgatttt ttttggtcta ttggtgccta acttatctga   2160
aaatcatgga acatgaggct agtttgatca tggtttagtt cattgtgatt aataatgtat   2220
gatttagtag ctattttggt gatcgtgtca ttttatttgt gaatggaatc attgtatgta   2280
aatgaagcta gttcaggggt tatgatgtag ctggctttgt attctaaagg ctgctattat   2340
tcatccatcg atttcaccta tatgtaatcc agagctttcg atgtgaaatt tgtctgatcc   2400
ttcactagga aggacagaac attgttaata ttttggcaca tctgtcttat tctcatcctt   2460
tgtttgaaca tgttagcctg ttcaaacaga tactgttgta atgtcctagt tatataggta   2520
catatgtgtt ctctattgag tttatggact tttgtgtgtg aagttatatt tcattttgct   2580
caaaactcat gtttgcaagc tttctgacat tattctattg ttctgaaaca ggtg          2634
```

<210> SEQ ID NO 111
<211> LENGTH: 1493
<212> TYPE: DNA
<213> ORGANISM: Setaria viridis

<400> SEQUENCE: 111

```
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc ccccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgtttttgaa gtatccagga    480
ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
```

gcgcgcgcta gcggagcacg gtcaggtgac acgggcgtcg tgacgcttcc gagttgaagg 900
ggttaacgcc agaaacagtg tttggccagg gtatgaacat aacaaaaaat attcacacga 960
aagaatggaa gtatggagct gctactgtgt aaatgccaag caggaaactc acgcccgcta 1020
acatccaacg gccaacagct cgacgtgccg gtcagcagag acatcggaac actggtgatt 1080
ggtggagccg gcagtatgcg ccccagcacg gccgaggtgg tggtggcccg tggccctgct 1140
gtctgcgcgg ctcgggacaa cttgaaactg ggccaccgcc tcgtcgcaac tcgcaacccg 1200
ttggcggaag aaaggaatgg ctcgtagggg cccgggtaga atccaagaat gttgcgctgg 1260
gcttcgattc acataacatg ggcctgaagc tctaaaacga cggcccggtc accgggcgat 1320
ggaaagagac cggatcctcc tcgtgaattc tggaaggcca cacgagagcg acccaccacc 1380
gacgcggagg agtcgtgcgt ggtccaacac ggccggcggg ctgggctgcg accttaacca 1440
gcaaggcacg ccacgacccg cctcgccctc gaggcataaa taccctccca tcc 1493

<210> SEQ ID NO 112
<211> LENGTH: 127
<212> TYPE: DNA
<213> ORGANISM: Setaria viridis

<400> SEQUENCE: 112
cgttgccgca agactcagat cagattccga tccccagttc ttccccaatc accttgtggt 60
ctctcgtgtc gcggttccca gggacgcctc cggctcgtcg ctcgacagcg atctccgccc 120
cagcaag 127

<210> SEQ ID NO 113
<211> LENGTH: 1014
<212> TYPE: DNA
<213> ORGANISM: Setaria viridis

<400> SEQUENCE: 113
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttgtttg caatttgcga tttgctcgtt tgttgcgcat cgtagtttat gtttggagta 180
atcgaggatt tgtatgcggc gtcggcgcta cctgcttaat cacgccatgt gacgcggtta 240
cttgcagagg ctgggttagt gggttctgtt atgtcgtgat ctaagaatct agattaggct 300
cagtcgttct tgctgtcgac tagtttgttt tgatatccat gtagtacaag ttacttaaaa 360
tttaggtcca atatatttg catgcttttg gcctgttatt cttgccaaca agttgtcctg 420
gtaaaaagta gatgtgaaag tcacgtattg ggacaaattg atggttaagt gctatagttc 480
tatagttctg tgatacatct atctgatttt ttttggtcta ttggtgccta acttatctga 540
aaatcatgga acatgaggct agtttgatca tggtttagtt cattgtgatt aataatgtat 600
gatttagtag ctattttggt gatcgtgtca ttttatttgt gaatggaatc attgtatgta 660
aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca ggtg 1014

<210> SEQ ID NO 114
<211> LENGTH: 2634
<212> TYPE: DNA
<213> ORGANISM: Setaria viridis

<400> SEQUENCE: 114

```
actgccgcga cacgcctcac tggcgggagg gctccgagcg ctctctcccc ggcggccggc     60

ggagcagcga tctggattgg agagaataga ggaaagagag ggaaaaggag agagatagcg    120

caaagagctg aaaagataag gttgtgcggg ctgtggtgat tagaggacca ctaatccctc    180

catctcctaa tgacgcggtg cccaagacca gtgccgcggc acaccagcgt ctaagtgaac    240

ttccgctaac cttccggtca ttgcgcctga aagatgtcat gtggcgaggc ccccctctca    300

gtagattgcc aactgcctac cgtgccactc ttccatgcat gattgctccc gtctatcccg    360

tttctcacaa cagatagaca acagtaagca tcactaaagc aagcatgtgt agaaccttaa    420

aaaaaggctt atactaccag tatactatca accagcatgc cgtttttgaa gtatccagga    480

ttagaagctt ctactgcgct tttatattat agctgtggac ctgtggtaac ctttctcttt    540

tggcgcttgc ttaatctcgg ccgtgctggt ccatgcttag gcactaggca gagatagagc    600

cgggggtgaa tggggctaaa gctcagctgc tcgaggggcc gtgggctggt ttccactagc    660

ctacagctgt gccacgtgcg gccgcgcaag ccgaagcaag cacgctgagc cgttggacag    720

cttgtcataa tgccattacg tggattacag gtaactggcc ctgtaactac tcgttcggcc    780

atcatcaaac gacgacgtcc gctaggcgac gacacgggta atgcacgcag ccacccaggc    840

gcgcgcgcta gcggagcacg gtcaggtgac acgggcgtcg tgacgcttcc gagttgaagg    900

ggttaacgcc agaaacagtg tttggccagg gtatgaacat aacaaaaaat attcacacga    960

aagaatggaa gtatggagct gctactgtgt aaatgccaag caggaaactc acgcccgcta   1020

acatccaacg gccaacagct cgacgtgccg gtcagcagag acatcggaac actggtgatt   1080

ggtggagccg gcagtatgcg ccccagcacg gccgaggtgg tggtggcccg tggccctgct   1140

gtctgcgcgg ctcgggacaa cttgaaactg ggccaccgcc tcgtcgcaac tcgcaacccg   1200

ttggcggaag aaaggaatgg ctcgtagggg cccgggtaga atccaagaat gttgcgctgg   1260

gcttcgattc acataacatg ggcctgaagc tctaaaacga cggcccggtc accgggcgat   1320

ggaaagagac cggatcctcc tcgtgaattc tggaaggcca cacgagagcg acccaccacc   1380

gacgcggagg agtcgtgcgt ggtccaacac ggccggcggg ctgggctgcg accttaacca   1440

gcaaggcacg ccacgacccg cctcgccctc gaggcataaa taccctccca tcccgttgcc   1500

gcaagactca gatcagattc cgatccccag ttcttcccca atcaccttgt ggtctctcgt   1560

gtcgcggttc ccagggacgc ctccggctcg tcgctcgaca gcgatctccg ccccagcaag   1620

gtatagattc agttccttgc tccgatccca atctggttga gatgttgctc cgatgcgact   1680

tgattatgtc atatatctgc ggtttgcacc gatctgaagc ctagggtttc tcgagcgacc   1740

cagttgtttg caatttgcga tttgctcgtt tgttgcgcat cgtagtttat gtttggagta   1800

atcgaggatt tgtatgcggc gtcggcgcta cctgcttaat cacgccatgt gacgcggtta   1860

cttgcagagg ctgggttagt gggttctgtt atgtcgtgat ctaagaatct agattaggct   1920

cagtcgttct tgctgtcgac tagtttgttt tgatatccat gtagtacaag ttacttaaaa   1980

tttaggtcca atatattttg catgcttttg gcctgttatt cttgccaaca agttgtcctg   2040

gtaaaaagta gatgtgaaag tcacgtattg ggacaaattg atggttaagt gctatagttc   2100

tatagttctg tgatacatct atctgatttt ttttggtcta ttggtgccta acttatctga   2160
```

aaatcatgga acatgaggct agtttgatca tggtttagtt cattgtgatt aataatgtat 2220
gatttagtag ctattttggt gatcgtgtca ttttatttgt gaatggaatc attgtatgta 2280
aatgaagcta gttcaggggt tatgatgtag ctggctttgt attctaaagg ctgctattat 2340
tcatccatcg atttcaccta tatgtaatcc agagctttcg atgtgaaatt tgtctgatcc 2400
ttcactagga aggacagaac attgttaata ttttggcaca tctgtcttat tctcatcctt 2460
tgtttgaaca tgttagcctg ttcaaacaga tactgttgta atgtcctagt tatataggta 2520
catatgtgtt ctctattgag tttatggact tttgtgtgtg aagttatatt tcattttgct 2580
caaaactcat gtttgcaagc tttctgacat tattctattg ttctgaaaca gggt 2634

<210> SEQ ID NO 115
<211> LENGTH: 1014
<212> TYPE: DNA
<213> ORGANISM: Setaria viridis

<400> SEQUENCE: 115
gtatagattc agttccttgc tccgatccca atctggttga gatgttgctc cgatgcgact 60
tgattatgtc atatatctgc ggtttgcacc gatctgaagc ctagggtttc tcgagcgacc 120
cagttgtttg caatttgcga tttgctcgtt tgttgcgcat cgtagtttat gtttggagta 180
atcgaggatt tgtatgcggc gtcggcgcta cctgcttaat cacgccatgt gacgcggtta 240
cttgcagagg ctgggttagt gggttctgtt atgtcgtgat ctaagaatct agattaggct 300
cagtcgttct tgctgtcgac tagtttgttt tgatatccat gtagtacaag ttacttaaaa 360
tttaggtcca atatattttg catgcttttg gcctgttatt cttgccaaca agttgtcctg 420
gtaaaaagta gatgtgaaag tcacgtattg ggacaaattg atggttaagt gctatagttc 480
tatagttctg tgatacatct atctgatttt ttttggtcta ttggtgccta acttatctga 540
aaatcatgga acatgaggct agtttgatca tggtttagtt cattgtgatt aataatgtat 600
gatttagtag ctattttggt gatcgtgtca ttttatttgt gaatggaatc attgtatgta 660
aatgaagcta gttcaggggt tatgatgtag ctggctttgt attctaaagg ctgctattat 720
tcatccatcg atttcaccta tatgtaatcc agagctttcg atgtgaaatt tgtctgatcc 780
ttcactagga aggacagaac attgttaata ttttggcaca tctgtcttat tctcatcctt 840
tgtttgaaca tgttagcctg ttcaaacaga tactgttgta atgtcctagt tatataggta 900
catatgtgtt ctctattgag tttatggact tttgtgtgtg aagttatatt tcattttgct 960
caaaactcat gtttgcaagc tttctgacat tattctattg ttctgaaaca gggt 1014

<210> SEQ ID NO 116
<211> LENGTH: 2176
<212> TYPE: DNA
<213> ORGANISM: Setaria viridis

<400> SEQUENCE: 116
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300
ccctgtaact actcgttcgg ccatcatcaa acgacgacgt ccgctaggcg acgacacggg 360

```
taatgcacgc agccacccag gcgcgcgcgc tagcggagca cggtcaggtg acacgggcgt    420
cgtgacgctt ccgagttgaa ggggttaacg ccagaaacag tgtttggcca gggtatgaac    480
ataacaaaaa atattcacac gaaagaatgg aagtatggag ctgctactgt gtaaatgcca    540
agcaggaaac tcacgcccgc taacatccaa cggccaacag ctcgacgtgc cggtcagcag    600
agacatcgga acactggtga ttggtggagc cggcagtatg cgccccagca cggccgaggt    660
ggtggtggcc cgtggccctg ctgtctgcgc ggctcgggac aacttgaaac tgggccaccg    720
cctcgtcgca actcgcaacc cgttggcgga agaaaggaat ggctcgtagg ggcccgggta    780
gaatccaaga atgttgcgct gggcttcgat tcacataaca tgggcctgaa gctctaaaac    840
gacggcccgg tcaccgggcg atggaaagag accggatcct cctcgtgaat tctggaaggc    900
cacacgagag cgacccacca ccgacgcgga ggagtcgtgc gtggtccaac acggccggcg    960
ggctgggctg cgaccttaac cagcaaggca cgccacgacc cgcctcgccc tcgaggcata   1020
aataccctcc catcccgttg ccgcaagact cagatcagat tccgatcccc agttcttccc   1080
caatcacctt gtggtctctc gtgtcgcggt tcccagggac gcctccggct cgtcgctcga   1140
cagcgatctc cgccccagca aggtatagat tcagttcctt gctccgatcc caatctggtt   1200
gagatgttgc tccgatgcga cttgattatg tcatatatct gcggtttgca ccgatctgaa   1260
gcctagggtt tctcgagcga cccagttgtt tgcaatttgc gatttgctcg tttgttgcgc   1320
atcgtagttt atgtttggag taatcgagga tttgtatgcg gcgtcggcgc tacctgctta   1380
atcacgccat gtgacgcggt tacttgcaga ggctgggtta gtgggttctg ttatgtcgtg   1440
atctaagaat ctagattagg ctcagtcgtt cttgctgtcg actagtttgt tttgatatcc   1500
atgtagtaca agttacttaa aatttaggtc caatatattt tgcatgcttt tggcctgtta   1560
ttcttgccaa caagttgtcc tggtaaaaag tagatgtgaa agtcacgtat tgggacaaat   1620
tgatggttaa gtgctatagt tctatagttc tgtgatacat ctatctgatt ttttttggtc   1680
tattggtgcc taacttatct gaaaatcatg gaacatgagg ctagtttgat catggtttag   1740
ttcattgtga ttaataatgt atgatttagt agctattttg gtgatcgtgt cattttattt   1800
gtgaatggaa tcattgtatg taaatgaagc tagttcaggg gttatgatgt agctggcttt   1860
gtattctaaa ggctgctatt attcatccat cgatttcacc tatatgtaat ccagagcttt   1920
cgatgtgaaa tttgtctgat ccttcactag gaaggacaga acattgttaa tattttggca   1980
catctgtctt attctcatcc tttgtttgaa catgttagcc tgttcaaaca gatactgttg   2040
taatgtccta gttatatagg tacatatgtg ttctctattg agtttatgga cttttgtgtg   2100
tgaagttata tttcattttg ctcaaaactc atgtttgcaa gctttctgac attattctat   2160
tgttctgaaa caggtg                                                   2176
```

<210> SEQ ID NO 117
<211> LENGTH: 1035
<212> TYPE: DNA
<213> ORGANISM: Setaria viridis

<400> SEQUENCE: 117

```
gccgtttttg aagtatccag gattagaagc ttctactgcg cttttatatt atagctgtgg     60
acctgtggta acctttctct tttggcgctt gcttaatctc ggccgtgctg gtccatgctt    120
aggcactagg cagagataga gccgggggtg aatggggcta aagctcagct gctcgagggg    180
ccgtgggctg gtttccacta gcctacagct gtgccacgtg cggccgcgca agccgaagca    240
agcacgctga gccgttggac agcttgtcat aatgccatta cgtggattac aggtaactgg    300
```

ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcc 1035

<210> SEQ ID NO 118
<211> LENGTH: 1822
<212> TYPE: DNA
<213> ORGANISM: Setaria viridis

<400> SEQUENCE: 118
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctc gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260
acaaattgat ggttaagtgc tatagttcta tagttctgtg atacatctat ctgatttttt 1320
ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg tg 1822

<210> SEQ ID NO 119
<211> LENGTH: 681
<212> TYPE: DNA
<213> ORGANISM: Setaria viridis

<400> SEQUENCE: 119
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctc gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 120
<211> LENGTH: 1822
<212> TYPE: DNA
<213> ORGANISM: Setaria viridis

<400> SEQUENCE: 120
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260
acaaattgat ggttaagtgc tatagttcta tagttctgtg atacatctat ctgatttttt 1320
ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg gt 1822

<210> SEQ ID NO 121
<211> LENGTH: 681
<212> TYPE: DNA
<213> ORGANISM: Setaria viridis

<400> SEQUENCE: 121
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc c 681

<210> SEQ ID NO 122
<211> LENGTH: 1925
<212> TYPE: DNA
<213> ORGANISM: Zea mays subsp. Mexicana

<400> SEQUENCE: 122
gtcgtgcccc tctctagaga taatgagcat tgcatgtcta agttataaaa aattaccaca 60
tattttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttttattt 420
aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc ccccctctct 960
ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg attttttttag ccctgccttc atacgctatt 1860
tatttgcttg gtactgtttc ttttgtcgat gctcaccctg ttgtttggtg atacttctgc 1920
aggtc 1925

<210> SEQ ID NO 123
<211> LENGTH: 850
<212> TYPE: DNA
<213> ORGANISM: Zea mays subsp. Mexicana

<400> SEQUENCE: 123
gtcgtgcccc tctctagaga taatgagcat tgcatgtcta agttataaaa aattaccaca 60
tattttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttttattt 420 aataatttag atataaaata gaataaaata aagtgactaa aaaataacta aatacctttt 480
aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc 850

<210> SEQ ID NO 124
<211> LENGTH: 78
<212> TYPE: DNA
<213> ORGANISM: Zea mays subsp. Mexicana

<400> SEQUENCE: 124
aacctcgtgt tcgttcggag cgcgcacaca cacaaccaga tctcccccaa atccacccgt 60
cggcacctcc gcttcaag 78

<210> SEQ ID NO 125
<211> LENGTH: 997
<212> TYPE: DNA
<213> ORGANISM: Zea mays subsp. Mexicana

<400> SEQUENCE: 125
gtacgccgct catcctcctc cccccccctct ctctaccttc tctagatcgg cgtttcggtc 60
catggttagg gcccggtagt tctacttctg ttcatgtttg tgttagatcc gtgtttgtgt 120
tagatccgtg ctgctagatt tcgtacacgg atgcgacctg tacatcagac atgttctgat 180
tgctaacttg ccagtgtttc tctttgggga atcctgggat ggctctagcc gttccgcaga 240
cgggatcgat ttcatgaatt ttttttgttt cgttgcatag ggtttggttt gcccttttcc 300
tttatttcaa tatatgccgt gcacttgttt gtcgggtcat cttttcatgt tttttttggc 360
ttggttgtga tgatgtggtc tggttgggcg gtcgttctag atcggagtag aatactgttt 420
caaactacct ggtggattta ttaaaggatc tgtatgtatg tgccatacat cttcatagtt 480
acgagtttaa gatgatggat ggaaatatcg atctaggata ggtatacatg ttgatgcggg 540
ttttactgat gcatatacag agatgctttt ttttcgcttg gttgtgatga tgtggtctgg 600
tcgggcggtc gttctagatc ggagtagaat actgtttcaa actacctggt ggatttatta 660
attttggatc tgtatgtgtg tcatacatct tcatagttac gagtttaaga tcgatggaaa 720
tatcgatcta ggataggtat acatgttgat gtgggtttta ctgatgcata tacatggcat 780
atgcagcatc tattcatatg ctctaacctt gagtacctat ctattataat aaacaagtat 840
gttttataat tattttgatc ttgatatact tggatgatgg catatgcagc agctatatgt 900
ggattttttt agccctgcct tcatacgcta tttatttgct tggtactgtt tcttttgtcg 960
atgctcaccc tgttgtttgg tgatacttct gcaggtc 997

<210> SEQ ID NO 126
<211> LENGTH: 1925
<212> TYPE: DNA
<213> ORGANISM: Zea mays subsp. Mexicana

<400> SEQUENCE: 126
gtcgtgcccc tctctagaga taatgagcat tgcatgtcta agttataaaa aattaccaca 60 tattttttt tgtcacactt gtgtttgaag tgcagtttat ctatctctat acatatattt 120
aaacttcact atatgaataa tatagtctat agtattaaaa taatatcaat gttttagatg 180
attatataac tgaactgcta gacatggtct aaaggacaac cgagtatttt gacaacatga 240
ctctacagtt ttatcttttt agtgtgcatg tgttcttttt acttttgcaa atagcttcac 300
ctatataata cttcatccat tttattagta catccattta ctaaattttt agtacatcta 360
ttttattcta ttttagcctc taaattaaga aaacttaaac tctattttag tttttatttt 420
aataatttag atataaaata gaataaaata aagtgactaa aaaataacta aataccttttt 480 aagaaataaa aaaactaagg aaccattttt cttgttccga gtagataatg acagcctgtt 540
caacgccgtc gacgagtcta acggacacca accagcgaac cagcagcgtc gcgtcgggcc 600
aagcgaagca gacggcacgg catctctgta gctgcctctg gacccctctc gagagttccg 660
ctccaccgtt ggacttgctc cgctgtcggc atccagaaat tgcgtggcgg agcggcagac 720
gtgagccggc acggcaggcg gcctcctctc acggcaccgg cagctacggg ggattccttt 780
cccaccgctc cttcgctttc ccttcctcgc ccgccgtaat aaatagaccc cctccacacc 840
ctctttcccc aacctcgtgt tcgttcggag cgcgcacaca cacaaccaga tctcccccaa 900
atccacccgt cggcacctcc gcttcaaggt acgccgctca tcctcctccc ccccctctct 960
ctaccttctc tagatcggcg tttcggtcca tggttagggc ccggtagttc tacttctgtt 1020
catgtttgtg ttagatccgt gtttgtgtta gatccgtgct gctagatttc gtacacggat 1080
gcgacctgta catcagacat gttctgattg ctaacttgcc agtgtttctc tttggggaat 1140
cctgggatgg ctctagccgt tccgcagacg ggatcgattt catgaatttt ttttgtttcg 1200
ttgcataggg tttggtttgc ccttttcctt tatttcaata tatgccgtgc acttgtttgt 1260
cgggtcatct tttcatgttt tttttggctt ggttgtgatg atgtggtctg gttgggcggt 1320
cgttctagat cggagtagaa tactgtttca aactacctgg tggatttatt aaaggatctg 1380
tatgtatgtg ccatacatct tcatagttac gagtttaaga tgatggatgg aaatatcgat 1440
ctaggatagg tatacatgtt gatgcgggtt ttactgatgc atatacagag atgctttttt 1500
ttcgcttggt tgtgatgatg tggtctggtc gggcggtcgt tctagatcgg agtagaatac 1560
tgtttcaaac tacctggtgg atttattaat tttggatctg tatgtgtgtc atacatcttc 1620
atagttacga gtttaagatc gatggaaata tcgatctagg ataggtatac atgttgatgt 1680
gggttttact gatgcatata catggcatat gcagcatcta ttcatatgct ctaaccttga 1740
gtacctatct attataataa acaagtatgt tttataatta ttttgatctt gatatacttg 1800
gatgatggca tatgcagcag ctatatgtgg atttttttag ccctgccttc atacgctatt 1860
tatttgcttg gtactgtttc ttttgtcgat gctcaccctg ttgtttggtg atacttctgc 1920
agggt 1925

<210> SEQ ID NO 127
<211> LENGTH: 997

<212> TYPE: DNA
<213> ORGANISM: Zea mays subsp. Mexicana

<400> SEQUENCE: 127

```
gtacgccgct catcctcctc cccccccctct ctctaccttc tctagatcgg cgtttcggtc     60
catggttagg gcccggtagt tctacttctg ttcatgtttg tgttagatcc gtgtttgtgt    120
tagatccgtg ctgctagatt tcgtacacgg atgcgacctg tacatcagac atgttctgat    180
tgctaacttg ccagtgtttc tctttgggga atcctgggat ggctctagcc gttccgcaga    240
cgggatcgat ttcatgaatt ttttttgttt cgttgcatag ggtttggttt gccctttttcc    300
tttatttcaa tatatgccgt gcacttgttt gtcgggtcat cttttcatgt tttttttggc    360
ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgtttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggattttttt agccctgcct tcatacgcta tttatttgct tggtactgtt tcttttgtcg    960
atgctcaccc tgttgtttgg tgatacttct gcagggt                              997
```

<210> SEQ ID NO 128
<211> LENGTH: 1974
<212> TYPE: DNA
<213> ORGANISM: Zea mays subsp. Mexicana

<400> SEQUENCE: 128

```
gtcgtgcccc tctctagaga taaagagcat tgcatgtcta agttataaaa aattaccaca     60
tatttttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tctttttagt gtgcatgtgt tctccttttt tttttgcaaa tagcttcacc    300
tatataatac ttcatccatt ttattagtac atccatttag ggtttagggt taatggtttt    360
tatagactaa ttttttttagt acatctattt tattctattt tagcctctaa attaagaaaa    420
ctaaaactct attttagttt ttttatttaa taatttagat ataaaataga ataaaataaa    480
gtgactaaaa attaaacaaa taccctttaa gaaattaaaa aaactaagga aacatttttc    540
ttgtttcgag tagataatgc cagcctgtta aacgccgtcg acgagtctaa cggacaccaa    600
ccagcgaacc agcagcgtcg cgtcgggcca agcgaagcag acggcacggc atctctgtcg    660
ctgcctctgg acccctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacaccccct ccacaccttc tttccccaac ctcgtgttgt    900
tcggagcgca cacacacaca accagatctc ccccaaatcc acccgtcggc acctccgctt    960
```

caaggtacgc cgctcatcct cccccccccc tctctacctt ctctagatcg gcgttccggt 1020
ccatggttag ggcccggtag ttctacttct gttcatgttt gtgttagatc cgtgtttgtg 1080
ttagatccgt gctgctagcg ttcgtacacg gatgcgacct gtacgtcaga cacgttctga 1140
ttgctaactt gccagtgttt ctctttgggg aatcctggga tggctctagc cgttccgcag 1200
acgggatcga tttcatgatt ttttttgttt cgttgcatag ggtttggttt gcccttttcc 1260
tttatttcaa tatatgccgt gcacttgttt gtcgggtcat cttttcatgc ttttttttgt 1320
cttggttgtg atgatgtggt ctggttgggc ggtcgttcta gatcggagaa gaattctgtt 1380
tcaaactacc tggtggattt attaattttg gatctgtatg tgtgtgccat acatattcat 1440
agttacgaat tgaagatgat ggatggaaat atcgatctag gataggtata catgttgatg 1500
cgggttttac tgatgcatat acagagatgc tttttgttcg cttggttgtg atgatgtggt 1560
ctggttgggc ggtcgttcat tcgttctaga tcggagtaga atactgtttc aaactacctg 1620
gtgtatttat taattttgga actgtatgtg tgtgtcatac atcttcatag ttacgagttt 1680
aagatggatg gaaatatcga tctaggatag gtatacatgt tgatgtgggt tttactgatg 1740
catatacatg atggcatatg cagcatctat tcatatgctc taaccttgag tacctatcta 1800
ttataataaa caagtatgtt ttataattat tttgatcttg atatacttgg atgatggcat 1860
atgcagcagc tatatgtgga ttttttagc cctgccttca tacgctattt atttgcttgg 1920
tactgtttct tttgtcgatg ctcaccctgt tgtttggtga tacttctgca ggtc 1974

<210> SEQ ID NO 129
<211> LENGTH: 887
<212> TYPE: DNA
<213> ORGANISM: Zea mays subsp. Mexicana

<400> SEQUENCE: 129
gtcgtgcccc tctctagaga taaagagcat tgcatgtcta agttataaaa aattaccaca 60
tatttttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa tttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720
tccagaaatt gcgtggcgga gcggcagacg tgagccggca cggcaggcgg cctcctcctc 780
ctctcacggc accggcagct acgggggatt cctttcccac cgctccttcg ctttcccttc 840
ctcgcccgcc gtaataaata gacaccccct ccacaccttc tttcccc 887

<210> SEQ ID NO 130
<211> LENGTH: 77
<212> TYPE: DNA
<213> ORGANISM: Zea mays subsp. Mexicana

<400> SEQUENCE: 130
aacctcgtgt tgttcggagc gcacacacac acaaccagat ctcccccaaa tccacccgtc 60
ggcacctccg cttcaag 77

<210> SEQ ID NO 131
<211> LENGTH: 1010
<212> TYPE: DNA
<213> ORGANISM: Zea mays subsp. Mexicana

<400> SEQUENCE: 131
gtacgccgct catcctcccc ccccctctc taccttctct agatcggcgt tccggtccat 60
ggttagggcc cggtagttct acttctgttc atgtttgtgt tagatccgtg tttgtgttag 120
atccgtgctg ctagcgttcg tacacggatg cgacctgtac gtcagacacg ttctgattgc 180
taacttgcca gtgtttctct ttggggaatc ctgggatggc tctagccgtt ccgcagacgg 240
gatcgatttc atgatttttt ttgtttcgtt gcatagggtt tggtttgccc ttttccttta 300
tttcaatata tgccgtgcac ttgtttgtcg ggtcatcttt tcatgctttt ttttgtcttg 360
gttgtgatga tgtggtctgg ttgggcggtc gttctagatc ggagaagaat tctgtttcaa 420
actacctggt ggatttatta attttggatc tgtatgtgtg tgccatacat attcatagtt 480
acgaattgaa gatgatggat ggaaatatcg atctaggata ggtatacatg ttgatgcggg 540
ttttactgat gcatatacag agatgctttt tgttcgcttg gttgtgatga tgtggtctgg 600
ttgggcggtc gttcattcgt tctagatcgg agtagaatac tgtttcaaac tacctggtgt 660
atttattaat tttggaactg tatgtgtgtg tcatacatct tcatagttac gagtttaaga 720
tggatggaaa tatcgatcta ggataggtat acatgttgat gtgggtttta ctgatgcata 780
tacatgatgg catatgcagc atctattcat atgctctaac cttgagtacc tatctattat 840
aataaacaag tatgttttat aattattttg atcttgatat acttggatga tggcatatgc 900
agcagctata tgtggatttt tttagccctg ccttcatacg ctatttattt gcttggtact 960
gtttcttttg tcgatgctca ccctgttgtt tggtgatact tctgcaggtc 1010

<210> SEQ ID NO 132
<211> LENGTH: 1974
<212> TYPE: DNA
<213> ORGANISM: Zea mays subsp. Mexicana

<400> SEQUENCE: 132
gtcgtgcccc tctctagaga taaagagcat tgcatgtcta agttataaaa aattaccaca 60
tatttttttt gtcacacttg tttgaagtgc agtttatcta tctttataca tatatttaaa 120
ctttactcta cgaataatat aatctatagt actacaataa tatcagtgtt ttagagaatc 180
atataaatga acagttagac atggtctaaa ggacaattga gtattttgac aacaggactc 240
tacagtttta tctttttagt gtgcatgtgt tctccttttt tttttgcaaa tagcttcacc 300
tatataatac ttcatccatt ttattagtac atccatttag ggtttagggt taatggtttt 360
tatagactaa tttttttagt acatctattt tattctattt tagcctctaa attaagaaaa 420
ctaaaactct attttagttt ttttatttaa taatttagat ataaaataga ataaaataaa 480
gtgactaaaa attaaacaaa taccctttaa gaaattaaaa aaactaagga aacatttttc 540
ttgtttcgag tagataatgc cagcctgtta aacgccgtcg acgagtctaa cggacaccaa 600
ccagcgaacc agcagcgtcg cgtcgggcca agcgaagcag acggcacggc atctctgtcg 660
ctgcctctgg acccctctcg agagttccgc tccaccgttg gacttgctcc gctgtcggca 720

```
tccagaaatt gcgtggcgga gcggcagacg tgagccggca cggcaggcgg cctcctcctc    780
ctctcacggc accggcagct acgggggatt cctttcccac cgctccttcg ctttcccttc    840
ctcgcccgcc gtaataaata gacaccccct ccacaccttc tttccccaac ctcgtgttgt    900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gccctttttcc  1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc tttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga tttttttagc cctgccttca tacgctattt atttgcttgg   1920
tactgtttct tttgtcgatg ctcaccctgt tgtttggtga tacttctgca gggt         1974
```

<210> SEQ ID NO 133
<211> LENGTH: 1010
<212> TYPE: DNA
<213> ORGANISM: Zea mays subsp. Mexicana

<400> SEQUENCE: 133

```
gtacgccgct catcctcccc ccccctctc  taccttctct agatcggcgt tccggtccat     60
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatttc atgatttttt ttgtttcgtt gcatagggtt tggtttgccc ttttccttta    300
tttcaatata tgccgtgcac ttgtttgtcg ggtcatcttt tcatgctttt ttttgtcttg    360
gttgtgatga tgtggtctgg ttgggcggtc gttctagatc ggagaagaat tctgtttcaa    420
actacctggt ggatttatta attttggatc tgtatgtgtg tgccatacat attcatagtt    480
acgaattgaa gatgatggat ggaaatatcg atctaggata ggtatacatg ttgatgcggg    540
ttttactgat gcatatacag agatgctttt tgttcgcttg gttgtgatga tgtggtctgg    600
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgatat acttggatga tggcatatgc    900
```

agcagctata tgtggatttt tttagccctg ccttcatacg ctatttattt gcttggtact 960
gtttcttttg tcgatgctca ccctgttgtt tggtgatact tctgcagggt 1010

<210> SEQ ID NO 134
<211> LENGTH: 2008
<212> TYPE: DNA
<213> ORGANISM: Zea mays subsp. Mexicana

<400> SEQUENCE: 134
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccctta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacaccccct ccacaccctc tttccccaac ctcgtgttcg ttcggagcgc 900
acacacacgc aaccagatct cccccaaatc cagccgtcgg cacctccgct tcaaggtacg 960
ccgctcatcc tccccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc tttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcaggtc 2008

<210> SEQ ID NO 135
<211> LENGTH: 877
<212> TYPE: DNA
<213> ORGANISM: Zea mays subsp. Mexicana

<400> SEQUENCE: 135
gtcgtgcccc tctctagaga taaagagcat tgcatgtcta aagtataaaa aattaccaca 60 tattttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gtttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccettta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacaccccct ccacaccctc tttcccc 877

<210> SEQ ID NO 136
<211> LENGTH: 78
<212> TYPE: DNA
<213> ORGANISM: Zea mays subsp. Mexicana

<400> SEQUENCE: 136
aacctcgtgt tcgttcggag cgcacacaca cgcaaccaga tctcccccaa atccagccgt 60
cggcacctcc gcttcaag 78

<210> SEQ ID NO 137
<211> LENGTH: 1053
<212> TYPE: DNA
<213> ORGANISM: Zea mays subsp. Mexicana

<400> SEQUENCE: 137
gtacgccgct catcctcccc cccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600

```
catatacaga gatgcttttt ttcgcttggt tgtgatgatg tggtctggtt gggcggtcgt    660

tctagatcgg agtagaatac tgtttcaaac tacctggtgg atttattaat tttgtatctt    720

tatgtgtgtg ccatacatct tcatagttac gagtttaaga tgatggatgg aaatattgat    780

ctaggatagg tatacatgtt gatgtgggtt ttactgatgc atatacatga tggcatatgc    840

ggcatctatt catatgctct aaccttgagt acctatctat tataataaac aagtatgttt    900

tataattatt ttgatcttga tatacttgga tgatggcata tgcagcagct atatgtggat    960

tttttagccc tgccttcata cgctatttat ttgcttggta ctgtttcttt tgtccgatgc   1020

tcaccctgtt gttgggtgat acttctgcag gtc                                1053
```

<210> SEQ ID NO 138
<211> LENGTH: 2008
<212> TYPE: DNA
<213> ORGANISM: Zea mays subsp. Mexicana

<400> SEQUENCE: 138

```
gtcgtgcccc tctctagaga taaagagcat tgcatgtcta aagtataaaa aattaccaca     60

tatttttttg tcacacttat ttgaagtgta gtttatctat ctctatacat atatttaaac    120

ttcactctac aaataatata gtctataata ctaaaataat attagtgttt tagaggatca    180

tataaataaa ctgctagaca tggtctaaag gataattgaa tattttgaca atctacagtt    240

ttatcttttt agtgtgcatg tgatctctct gttttttttg caaatagctt gacctatata    300

atacttcatc cattttatta gtacatccat ttaggattta gggttgatgg tttctataga    360

ctaattttta gtacatccat tttattcttt ttagtctcta aatttttttaa aactaaaact    420

ctattttagt tttttattta ataatttaga tataaaatga aataaaataa attgactaca    480

aataaaacaa ataccottta agaaataaaa aaactaagca aacatttttc ttgtttcgag    540

tagataatga caggctgttc aacgccgtcg acgagtctaa cggacaccaa ccagcgaacc    600

agcagcgtcg cgtcgggcca agcgaagcag acggcacggc atctctgtag ctgcctctgg    660

acccctctcg agagttccgc tccaccgttg gacttgctcc gctgtcggca tccagaaatt    720

gcgtggcgga gcggcagacg tgaggcggca cggcaggcgg cctcttcctc ctctcacggc    780

accggcagct acgggggatt cctttcccac cgctccttcg ctttcccttc ctcgcccgcc    840

gtaataaata gacacccccct ccacaccctc tttccccaac ctcgtgttcg ttcggagcgc    900

acacacacgc aaccagatct cccccaaatc cagccgtcgg cacctccgct tcaaggtacg    960

ccgctcatcc tccccccccc cctctctcta ccttctctag atcggcgatc cggtccatgg   1020

ttagggcccg gtagttctac ttctgttcat gtttgtgtta gagcaaacat gttcatgttc   1080

atgtttgtga tgatgtggtc tggttgggcg gtcgttctag atcggagtag gatactgttt   1140

caagctacct ggtggattta ttaattttgt atctgtatgt gtgtgccata catcttcata   1200

gttacgagtt taagatgatg gatggaaata tcgatctagg ataggtatac atgttgatgc   1260

gggttttact gatgcatata cagagatgct ttttttctcg cttggttgtg atgatatggt   1320

ctggttgggc ggtcgttcta gatcggagta gaatactgtt tcaaactacc tggtggattt   1380

attaaaggat aaagggtcgt tctagatcgg agtagaatac tgtttcaaac tacctggtgg   1440

atttattaaa ggatctgtat gtatgtgcct acatcttcat agttacgagt ttaagatgat   1500

ggatggaaat atcgatctag gataggtata catgttgatg cgggttttac tgatgcatat   1560

acagagatgc ttttttttcgc ttggttgtga tgatgtggtc tggttgggcg gtcgttctag   1620
```

atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcagggt 2008

<210> SEQ ID NO 139
<211> LENGTH: 1053
<212> TYPE: DNA
<213> ORGANISM: Zea mays subsp. Mexicana

<400> SEQUENCE: 139
gtacgccgct catcctcccc cccccccctct ctctaccttc tctagatcgg cgatccggtc 60
catggttagg gcccggtagt tctacttctg ttcatgtttg tgttagagca aacatgttca 120
tgttcatgtt tgtgatgatg tggtctggtt gggcggtcgt tctagatcgg agtaggatac 180
tgtttcaagc tacctggtgg atttattaat tttgtatctg tatgtgtgtg ccatacatct 240
tcatagttac gagtttaaga tgatggatgg aaatatcgat ctaggatagg tatacatgtt 300
gatgcgggtt ttactgatgc atatacagag atgctttttt tctcgcttgg ttgtgatgat 360
atggtctggt tgggcggtcg ttctagatcg gagtagaata ctgtttcaaa ctacctggtg 420
gatttattaa aggataaagg gtcgttctag atcggagtag aatactgttt caaactacct 480
ggtggattta ttaaaggatc tgtatgtatg tgcctacatc ttcatagtta cgagtttaag 540
atgatggatg gaaatatcga tctaggatag gtatacatgt tgatgcgggt tttactgatg 600
catatacaga gatgcttttt ttcgcttggt tgtgatgatg tggtctggtt gggcggtcgt 660
tctagatcgg agtagaatac tgtttcaaac tacctggtgg atttattaat tttgtatctt 720
tatgtgtgtg ccatacatct tcatagttac gagtttaaga tgatggatgg aaatattgat 780
ctaggatagg tatacatgtt gatgtgggtt ttactgatgc atatacatga tggcatatgc 840
ggcatctatt catatgctct aaccttgagt acctatctat tataataaac aagtatgttt 900
tataattatt ttgatcttga tatacttgga tgatggcata tgcagcagct atatgtggat 960
tttttagccc tgccttcata cgctatttat ttgcttggta ctgtttcttt tgtccgatgc 1020
tcaccctgtt gttgggtgat acttctgcag ggt 1053

<210> SEQ ID NO 140
<211> LENGTH: 1635
<212> TYPE: DNA
<213> ORGANISM: Sorghum bicolor

<400> SEQUENCE: 140
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga cgtaaccctc cgttgcccac 420
gataaaagct ccaccccega ccccggcccc ccgatttccc ctacggacca gtctcccccc 480
gatcgcaatc gcgaattcgt cgcaccatcg gcacgcagac gaacgaagca aggctctccc 540
catcggctcg tcaaggtatg cgttccctag atttgttccc ttcctctctc ggtttgtcta 600
tatatatgca tgtatggtcg attcccgatc tcgtcgattc tcggtttcgc cttccgtacg 660
aagattcgtt tagattgttc atatgttctg ttgtgttacc agattgatcg gatcaacttg 720
atccagttat cttcgctcct ccgattagat ccgtttctat ttcagtatat atatactagt 780
atagtatcta gggttcacac tgttgaccga ctggttactt ggaattgatc cgtgctgagt 840
tcagttgttg ccgtccataa aggcccgtgc tattgtctgt tctgaaacga aatcctgtag 900
atttcttagg gttagtgttc aattcatcaa aaggttgatt agtgaattat caaatttgag 960
agggttaaat cattctcatc atgttgtctc gaatgtaatc ccaaagatat tatagactgt 1020
gtttcgattt gatggattga tttgtgtatc atctaaatca acaaggctaa gtcatcagtt 1080
catagaatca tgtttaggtt tccgttcaat agactagttt tatcaatata taaaattata 1140
agaagggtag ggtaaatcac gttgcctcaa atgccatcct gtatggtttg gtttcaattc 1200
aattagtttg gttgattagg gtatgctctg gattaagatg gttaaatctt ccctagcatc 1260
ttccctgcct atccttactt gatccgtttc ggatatgttg gaagtacagc gagcttattt 1320
catgttgata gtgacccctt tcagattata ctattgaata ttgtatgttt gccacttctg 1380
tatgttgaat tatcctgcta aattagcaat ggaattagca tattggcaat tggtatgcat 1440
ggacctaatc aggacggatg tggttatgtt agtttcaatt cattgtcaat tcattgttca 1500
cctgcgttag atatatatga tgatttttac gtgtagttca tagttcttga gttttggatc 1560
tttcttatct gatatatgct ttcctgtgcc tgtgctttat tgtgtcttac catgcgattt 1620
ttgtctatgc aggtc 1635

<210> SEQ ID NO 141
<211> LENGTH: 401
<212> TYPE: DNA
<213> ORGANISM: Sorghum bicolor

<400> SEQUENCE: 141
ccaagtccaa atgtcaattc ccttgaagat gatctatttt tatcttttgc attttgttat 60
ggaagtttgc aaatagcaac aaatgctaag tcaatttgcc aaagtctttg gagatgctct 120
tagtctataa ttgaacaata tttgtaaaat acaaaaaaaa atagtactat ttttatttta 180
aaaaattttt ggaagtaaac aaggccgagg atggggaaac ggaagtccaa cacgtcgttt 240
tctaagttgg gctcaaaagc ccatcacgga actgacctgc tatgggtcgg aggagagcgc 300
gtccagatgg ttccagaggc tggtggtggt gggccaaacg cggaactccg ccaccgccac 360
ggcctcgtgc gcaagcgcag cgcgttgccg tgagccgtga c 401

<210> SEQ ID NO 142
<211> LENGTH: 154
<212> TYPE: DNA
<213> ORGANISM: Sorghum bicolor

<400> SEQUENCE: 142
gtaaccctcc gttgcccacg ataaaagctc caccccccgac cccggccccc cgatttcccc 60
tacggaccag tctccccccg atcgcaatcg cgaattcgtc gcaccatcgg cacgcagacg 120
aacgaagcaa ggctctcccc atcggctcgt caag 154

<210> SEQ ID NO 143
<211> LENGTH: 1080
<212> TYPE: DNA
<213> ORGANISM: Sorghum bicolor

<400> SEQUENCE: 143
gtatgcgttc cctagatttg ttcccttcct ctctcggttt gtctatatat atgcatgtat 60
ggtcgattcc cgatctcgtc gattctcggt ttcgccttcc gtacgaagat tcgtttagat 120
tgttcatatg ttctgttgtg ttaccagatt gatcggatca acttgatcca gttatcttcg 180
ctcctccgat tagatccgtt tctatttcag tatatatata ctagtatagt atctagggtt 240
cacactgttg accgactggt tacttggaat tgatccgtgc tgagttcagt tgttgccgtc 300
cataaaggcc cgtgctattg tctgttctga aacgaaatcc tgtagatttc ttagggttag 360
tgttcaattc atcaaaaggt tgattagtga attatcaaat ttgagagggt taaatcattc 420
tcatcatgtt gtctcgaatg taatcccaaa gatattatag actgtgtttc gatttgatgg 480
attgatttgt gtatcatcta aatcaacaag gctaagtcat cagttcatag aatcatgttt 540
aggtttccgt tcaatagact agttttatca atatataaaa ttataagaag ggtagggtaa 600
atcacgttgc ctcaaatgcc atcctgtatg gtttggtttc aattcaatta gtttggttga 660
ttagggtatg ctctggatta agatggttaa atcttcccta gcatcttccc tgcctatcct 720
tacttgatcc gtttcggata tgttggaagt acagcgagct tatttcatgt tgatagtgac 780
ccctttcaga ttatactatt gaatattgta tgtttgccac ttctgtatgt tgaattatcc 840
tgctaaatta gcaatggaat tagcatattg gcaattggta tgcatggacc taatcaggac 900
ggatgtggtt atgttagttt caattcattg tcaattcatt gttcacctgc gttagatata 960
tatgatgatt tttacgtgta gttcatagtt cttgagtttt ggatctttct tatctgatat 1020
atgctttcct gtgcctgtgc tttattgtgt cttaccatgc gatttttgtc tatgcaggtc 1080

<210> SEQ ID NO 144
<211> LENGTH: 2067
<212> TYPE: DNA
<213> ORGANISM: Sorghum bicolor

<400> SEQUENCE: 144
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480
ccccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgcagagc ctcagaccag attccgatca atcacccata agctcccccc 900
aaatctgttc ctcgtctccc gtctcgcggt ttcctacttc cctcggacgc ctccggcaag 960
tcgctcgacc gcgcgattcc gcccgctcaa ggtatcaact cggttcacca ctccaatcta 1020
cgtctgattt agatgttact tccatctatg tctaatttag atgttactcc gatgcgattg 1080
gattatgttt atgcggtttg cactgctctg gaaactggaa tctagggttt cgagtgattt 1140
gatcgatcgc gatctgtgat ttcgttgcgc cttgtgtatg cttggagtga tctaggcttg 1200
tatatgcggc atcgcgatct gacgcggttg ctttgtagag gctgggggtc taggctgtga 1260
ttttagaatc aaataaagct gttccttacc gtagatgttt cctacatgtt ctgtccagta 1320
ctccagtgct atattcacat tgtttgaggc ttgagttttg tcgatcagtg gtcatgagaa 1380
aaatatatct catgatttta gaggcaccta ttgggaaagg tagatggttc cgttttacat 1440
gttttataga ccttgtggca tggctccttt gttctatggg tgctttattt tcctgaataa 1500
cagtaatgcg agactggtct atgggtgctt tgaccagtaa tgcgagacta gttatttgat 1560
catggtgcag ttcctagtga ttacgaacaa caatttggta gctcagttca ttcagcattg 1620
gtttctacga tccttatcat tttacttctg aatgaattta tttatttaag atattacagt 1680
gcaataaact gctgtataat atcagtaaca aactgctatt actagtaaat gcctagattc 1740
ataataattc attattctac ttgaaaatga tcttaggcct ttttatgcgg tcctacgcat 1800
ccttccacag gacttgctgt ttgtttgttt tttgtaatcc ctcgctggga cgcagaatgg 1860
ttcatctgtg ctaataattt ttttgcatat ataagtttat agttctcatt attcatgtgg 1920
ctatggtagc ctgtaaaatc tattgtaata acatattagt cagccataca tctgttccaa 1980
cttgctcaat tgcaaatcat atctccactt aaagcacatg tttgcaagct ttctgacaag 2040
tttctttgtg tttgattgaa acaggtg 2067

<210> SEQ ID NO 145
<211> LENGTH: 855
<212> TYPE: DNA
<213> ORGANISM: Sorghum bicolor

<400> SEQUENCE: 145
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360
gcacggtgct atttgatctt ttaaaggaaa aagaggaata gtcgtgggcg ccaggcggga 420
attggggcgc gggagtctgc cggacgacgc gttccgtccg aacggccgga cccgacgagg 480 ccccccgcc gccccacgtc gcagaaccgt ccgtgggtgg taatctggcc gggtacacca 540
gccgtcccct tgggcggcct cacagcactg ggctcacacg tgagttttgt tctgggcttc 600
ggatcgcacc atatgggcct cggcatcaga aagacggggc ccgtctggga tagaagagac 660
aggaacctcc tcgtggattc cagaagccag ccacgagcga ccaccgacgc ggaggatact 720
cgtcgtccaa gtccaacacg gcgggcgggc gggcggacgc gtgggctggg ctaactgcct 780
aaccttaacc tccaaggcac gccaaggccc gcttctccca cccgacataa atatcccccc 840
atccaggcaa ggcgc 855

<210> SEQ ID NO 146
<211> LENGTH: 136
<212> TYPE: DNA
<213> ORGANISM: Sorghum bicolor

<400> SEQUENCE: 146
agagcctcag accagattcc gatcaatcac ccataagctc cccccaaatc tgttcctcgt 60
ctcccgtctc gcggtttcct acttccctcg gacgcctccg gcaagtcgct cgaccgcgcg 120
attccgcccg ctcaag 136

<210> SEQ ID NO 147
<211> LENGTH: 1076
<212> TYPE: DNA
<213> ORGANISM: Sorghum bicolor

<400> SEQUENCE: 147
gtatcaactc ggttcaccac tccaatctac gtctgattta gatgttactt ccatctatgt 60
ctaatttaga tgttactccg atgcgattgg attatgttta tgcggtttgc actgctctgg 120
aaactggaat ctagggtttc gagtgatttg atcgatcgcg atctgtgatt tcgttgcgcc 180
ttgtgtatgc ttggagtgat ctaggcttgt atatgcggca tcgcgatctg acgcggttgc 240
tttgtagagg ctgggggtct aggctgtgat tttagaatca aataaagctg ttccttaccg 300
tagatgtttc ctacatgttc tgtccagtac tccagtgcta tattcacatt gtttgaggct 360
tgagttttgt cgatcagtgg tcatgagaaa aatatatctc atgattttag aggcacctat 420
tgggaaaggt agatggttcc gttttacatg ttttatagac cttgtggcat ggctcctttg 480
ttctatgggt gctttatttt cctgaataac agtaatgcga gactggtcta tgggtgcttt 540
gaccagtaat gcgagactag ttatttgatc atggtgcagt tcctagtgat tacgaacaac 600
aatttggtag ctcagttcat tcagcattgg tttctacgat ccttatcatt ttacttctga 660
atgaatttat ttatttaaga tattacagtg caataaactg ctgtataata tcagtaacaa 720
actgctatta ctagtaaatg cctagattca taataattca ttattctact tgaaaatgat 780
cttaggcctt tttatgcggt cctacgcatc cttccacagg acttgctgtt tgtttgtttt 840
ttgtaatccc tcgctgggac gcagaatggt tcatctgtgc taataatttt tttgcatata 900
taagtttata gttctcatta ttcatgtggc tatggtagcc tgtaaaatct attgtaataa 960
catattagtc agccatacat ctgttccaac ttgctcaatt gcaaatcata tctccactta 1020
aagcacatgt ttgcaagctt tctgacaagt ttctttgtgt ttgattgaaa caggtg 1076

<210> SEQ ID NO 148
<211> LENGTH: 2067
<212> TYPE: DNA
<213> ORGANISM: Sorghum bicolor

<400> SEQUENCE: 148
cattaaaagt cattatgtgc atgcgtcgta actaacatgg atatgttgct gcactatctc 60
ctcgcactag ctgcgcatga taaagccaca agccaaaatt aattattatg ggtgagaata 120
aatacgtacc agcaccggcc atagaaaaag tacattatta aaggtctaat ttggaaacag 180
tctgaaaacg acgtgcgctg cagaggtaaa tgtaattttc ggcactaaaa ccattatcaa 240
ctaattcatt caataacagt tatttagaaa atgtatagct cgctctaaaa aaacagttta 300
gaaaaacagt caaaataatt cgaccaacaa acagttaata aggttcatta aatatataat 360

```
gcacggtgct atttgatctt ttaaaggaaa aagaggaata gtcgtgggcg ccaggcggga    420

attggggcgc gggagtctgc cggacgacgc gttccgtccg aacggccgga cccgacgagg    480

cccccccgcc gccccacgtc gcagaaccgt ccgtgggtgg taatctggcc gggtacacca    540

gccgtcccct tgggcggcct cacagcactg ggctcacacg tgagttttgt tctgggcttc    600

ggatcgcacc atatgggcct cggcatcaga aagacggggc ccgtctggga tagaagagac    660

aggaacctcc tcgtggattc cagaagccag ccacgagcga ccaccgacgc ggaggatact    720

cgtcgtccaa gtccaacacg gcgggcgggc gggcggacgc gtgggctggg ctaactgcct    780

aaccttaacc tccaaggcac gccaaggccc gcttctccca cccgacataa atatcccccc    840

atccaggcaa ggcgcagagc ctcagaccag attccgatca atcacccata agctcccccc    900

aaatctgttc ctcgtctccc gtctcgcggt ttcctacttc cctcggacgc ctccggcaag    960

tcgctcgacc gcgcgattcc gcccgctcaa ggtatcaact cggttcacca ctccaatcta   1020

cgtctgattt agatgttact tccatctatg tctaatttag atgttactcc gatgcgattg   1080

gattatgttt atgcggtttg cactgctctg gaaactggaa tctagggttt cgagtgattt   1140

gatcgatcgc gatctgtgat ttcgttgcgc cttgtgtatg cttggagtga tctaggcttg   1200

tatatgcggc atcgcgatct gacgcggttg ctttgtagag gctgggggtc taggctgtga   1260

ttttagaatc aaataaagct gttccttacc gtagatgttt cctacatgtt ctgtccagta   1320

ctccagtgct atattcacat tgtttgaggc ttgagttttg tcgatcagtg gtcatgagaa   1380

aaatatatct catgatttta gaggcaccta ttgggaaagg tagatggttc cgttttacat   1440

gttttataga ccttgtggca tggctccttt gttctatggg tgctttattt tcctgaataa   1500

cagtaatgcg agactggtct atgggtgctt tgaccagtaa tgcgagacta gttatttgat   1560

catggtgcag ttcctagtga ttacgaacaa caatttggta gctcagttca ttcagcattg   1620

gtttctacga tccttatcat tttacttctg aatgaattta tttatttaag atattacagt   1680

gcaataaact gctgtataat atcagtaaca aactgctatt actagtaaat gcctagattc   1740

ataataattc attattctac ttgaaaatga tcttaggcct ttttatgcgg tcctacgcat   1800

ccttccacag gacttgctgt ttgtttgttt tttgtaatcc ctcgctggga cgcagaatgg   1860

ttcatctgtg ctaataattt ttttgcatat ataagtttat agttctcatt attcatgtgg   1920

ctatggtagc ctgtaaaatc tattgtaata acatattagt cagccataca tctgttccaa   1980

cttgctcaat tgcaaatcat atctccactt aaagcacatg tttgcaagct ttctgacaag   2040

tttctttgtg tttgattgaa acagggt                                       2067
```

<210> SEQ ID NO 149
<211> LENGTH: 1076
<212> TYPE: DNA
<213> ORGANISM: Sorghum bicolor

<400> SEQUENCE: 149

```
gtatcaactc ggttcaccac tccaatctac gtctgattta gatgttactt ccatctatgt     60

ctaatttaga tgttactccg atgcgattgg attatgttta tgcggtttgc actgctctgg    120

aaactggaat ctagggtttc gagtgatttg atcgatcgcg atctgtgatt tcgttgcgcc    180

ttgtgtatgc ttggagtgat ctaggcttgt atatgcggca tcgcgatctg acgcggttgc    240

tttgtagagg ctgggggtct aggctgtgat tttagaatca aataaagctg ttccttaccg    300

tagatgtttc ctacatgttc tgtccagtac tccagtgcta tattcacatt gtttgaggct    360
```

```
tgagttttgt cgatcagtgg tcatgagaaa aatatatctc atgattttag aggcacctat    420

tgggaaaggt agatggttcc gttttacatg ttttatagac cttgtggcat ggctcctttg    480

ttctatgggt gctttatttt cctgaataac agtaatgcga gactggtcta tgggtgcttt    540

gaccagtaat gcgagactag ttatttgatc atggtgcagt tcctagtgat tacgaacaac    600

aatttggtag ctcagttcat tcagcattgg tttctacgat ccttatcatt ttacttctga    660

atgaatttat ttatttaaga tattacagtg caataaactg ctgtataata tcagtaacaa    720

actgctatta ctagtaaatg cctagattca taataattca ttattctact tgaaaatgat    780

cttaggcctt tttatgcggt cctacgcatc cttccacagg acttgctgtt tgtttgtttt    840

ttgtaatccc tcgctgggac gcagaatggt tcatctgtgc taataatttt tttgcatata    900

taagtttata gttctcatta ttcatgtggc tatggtagcc tgtaaaatct attgtaataa    960

catattagtc agccatacat ctgttccaac ttgctcaatt gcaaatcata tctccactta   1020

aagcacatgt ttgcaagctt tctgacaagt ttctttgtgt ttgattgaaa cagggt       1076
```

<210> SEQ ID NO 150
<211> LENGTH: 2003
<212> TYPE: DNA
<213> ORGANISM: Sorghum bicolor

<400> SEQUENCE: 150

```
agaagtaaaa aaaaagttcg tttcagaatc ataaaggtaa gttaaaaaaa gaccatacaa     60

aaaagaggta tttaatgata aactataatc cagaatttgt taggatagta tataagaata    120

agaccttgtt tagtttcaaa aaaatttgca aaattttcca gattcctcgt cacatcaaat    180

ctttagaggt atgcatggag tattaaatat agacaagacc taaataagaa aacatgaaat    240

gttcacgaaa aaaatcaagc caatgcatga tcgaagcaaa cggtatagta acggtgttaa    300

cctgatccat tgatctttgt aatctttaac ggccacctac cgcgggcagc aaacggcgtc    360

cccctcctcg atatctccgc ggcggcctct ggctttttcc gcggaattgc gcggtgggga    420

cggattccac gagaccgcaa cgcaaccgcc tctcgccgct gggccccaca ccgctcggtg    480

ccgtagcccg tagcctcacg ggattctttc tccctcctcc cccgtgtata aattggcttc    540

atcccctccc tgcctcatcc atccaaatcc cactccccaa tcccatcccg tcggagaaat    600

tcatcgaagc gaagcgaagc gaatcctccc gatcctctca aggtacgcga gttttcgaat    660

cccctccaga cccctcgtat gctttccctg ttcgttttcg tcgtagcgtt tgattaggta    720

tgctttccct gttcgtgttc gtcgtagggt tcgattaggt cgtgtgaggc catggcctgc    780

tgtgataaat ttatttgttg ttatatcgga tctgtagtcg atttgggggt cgtggtgtag    840

atccgcgggc tgtgatgaag ttatttggtg tgattgtgct cgcgtgattc tgcgcgttga    900

gctcgagtag atctgatggt tggacgaccg attggttcgt tggctggctg cgctaaggtt    960

gggctgggct catgttgcgt tcgctgttgc gcgtgattcc gcggatggac ttgcgcttga   1020

ttgccgccag atcacgttac gattatgtga tttcgtttgg aactttttag atttgtagct   1080

tctgcttatt atatgacaga tgcgcctact gctcatatgc ctgtggtaaa taatggatgg   1140

ctgtgggtca aactagttga ttgtcgagtc atgtatcata tacaggtgta tagacttgcg   1200

tctaattgtt tgcatgttgc agttatatga tttgttttag attgtttgtt ccactcatct   1260

aggctgtaaa agggacacta cttattagct tgttgtttaa tctttttatt agtagattat   1320

attggtaatg ttttactaat tattattatg ttatatgtga cttctgctca tgcctgatta   1380

taatcataga tcactgtagt tgattgttga atcatgtgtc aaatacccgt atacataaca   1440
```

ctacacattt gcttagttgt ttccttaact catgcaaatt gaacaccatg tatgatttgc 1500
atggtgctgt aatgttaaat actacagtcc tgttggtact tgtttagtaa gaatctgctt 1560
catacaacta tatgctatgc ctgatgataa tcatatatct ttgtgtaatt aataattagt 1620
tgactgttga ataatgtatc gagtacatac catggcacaa ttgcttagtc acttccttaa 1680
ccatgcatat tgaactgacc ccttcatgtt ctgctgaatt gttctattct gattagacca 1740
tacatcatgt attgcaatct ttatttgcaa ttgtaatgta atggttcggt tctcaaatgt 1800
taaatgctat agttgtgcta ctttctaatg ttaaatgcta tagctgtgct acttgtaaga 1860
tctgcttcat agtttagtta aattaggatg atgagctttg atgctgtaac tttgtttgat 1920
tatgttcata gttgatcagt tttgttaga ctcacagtaa cttatggtct cactcttctt 1980
ctggtctttg atgtttgcag cgg 2003

<210> SEQ ID NO 151
<211> LENGTH: 565
<212> TYPE: DNA
<213> ORGANISM: Sorghum bicolor

<400> SEQUENCE: 151
agaagtaaaa aaaaagttcg tttcagaatc ataaaggtaa gttaaaaaaa gaccatacaa 60
aaaagaggta tttaatgata aactataatc cagaatttgt taggatagta tataagaata 120
agaccttgtt tagtttcaaa aaaatttgca aaattttcca gattcctcgt cacatcaaat 180
ctttagaggt atgcatggag tattaaatat agacaagacc taaataagaa aacatgaaat 240
gttcacgaaa aaaatcaagc caatgcatga tcgaagcaaa cggtatagta acggtgttaa 300
cctgatccat tgatctttgt aatctttaac ggccacctac cgcgggcagc aaacggcgtc 360
cccctcctcg atatctccgc ggcggcctct ggctttttcc gcggaattgc gcggtgggga 420
cggattccac gagaccgcaa cgcaaccgcc tctcgccgct gggcccccaca ccgctcggtg 480 ccgtagcccg tagcctcacg ggattctttc tccctcctcc cccgtgtata aattggcttc 540
atcccctccc tgcctcatcc atcca 565

<210> SEQ ID NO 152
<211> LENGTH: 77
<212> TYPE: DNA
<213> ORGANISM: Sorghum bicolor

<400> SEQUENCE: 152
aatcccactc cccaatccca tcccgtcgga gaaattcatc gaagcgaagc gaagcgaatc 60
ctcccgatcc tctcaag 77

<210> SEQ ID NO 153
<211> LENGTH: 1361
<212> TYPE: DNA
<213> ORGANISM: Sorghum bicolor

<400> SEQUENCE: 153
gtacgcgagt tttcgaatcc cctccagacc cctcgtatgc tttccctgtt cgttttcgtc 60
gtagcgtttg attaggtatg ctttccctgt tcgtgttcgt cgtagggttc gattaggtcg 120
tgtgaggcca tggcctgctg tgataaattt atttgttgtt atatcggatc tgtagtcgat 180
ttgggggtcg tggtgtagat ccgcgggctg tgatgaagtt atttggtgtg attgtgctcg 240
cgtgattctg cgcgttgagc tcgagtagat ctgatggttg gacgaccgat tggttcgttg 300

-continued

```
gctggctgcg ctaaggttgg gctgggctca tgttgcgttc gctgttgcgc gtgattccgc    360

ggatggactt gcgcttgatt gccgccagat cacgttacga ttatgtgatt tcgtttggaa    420

ctttttagat ttgtagcttc tgcttattat atgacagatg cgcctactgc tcatatgcct    480

gtggtaaata atggatggct gtgggtcaaa ctagttgatt gtcgagtcat gtatcatata    540

caggtgtata gacttgcgtc taattgtttg catgttgcag ttatatgatt tgttttagat    600

tgtttgttcc actcatctag gctgtaaaag ggacactact tattagcttg ttgtttaatc    660

tttttattag tagattatat tggtaatgtt ttactaatta ttattatgtt atatgtgact    720

tctgctcatg cctgattata atcatagatc actgtagttg attgttgaat catgtgtcaa    780

atacccgtat acataacact acacatttgc ttagttgttt ccttaactca tgcaaattga    840

acaccatgta tgatttgcat ggtgctgtaa tgttaaatac tacagtcctg ttggtacttg    900

tttagtaaga atctgcttca tacaactata tgctatgcct gatgataatc atatatcttt    960

gtgtaattaa taattagttg actgttgaat aatgtatcga gtacatacca tggcacaatt   1020

gcttagtcac ttccttaacc atgcatattg aactgacccc ttcatgttct gctgaattgt   1080

tctattctga ttagaccata catcatgtat tgcaatcttt atttgcaatt gtaatgtaat   1140

ggttcggttc tcaaatgtta aatgctatag ttgtgctact ttctaatgtt aaatgctata   1200

gctgtgctac ttgtaagatc tgcttcatag tttagttaaa ttaggatgat gagctttgat   1260

gctgtaactt tgtttgatta tgttcatagt tgatcagttt ttgttagact cacagtaact   1320

tatggtctca ctcttcttct ggtctttgat gtttgcagcg g                       1361
```

<210> SEQ ID NO 154
<211> LENGTH: 1812
<212> TYPE: DNA
<213> ORGANISM: Artificial sequence
<220> FEATURE:
<223> OTHER INFORMATION: Codon optimized coding sequence.

<400> SEQUENCE: 154

```
atggtccgtc ctgtagaaac cccaacccgt gaaatcaaaa aactcgacgg cctgtgggca     60

ttcagtctgg atcgcgaaaa ctgtggaatt gatcagcgtt ggtgggaaag cgcgttacaa    120

gaaagccggg caattgctgt gccaggcagt tttaacgatc agttcgccga tgcagatatt    180

cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtatc accgtttgtg tgaacaacga actgaactgg    420

cagactatcc cgccgggaat ggtgattacc gacgaaaacg gcaagaaaaa gcagtcttac    480

ttccatgatt tctttaacta tgccggaatc catcgcagcg taatgctcta caccacgccg    540

aacacctggg tggacgatat caccgtggtg acgcatgtcg cgcaagactg taaccacgcg    600

tctgttgact ggcaggtggt ggccaatggt gatgtcagcg ttgaactgcg tgatgcggat    660

caacaggtgg ttgcaactgg acaaggcact agcgggactt tgcaagtggt gaatccgcac    720

ctctggcaac cgggtgaagg ttatctctat gaactgtgcg tcacagccaa aagccagaca    780

gagtgtgata tctacccgct tcgcgtcggc atccggtcag tggcagtgaa gggcgaacag    840

ttcctgatta accacaaacc gttctacttt actggctttg gtcgtcatga agatgcggac    900

ttgcgtggca aaggattcga taacgtgctg atggtgcacg accacgcatt aatggactgg    960

attggggcca actcctaccg tacctcgcat taccettacg ctgaagagat gctcgactgg   1020
```

```
gcagatgaac atggcatcgt ggtgattgat gaaactgctg ctgtcggctt taacctctct   1080

ttaggcattg gtttcgaagc gggcaacaag ccgaaagaac tgtacagcga agaggcagtc   1140

aacggggaaa ctcagcaagc gcacttacag gcgattaaag agctgatagc gcgtgacaaa   1200

aaccacccaa gcgtggtgat gtggagtatt gccaacgaac cggatacccg tccgcaaggt   1260

gcacgggaat atttcgcgcc actggcggaa gcaacgcgta aactcgaccc gacgcgtccg   1320

atcacctgcg tcaatgtaat gttctgcgac gctcacaccg ataccatcag cgatctcttt   1380

gatgtgctgt gcctgaaccg ttattacgga tggtatgtcc aaagcggcga tttggaaacg   1440

gcagagaagg tactggaaaa agaacttctg gcctggcagg agaaactgca tcagccgatt   1500

atcatcaccg aatacggcgt ggatacgtta gccgggctgc actcaatgta caccgacatg   1560

tggagtgaag agtatcagtg tgcatggctg gatatgtatc accgcgtctt tgatcgcgtc   1620

agcgccgtcg tcggtgaaca ggtatggaat ttcgccgatt ttgcgacctc gcaaggcata   1680

ttgcgcgttg gcggtaacaa gaaagggatc ttcactcgcg accgcaaacc gaagtcggcg   1740

gcttttctgc tgcaaaaacg ctggactggc atgaacttcg gtgaaaaacc gcagcaggga   1800

ggcaaacaat ga                                                         1812
```

```
<210> SEQ ID NO 155
<211> LENGTH: 2001
<212> TYPE: DNA
<213> ORGANISM: Artificial sequence
<220> FEATURE:
<223> OTHER INFORMATION: Chimeric coding sequence with processable
      intron.

<400> SEQUENCE: 155

atggtccgtc ctgtagaaac cccaacccgt gaaatcaaaa aactcgacgg cctgtgggca     60

ttcagtctgg atcgcgaaaa ctgtggaatt gatcagcgtt ggtgggaaag cgcgttacaa    120

gaaagccggg caattgctgt gccaggcagt tttaacgatc agttcgccga tgcagatatt    180

cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtaag tttctgcttc tacctttgat atatatataa    420

taattatcat taattagtag taatataata tttcaaatat ttttttcaaa ataaaagaat    480

gtagtatata gcaattgctt ttctgtagtt tataagtgtg tatattttaa tttataactt    540

ttctaatata tgaccaaaat ttgttgatgt gcaggtatca ccgtttgtgt gaacaacgaa    600

ctgaactggc agactatccc gccgggaatg gtgattaccg acgaaaacgg caagaaaaag    660

cagtcttact tccatgattt ctttaactat gccggaatcc atcgcagcgt aatgctctac    720

accacgccga acacctgggt ggacgatatc accgtggtga cgcatgtcgc gcaagactgt    780

aaccacgcgt ctgttgactg gcaggtggtg gccaatggtg atgtcagcgt tgaactgcgt    840

gatgcggatc aacaggtggt tgcaactgga caaggcacta gcgggacttt gcaagtggtg    900

aatccgcacc tctggcaacc gggtgaaggt tatctctatg aactgtgcgt cacagccaaa    960

agccagacag agtgtgatat ctacccgctt cgcgtcggca tccggtcagt ggcagtgaag   1020

ggcgaacagt tcctgattaa ccacaaaccg ttctacttta ctggctttgg tcgtcatgaa   1080

gatgcggact tgcgtggcaa aggattcgat aacgtgctga tggtgcacga ccacgcatta   1140

atggactgga ttggggccaa ctcctaccgt acctcgcatt acccttacgc tgaagagatg   1200
```

```
ctcgactggg cagatgaaca tggcatcgtg gtgattgatg aaactgctgc tgtcggcttt   1260

aacctctctt taggcattgg tttcgaagcg ggcaacaagc cgaaagaact gtacagcgaa   1320

gaggcagtca acggggaaac tcagcaagcg cacttacagg cgattaaaga gctgatagcg   1380

cgtgacaaaa accacccaag cgtggtgatg tggagtattg ccaacgaacc ggatacccgt   1440

ccgcaaggtg cacgggaata tttcgcgcca ctggcggaag caacgcgtaa actcgacccg   1500

acgcgtccga tcacctgcgt caatgtaatg ttctgcgacg ctcacaccga taccatcagc   1560

gatctctttg atgtgctgtg cctgaaccgt tattacggat ggtatgtcca aagcggcgat   1620

ttggaaacgg cagagaaggt actggaaaaa gaacttctgg cctggcagga gaaactgcat   1680

cagccgatta tcatcaccga atacggcgtg gatacgttag ccgggctgca ctcaatgtac   1740

accgacatgt ggagtgaaga gtatcagtgt gcatggctgg atatgtatca ccgcgtcttt   1800

gatcgcgtca gcgccgtcgt cggtgaacag gtatggaatt tcgccgattt tgcgacctcg   1860

caaggcatat tgcgcgttgg cggtaacaag aaagggatct tcactcgcga ccgcaaaccg   1920

aagtcggcgg cttttctgct gcaaaaacgc tggactggca tgaacttcgg tgaaaaaccg   1980

cagcagggag gcaaacaatg a                                              2001
```

<210> SEQ ID NO 156
<211> LENGTH: 1653
<212> TYPE: DNA
<213> ORGANISM: Artificial sequence
<220> FEATURE:
<223> OTHER INFORMATION: Codon optimized coding sequence.

<400> SEQUENCE: 156

```
atggaagacg ccaaaaacat aaagaaaggc ccggcgccat tctatcctct agaggatgga     60

accgctggag agcaactgca taaggctatg aagagatacg ccctggttcc tggaacaatt    120

gcttttacag atgcacatat cgaggtgaac atcacgtacg cggaatactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgaacatt    360

tcgcagccta ccgtagtgtt tgtttccaaa aaggggttgc aaaaaatttt gaacgtgcaa    420

aaaaaattac caataatcca gaaaattatt atcatggatt ctaaaacgga ttaccaggga    480

tttcagtcga tgtacacgtt cgtcacatct catctacctc ccggttttaa tgaatacgat    540

tttgtaccag agtcctttga tcgtgacaaa acaattgcac tgataatgaa ttcctctgga    600

tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcagag aggcgaatta tgtgtcagag gacctatgat tatgtccggt   1200
```

```
tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg taa                                1653
```

<210> SEQ ID NO 157
<211> LENGTH: 936
<212> TYPE: DNA
<213> ORGANISM: Artificial sequence
<220> FEATURE:
<223> OTHER INFORMATION: Codon optimized coding sequence.

<400> SEQUENCE: 157

```
atggcttcca aggtgtacga ccccgagcaa cgcaaacgca tgatcactgg gcctcagtgg     60

tgggctcgct gcaagcaaat gaacgtgctg gactccttca tcaactacta tgattccgag    120

aagcacgccg agaacgccgt gatttttctg catggtaacg ctgcctccag ctacctgtgg    180

aggcacgtcg tgcctcacat cgagcccgtg gctagatgca tcatccctga tctgatcgga    240

atgggtaagt ccggcaagag cgggaatggc tcatatcgcc tcctggatca ctacaagtac    300

ctcaccgctt ggttcgagct gctgaacctt ccaaagaaaa tcatctttgt gggccacgac    360

tggggggctt gtctggcctt tcactactcc tacgagcacc aagacaagat caaggccatc    420

gtccatgctg agagtgtcgt ggacgtgatc gagtcctggg acgagtggcc tgacatcgag    480

gaggatatcg ccctgatcaa gagcgaagag ggcgagaaaa tggtgcttga gaataacttc    540

ttcgtcgaga ccatgctccc aagcaagatc atgcggaaac tggagcctga ggagttcgct    600

gcctacctgg agccattcaa ggagaagggc gaggttagac ggcctaccct ctcctggcct    660

cgcgagatcc ctctcgttaa gggaggcaag cccgacgtcg tccagattgt ccgcaactac    720

aacgcctacc ttcgggccag cgacgatctg cctaagatgt tcatcgagtc cgaccctggg    780

ttcttttcca acgctattgt cgagggagct aagaagttcc ctaacaccga gttcgtgaag    840

gtgaagggcc tccacttcag ccaggaggac gctccagatg aaatgggtaa gtacatcaag    900

agcttcgtgg agcgcgtgct gaagaacgag cagtaa                             936
```

<210> SEQ ID NO 158
<211> LENGTH: 253
<212> TYPE: DNA
<213> ORGANISM: Agrobacterium tumefaciens

<400> SEQUENCE: 158

```
gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253
```

<210> SEQ ID NO 159
<211> LENGTH: 210

<212> TYPE: DNA
<213> ORGANISM: Triticum aestivum

<400> SEQUENCE: 159
ctgcatgcgt ttggacgtat gctcattcag gttggagcca atttggttga tgtgtgtgcg 60
agttcttgcg agtctgatga gacatctctg tattgtgttt ctttccccag tgttttctgt 120
acttgtgtaa tcggctaatc gccaacagat tcggcgatga ataaatgaga aataaattgt 180
tctgattttg agtgcaaaaa aaaaggaatt 210

<210> SEQ ID NO 160
<211> LENGTH: 300
<212> TYPE: DNA
<213> ORGANISM: Oryza sativa

<400> SEQUENCE: 160
attaatcgat cctccgatcc cttaattacc ataccattac accatgcatc aatatccata 60
tatatataaa ccctttcgca cgtacttata ctatgttttg tcatacatat atatgtgtcg 120
aacgatcgat ctatcactga tatgatatga ttgatccatc agcctgatct ctgtatcttg 180
ttatttgtat accgtcaaat aaaagtttct tccacttgtg ttaataatta gctactctca 240
tctcatgaac cctatatata actagtttaa tttgctgtca attgaacatg atgatcgatg 300

<210> SEQ ID NO 161
<211> LENGTH: 1204
<212> TYPE: DNA
<213> ORGANISM: Artificial sequence
<220> FEATURE:
<223> OTHER INFORMATION: Chimeric transcriptional regulatory expression
element group.

<400> SEQUENCE: 161
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tccttcgcaa gacccttcct ctatataagg aagttcattt 600
catttggaga ggacacgctg acaagctgac tctagcagat cctctagaac catcttccac 660
acactcaagc cacactattg gagaacacac agggacaaca caccataaga tccaagggag 720
gcctccgccg ccgccggtaa ccaccccgcc cctctcctct ttctttctcc gttttttttt 780
ccgtctcggt ctcgatcttt ggccttggta gtttgggtgg gcgagaggcg gcttcgtgcg 840
cgcccagatc ggtgcgcggg aggggcggga tctcgcggct ggggctctcg ccggcgtgga 900
tccggcccgg atctcgcggg gaatggggct ctcggatgta gatctgcgat ccgccgttgt 960
tgggggagat gatggggggt ttaaaatttc cgccgtgcta aacaagatca ggaagagggg 1020
aaaagggcac tatggtttat atttttatat atttctgctg cttcgtcagg cttagatgtg 1080
ctagatcttt ctttcttctt tttgtgggta gaatttgaat ccctcagcat tgttcatcgg 1140

```
tagtttttct tttcatgatt tgtgacaaat gcagcctcgt gcggagcttt tttgtaggta   1200

gaag                                                                1204


<210> SEQ ID NO 162
<211> LENGTH: 1396
<212> TYPE: DNA
<213> ORGANISM: Oryza sativa

<400> SEQUENCE: 162

tcgaggtcat tcatatgctt gagaagagag tcgggatagt ccaaaataaa acaaaggtaa     60

gattacctgg tcaaaagtga aaacatcagt taaaaggtgg tataaagtaa aatatcggta    120

ataaaaggtg gcccaaagtg aaatttactc ttttctacta ttataaaaat tgaggatgtt    180

tttgtcggta ctttgatacg tcatttttgt atgaattggt ttttaagttt attcgctttt    240

ggaaatgcat atctgtattt gagtcgggtt ttaagttcgt ttgcttttgt aaatacagag    300

ggatttgtat aagaaatatc tttagaaaaa cccatatgct aatttgacat aatttttgag    360

aaaaatatat attcaggcga attctcacaa tgaacaataa taagattaaa atagctttcc    420

cccgttgcag cgcatgggta ttttttctag taaaaataaa agataaactt agactcaaaa    480

catttacaaa aacaacccct aaagttccta aagcccaaag tgctatccac gatccatagc    540

aagcccagcc caacccaacc caacccagcc caccccagtc cagccaactg gacaatagtc    600

tccacacccc cccactatca ccgtgagttg tccgcacgca ccgcacgtct cgcagccaaa    660

aaaaaaaaga aagaaaaaaa agaaaaagaa aaaacagcag gtgggtccgg gtcgtggggg    720

ccggaaacgc gaggaggatc gcgagccagc gacgaggccg gccctccctc cgcttccaaa    780

gaaacgcccc ccatcgccac tatatacata cccccccctc tcctcccatc cccccaaccc    840

taccaccacc accaccacca cctccacctc ctccccccctc gctgccggac gacgagctcc    900

tccccccctcc ccctccgccg ccgccgcgcc ggtaaccacc ccgcccctct cctctttctt    960

tctccgtttt tttttccgtc tcggtctcga tctttggcct tggtagtttg ggtgggcgag   1020

aggcggcttc gtgccgccca gatcggtgcg cgggaggggc gggatctcgc ggctggctct   1080

cgcccccgtg gatccggccc ggatctcgcg gggaatgggg ctctcggatg tagatctgcg   1140

atccgccgtt gttggggccg atgatggggc ccttaaaatt tccgccgtgc taaacaagat   1200

caggaagagg ggaaaagggc actatggttt atattttat atatttctgc tgcttcgtca    1260

ggcttagatg tgctagatct ttctttcttc tttttgtggg tagaatttaa tccctcagca   1320

ttgttcatcg gtagtttttc ttttcatgat tcgtgacaaa tgcagcctcg tgcggacgtt   1380

tttttgtagg tagaag                                                   1396


<210> SEQ ID NO 163
<211> LENGTH: 1446
<212> TYPE: DNA
<213> ORGANISM: Artificial sequence
<220> FEATURE:
<223> OTHER INFORMATION: Chimeric transcriptional regulatory expression
      element group.

<400> SEQUENCE: 163

ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240
```

```
aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga ggacacgctg acaagctgac tctagcagat ctaccgtctt cggtacgcgc    660

tcactccgcc ctctgccttt gttactgcca cgtttctctg aatgctctct tgtgtggtga    720

ttgctgagag tggtttagct ggatctagaa ttacactctg aaatcgtgtt ctgcctgtgc    780

tgattacttg ccgtcctttg tagcagcaaa atatagggac atggtagtac gaaacgaaga    840

tagaacctac acagcaatac gagaaatgtg taatttggtg cttagcggta tttatttaag    900

cacatgttgg tgttataggg cacttggatt cagaagtttg ctgttaattt aggcacaggc    960

ttcatactac atgggtcaat agtataggga ttcatattat aggcgatact ataataattt   1020

gttcgtctgc agagcttatt atttgccaaa attagatatt cctattctgt ttttgtttgt   1080

gtgctgttaa attgttaacg cctgaaggaa taaatataaa tgacgaaatt ttgatgttta   1140

tctctgctcc tttattgtga ccataagtca agatcagatg cacttgtttt aaatattgtt   1200

gtctgaagaa ataagtactg acagtatttt gatgcattga tctgcttgtt tgttgtaaca   1260

aaatttaaaa ataaagagtt tcctttttgt tgctctcctt acctcctgat ggtatctagt   1320

atctaccaac tgacactata ttgcttctct ttacatacgt atcttgctcg atgccttctc   1380

cctagtgttg accagtgtta ctcacatagt ctttgctcat ttcattgtaa tgcagatacc   1440

aagcgg                                                              1446
```

```
<210> SEQ ID NO 164
<211> LENGTH: 675
<212> TYPE: DNA
<213> ORGANISM: Artificial sequence
<220> FEATURE:
<223> OTHER INFORMATION: Chimeric transcriptional regulatory expression
      element group.

<400> SEQUENCE: 164

ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat gtgagacttt tcaacaaagg gtaatatccg    300

gaaacctcct cggattccat tgcccagcta tctgtcactt tattgtgaag atagtggaaa    360

aggaaggtgg ctcctacaaa tgccatcatt gcgataaagg aaaggccatc gttgaagatg    420

cctctgccga cagtggtccc aaagatggac ccccacccac gaggagcatc gtggaaaaag    480

aagacgttcc aaccacgtct tcaaagcaag tggattgatg tgatatctcc actgacgtaa    540

gggatgacgc acaatcccac tatccttcgc aagacccttc ctctatataa ggaagttcat    600

ttcatttgga gaggaaccat cttccacaca ctcaagccac actattggag aacacacagg    660

gacaacacac cataa                                                     675
```

<210> SEQ ID NO 165
<211> LENGTH: 804
<212> TYPE: DNA
<213> ORGANISM: Zea mays

<400> SEQUENCE: 165
accgtcttcg gtacgcgctc actccgccct ctgcctttgt tactgccacg tttctctgaa 60
tgctctcttg tgtggtgatt gctgagagtg gtttagctgg atctagaatt acactctgaa 120
atcgtgttct gcctgtgctg attacttgcc gtcctttgta gcagcaaaat atagggacat 180
ggtagtacga aacgaagata gaacctacac agcaatacga gaaatgtgta atttggtgct 240
tagcggtatt tatttaagca catgttggtg ttatagggca cttggattca gaagtttgct 300
gttaatttag gcacaggctt catactacat gggtcaatag tatagggatt catattatag 360
gcgatactat aataatttgt tcgtctgcag agcttattat ttgccaaaat tagatattcc 420
tattctgttt ttgtttgtgt gctgttaaat tgttaacgcc tgaaggaata aatataaatg 480
acgaaatttt gatgtttatc tctgctcctt tattgtgacc ataagtcaag atcagatgca 540
cttgttttaa atattgttgt ctgaagaaat aagtactgac agtattttga tgcattgatc 600
tgcttgtttg ttgtaacaaa atttaaaaat aaagagtttc ctttttgttg ctctccttac 660
ctcctgatgg tatctagtat ctaccaactg acactatatt gcttctcttt acatacgtat 720
cttgctcgat gccttctccc tagtgttgac cagtgttact cacatagtct ttgctcattt 780
cattgtaatg cagataccaa gcgg 804

<210> SEQ ID NO 166
<211> LENGTH: 623
<212> TYPE: DNA
<213> ORGANISM: Cauliflower mosaic virus

<400> SEQUENCE: 166
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgatatctcc actgacgtaa 540
gggatgacgc acaatcccac tatccttcgc aagacccttc ctctatataa ggaagttcat 600
ttcatttgga gaggacacgc tga 623

<210> SEQ ID NO 167
<211> LENGTH: 8
<212> TYPE: DNA
<213> ORGANISM: Cauliflower mosaic virus

<400> SEQUENCE: 167 acacgctg 8

<210> SEQ ID NO 168
<211> LENGTH: 1790
<212> TYPE: DNA

<213> ORGANISM: Coix lacryma-jobi

<400> SEQUENCE: 168
gtgatgttca agatattgta atggtgttta ttttctatca aatagccata aaatgatata 60
caaaatgtta ttcatgattg atcctagtta cattcaaagt attaaatagc ttgcagatag 120
taaatagaca gtcattgtat aacctgtttt tttgactgtc tatgttcagt tccaagaact 180
tacagacaag aggttatgtg tagattgaac gtgcccttga cggcatccaa ctagcgaacc 240
acgagggaag cagatggtgg ccgttgaggg gctgttgacg caaagcatct ctctcggctg 300
ctctcgaaag ctccattgcg ggtggcggtc tggtggcacc aggaaattgc gtgagccaag 360
gcgggctcgt ctcggtctca caacacggca cgaaaccgtc acggcacacg gcaccaggat 420
ttccttcccc tcccctgccg ttctcctcat cataaatagc cacccccctcc tcgcctcttt 480 tccccaactc atctgttctt cgtctcacac agccagatcc caatccctct cctcgcgaac 540
ttcgtcgatc tcccttccct cgcctcgctt caaggtacgg cgatcatcct cccgctttcc 600
ctcctcctcc tctagatgta gtacggagta cttgccatca tgcatcatgc tacatcacgc 660
tcgtgcgagc tctgggtcct cgatctggga acggaactgt gggatgctgc tcgtgcgatt 720
tattattggg gatctgggtt ctcgatctgg gaacggaact gtgggatgct gctcgtgcga 780
tttattattg gggatctggg ttctcgatct gggaacggaa ctgtgggatg cttgtaggca 840
ggtcggagat gggtcggatc gttgcttagg gttcgatctg ctcgtggttt tcttttaatc 900
cctgatgcat gatttatcgg tcatcctatt agatggaacc agtagggtga ctctgatccg 960
atatacttaa cctcgatctg gttcgatgtt cctggctagg cttgtgcgtc tgtttcgtca 1020
gaccagtttt gctgtttttg gtatggttgt gatgcccgtc caaatatgac taagcgagtg 1080
tagaatcatt ttatgaacta actgctggtc ttattaaatc tagatctgca tacgttgatg 1140
tactacgttc atagttgata cagtatgtat gaactagttg ctggtcgtat taattttgga 1200
tctgcatgtg tggtagcata taatgttcat aatacaattg atacagtatg atgtatgaac 1260
tatctgctgg tttattaaat ttggatctgc ttgtggtaaa aaatatgttt tttatatagt 1320
taccatgatg gattaatcta tacttctgat gtatatgctg cagttttctg ctgaggctgt 1380 agtttttttcc agattaaaat acagcatgca tatttgctaa gctctgggcg tgtgaacgcc 1440
caccatggca ttgtccagta atagtaatga attttttttgt ttgcctgatg tgggagaaaa 1500
cacgcattgt ccagttattt tgttccatat gcattgtcct gttttgttgg atatgcatgc 1560
ttagaaaaca tatgcagcca ctgtttgata atgctttagc atctgcctgt tgaacatgca 1620
tgatctacct atctttattt tgtatgtact tgggtagtgg catgttgcta gttttccttg 1680
attctgtggc gtctacatgt tgagcttgca tatatgtttg ttgtccttct tttcctcctt 1740
ggtctactgc tatatgctta cccttttgtt tggctaattt tcaggtgcag 1790

<210> SEQ ID NO 169
<211> LENGTH: 481
<212> TYPE: DNA
<213> ORGANISM: Coix lacryma-jobi

<400> SEQUENCE: 169
gtgatgttca agatattgta atggtgttta ttttctatca aatagccata aaatgatata 60
caaaatgtta ttcatgattg atcctagtta cattcaaagt attaaatagc ttgcagatag 120
taaatagaca gtcattgtat aacctgtttt tttgactgtc tatgttcagt tccaagaact 180
tacagacaag aggttatgtg tagattgaac gtgcccttga cggcatccaa ctagcgaacc 240
acgagggaag cagatggtgg ccgttgaggg gctgttgacg caaagcatct ctctcggctg 300
ctctcgaaag ctccattgcg ggtggcggtc tggtggcacc aggaaattgc gtgagccaag 360
gcgggctcgt ctcggtctca caacacggca cgaaaccgtc acggcacacg gcaccaggat 420
ttccttcccc tcccctgccg ttctcctcat cataaatagc cacccctcc tcgcctcttt 480 t 481

<210> SEQ ID NO 170
<211> LENGTH: 93
<212> TYPE: DNA
<213> ORGANISM: Coix lacryma-jobi

<400> SEQUENCE: 170
ccccaactca tctgttcttc gtctcacaca gccagatccc aatccctctc ctcgcgaact 60
tcgtcgatct cccttccctc gcctcgcttc aag 93

<210> SEQ ID NO 171
<211> LENGTH: 1216
<212> TYPE: DNA
<213> ORGANISM: Coix lacryma-jobi

<400> SEQUENCE: 171
gtacggcgat catcctcccg ctttccctcc tcctcctcta gatgtagtac ggagtacttg 60
ccatcatgca tcatgctaca tcacgctcgt gcgagctctg ggtcctcgat ctgggaacgg 120
aactgtggga tgctgctcgt gcgatttatt attggggatc tgggttctcg atctgggaac 180
ggaactgtgg gatgctgctc gtgcgattta ttattgggga tctgggttct cgatctggga 240
acggaactgt gggatgcttg taggcaggtc ggagatgggt cggatcgttg cttagggttc 300
gatctgctcg tggttttctt ttaatccctg atgcatgatt tatcggtcat cctattagat 360
ggaaccagta gggtgactct gatccgatat acttaacctc gatctggttc gatgttcctg 420
gctaggcttg tgcgtctgtt tcgtcagacc agttttgctg tttttggtat ggttgtgatg 480
cccgtccaaa tatgactaag cgagtgtaga atcattttat gaactaactg ctggtcttat 540
taaatctaga tctgcatacg ttgatgtact acgttcatag ttgatacagt atgtatgaac 600
tagttgctgg tcgtattaat tttggatctg catgtgtggt agcatataat gttcataata 660
caattgatac agtatgatgt atgaactatc tgctggttta ttaaatttgg atctgcttgt 720
ggtaaaaaat atgtttttta tatagttacc atgatggatt aatctatact tctgatgtat 780
atgctgcagt tttctgctga ggctgtagtt ttttccagat taaaatacag catgcatatt 840
tgctaagctc tgggcgtgtg aacgcccacc atggcattgt ccagtaatag taatgaattt 900
ttttgtttgc ctgatgtggg agaaaacacg cattgtccag ttattttgtt ccatatgcat 960
tgtcctgttt tgttggatat gcatgcttag aaaacatatg cagccactgt ttgataatgc 1020
tttagcatct gcctgttgaa catgcatgat ctacctatct ttattttgta tgtacttggg 1080
tagtggcatg ttgctagttt tccttgattc tgtggcgtct acatgttgag cttgcatata 1140
tgtttgttgt ccttcttttc ctccttggtc tactgctata tgcttaccct tttgtttggc 1200
taattttcag gtgcag 1216

PLANT REGULATORY ELEMENTS FROM A UBIQUITIN GENE FROM BOUTELOUA GRACILIS

REFERENCE TO RELATED APPLICATIONS

This application is a divisional of co-pending U.S. application Ser. No. 14/133,599, filed Dec. 18, 2013 (pending), which claims the benefit of priority to United States provisional application Ser. No. 61/739,720, filed Dec. 19, 2012, the disclosures of which are incorporated by reference herein in their entirety.

INCORPORATION OF SEQUENCE LISTING

The sequence listing that is contained in the file named "38-21-59465-0000Seq.txt", which is 341,857 bytes (as measured in Microsoft Windows®) and was created on Sep. 27, 2012, is filed herewith by electronic submission and is incorporated by reference herein.

FIELD OF THE INVENTION

The invention relates to the field of plant molecular biology, plant genetic engineering, and DNA molecules useful for modulating gene expression in plants.

BACKGROUND

Regulatory elements are genetic elements that regulate gene activity by modulating the transcription of an operably linked transcribable DNA molecule. Such elements include promoters, leaders, enhancers, introns, and 3' untranslated regions, and are useful in the field of plant molecular biology and plant genetic engineering.

SUMMARY OF THE INVENTION

The invention provides novel regulatory elements for use in plants and constructs comprising the regulatory elements. The invention also provides transgenic plant cells, plants, plant parts, and seeds comprising the regulatory elements. In one embodiment, the invention provides the regulatory elements disclosed herein operably linked to a transcribable DNA molecule. In certain embodiments, the transcribable DNA molecule is heterologous with respect to a regulatory element sequence provided herein. Also provided herein are methods for making and using the regulatory elements disclosed herein, including constructs comprising the regulatory elements, and transgenic plants, plant cells, plant parts, and seeds comprising the regulatory elements operably linked to a transcribable DNA molecule that is heterologous with respect to the regulatory element.

Thus, in one aspect, the invention provides a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. By "heterologous transcribable DNA molecule," it is meant that the transcribable DNA molecule is heterologous with respect to the DNA sequence. In specific embodiments, the recombinant DNA molecule comprises a DNA sequence having at least 90 percent, at least 91 percent, at least 92 percent, at least 93 percent, at least 94 percent, at least about 95 percent, at least 96 percent, at least 97 percent, at least 98 percent, or at least 99 percent sequence identity to the DNA sequence of any of SEQ ID NOs: 1-98 and 168-171. In particular embodiments, the heterologous transcribable DNA molecule comprises a gene of agronomic interest, such as a gene capable of conferring herbicide resistance or pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a DNA sequence with at least about 85 percent sequence identity to any of SEQ ID NOs: 1-98 and 168-171; b) a DNA sequence comprising any of SEQ ID NOs: 1-98 and 168-171; and c) a fragment of any of SEQ ID NOs: 1-98 and 168-171, wherein the fragment has gene-regulatory activity; wherein the DNA sequence is operably linked to a heterologous transcribable DNA molecule. In specific embodiments, the transgenic plant is a progeny plant of any generation relative to a starting transgenic plant and comprises the recombinant DNA molecule. A transgenic seed comprising the recombinant DNA molecule that produces such a transgenic plant when grown is also provided by the invention.

In still yet another aspect, the invention provides a method of expressing a transcribable DNA molecule, such as a gene of agronomic interest, in a transgenic plant by obtaining a transgenic plant containing a recombinant DNA molecule of the invention and cultivating the plant.

Also provided herein is a method of providing a transgenic plant by transforming a plant cell with a recombinant DNA molecule of the invention to produce a transformed plant cell, and regenerating the transformed plant cell to produce a transgenic plant.

BRIEF DESCRIPTION OF THE FIGURES

FIG. 1 shows an alignment of a 2005 base pair (bp) promoter P-AGRne.Ubq1-1:1:5 (SEQ ID NO: 2), contained in the regulatory expression element group (EXP) EXP-AGRne.Ubq1:1:7 (SEQ ID NO: 1), with promoter variants of P-AGRne.Ubq1-1:1:5. Deletion, for instance of the 5' end of P-AGRne.Ubq1-1:1:5, produced the promoter P-AGRne.Ubq1-1:1:4 (SEQ ID NO: 6), a 999 bp sequence that is contained in EXP-AGRne.Ubq1:1:8 (SEQ ID NO: 5). Another promoter variant shown in FIG. 1 is P-AGRne.Ubq1-1:1:6 (SEQ ID NO: 8), a 762 bp sequence contained in EXP-AGRne.Ubq1:1:9 (SEQ ID NO: 7).

FIG. 2 shows an alignment of a 4114 bp promoter P-ARUdo.Ubq1-1:1:4 (SEQ ID NO: 10), contained in the regulatory expression element group EXP-ARUdo.Ubq1:1:4 (SEQ ID NO: 9), with promoter variants of P-ARUdo.Ubq1-1:1:4. Included in the alignment are a 2012 bp promoter P-ARUdo.Ubq1-1:1:5 (SEQ ID NO: 14); a 1000 bp promoter P-ARUdo.Ubq1-1:1:6 (SEQ ID NO: 17); and a 755 bp promoter P-ARUdo.Ubq1-1:1:8 (SEQ ID NO: 22).

FIG. 3 shows an alignment of a 2033 bp promoter P-ARUdo.Ubq2-1:1:4 (SEQ ID NO: 24) with promoter variants of P-ARUdo.Ubq2-1:1:4. Included in the alignment are a 2004 bp promoter P-ARUdo.Ubq2-1:1:6 (SEQ ID NO: 28); a 1001 bp promoter P-ARUdo.Ubq2-1:1:5 (SEQ ID NO: 31); and a 696 bp promoter P-ARUdo.Ubq2-1:1:7 (SEQ ID NO: 33).

FIG. 4 shows an alignment of a 2371 bp promoter P-BOUgr.Ubq1-1:1:2 (SEQ ID NO: 35) with promoter variants of the 5' end of P-BOUgr.Ubq1-1:1:2. Included in the alignment are a 1999 bp promoter P-BOUgr.Ubq1-1:1:3 (SEQ ID NO: 39); a 1022 bp promoter P-BOUgr.Ubq1-1:1:5 (SEQ ID NO: 42); and a 760 bp promoter P-BOUgr.Ubq1-1:1:6 (SEQ ID NO: 44).

FIG. 5 shows alignment of a 2100 bp promoter element, P-BOUgr.Ubq2-1:1:4 (SEQ ID NO: 46) with promoter variants of P-BOUgr.Ubq2-1:1:4. Included in the alignment are a 2043 bp promoter P-BOUgr.Ubq2-1:1:7 (SEQ ID NO: 50); a 2002 bp promoter P-BOUgr.Ubq2-1:1:5 (SEQ ID NO: 53); a 1024 bp promoter P-BOUgr.Ubq2-1:1:6 (SEQ ID NO: 56); and a 749 bp promoter P-BOUgr.Ubq2-1:1:8 (SEQ ID NO: 61).

FIG. 6 shows an alignment of a 5359 bp promoter element, P-MISsi.Ubq1-1:1:2 (SEQ ID NO: 63) with promoter variants of P-MISsi.Ubq1-1:1:2. Included in the alignment are a 2423 bp promoter P-MISsi.Ubq1-1:1:11 (SEQ ID NO: 67); a 1447 bp promoter P-MISsi.Ubq1-1:1:10 (SEQ ID NO: 71); a 899 bp promoter P-MISsi.Ubq1-1:1:13 (SEQ ID NO: 73); a 691 bp promoter P-MISsi.Ubq1-1:1:14 (SEQ ID NO: 75); and a 506 bp promoter P-MISsi.Ubq1-1:1:9 (SEQ ID NO: 77).

FIG. 7 shows an alignment of a 2831 bp promoter element, P-SCHsc.Ubq1-1:1:12 (SEQ ID NO: 79) with promoter variants of P-SCHsc.Ubq1-1:1:12. Included in the alignment are a 2033 bp promoter P-SCHsc.Ubq1-1:1:11 (SEQ ID NO: 83); a 1046 bp promoter P-SCHsc.Ubq1-1:1:10 (SEQ ID NO: 85); and a 547 bp promoter P-SCHsc.Ubq1-1:1:14 (SEQ ID NO: 87).

FIG. 8 shows an alignment of a 2218 bp promoter element, P-SORnu.Ubq1-1:1:4 (SEQ ID NO: 89) with promoter variants of P-SORnu.Ubq1-1:1:4. Included in the alignment are a 1964 bp promoter P-SORnu.Ubq1-1:1:5 (SEQ ID NO: 93); a 1023 bp promoter P-SORnu.Ubq1-1:1:6 (SEQ ID NO: 96); and a 724 bp promoter P-SORnu.Ubq1-1:1:7 (SEQ ID NO: 98).

BRIEF DESCRIPTION OF THE SEQUENCES

Figure 1:
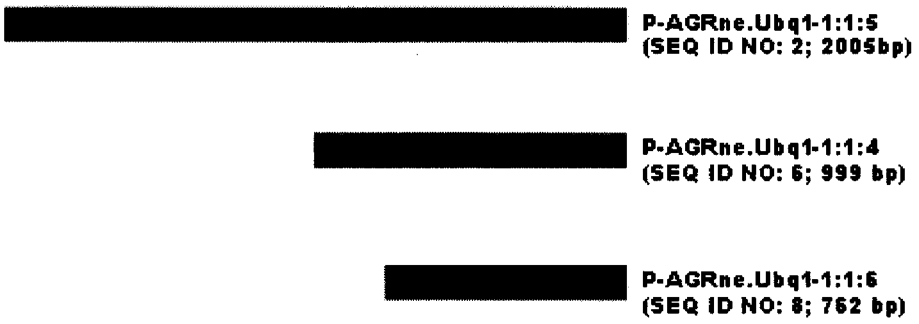
FIG. 1: Shows an alignment of multiple promoter variants of various sizes corresponding to promoter elements from *Agrostis nebulosa*. In particular.
Figure 2:
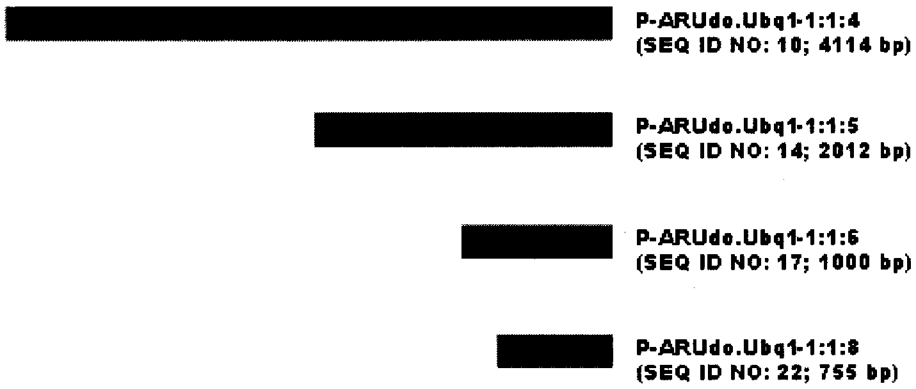
FIG. 2: Shows an alignment of multiple promoter variants of various sizes corresponding to promoter elements from *Arundo donax*. In particular.
Figure 3:
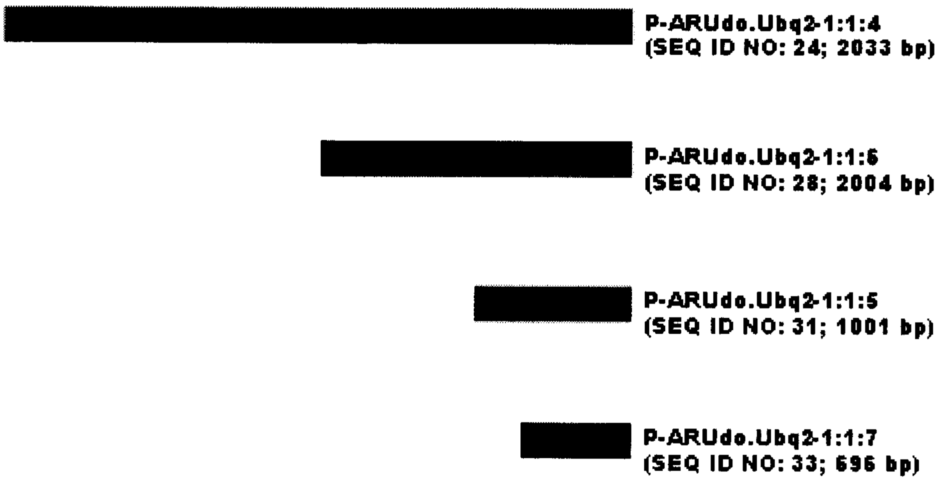
FIG. 3: Shows an alignment of multiple promoter variants of various sizes corresponding to promoter elements from *Arundo donax*. In particular.
Figure 4:
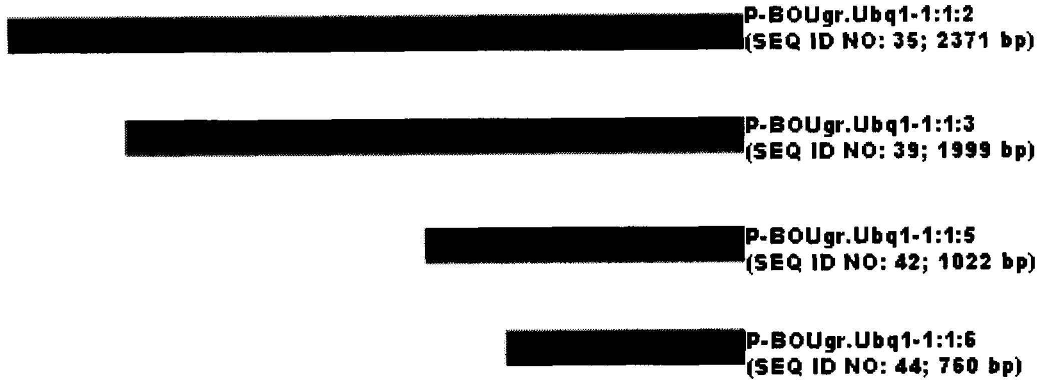
FIG. 4: Shows an alignment of multiple promoter variants of various sizes corresponding to promoter elements from *Bouteloua gracilis*. In particular.
Figure 5:
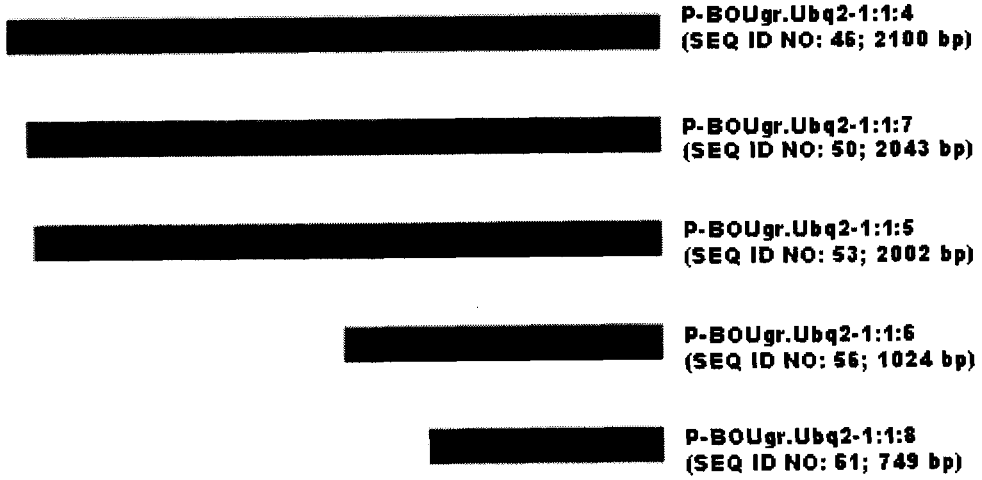
FIG. 5: Shows an alignment of multiple promoter variants of various sizes corresponding to promoter elements from *Bouteloua gracilis*. In particular.
Figure 6:
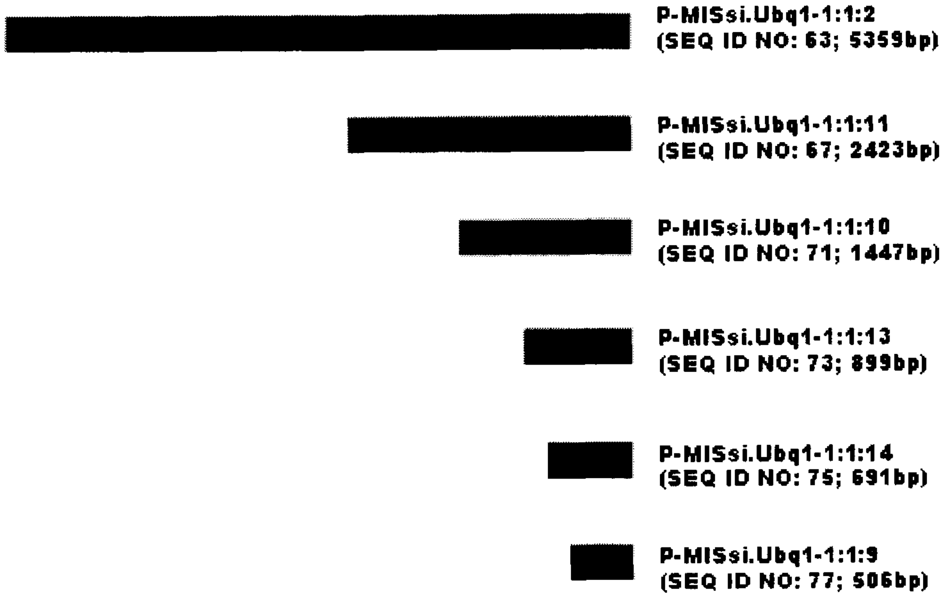
FIG. 6: Shows an alignment of multiple promoter variants of various sizes corresponding to promoter elements from *Miscanthus sinesis*. In particular.
Figure 7:
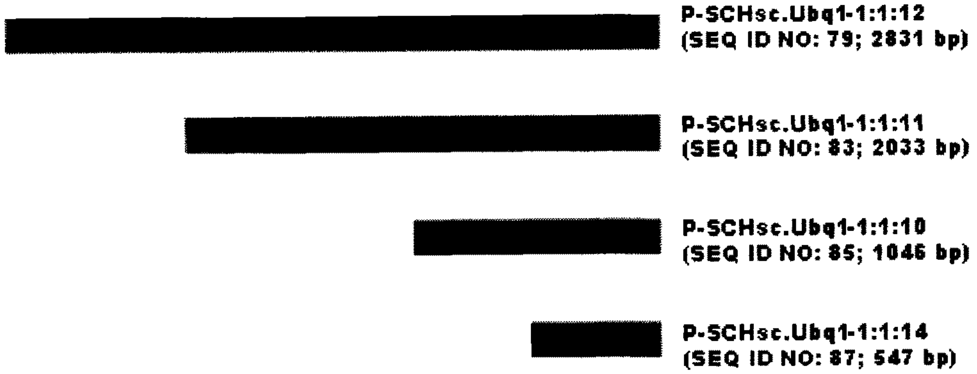
FIG. 7: Shows an alignment of multiple promoter variants of various sizes corresponding to promoter elements from *Schizachyium scoparium*. In particular.
Figure 8:
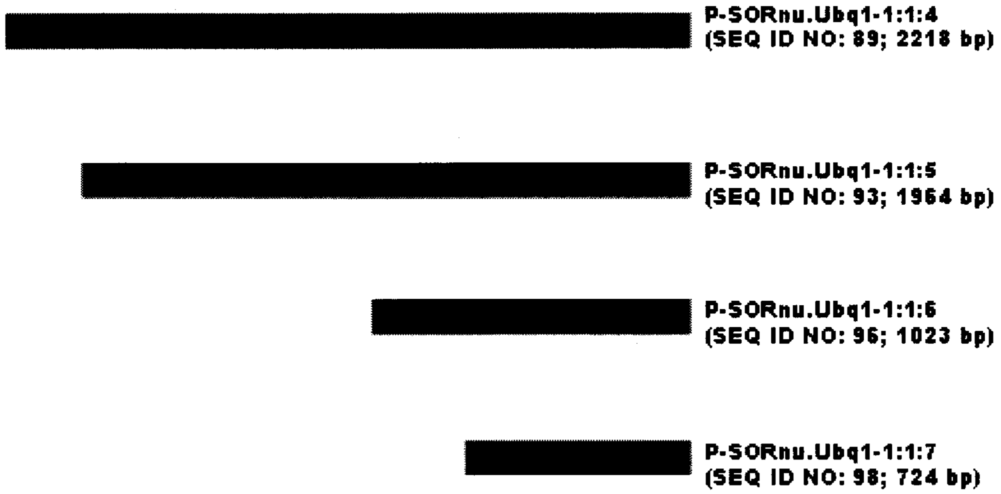
FIG. 8: Shows an alignment of multiple promoter variants of various sizes corresponding to promoter elements from *Sorghastrum nutans*. In particular.

SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168 are DNA sequences of regulatory expression element groups (EXPs) comprising a promoter sequence operably linked 5' to a leader sequence which is operably linked 5' to an intron sequence.

SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169 are promoter sequences.

SEQ ID NOs: 3, 11, 25, 36, 47, 64, 68, 80, 90, 101, 112, 124, 130, 136, 142, 146, 152 and 170 are leader sequences.

SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171 are intron sequences.

DETAILED DESCRIPTION OF THE INVENTION

The invention provides DNA molecules having gene-regulatory activity in plants. The nucleotide sequences of these DNA molecules are provided as SEQ ID NOs: 1-98 and 168-171. These DNA molecules are, for instance, capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing recombinant DNA molecules of the invention, and methods for preparing and using the same.

The following definitions and methods are provided to better define the invention and to guide those of ordinary skill in the art in the practice of the invention. Unless otherwise noted, terms are to be understood according to conventional usage by those of ordinary skill in the relevant art.

DNA Molecules

As used herein, the term "DNA" or "DNA molecule" refers to a double-stranded DNA molecule of cellular or synthetic origin, i.e., a polymer of deoxyribonucleotide bases. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

As used herein, the term "sequence identity" refers to the extent to which two optimally aligned DNA sequences are identical. An optimal sequence alignment is created by manually aligning two DNA sequences, e.g., a reference sequence and another DNA sequence, to maximize the number of nucleotide matches in the sequence alignment with appropriate internal nucleotide insertions, deletions, or gaps. As used herein, the term "reference sequence" refers to a DNA sequence provided as SEQ ID NOs: 1-98 and 168-171.

As used herein, the term "percent sequence identity" or "percent identity" or "% identity" is the identity fraction multiplied by 100. The "identity fraction" for a DNA sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a DNA sequence that when optimally aligned to a reference sequence, provided herein as SEQ ID NOs: 1-98 and 168-171, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders, enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence, which is in turn operably linked 5' to an intron sequence.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. Chimeric promoters are produced through the fusion of two or more heterologous DNA molecules. Promoters useful in practicing the invention include SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, including fragments or variants thereof. In specific embodiments of the invention, such DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169, such as internal or 5' deletions, for example, can be produced using well known methods in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 comprised of 3' deletions in which the TATA box element or equivalent DNA sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and fragments or enhancers derived therefrom can be used to make chimeric regulatory element compositions comprised of any of the promoters presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169 and the fragments or enhancers derived therefrom operably linked to other enhancers and promoters.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Promoter molecules of the invention may thus be operably linked to their native leader or may be operably linked to a heterologous leader. Leaders useful in practicing the invention include SEQ ID NOs: 3, 11, 25, 36, 47, 64, 68, 80, 90 and 170 or fragments or variants thereof. In specific embodiments, such DNA sequences may be defined as being capable of acting as a leader in a host cell, including, for example, a transgenic plant cell. In one embodiment, such DNA sequences may be decoded as comprising leader activity.

The leader sequences (5' UTR) presented as SEQ ID NOs: 3, 11, 25, 36, 47, 64, 68, 80, 90 and 170 may be comprised of regulatory elements or may adopt secondary structures that can have an effect on transcription or translation of an operably linked DNA molecule. The leader sequences presented as SEQ ID NOs: 3, 11, 25, 36, 47, 64, 68, 80, 90 and 170 can be used in accordance with the invention to make chimeric regulatory elements that affect transcription or translation of an operably linked DNA molecule. In addition, the leader sequences presented as SEQ ID NOs: 3, 11, 25, 36, 47, 64, 68, 80, 90 and 170 can be used to make chimeric leader sequences that affect transcription or translation of an operably linked DNA molecule.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements.

Introns useful in practicing the invention include SEQ ID NOs: 4, 12, 15, 20, 26, 29, 37, 40, 48, 51, 54, 57, 59, 65, 69, 81, 91, 94 and 171. Compositions derived from any of the introns presented as SEQ ID NOs: 4, 12, 15, 20, 26, 29, 37, 40, 48, 51, 54, 57, 59, 65, 69, 81, 91, 94 and 171 can be comprised of internal deletions or duplications of cis regulatory elements; and/or alterations of the 5' and 3' DNA sequences comprising the intron/exon splice junctions can be used to improve expression or specificity of expression when operably linked to a promoter+leader or chimeric promoter+leader and coding sequence. When modifying intron/exon boundary sequences, it may be beneficial to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified in this manner. Introns and intron variants altered as described herein and through methods known in the art, can be tested empirically as described in the working examples to determine an intron's effect on expression of an operably linked DNA molecule.

As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. The 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. The 3' UTR should not cause a reduction in the transcriptional activity imparted by the promoter, leader, enhancers, and introns that are used to drive expression of the DNA molecule. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the invention.

As used herein, the term "variant" refers to a second DNA molecule, such as a regulatory element, that is similar in composition, but not identical to, a first DNA molecule, and wherein the second DNA molecule still maintains the general functionality, i.e., same or similar expression pattern, for instance through more or less or equivalent transcriptional or translational activity, of the first DNA molecule. A variant may be a shortened or truncated version of the first DNA molecule and/or an altered version of the DNA sequence of the first DNA molecule, such as one with different restriction enzyme sites and/or internal deletions, substitutions, and/or insertions. Regulatory element "variants" also encompass variants arising from mutations that occur during or as a result of bacterial and plant cell transformation. In the invention, a DNA sequence provided as SEQ ID NOs: 1-98 and 168-171 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-98 and 168-171 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-98 and 168-171, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Expression of a transcribable DNA molecule in a plant cell can also be used to suppress plant pests feeding on the plant cell, for example, compositions isolated from coleopteran pests and compositions isolated from nematode pests. Plant pests include, but are not limited to, arthropod pests, nematode pests, and fungal or microbial pests.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also includes progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants, of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique,* (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention.

However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel ubiquitin regulatory elements, or regulatory expression element group (EXP) sequences, were identified and isolated from genomic DNA of the monocot Cloud grass (*Agrostis nebulosa*), giant reed (*Arundo donax*), Blue grama (*Bouteloua gracilis*), Chinese silvergrass (*Miscanthus sinesis*), Little bluestem (*Schizachyium scoparium*), Yellow Indiangrass (*Sorghastrum nutans*) and *Coix* (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding regulatory elements for the identified Ubiquitin gene, which comprises a promoter, leader (5' UTR), and first intron operably linked. The primers were used with GenomeWalker™ (Clontech Laboratories, Inc, Mountain View, Calif.) libraries constructed following the manufacturer's protocol to clone the 5' region of the corresponding genomic DNA sequence. Ubiquitin regulatory elements were also isolated from the monocots *Setaria italica, Setaria viridis*, and *Zea mays* subsp. *Mexicana* (Teosinte) using GenomeWalker™ libraries as described above. In addition, ubiquitin regulatory elements were isolated from the monocot *Sorghum bicolor* using public sequences that are homologs to the Ubiquitin 4, 6, and 7 genes.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction (PCR) conditions with primers containing unique restriction enzyme sites and genomic DNA isolated from *A. nebulosa, A donax, B. gracilis, M. sinesis, S. scoparium, S. nutans*, and *C. lacryma-jobi*. The resulting DNA fragments were ligated into base plant expression vectors and sequenced. An analysis of the regulatory element transcription start site (TSS) and intron/exon splice junctions was then done using transformed plant protoplasts. Briefly, the protoplasts were transformed with the plant expression vectors comprising the cloned DNA fragments operably linked to a heterologous transcribable DNA molecule and the 5' RACE System for Rapid Amplification of cDNA Ends, Version 2.0 (Invitrogen, Carlsbad, Calif. 92008) was used to confirm the regulatory element TSS and intron/exon splice junctions by analyzing the sequence of the messenger RNA (mRNA) transcripts produced thereby.

DNA sequences of the identified EXPs are provided herein as SEQ ID NOs: 1, 5, 7, 9, 13, 16, 18, 19, 21, 23, 27, 30, 32, 34, 38, 41, 43, 45, 49, 52, 55, 58, 60, 62, 66, 70, 72, 74, 76, 78, 82, 84, 86, 88, 92, 95, 97, 99, 103, 106, 108, 110, 114, 116, 118, 120, 122, 126, 128, 132, 134, 138, 140, 144, 148, 150 and 168, as listed in Table 1 below. Promoter sequences are provided herein as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98, 100, 104, 107, 109, 111, 117, 119, 121, 123, 129, 135, 141, 145, 151 and 169. Leader sequences are provided herein as SEQ ID NOs: 3, 11, 25, 36, 47, 64, 68, 80, 90, 101, 112, 124, 130, 136, 142, 146, 152 and 170. Intron sequences are provided herein as SEQ ID NOs: 4, 12, 15, 20, 26, 29, 37, 40, 48, 51, 54, 57, 59, 65, 69, 81, 91, 94, 102, 105, 113, 115, 125, 127, 131, 133, 137, 139, 143, 147, 149, 153 and 171.

TABLE 1

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| EXP-AGRne.Ubq1:1:7 | 1 | 3143 | *A. nebulosa* | EXP: P-AGRne.Ubq1-1:1:5 (SEQ ID NO: 2); L-AGRne.Ubq1-1:1:1 (SEQ ID NO: 3); I-AGRne.Ubq1-1:1:3 (SEQ ID NO: 4) |
| P-AGRne.Ubq1-1:1:5 | 2 | 2005 | *A. nebulosa* | Promoter |
| L-AGRne.Ubq1-1:1:1 | 3 | 85 | *A. nebulosa* | Leader |
| I-AGRne.Ubq1-1:1:3 | 4 | 1053 | *A. nebulosa* | Intron |
| EXP-AGRne.Ubq1:1:8 | 5 | 2137 | *A. nebulosa* | EXP: P-AGRne.Ubq1-1:1:4 (SEQ ID NO: 6); L-AGRne.Ubq1-1:1:1 (SEQ ID NO: 3); I-AGRne.Ubq1-1:1:3 (SEQ ID NO: 4) |
| P-AGRne.Ubq1-1:1:4 | 6 | 999 | *A. nebulosa* | Promoter |
| EXP-AGRne.Ubq1:1:9 | 7 | 1900 | *A. nebulosa* | EXP: P-AGRne.Ubq1-1:1:6 (SEQ ID NO: 8); L-AGRne.Ubq1-1:1:1 (SEQ ID NO: 3); I-AGRne.Ubq1-1:1:3 (SEQ ID NO: 4) |
| P-AGRne.Ubq1-1:1:6 | 8 | 762 | *A. nebulosa* | Promoter |
| EXP-ARUdo.Ubq1:1:4 | 9 | 5068 | *A. donax* | EXP: P-ARUdo.Ubq1-1:1:4 (SEQ ID NO: 10); L-ARUdo.Ubq1-1:1:1 (SEQ ID NO: 11); I-ARUdo.Ubq1-1:1:2 (SEQ ID NO: 12) |
| P-ARUdo.Ubq1-1:1:4 | 10 | 4114 | *A. donax* | Promoter |
| L-ARUdo.Ubq1-1:1:1 | 11 | 85 | *A. donax* | Leader |
| I-ARUdo.Ubq1-1:1:2 | 12 | 869 | *A. donax* | Intron |
| EXP-ARUdo.Ubq1:1:8 | 13 | 2969 | *A. donax* | EXP: P-ARUdo.Ubq1-1:1:5 (SEQ ID NO: 14); L-ARUdo.Ubq1-1:1:1 (SEQ ID NO: 11); I-ARUdo.Ubq1-1:1:3 (SEQ ID NO: 15) |
| P-ARUdo.Ubq1-1:1:5 | 14 | 2012 | *A. donax* | Promoter |
| I-ARUdo.Ubq1-1:1:3 | 15 | 872 | *A. donax* | Intron |
| EXP-ARUdo.Ubq1:1:6 | 16 | 1954 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:2 (SEQ ID NO: 12) |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| P-ARUdo.Ubq1-1:1:6 | 17 | 1000 | *A. donax* | Promoter |
| EXP-ARUdo.Ubq1:1:9 | 18 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:3 (SEQ ID NO: 15) |
| EXP-ARUdo.Ubq1:1:12 | 19 | 1957 | *A. donax* | EXP: P-ARUdo.Ubq1-1:1:6 (SEQ ID NO: 17); L-ARUdo.Ubq1-1:1:1 (SEQ ID NO: 11); I-ARUdo.Ubq1-1:1:4 (SEQ ID NO: 20) |
| I-ARUdo.Ubq1-1:1:4 | 20 | 872 | *A. donax* | Intron |
| EXP-ARUdo.Ubq1:1:11 | 21 | 1712 | *A. donax* | EXP: P-ARUdo.Ubq1-1:1:8 (SEQ ID NO: 22); L-ARUdo.Ubq1-1:1:1 (SEQ ID NO: 11); I-ARUdo.Ubq1-1:1:3 (SEQ ID NO: 15) |
| P-ARUdo.Ubq1-1:1:8 | 22 | 755 | *A. donax* | Promoter |
| EXP-ARUdo.Ubq2:1:4 | 23 | 3276 | *A. donax* | EXP: P-ARUdo.Ubq2-1:1:4 (SEQ ID NO: 24); L-ARUdo.Ubq2-1:1:1 (SEQ ID NO: 25); I-ARUdo.Ubq2-1:1:1 (SEQ ID NO: 26) |
| P-ARUdo.Ubq2-1:1:4 | 24 | 2033 | *A. donax* | Promoter |
| L-ARUdo.Ubq2-1:1:1 | 25 | 88 | *A. donax* | Leader |
| I-ARUdo.Ubq2-1:1:1 | 26 | 1155 | *A. donax* | Intron |
| EXP-ARUdo.Ubq2:1:8 | 27 | 3250 | *A. donax* | EXP: P-ARUdo.Ubq2-1:1:6 (SEQ ID NO: 28); L-ARUdo.Ubq2-1:1:1 (SEQ ID NO: 25); I-ARUdo.Ubq2-1:1:2 (SEQ ID NO: 29) |
| P-ARUdo.Ubq2-1:1:6 | 28 | 2004 | *A. donax* | Promoter |
| I-ARUdo.Ubq2-1:1:2 | 29 | 1158 | *A. donax* | Intron |
| EXP-ARUdo.Ubq2:1:9 | 30 | 2247 | *A. donax* | EXP: P-ARUdo.Ubq2-1:1:5 (SEQ ID NO: 31); L-ARUdo.Ubq2-1:1:1 (SEQ ID NO: 25); I-ARUdo.Ubq2-1:1:2 (SEQ ID NO: 29) |
| P-ARUdo.Ubq2-1:1:5 | 31 | 1001 | *A. donax* | Promoter |
| EXP-ARUdo.Ubq2:1:10 | 32 | 1942 | *A. donax* | EXP: P-ARUdo.Ubq2-1:1:7 (SEQ ID NO: 33); L-ARUdo.Ubq2-1:1:1 (SEQ ID NO: 25); I-ARUdo.Ubq2-1:1:2 (SEQ ID NO: 29) |
| P-ARUdo.Ubq2-1:1:7 | 33 | 696 | *A. donax* | Promoter |
| EXP-BOUgr.Ubq1:1:1 | 34 | 3511 | *B. gracilis* | EXP: P-BOUgr.Ubq1-1:1:2 (SEQ ID NO: 35); L-BOUgr.Ubq1-1:1:1 (SEQ ID NO: 36); I-BOUgr.Ubq1-1:1:2 (SEQ ID NO: 37) |
| P-BOUgr.Ubq1-1:1:2 | 35 | 2371 | *B. gracilis* | Promoter |
| L-BOUgr.Ubq1-1:1:1 | 36 | 86 | *B. gracilis* | Leader |
| I-BOUgr.Ubq1-1:1:2 | 37 | 1054 | *B. gracilis* | Intron |
| EXP-BOUgr.Ubq1:1:6 | 38 | 3142 | *B. gracilis* | EXP: P-BOUgr.Ubq1-1:1:3 (SEQ ID NO: 39); L-BOUgr.Ubq1-1:1:1 (SEQ ID NO: 36); I-BOUgr.Ubq1-1:1:3 (SEQ ID NO: 40) |
| P-BOUgr.Ubq1-1:1:3 | 39 | 1999 | *B. gracilis* | Promoter |
| I-BOUgr.Ubq1-1:1:3 | 40 | 1057 | *B. gracilis* | Intron |
| EXP-BOUgr.Ubq1:1:7 | 41 | 2165 | *B. gracilis* | EXP: P-BOUgr.Ubq1-1:1:5 (SEQ ID NO: 42); L-BOUgr.Ubq1-1:1:1 (SEQ ID NO: 36); I-BOUgr.Ubq1-1:1:3 (SEQ ID NO: 40) |
| P-BOUgr.Ubq1-1:1:5 | 42 | 1022 | *B. gracilis* | Promoter |
| EXP-BOUgr.Ubq1:1:8 | 43 | 1903 | *B. gracilis* | EXP: P-BOUgr.Ubq1-1:1:6 (SEQ ID NO: 44); L-BOUgr.Ubq1-1:1:1 (SEQ ID NO: 36); I-BOUgr.Ubq1-1:1:3 (SEQ ID NO: 40) |
| P-BOUgr.Ubq1-1:1:6 | 44 | 760 | *B. gracilis* | Promoter |
| EXP-BOUgr.Ubq2:1:11 | 45 | 3234 | *B. gracilis* | EXP: P-BOUgr.Ubq2-1:1:4 (SEQ ID NO: 46); L-BOUgr.Ubq2-1:1:1 (SEQ ID NO: 47); I-BOUgr.Ubq2-1:1:3 (SEQ ID NO: 48) |
| P-BOUgr.Ubq2-1:1:4 | 46 | 2100 | *B. gracilis* | Promoter |
| L-BOUgr.Ubq2-1:1:1 | 47 | 91 | *B. gracilis* | Leader |
| I-BOUgr.Ubq2-1:1:3 | 48 | 1043 | *B. gracilis* | Intron |
| EXP-BOUgr.Ubq2:1:7 | 49 | 3176 | *B. gracilis* | EXP: P-BOUgr.Ubq2-1:1:7 (SEQ ID NO: 50); L-BOUgr.Ubq2-1:1:1 (SEQ ID NO: 47); I-BOUgr.Ubq2-1:1:1 (SEQ ID NO: 51) |
| P-BOUgr.Ubq2-1:1:7 | 50 | 2043 | *B. gracilis* | Promoter |
| I-BOUgr.Ubq2-1:1:1 | 51 | 1042 | *B. gracilis* | Intron |
| EXP-BOUgr.Ubq2:1:14 | 52 | 3139 | *B. gracilis* | EXP: P-BOUgr.Ubq2-1:1:5 (SEQ ID NO: 53); L-BOUgr.Ubq2-1:1:1 (SEQ ID NO: 47); I-BOUgr.Ubq2-1:1:4 (SEQ ID NO: 54) |
| P-BOUgr.Ubq2-1:1:5 | 53 | 2002 | *B. gracilis* | Promoter |
| I-BOUgr.Ubq2-1:1:4 | 54 | 1046 | *B. gracilis* | Intron |
| EXP-BOUgr.Ubq2:1:15 | 55 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:5 (SEQ ID NO: 57) |
| P-BOUgr.Ubq2-1:1:6 | 56 | 1024 | *B. gracilis* | Promoter |
| I-BOUgr.Ubq2-1:1:5 | 57 | 1045 | *B. gracilis* | Intron |
| EXP-BOUgr.Ubq2:1:16 | 58 | 2160 | *B. gracilis* | EXP: P-BOUgr.Ubq2-1:1:6 (SEQ ID NO: 56); L-BOUgr.Ubq2-1:1:1 (SEQ ID NO: 47); I-BOUgr.Ubq2-1:1:6 (SEQ ID NO: 59) |
| I-BOUgr.Ubq2-1:1:6 | 59 | 1045 | *B. gracilis* | Intron |
| EXP-BOUgr.Ubq2:1:17 | 60 | 1885 | *B. gracilis* | EXP: P-BOUgr.Ubq2-1:1:8 (SEQ ID NO: 61); L-BOUgr.Ubq2-1:1:1 (SEQ ID NO: 47); I-BOUgr.Ubq2-1:1:6 (SEQ ID NO: 59) |
| P-BOUgr.Ubq2-1:1:8 | 61 | 749 | *B. gracilis* | Promoter |
| EXP-MISsi.Ubq1:1:2 | 62 | 6813 | *M. sinesis* | EXP: P-MISsi.Ubq1-1:1:2 (SEQ ID NO: 63); L-MISsi.Ubq1-1:1:1 (SEQ ID NO: 64); I-MISsi.Ubq1-1:1:1 (SEQ ID NO: 65) |
| P-MISsi.Ubq1-1:1:2 | 63 | 5359 | *M. sinesis* | Promoter |
| L-MISsi.Ubq1-1:1:1 | 64 | 63 | *M. sinesis* | Leader |
| I-MISsi.Ubq1-1:1:1 | 65 | 1391 | *M. sinesis* | Intron |
| EXP-MISsi.Ubq1:1:9 | 66 | 4402 | *M. sinesis* | EXP: P-MISsi.Ubq1-1:1:11 (SEQ ID NO: 67); L-MISsi.Ubq1-1:1:2 (SEQ ID NO: 68); I-MISsi.Ubq1-1:1:3 (SEQ ID NO: 69) |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| P-MISsi.Ubq1-1:1:11 | 67 | 2423 | *M. sinesis* | Promoter |
| L-MISsi.Ubq1-1:1:2 | 68 | 55 | *M. sinesis* | Leader |
| I-MISsi.Ubq1-1:1:3 | 69 | 1924 | *M. sinesis* | Intron |
| EXP-MISsi.Ubq1:1:8 | 70 | 3426 | *M. sinesis* | EXP: P-MISsi.Ubq1-1:1:10 (SEQ ID NO: 71); L-MISsi.Ubq1-1:1:2 (SEQ ID NO: 68); I-MISsi.Ubq1-1:1:3 (SEQ ID NO: 69) |
| P-MISsi.Ubq1-1:1:10 | 71 | 1447 | *M. sinesis* | Promoter |
| EXP-MISsi.Ubq1:1:10 | 72 | 2878 | *M. sinesis* | EXP: P-MISsi.Ubq1-1:1:13 (SEQ ID NO: 73); L-MISsi.Ubq1-1:1:2 (SEQ ID NO: 68); I-MISsi.Ubq1-1:1:3 (SEQ ID NO: 69) |
| P-MISsi.Ubq1-1:1:13 | 73 | 899 | *M. sinesis* | Promoter |
| EXP-MISsi.Ubq1:1:11 | 74 | 2670 | *M. sinesis* | EXP: P-MISsi.Ubq1-1:1:14 (SEQ ID NO: 75); L-MISsi.Ubq1-1:1:2 (SEQ ID NO: 68); I-MISsi.Ubq1-1:1:3 (SEQ ID NO: 69) |
| P-MISsi.Ubq1-1:1:14 | 75 | 691 | *M. sinesis* | Promoter |
| EXP-MISsi.Ubq1:1:7 | 76 | 2485 | *M. sinesis* | EXP: P-MISsi.Ubq1-1:1:9 (SEQ ID NO: 77); L-MISsi.Ubq1-1:1:2 (SEQ ID NO: 68); I-MISsi.Ubq1-1:1:3 (SEQ ID NO: 69) |
| P-MISsi.Ubq1-1:1:9 | 77 | 506 | *M. sinesis* | Promoter |
| EXP-SCHsc.Ubq1:1:9 | 78 | 4079 | *S. scoparium* | EXP: P-SCHsc.Ubq1-1:1:12 (SEQ ID NO: 79); L-SCHsc.Ubq1-1:1:3 (SEQ ID NO: 80); I-SCHsc.Ubq1-1:1:2 (SEQ ID NO: 81) |
| P-SCHsc.Ubq1-1:1:12 | 79 | 2831 | *S. scoparium* | Promoter |
| L-SCHsc.Ubq1-1:1:3 | 80 | 95 | *S. scoparium* | Leader |
| I-SCHsc.Ubq1-1:1:2 | 81 | 1153 | *S. scoparium* | Intron |
| EXP-SCHsc.Ubq1:1:8 | 82 | 3281 | *S. scoparium* | EXP: P-SCHsc.Ubq1-1:1:11 (SEQ ID NO: 83); L-SCHsc.Ubq1-1:1:3 (SEQ ID NO: 80); I-SCHsc.Ubq1-1:1:2 (SEQ ID NO: 81) |
| P-SCHsc.Ubq1-1:1:11 | 83 | 2033 | *S. scoparium* | Promoter |
| EXP-SCHsc.Ubq1:1:7 | 84 | 2294 | *S. scoparium* | EXP: P-SCHsc.Ubq1-1:1:10 (SEQ ID NO: 85); L-SCHsc.Ubq1-1:1:3 (SEQ ID NO: 80); I-SCHsc.Ubq1-1:1:2 (SEQ ID NO: 81) |
| P-SCHsc.Ubq1-1:1:10 | 85 | 1046 | *S. scoparium* | Promoter |
| EXP-SCHsc.Ubq1:1:10 | 86 | 1795 | *S. scoparium* | EXP: P-SCHsc.Ubq1-1:1:14 (SEQ ID NO: 87); L-SCHsc.Ubq1-1:1:3 (SEQ ID NO: 80); I-SCHsc.Ubq1-1:1:2 (SEQ ID NO: 81) |
| P-SCHsc.Ubq1-1:1:14 | 87 | 547 | *S. scoparium* | Promoter |
| EXP-SORnu.Ubq1:1:2 | 88 | 3357 | *S. nutans* | EXP: P-SORnu.Ubq1-1:1:4 (SEQ ID NO: 89); L-SORnu.Ubq1-1:1:1 (SEQ ID NO: 90); I-SORnu.Ubq1-1:1:1 (SEQ ID NO: 91) |
| P-SORnu.Ubq1-1:1:4 | 89 | 2218 | *S. nutans* | Promoter |
| L-SORnu.Ubq1-1:1:1 | 90 | 86 | *S. nutans* | Leader |
| I-SORnu.Ubq1-1:1:1 | 91 | 1053 | *S. nutans* | Intron |
| EXP-SORnu.Ubq1:1:6 | 92 | 3106 | *S. nutans* | EXP: P-SORnu.Ubq1-1:1:5 (SEQ ID NO: 93); L-SORnu.Ubq1-1:1:1 (SEQ ID NO: 90); I-SORnu.Ubq1-1:1:2 (SEQ ID NO: 94) |
| P-SORnu.Ubq1-1:1:5 | 93 | 1964 | *S. nutans* | Promoter |
| I-SORnu.Ubq1-1:1:2 | 94 | 1056 | *S. nutans* | Intron |
| EXP-SORnu.Ubq1:1:7 | 95 | 2165 | *S. nutans* | EXP: P-SORnu.Ubq1-1:1:6 (SEQ ID NO: 96); L-SORnu.Ubq1-1:1:1 (SEQ ID NO: 90); I-SORnu.Ubq1-1:1:2 (SEQ ID NO: 94) |
| P-SORnu.Ubq1-1:1:6 | 96 | 1023 | *S. nutans* | Promoter |
| EXP-SORnu.Ubq1:1:8 | 97 | 1866 | *S. nutans* | EXP: P-SORnu.Ubq1-1:1:7 (SEQ ID NO: 98); L-SORnu.Ubq1-1:1:1 (SEQ ID NO: 90); I-SORnu.Ubq1-1:1:2 (SEQ ID NO: 94) |
| P-SORnu.Ubq1-1:1:7 | 98 | 724 | *S. nutans* | Promoter |
| EXP-SETit.Ubq1:1:10 | 99 | 2625 | *S. italica* | EXP: P-SETit.Ubq1-1:1:4 (SEQ ID NO: 100); L-SETit.Ubq1-1:1:1 (SEQ ID NO: 101); I-SETit.Ubq1-1:1:3 (SEQ ID NO: 102) |
| P-SETit.Ubq1-1:1:4 | 100 | 1492 | *S. italica* | Promoter |
| L-SETit.Ubq1-1:1:1 | 101 | 127 | *S. italica* | Leader |
| I-SETit.Ubq1-1:1:3 | 102 | 1006 | *S. italica* | Intron |
| EXP-SETit.Ubq1:1:5 | 103 | 2625 | *S. italica* | EXP: P-SETit.Ubq1-1:1:1 (SEQ ID NO: 104); L-SETit.Ubq1-1:1:1 (SEQ ID NO: 101); I-SETit.Ubq1-1:1:2 (SEQ ID NO: 105) |
| P-SETit.Ubq1-1:1:1 | 104 | 1492 | *S. italica* | Promoter |
| I-SETit.Ubq1-1:1:2 | 105 | 1006 | *S. italica* | Intron |
| EXP-SETit.Ubq1:1:7 | 106 | 2167 | *S. italica* | EXP: P-SETit.Ubq1-1:1:2 (SEQ ID NO: 107); L-SETit.Ubq1-1:1:1 (SEQ ID NO: 101); I-SETit.Ubq1-1:1:2 (SEQ ID NO: 105) |
| P-SETit.Ubq1-1:1:2 | 107 | 1034 | *S. italica* | Promoter |
| EXP-SETit.Ubq1:1:6 | 108 | 1813 | *S. italica* | EXP: P-SETit.Ubq1-1:1:3 (SEQ ID NO: 109); L-SETit.Ubq1-1:1:1 (SEQ ID NO: 101); I-SETit.Ubq1-1:1:2 (SEQ ID NO: 105) |
| P-SETit.Ubq1-1:1:3 | 109 | 680 | *S. italica* | Promoter |
| EXP-Sv.Ubq1:1:7 | 110 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:2 (SEQ ID NO: 113) |
| P-Sv.Ubq1-1:1:1 | 111 | 1493 | *S. viridis* | Promoter |
| L-Sv.Ubq1-1:1:2 | 112 | 127 | *S. viridis* | Leader |
| I-Sv.Ubq1-1:1:2 | 113 | 1014 | *S. viridis* | Intron |
| EXP-Sv.Ubq1:1:11 | 114 | 2634 | *S. viridis* | EXP: P-Sv.Ubq1-1:1:1 (SEQ ID NO: 111); L-Sv.Ubq1-1:1:2 (SEQ ID NO: 112); I-Sv.Ubq1-1:1:3 (SEQ ID NO: 115) |
| I-Sv.Ubq1-1:1:3 | 115 | 1014 | *S. viridis* | Intron |
| EXP-Sv.Ubq1:1:8 | 116 | 2176 | *S. viridis* | EXP: P-Sv.Ubq1-1:1:2 (SEQ ID NO: 117); L-Sv.Ubq1-1:1:2 (SEQ ID NO: 112); I-Sv.Ubq1-1:1:2 (SEQ ID NO: 113) |
| P-Sv.Ubq1-1:1:2 | 117 | 1035 | *S. viridis* | Promoter |
| EXP-Sv.Ubq1:1:10 | 118 | 1822 | *S. viridis* | EXP: P-Sv.Ubq1-1:1:4 (SEQ ID NO: 119); L-Sv.Ubq1-1:1:2 (SEQ ID NO: 112); I-Sv.Ubq1-1:1:2 (SEQ ID NO: 113) |

TABLE 1-continued

Regulatory expression element groups ("EXPs"), promoters, enhancers, leaders and introns isolated from various grass species.

| Description | SEQ ID NO: | Size (bp) | Genus/Species | Description and/or regulatory elements of EXP linked in 5' → 3' direction (SEQ ID NOs): |
|---|---|---|---|---|
| P-Sv.Ubq1-1:1:4 | 119 | 681 | *S. viridis* | Promoter |
| EXP-Sv.Ubq1:1:12 | 120 | 1822 | *S. viridis* | EXP: P-Sv.Ubq1-1:1:3 (SEQ ID NO: 121); L-Sv.Ubq1-1:1:2 (SEQ ID NO: 112); I-Sv.Ubq1-1:1:3 (SEQ ID NO: 115) |
| P-Sv.Ubq1-1:1:3 | 121 | 681 | *S. viridis* | Promoter |
| EXP-Zm.UbqM1:1:6 (Allele-1) | 122 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:13 (SEQ ID NO: 125) |
| P-Zm.UbqM1-1:1:1 (Allele-1) | 123 | 850 | *Z. mays* subsp. *Mexicana* | Promoter |
| L-Zm.UbqM1-1:1:1 (Allele-1) | 124 | 78 | *Z. mays* subsp. *Mexicana* | Leader |
| I-Zm.UbqM1-1:1:13 (Allele-1) | 125 | 997 | *Z. mays* subsp. *Mexicana* | Intron |
| EXP-Zm.UbqM1:1:10 (Allele-1) | 126 | 1925 | *Z. mays* subsp. *Mexicana* | EXP: P-Zm.UbqM1-1:1:1 (SEQ ID NO: 123); L-Zm.UbqM1-1:1:1 (SEQ ID NO: 124); I-Zm.UbqM1-1:1:17 (SEQ ID NO: 127) |
| I-Zm.UbqM1-1:1:17 (Allele-1) | 127 | 997 | *Z. mays* subsp. *Mexicana* | Intron |
| EXP-Zm.UbqM1:1:7 (Allele-2) | 128 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:14 (SEQ ID NO: 131) |
| P-Zm.UbqM1-1:1:4 (Allele-2) | 129 | 887 | *Z. mays* subsp. *Mexicana* | Promoter |
| L-Zm.UbqM1-1:1:5 (Allele-2) | 130 | 77 | *Z. mays* subsp. *Mexicana* | Leader |
| I-Zm.UbqM1-1:1:14 (Allele-2) | 131 | 1010 | *Z. mays* subsp. *Mexicana* | Intron |
| EXP-Zm.UbqM1:1:12 (Allele-2) | 132 | 1974 | *Z. mays* subsp. *Mexicana* | EXP: P-Zm.UbqM1-1:1:4 (SEQ ID NO: 129); L-Zm.UbqM1-1:1:5 (SEQ ID NO: 130); I-Zm.UbqM1-1:1:19 (SEQ ID NO: 133) |
| I-Zm.UbqM1-1:1:19 (Allele-2) | 133 | 1010 | *Z. mays* subsp. *Mexicana* | Intron |
| EXP-Zm.UbqM1:1:8 (Allele-2) | 134 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:15 (SEQ ID NO: 137) |
| P-Zm.UbqM1-1:1:5 (Allele-2) | 135 | 877 | *Z. mays* subsp. *Mexicana* | Promoter |
| L-Zm.UbqM1-1:1:4 (Allele-2) | 136 | 78 | *Z. mays* subsp. *Mexicana* | Leader |
| I-Zm.UbqM1-1:1:15 (Allele-2) | 137 | 1053 | *Z. mays* subsp. *Mexicana* | Intron |
| EXP-Zm.UbqM1:1:11 (Allele-2) | 138 | 2008 | *Z. mays* subsp. *Mexicana* | EXP: P-Zm.UbqM1-1:1:5 (SEQ ID NO: 135); L-Zm.UbqM1-1:1:4 (SEQ ID NO: 136); I-Zm.UbqM1-1:1:18 (SEQ ID NO: 139) |
| I-Zm.UbqM1-1:1:18 (Allele-2) | 139 | 1053 | *Z. mays* subsp. *Mexicana* | Intron |
| EXP-Sb.Ubq4:1:2 | 140 | 1635 | *S. bicolor* | EXP: P-Sb.Ubq4-1:1:1 (SEQ ID NO: 141); L-Sb.Ubq4-1:1:1 (SEQ ID NO: 142); I-Sb.Ubq4-1:1:2 (SEQ ID NO: 143) |
| P-Sb.Ubq4-1:1:1 | 141 | 401 | *S. bicolor* | Promoter |
| L-Sb.Ubq4-1:1:1 | 142 | 154 | *S. bicolor* | Leader |
| I-Sb.Ubq4-1:1:2 | 143 | 1080 | *S. bicolor* | Intron |
| EXP-Sb.Ubq6:1:2 | 144 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:2 (SEQ ID NO: 147) |
| P-Sb.Ubq6-1:1:1 | 145 | 855 | *S. bicolor* | Promoter |
| L-Sb.Ubq6-1:1:1 | 146 | 136 | *S. bicolor* | Leader |
| I-Sb.Ubq6-1:1:2 | 147 | 1076 | *S. bicolor* | Intron |
| EXP-Sb.Ubq6:1:3 | 148 | 2067 | *S. bicolor* | EXP: P-Sb.Ubq6-1:1:1 (SEQ ID NO: 145); L-Sb.Ubq6-1:1:1 (SEQ ID NO: 146); I-Sb.Ubq6-1:1:3 (SEQ ID NO: 149) |
| I-Sb.Ubq6-1:1:3 | 149 | 1076 | *S. bicolor* | Intron |
| EXP-Sb.Ubq7:1:2 | 150 | 2003 | *S. bicolor* | EXP: P-Sb.Ubq7-1:1:1 (SEQ ID NO: 151); L-Sb.Ubq7-1:1:1 (SEQ ID NO: 152); I-Sb.Ubq7-1:1:2 (SEQ ID NO: 153) |
| P-Sb.Ubq7-1:1:1 | 151 | 565 | *S. bicolor* | Promoter |
| L-Sb.Ubq7-1:1:1 | 152 | 77 | *S. bicolor* | Leader |
| I-Sb.Ubq7-1:1:2 | 153 | 1361 | *S. bicolor* | Intron |
| EXP-Cl.Ubq10 | 168 | 1790 | *C. lacryma-jobi* | EXP: P-Cl.UBQ10 (SEQ ID NO: 169); L-Cl.UBQ10 (SEQ ID NO: 170); I-Cl.UBQ10 (SEQ ID NO: 171) |
| P-Cl.Ubq10 | 169 | 481 | *C. lacryma-jobi* | Promoter |
| L-Cl.Ubq10 | 170 | 93 | *C. lacryma-jobi* | Leader |
| I-Cl.Ubq10 | 171 | 1216 | *C. lacryma-jobi* | Intron |

As shown in Table 1, for example, the regulatory EXP sequence designated EXP-AGRne.Ubq1:1:7 (SEQ ID NO: 1), with components isolated from *A. nebulosa*, comprises a promoter element, P-AGRne.Ubq1-1:1:5 (SEQ ID NO: 2), operably linked 5' to a leader element, L-AGRne.Ubq1-1:1:1 (SEQ ID NO: 3), operably linked 5' to an intron element, I-AGRne.Ubq1-1:1:3 (SEQ ID NO: 4). Other EXP sequences are linked similarly, as outlined in Table 1.

As shown in Table 1, the sequence listing, and FIGS. 1-8, variants of promoter sequences from *A. nebulosa, A donax, B. gracilis, M. sinesis, S. scoparium*, and *S. nutans* were engineered, which comprise shorter promoter fragments of, for instance, P-AGRne.Ubq1-1:1:5 (SEQ ID NO:2), P-ARUdo.Ubq1-1:1:4 (SEQ ID NO:10), or other respective promoters from other species, and for instance resulting in P-AGRne.Ubq1-1:1:4 (SEQ ID NO: 6) and P-ARUdo.Ubq1-1:1:5 (SEQ ID NO: 14), as well as other promoter fragments.

Also listed in Table 1 are three allelic variants isolated using the same primer sets designed for amplification of genomic DNA from *Z. mays* subsp. *mexicana*. Allelic variants of the *Z. mays* subsp. *mexicana* EXP sequences are comprised of DNA sequences that share some identity within various regions of other DNA sequences, but insertions, deletions, and nucleotide mismatches may also be apparent within each promoter, leader and/or intron of each of the EXP sequences. The EXP sequences designated EXP-Zm.UbqM1:1:6 (SEQ ID NO: 122) and EXP-Zm.UbqM1:1:10 (SEQ ID NO: 126) represent a first allele (Allele-1) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction. The EXP sequences designated EXP-Zm.UbqM1:1:7 (SEQ ID NO: 128) and EXP-Zm.UbqM1:1:12 (SEQ ID NO: 132) represent a second allele (Allele-2) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction. The EXP sequences EXP-Zm.UbqM1:1:8 (SEQ ID NO: 134) and EXP-Zm.UbqM1:1:11 (SEQ ID NO: 138) represent a third allele (Allele-3) of the *Z. mays* subsp. *mexicana* Ubq1 gene regulatory expression element group, with the only difference between the two EXP sequences occurring in the last 3' nucleotides of each respective intron following the sequence 5'-AG-3' of the 3' intron splice junction.

Example 2

Analysis of Regulatory Elements Driving GUS in Corn Protoplasts Using GUS Expression Cassette Amplicons Corn leaf protoplasts were transformed with DNA amplicons derived from plant expression vectors containing an EXP sequence, driving expression of the β-glucuronidase transgene (GUS), and compared to leaf protoplasts in which expression of GUS is driven by known constitutive promoters in a series of experiments presented below.

In a first set of experiments, corn protoplast cells derived from leaf tissue were transformed as above with amplicons produced from amplification of GUS expression cassettes comprising plant expression vectors to compare expression of a transgene (GUS) driven by one of EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 20), EXP-ARUdo.Ubq2:1:8 (SEQ ID NO: 26), EXP-ARUdo.Ubq2:1:9 (SEQ ID NO: 29), EXP-ARUdo.Ubq2:1:10 (SEQ ID NO: 31), EXP-BOUgr.Ubq1:1:6 (SEQ ID NO: 37), EXP-BOUgr.Ubq1:1:7 (SEQ ID NO: 40), EXP-BOUgr.Ubq1:1:8 (SEQ ID NO: 42), EXP-BOUgr.Ubq2:1:14 (SEQ ID NO: 51), EXP-BOUgr.Ubq2:1:16 (SEQ ID NO: 57), EXP-BOUgr.Ubq2:1:17 (SEQ ID NO: 59), EXP-MISsi.Ubq1:1:8 (SEQ ID NO: 69), EXP-MISsi.Ubq1:1:10 (SEQ ID NO: 71), EXP-MISsi.Ubq1:1:11 (SEQ ID NO: 73), EXP-MISsi.Ubq1:1:7 (SEQ ID NO: 75), EXP-SCHsc.Ubq1:1:9 (SEQ ID NO: 77), EXP-SCHsc.Ubq1:1:7 (SEQ ID NO: 83), EXP-SCHsc.Ubq1:1:10 (SEQ ID NO: 85), EXP-SORnu.Ubq1:1:6 (SEQ ID NO: 91), EXP-SORnu.Ubq1:1:7 (SEQ ID NO: 94), EXP-SORnu.Ubq1:1:8 (SEQ ID NO: 96), EXP-SETit.Ubq1:1:5 (SEQ ID NO: 102), EXP-SETit.Ubq1:1:7 (SEQ ID NO: 105), EXP-SETit.Ubq1:1:6 (SEQ ID NO: 107), EXP-Sv.Ubq1:1:7 (SEQ ID NO: 109), EXP-Sv.Ubq1:1:8 (SEQ ID NO: 115), EXP-Sv.Ubq1:1:10 (SEQ ID NO: 117), EXP-Zm.UbqM1:1:6 (SEQ ID NO: 121), EXP-Zm.UbqM1:1:7 (SEQ ID NO: 127), EXP-Zm.UbqM1:1:8 (SEQ ID NO: 133), Exp-Sb.Ubq4:1:2 (SEQ ID NO: 139), and Exp-Sb.Ubq6:1:2 (SEQ ID NO: 143) with that of known constitutive promoters. Each EXP sequence comprising the amplification template from which the expression cassette amplicon is produced was cloned using methods known in the art into a plant expression vector shown in Table 2 below under the heading of "Amplicon Template." The resulting plant expression vectors comprise a expression cassette comprised of a EXP sequence, operably linked 5' to a coding sequence for GUS that either contains a processable intron ("GUS-2", SEQ ID NO: 154), or a contiguous GUS coding sequence ("GUS-1", SEQ ID NO: 153), operably linked 5' to a 3' UTR T-AGRtu.nos-1:1:13 (SEQ ID NO: 157) or T-Ta.Hsp17-1:1:1 (SEQ ID NO: 158). Amplicons were produced using methods known to those skilled in the art using the plasmid construct templates presented in Table 2 below. Briefly, a 5' oligonucleotide primer was designed to anneal to the promoter sequence and a 3' oligonucleotide primer, which anneals at the 3' end of the 3' UTR, was used for amplification of each expression cassette. Successive 5' deletions were introduced into the promoter sequences comprising the expression cassettes, giving rise to different EXP sequences, by the use of different oligonucleotide primers which were designed to anneal at different positions within the promoter sequence comprising each amplicon template.

TABLE 2

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 162 | GUS-1 | T-AGRtu.nos-1:1:13 |
| PCR0145943 | pMON65328 | EXP-CaMV.35S-enh + Ta.Lhcb1 + Os.Act1:1:1 | 161 | GUS-2 | T-Ta.Hsp17-1:1:1 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145935 | pMON140890 | EXP-AGRne.Ubq1:1:7 | 1 | GUS-1 | T-AGRtu.nos-1:1:13 |
| PCR0145827 | pMON140890 | EXP-AGRne.Ubq1:1:8 | 5 | GUS-1 | T-AGRtu.nos-1:1:13 |
| PCR0145828 | pMON140890 | EXP-AGRne.Ubq1:1:9 | 7 | GUS-1 | T-AGRtu.nos-1:1:13 |
| PCR0145939 | pMON140894 | EXP-ARUdo.Ubq1:1:8 | 13 | GUS-1 | T-AGRtu.nos-1:1:13 |
| PCR0145837 | pMON140894 | EXP-ARUdo.Ubq1:1:9 | 18 | GUS-1 | T-AGRtu.nos-1:1:13 |
| PCR0145838 | pMON140894 | EXP-ARUdo.Ubq1:1:11 | 21 | GUS-1 | T-AGRtu.nos-1:1:13 |
| PCR0145940 | pMON140895 | EXP-ARUdo.Ubq2:1:8 | 27 | GUS-1 | T-AGRtu.nos-1:1:13 |
| PCR0145841 | pMON140895 | EXP-ARUdo.Ubq2:1:9 | 30 | GUS-1 | T-AGRtu.nos-1:1:13 |
| PCR0145842 | pMON140895 | EXP-ARUdo.Ubq2:1:10 | 32 | GUS-1 | T-AGRtu.nos-1:1:13 |
| PCR0145936 | pMON140891 | EXP-BOUgr.Ubq1:1:6 | 38 | GUS-1 | T-AGRtu.nos-1:1:13 |
| PCR0145829 | pMON140891 | EXP-BOUgr.Ubq1:1:7 | 41 | GUS-1 | T-AGRtu.nos-1:1:13 |
| PCR0145831 | pMON140891 | EXP-BOUgr.Ubq1:1:8 | 43 | GUS-1 | T-AGRtu.nos-1:1:13 |
| PCR0145937 | pMON140892 | EXP-BOUgr.Ubq2:1:14 | 52 | GUS-1 | T-AGRtu.nos-1:1:13 |
| PCR0145833 | pMON140892 | EXP-BOUgr.Ubq2:1:16 | 58 | GUS-1 | T-AGRtu.nos-1:1:13 |
| PCR0145836 | pMON140892 | EXP-BOUgr.Ubq2:1:17 | 60 | GUS-1 | T-AGRtu.nos-1:1:13 |
| PCR0145898 | pMON136265 | EXP-MISsi.Ubq1:1:8 | 70 | GUS-1 | T-AGRtu.nos-1:1:13 |
| PCR0145823 | pMON136265 | EXP-MISsi.Ubq1:1:10 | 72 | GUS-1 | T-AGRtu.nos-1:1:13 |
| PCR0145824 | pMON136265 | EXP-MISsi.Ubq1:1:11 | 74 | GUS-1 | T-AGRtu.nos-1:1:13 |
| PCR0145899 | pMON136260 | EXP-MISsi.Ubq1:1:7 | 76 | GUS-1 | T-AGRtu.nos-1:1:13 |
| PCR0145894 | pMON136262 | EXP-SCHsc.Ubq1:1:9 | 78 | GUS-1 | T-AGRtu.nos-1:1:13 |
| PCR0145895 | pMON136257 | EXP-SCHsc.Ubq1:1:7 | 84 | GUS-1 | T-AGRtu.nos-1:1:13 |
| PCR0145813 | pMON136257 | EXP-SCHsc.Ubq1:1:10 | 86 | GUS-1 | T-AGRtu.nos-1:1:13 |
| PCR0145938 | pMON140893 | EXP-SORnu.Ubq1:1:6 | 92 | GUS-1 | T-AGRtu.nos-1:1:13 |
| PCR0145839 | pMON140893 | EXP-SORnu.Ubq1:1:7 | 95 | GUS-1 | T-AGRtu.nos-1:1:13 |

TABLE 2-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145840 | pMON140893 | EXP-SORnu.Ubq1:1:8 | 97 | GUS-1 | T-AGRtu.nos-1:1:13 |
| PCR0145900 | pMON140877 | EXP-SETit.Ubq1:1:5 | 103 | GUS-1 | T-AGRtu.nos-1:1:13 |
| PCR0145928 | pMON140877 | EXP-SETit.Ubq1:1:7 | 106 | GUS-1 | T-AGRtu.nos-1:1:13 |
| PCR0145905 | pMON140877 | EXP-SETit.Ubq1:1:6 | 108 | GUS-1 | T-AGRtu.nos-1:1:13 |
| PCR0145909 | pMON140878 | EXP-Sv.Ubq1:1:7 | 110 | GUS-1 | T-AGRtu.nos-1:1:13 |
| PCR0145929 | pMON140878 | EXP-Sv.Ubq1:1:8 | 116 | GUS-1 | T-AGRtu.nos-1:1:13 |
| PCR0145911 | pMON140878 | EXP-Sv.Ubq1:1:10 | 118 | GUS-1 | T-AGRtu.nos-1:1:13 |
| PCR0145914 | pMON140881 | EXP-Zm.UbqM1:1:6 | 122 | GUS-1 | T-AGRtu.nos-1:1:13 |
| PCR0145916 | pMON140883 | EXP-Zm.UbqM1:1:7 | 128 | GUS-1 | T-AGRtu.nos-1:1:13 |
| PCR0145915 | pMON140882 | EXP-Zm.UbqM1:1:8 | 134 | GUS-1 | T-AGRtu.nos-1:1:13 |
| PCR0145921 | pMON140887 | Exp-Sb.Ubq4:1:2 | 140 | GUS-1 | T-AGRtu.nos-1:1:13 |
| PCR0145920 | pMON140886 | Exp-Sb.Ubq6:1:2 | 144 | GUS-1 | T-AGRtu.nos-1:1:13 |

Plasmid constructs listed as amplicon templates in Table 2 served as templates for amplification of transgene expression cassettes comprising the listed EXP sequences of Table 2. Control plasmids used to generate GUS transgene amplicons for comparison were constructed as previously described with the constitutive EXP sequences EXP-Os-.Act1:1:9 (SEQ ID NO: 162) and EXP-CaMV.35S-enh+Ta.Lhcb1+Os.Act1:1:1 (SEQ ID NO: 161). An empty vector not designed for transgene expression was used as a negative control to assess background GUS and luciferase expression.

Two plasmids, for use in co-transformation and normalization of data, were also constructed using methods known in the art. Each plasmid contained a specific luciferase coding sequence that was driven by a constitutive EXP sequence. The plant vector pMON19437 comprises a expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises a expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.hRenilla Lucife-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the amplicons presented in Table 2, and were incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence amplicon per one of two transformation experiments. The mean GUS and luciferase expression levels are provided in Table 3. In this table, the firefly luciferase values (e.g., from expression of pMON19437) are provided in the column labeled “FLuc” and the *Renilla* luciferase values are provided as in the column labeled “RLuc.”

TABLE 3

Mean GUS and Luciferase activity in transformed corn leaf protoplast cells.

| EXP Sequence | SEQ ID NO: | GUS | FLuc | RLuc |
|---|---|---|---|---|
| EMPTY | | 5 | 7840.58 | 205661 |
| EXP-Os.Act1:1:9 | 162 | 1540.25 | 2671.83 | 105417 |
| EXP-CaMV.35S-enh + Ta.Lhcb1 + Os.Act1:1:1 | 161 | 12530.8 | 3067.08 | 137723 |
| EXP-AGRne.Ubq1:1:7 | 1 | 39665 | 3645.83 | 137384 |
| EXP-AGRne.Ubq1:1:8 | 5 | 22805.5 | 4183.58 | 140991 |
| EXP-AGRne.Ubq1:1:9 | 7 | 5861.5 | 887.08 | 34034.3 |
| EXP-ARUdo.Ubq1:1:8 | 13 | 26965.5 | 1052.33 | 37774.8 |
| EXP-ARUdo.Ubq1:1:9 | 18 | 66126 | 3251.08 | 114622 |
| EXP-ARUdo.Ubq1:1:11 | 21 | 136163 | | 453851 |
| EXP-ARUdo.Ubq2:1:8 | 27 | 13222.3 | 2203.58 | 72339.1 |
| EXP-ARUdo.Ubq2:1:9 | 30 | 30095 | 6538.58 | 229201 |
| EXP-ARUdo.Ubq2:1:10 | 32 | 16448.5 | 1842.58 | 65325.1 |
| EXP-BOUgr.Ubq1:1:6 | 38 | 32544.3 | 2765.08 | 80330.8 |
| EXP-BOUgr.Ubq1:1:7 | 41 | 3826.33 | 697.11 | 20709 |
| EXP-BOUgr.Ubq1:1:8 | 43 | 9935.5 | 3372.58 | 110965 |
| EXP-BOUgr.Ubq2:1:14 | 52 | 17828 | 1575.83 | 62286.8 |
| EXP-BOUgr.Ubq2:1:16 | 58 | 54970.3 | 3389.08 | 117616 |
| EXP-BOUgr.Ubq2:1:17 | 60 | 48601.3 | 7139.08 | 245785 |
| EXP-MISsi.Ubq1:1:8 | 70 | 11788.3 | 3264.58 | 87751.6 |
| EXP-MISsi.Ubq1:1:10 | 72 | 33329.5 | 2388.58 | 81000.6 |
| EXP-MISsi.Ubq1:1:11 | 74 | 4723.75 | 3135.33 | 98059.1 |
| EXP-MISsi.Ubq1:1:7 | 76 | 4499 | 3073.58 | 84015.1 |
| EXP-SCHsc.Ubq1:1:9 | 78 | 5972 | 1703.33 | 62310.6 |
| EXP-SCHsc.Ubq1:1:7 | 84 | 24173.5 | 5306.08 | 155122 |
| EXP-SCHsc.Ubq1:1:10 | 86 | 7260 | 1171.08 | 38698.1 |
| EXP-SORnu.Ubq1:1:6 | 92 | 3966.5 | 4175.08 | 129365 |
| EXP-SORnu.Ubq1:1:7 | 95 | 23375.5 | 616.83 | 25125.3 |
| EXP-SORnu.Ubq1:1:8 | 97 | 8431.75 | 1630.08 | 55095.6 |
| EXP-SETit.Ubq1:1:5 | 103 | 20496.5 | 2358.83 | 88695.8 |
| EXP-SETit.Ubq1:1:7 | 106 | 75728.5 | 4723.08 | 185224 |
| EXP-SETit.Ubq1:1:6 | 108 | 44148.3 | 4962.08 | 161216 |
| EXP-Sv.Ubq1:1:7 | 110 | 15043.8 | 1888.33 | 74670.6 |
| EXP-Sv.Ubq1:1:8 | 116 | 31997.8 | 3219.83 | 113787 |
| EXP-Sv.Ubq1:1:10 | 118 | 38952.8 | 7011.33 | 220209 |
| EXP-Zm.UbqM1:1:6 | 122 | 30528.3 | 2453.58 | 90113.1 |
| EXP-Zm.UbqM1:1:8 | 134 | 34986.3 | 2553.78 | 105725 |
| Exp-Sb.Ubq4:1:2 | 140 | 9982.25 | 2171.58 | 72593.8 |
| Exp-Sb.Ubq6:1:2 | 144 | 33689 | 3879.58 | 114710 |

To compare the relative activity of each EXP sequence, GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 4 below shows the GUS/RLuc ratios of expression normalized with respect to EXP-Os.Act1:1:1 and EXP-CaMV.35S-enh+Ta.Lhcb1+Os.Act1:1:1 driven expression in corn protoplasts. Table 5 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 4

GUS/RLuc and GUS/FLuc ratios of expression normalized with respect to EXP-CaMV.35S-enh + Ta.Lhcb1 + Os.Act1:1:1 (SEQ ID NO: 161) in corn protoplasts.

| EXP Sequence | SEQ ID NO: | GUS/FLuc Relative to EXP-CaMV.35S-enh + Ta.Lhcb1 + Os.Act1:1:1 | GUS/RLuc Relative to EXP-CaMV.35S-enh + Ta.Lhcb1 + Os.Act1:1:1 |
|---|---|---|---|
| EXP-Os.Act1:1:9 | 162 | 0.14 | 0.16 |
| EXP-CaMV.35S-enh + Ta.Lhcb1 + Os.Act1:1:1 | 161 | 1 | 1 |

TABLE 4-continued

GUS/RLuc and GUS/FLuc ratios of expression normalized with respect to EXP-CaMV.35S-enh + Ta.Lhcb1 + Os.Act1:1:1 (SEQ ID NO: 161) in corn protoplasts.

| EXP Sequence | SEQ ID NO: | GUS/FLuc Relative to EXP-CaMV.35S-enh + Ta.Lhcb1 + Os.Act1:1:1 | GUS/RLuc Relative to EXP-CaMV.35S-enh + Ta.Lhcb1 + Os.Act1:1:1 |
|---|---|---|---|
| EXP-AGRne.Ubq1:1:7 | 1 | 2.66 | 3.17 |
| EXP-AGRne.Ubq1:1:8 | 5 | 1.33 | 1.78 |
| EXP-AGRne.Ubq1:1:9 | 7 | 1.62 | 1.89 |
| EXP-ARUdo.Ubq1:1:8 | 13 | 6.27 | 7.85 |
| EXP-ARUdo.Ubq1:1:9 | 18 | 4.98 | 6.34 |
| EXP-ARUdo.Ubq1:1:11 | 21 | | 3.3 |
| EXP-ARUdo.Ubq2:1:8 | 27 | 1.47 | 2.01 |
| EXP-ARUdo.Ubq2:1:9 | 30 | 1.13 | 1.44 |
| EXP-ARUdo.Ubq2:1:10 | 32 | 2.18 | 2.77 |
| EXP-BOUgr.Ubq1:1:6 | 38 | 2.88 | 4.45 |
| EXP-BOUgr.Ubq1:1:7 | 41 | 1.34 | 2.03 |
| EXP-BOUgr.Ubq1:1:8 | 43 | 0.72 | 0.98 |
| EXP-BOUgr.Ubq2:1:14 | 52 | 2.77 | 3.15 |
| EXP-BOUgr.Ubq2:1:16 | 58 | 3.97 | 5.14 |
| EXP-BOUgr.Ubq2:1:17 | 60 | 1.67 | 2.17 |
| EXP-MISsi.Ubq1:1:8 | 70 | 0.88 | 1.48 |
| EXP-MISsi.Ubq1:1:10 | 72 | 3.42 | 4.52 |
| EXP-MISsi.Ubq1:1:11 | 74 | 0.37 | 0.53 |
| EXP-MISsi.Ubq1:1:7 | 76 | 0.36 | 0.59 |
| EXP-SCHsc.Ubq1:1:9 | 78 | 0.86 | 1.05 |
| EXP-SCHsc.Ubq1:1:7 | 84 | 1.12 | 1.71 |
| EXP-SCHsc.Ubq1:1:10 | 86 | 1.52 | 2.06 |
| EXP-SORnu.Ubq1:1:6 | 92 | 0.23 | 0.34 |
| EXP-SORnu.Ubq1:1:7 | 95 | 9.28 | 10.23 |
| EXP-SORnu.Ubq1:1:8 | 97 | 1.27 | 1.68 |
| EXP-SETit.Ubq1:1:5 | 103 | 2.13 | 2.54 |
| EXP-SETit.Ubq1:1:7 | 106 | 3.92 | 4.49 |
| EXP-SETit.Ubq1:1:6 | 108 | 2.18 | 3.01 |
| EXP-Sv.Ubq1:1:7 | 110 | 1.95 | 2.21 |
| EXP-Sv.Ubq1:1:8 | 116 | 2.43 | 3.09 |
| EXP-Sv.Ubq1:1:10 | 118 | 1.36 | 1.94 |
| EXP-Zm.UbqM1:1:6 | 122 | 3.05 | 3.72 |
| EXP-Zm.UbqM1:1:8 | 134 | 3.35 | 3.64 |
| Exp-Sb.Ubq4:1:2 | 140 | 1.13 | 1.51 |
| Exp-Sb.Ubq6:1:2 | 144 | 2.13 | 3.23 |

TABLE 5

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 7.09 | 6.23 |
| EXP-AGRne.Ubq1:1:7 | 1 | 18.87 | 19.76 |
| EXP-AGRne.Ubq1:1:8 | 5 | 9.46 | 11.07 |
| EXP-AGRne.Ubq1:1:9 | 7 | 11.46 | 11.79 |
| EXP-ARUdo.Ubq1:1:8 | 13 | 44.45 | 48.86 |
| EXP-ARUdo.Ubq1:1:9 | 18 | 35.28 | 39.48 |
| EXP-ARUdo.Ubq1:1:11 | 21 | | 20.53 |
| EXP-ARUdo.Ubq2:1:8 | 27 | 10.41 | 12.51 |
| EXP-ARUdo.Ubq2:1:9 | 30 | 7.98 | 8.99 |
| EXP-ARUdo.Ubq2:1:10 | 32 | 15.49 | 17.23 |
| EXP-BOUgr.Ubq1:1:6 | 38 | 20.42 | 27.73 |
| EXP-BOUgr.Ubq1:1:7 | 41 | 9.52 | 12.65 |
| EXP-BOUgr.Ubq1:1:8 | 43 | 5.11 | 6.13 |
| EXP-BOUgr.Ubq2:1:14 | 52 | 19.63 | 19.59 |
| EXP-BOUgr.Ubq2:1:16 | 58 | 28.14 | 31.99 |
| EXP-BOUgr.Ubq2:1:17 | 60 | 11.81 | 13.53 |
| EXP-MISsi.Ubq1:1:8 | 70 | 6.26 | 9.19 |

TABLE 5-continued

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-MISsi.Ubq1:1:10 | 72 | 24.21 | 28.16 |
| EXP-MISsi.Ubq1:1:11 | 74 | 2.61 | 3.3 |
| EXP-MISsi.Ubq1:1:7 | 76 | 2.54 | 3.67 |
| EXP-SCHsc.Ubq1:1:9 | 78 | 6.08 | 6.56 |
| EXP-SCHsc.Ubq1:1:7 | 84 | 7.9 | 10.67 |
| EXP-SCHsc.Ubq1:1:10 | 86 | 10.75 | 12.84 |
| EXP-SORnu.Ubq1:1:6 | 92 | 1.65 | 2.1 |
| EXP-SORnu.Ubq1:1:7 | 95 | 65.74 | 63.67 |
| EXP-SORnu.Ubq1:1:8 | 97 | 8.97 | 10.47 |
| EXP-SETit.Ubq1:1:5 | 103 | 15.07 | 15.82 |
| EXP-SETit.Ubq1:1:7 | 106 | 27.81 | 27.98 |
| EXP-SETit.Ubq1:1:6 | 108 | 15.43 | 18.74 |
| EXP-Sv.Ubq1:1:7 | 110 | 13.82 | 13.79 |
| EXP-Sv.Ubq1:1:8 | 116 | 17.24 | 19.25 |
| EXP-Sv.Ubq1:1:10 | 118 | 9.64 | 12.11 |
| EXP-Zm.UbqM1:1:6 | 122 | 21.58 | 23.19 |
| EXP-Zm.UbqM1:1:8 | 134 | 23.76 | 22.65 |
| Exp-Sb.Ubq4:1:2 | 140 | 7.97 | 9.41 |
| Exp-Sb.Ubq6:1:2 | 144 | 15.06 | 20.1 |

As can be seen in Tables 9 and 10, all of the EXP sequences were capable of driving GUS transgene expression in corn cells. Average GUS expression was higher for all of the EXP sequences relative to EXP-Os.Act1:1:9. The EXP sequences, EXP-AGRne.Ubq1:1:7 (SEQ ID NO: 1), EXP-AGRne.Ubq1:1:8 (SEQ ID NO: 5), EXP-AGRne.Ubq1:1:9 (SEQ ID NO: 7), EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 21), EXP-ARUdo.Ubq2:1:8 (SEQ ID NO: 27), EXP-ARUdo.Ubq2:1:9 (SEQ ID NO: 30), EXP-ARUdo.Ubq2:1:10 (SEQ ID NO: 32), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SCHsc.Ubq1:1:7 (SEQ ID NO: 84), EXP-SCHsc.Ubq1:1:10 (SEQ ID NO: 86), EXP-SORnu.Ubq1:1:7 (SEQ ID NO: 95), EXP-SORnu.Ubq1:1:8 (SEQ ID NO: 97), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), EXP-Zm.UbqM1:1:8 (SEQ ID NO: 134), EXP-Sb.Ubq4:1:2 (SEQ ID NO: 140), and EXP-Sb.Ubq6:1:2 (SEQ ID NO: 144) demonstrated GUS expression levels above that of EXP-CaMV.35S-enh+Ta.Lhcb1+Os.Act1:1:1.

In a second set of experiments, a GUS expression cassette amplicon comprising the EXP sequence EXP-Zm.UbqM1:1:7 (SEQ ID NO: 128) was compared to the control amplicons, PCR0145942 (EXP-Os.Act1:1:9, SEQ ID NO: 162) and PCR0145944 (EXP-CaMV.35S-enh+Zm.DnaK:1:1, SEQ ID NO: 161) with respect to GUS expression. GUS expression driven by the EXP sequence EXP-Zm.UbqM1:1:7 was higher than that of the two controls. Table 6 below shows the mean GUS and luciferase values determined for each amplicon. Table 7 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 6

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

TABLE 7

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in corn leaf protoplasts.

| EXP Sequence | SEQ ID NO: | GUS | FLuc | RLuc |
|---|---|---|---|---|
| EXP-Os.Act1:1:9 | 162 | 1512.25 | 11333.75 | 190461.00 |
| EXP-CaMV.35S-enh + Ta.Lhcb1 + Os.Act1:1:1 | 161 | 41176.50 | 13885.75 | 330837.25 |
| EXP-Zm.UbqM1:1:7 | 128 | 79581.50 | 15262.50 | 330755.75 |

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the GUS transgene, and compared to leaf protoplast in which expression of GUS is driven by known constitutive promoters.

Example 3

Analysis of Regulatory Elements Driving GUS in Wheat Protoplasts Using GUS Expression Cassette Amplicons Wheat leaf protoplasts were transformed with DNA amplicons derived from plant expression vectors containing an EXP sequence, driving expression of the GUS transgene, and compared to leaf protoplast in which expression of GUS was driven by known constitutive promoters.

Wheat protoplast cells derived from leaf tissue were transformed using methods known in the art with amplicons produced from amplification of GUS expression cassettes comprising plant expression vectors to compare expression of a transgene (GUS) driven by the EXP sequences listed in Table 3 with that of known constitutive promoters with methodology as described in a previous example (Example 2), using the same GUS expression cassette amplicons as that used for assay in corn in Example 2 above. Control GUS expression cassette amplicons and Luciferase plasmids used for wheat protoplast transformation were also the same as those presented in the previous example and provided in Table 3 above in Example 2. Likewise, negative controls were used for the determination of GUS and Luciferase background, as described above. Wheat leaf protoplasts were transformed using a PEG-based transformation method, as described in Example 2 above. Table 8 lists mean GUS and LUC activity seen in transformed wheat leaf protoplast cells, and Table 9 and 10 shows normalized GUS/FLuc and GUS/RLuc ratios of expression in wheat protoplasts relative to the constitutive EXP controls.

TABLE 8

Mean GUS and Luciferase activity in transformed wheat leaf protoplast cells.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 9

GUS/RLuc and GUS/FLuc ratios of expression normalized with respect to EXP-CaMV.35S-enh + Ta.Lhcb1 + Os.Act1:1:1 (SEQ ID NO: 161) in wheat protoplasts.

| EXP Sequence | SEQ ID NO: | GUS | FLuc | RLuc |
|---|---|---|---|---|
| EMPTY | | 262.56 | 1109.78 | 61422.1 |
| EXP-Os.Act1:1:9 | 162 | 2976.33 | 730.11 | 53334.8 |
| EXP-CaMV.35S-enh + Ta.Lhcb1 + Os.Act1:1:1 | 161 | 29299.3 | 741.78 | 50717.4 |
| EXP-AGRne.Ubq1:1:7 | 1 | 27078.3 | 754.44 | 44235.8 |
| EXP-AGRne.Ubq1:1:8 | 5 | 22082.7 | 958.11 | 55774.8 |
| EXP-AGRne.Ubq1:1:9 | 7 | 13882.7 | 699.78 | 49273.4 |
| EXP-ARUdo.Ubq1:1:8 | 13 | 65628 | 791.44 | 56358.8 |
| EXP-ARUdo.Ubq1:1:9 | 18 | 87615 | 801.44 | 53246.4 |
| EXP-ARUdo.Ubq1:1:11 | 21 | 19224.3 | 143.44 | 14104.1 |
| EXP-ARUdo.Ubq2:1:8 | 27 | 25453.3 | 835.11 | 57679.4 |
| EXP-ARUdo.Ubq2:1:9 | 30 | 26720.7 | 702.44 | 47455.4 |
| EXP-ARUdo.Ubq2:1:10 | 32 | 37089.3 | 859.11 | 57814.4 |
| EXP-BOUgr.Ubq1:1:6 | 38 | 35146 | 995.44 | 64418.8 |
| EXP-BOUgr.Ubq1:1:7 | 41 | 18077 | 857.78 | 55793.4 |
| EXP-BOUgr.Ubq1:1:8 | 43 | 11723.7 | 938.44 | 59362.1 |
| EXP-BOUgr.Ubq2:1:14 | 52 | 38109.3 | 875.11 | 58048.1 |
| EXP-BOUgr.Ubq2:1:16 | 58 | 37384 | 860.44 | 52447.8 |
| EXP-BOUgr.Ubq2:1:17 | 60 | 24090.7 | 968.78 | 53057.8 |
| EXP-MISsi.Ubq1:1:8 | 70 | 16456.7 | 1021.78 | 61684.1 |
| EXP-MISsi.Ubq1:1:10 | 72 | 42816.7 | 839.78 | 46688.1 |
| EXP-MISsi.Ubq1:1:11 | 74 | 20625.7 | 987.78 | 61842.1 |
| EXP-MISsi.Ubq1:1:7 | 76 | 4913.67 | 764.78 | 64720.1 |
| EXP-SCHsc.Ubq1:1:9 | 78 | 9726 | 937.11 | 54725.4 |
| EXP-SCHsc.Ubq1:1:7 | 84 | 13374.7 | 1112.44 | 73815.4 |
| EXP-SCHsc.Ubq1:1:10 | 86 | 13650 | 936.78 | 62242.1 |
| EXP-SORnu.Ubq1:1:6 | 92 | 8188.17 | 753.83 | 50572.5 |
| EXP-SORnu.Ubq1:1:7 | 95 | 83233.7 | 854.44 | 54410.1 |
| EXP-SORnu.Ubq1:1:8 | 97 | 21904.7 | 1011.83 | 60852 |
| EXP-SETit.Ubq1:1:5 | 103 | 39427.7 | 908.78 | 57463.1 |
| EXP-SETit.Ubq1:1:7 | 106 | 108091 | 809.44 | 49330.4 |
| EXP-SETit.Ubq1:1:6 | 108 | 58703 | 809.11 | 46110.1 |
| EXP-Sv.Ubq1:1:7 | 110 | 29330 | 684.11 | 43367.1 |
| EXP-Sv.Ubq1:1:8 | 116 | 53359 | 698.11 | 40076.4 |
| EXP-Sv.Ubq1:1:10 | 118 | 49122.7 | 901.44 | 53180.8 |
| EXP-Zm.UbqM1:1:6 | 122 | 37268 | 945.78 | 54088.1 |
| EXP-Zm.UbqM1:1:8 | 134 | 51408 | 677.78 | 47297.4 |
| Exp-Sb.Ubq4:1:2 | 140 | 35660.3 | 1114.11 | 62591.1 |
| Exp-Sb.Ubq6:1:2 | 144 | 27543 | 915.11 | 57826.4 |

TABLE 10

GUS/RLuc and GUS/FLuc ratios of expression normalized with respect to EXP-Os.Act1:1:9 (SEQ ID NO: 162) in corn leaf protoplasts.

| EXP Sequence | SEQ ID NO: | GUS/FLuc Relative to EXP-Os.Act1:1:9 | GUS/RLuc Relative to EXP-Os.Act1:1:9 |
|---|---|---|---|
| EXP-Os.Act1:1:9 | 162 | 1 | 1 |
| EXP-CaMV.35S-enh + Ta.Lhcb1 + Os.Act1:1:1 | 161 | 9.69 | 10.35 |
| EXP-AGRne.Ubq1:1:7 | 1 | 8.8 | 10.97 |
| EXP-AGRne.Ubq1:1:8 | 5 | 5.65 | 7.09 |
| EXP-AGRne.Ubq1:1:9 | 7 | 4.87 | 5.05 |
| EXP-ARUdo.Ubq1:1:8 | 13 | 20.34 | 20.87 |
| EXP-ARUdo.Ubq1:1:9 | 18 | 26.82 | 29.49 |
| EXP-ARUdo.Ubq1:1:11 | 21 | 32.88 | 24.43 |
| EXP-ARUdo.Ubq2:1:8 | 27 | 7.48 | 7.91 |
| EXP-ARUdo.Ubq2:1:9 | 30 | 9.33 | 10.09 |
| EXP-ARUdo.Ubq2:1:10 | 32 | 10.59 | 11.5 |
| EXP-BOUgr.Ubq1:1:6 | 38 | 8.66 | 9.78 |
| EXP-BOUgr.Ubq1:1:7 | 41 | 5.17 | 5.81 |
| EXP-BOUgr.Ubq1:1:8 | 43 | 3.06 | 3.54 |
| EXP-BOUgr.Ubq2:1:14 | 52 | 10.68 | 11.76 |
| EXP-BOUgr.Ubq2:1:16 | 58 | 10.66 | 12.77 |
| EXP-BOUgr.Ubq2:1:17 | 60 | 6.1 | 8.14 |
| EXP-MISsi.Ubq1:1:8 | 70 | 3.95 | 4.78 |
| EXP-MISsi.Ubq1:1:10 | 72 | 12.51 | 16.43 |
| EXP-MISsi.Ubq1:1:11 | 74 | 5.12 | 5.98 |
| EXP-MISsi.Ubq1:1:7 | 76 | 1.58 | 1.36 |
| EXP-SCHsc.Ubq1:1:9 | 78 | 2.55 | 3.18 |
| EXP-SCHsc.Ubq1:1:7 | 84 | 2.95 | 3.25 |
| EXP-SCHsc.Ubq1:1:10 | 86 | 3.57 | 3.93 |
| EXP-SORnu.Ubq1:1:6 | 92 | 2.66 | 2.9 |
| EXP-SORnu.Ubq1:1:7 | 95 | 23.9 | 27.41 |
| EXP-SORnu.Ubq1:1:8 | 97 | 5.31 | 6.45 |
| EXP-SETit.Ubq1:1:5 | 103 | 10.64 | 12.3 |
| EXP-SETit.Ubq1:1:7 | 106 | 32.76 | 39.26 |
| EXP-SETit.Ubq1:1:6 | 108 | 17.8 | 22.81 |
| EXP-Sv.Ubq1:1:7 | 110 | 10.52 | 12.12 |
| EXP-Sv.Ubq1:1:8 | 116 | 18.75 | 23.86 |
| EXP-Sv.Ubq1:1:10 | 118 | 13.37 | 16.55 |
| EXP-Zm.UbqM1:1:6 | 122 | 9.67 | 12.35 |
| EXP-Zm.UbqM1:1:8 | 134 | 18.61 | 19.48 |
| Exp-Sb.Ubq4:1:2 | 140 | 7.85 | 10.21 |
| Exp-Sb.Ubq6:1:2 | 144 | 7.38 | 8.54 |

As can be seen in Tables 9 and 10 above, all of the EXP sequences were capable of driving GUS transgene expression in wheat cells. All of the EXP sequences drove GUS expression at levels higher than that of EXP-Os.Act1:1:9 in wheat cells. The EXP sequences EXP-ARUdo.Ubq1:1:8 (SEQ ID NO: 13), EXP-ARUdo.Ubq1:1:9 (SEQ ID NO: 18), EXP-ARUdo.Ubq1:1:11 (SEQ ID NO: 21), EXP-ARUdo.Ubq2:1:10 (SEQ ID NO: 32), EXP-BOUgr.Ubq2:1:14 (SEQ ID NO: 52), EXP-BOUgr.Ubq2:1:16 (SEQ ID NO: 58), EXP-BOUgr.Ubq2:1:17 (SEQ ID NO: 60), EXP-MISsi.Ubq1:1:10 (SEQ ID NO: 72), EXP-SORnu.Ubq1:1:7 (SEQ ID NO: 95), EXP-SETit.Ubq1:1:5 (SEQ ID NO: 103), EXP-SETit.Ubq1:1:7 (SEQ ID NO: 106), EXP-SETit.Ubq1:1:6 (SEQ ID NO: 108), EXP-Sv.Ubq1:1:7 (SEQ ID NO: 110), EXP-Sv.Ubq1:1:8 (SEQ ID NO: 116), EXP-Sv.Ubq1:1:10 (SEQ ID NO: 118), EXP-Zm.UbqM1:1:6 (SEQ ID NO: 122), and EXP-Zm.UbqM1:1:8 (SEQ ID NO: 134) demonstrated levels of GUS expression equal to or greater than GUS expression driven by EXP-CaMV.35S-enh+Ta.Lhcb1+Os.Act1:1:1 in wheat cells.

In a second set of experiments, the amplicon GUS expression cassette comprising EXP-ARUdo.Ubq1:1:11 (SEQ ID NO: 21) was compared to the controls EXP-Os.Act1:1:9 (SEQ ID NO: 162) and EXP-CaMV.35S-enh+Zm.DnaK:1:1 (SEQ ID NO: 161). Table 11 below shows the mean GUS and luciferase values determined for each amplicon. Table 12 below shows the GUS/RLuc ratios of expression normalized with respect to EXP-Os.Act1:1:9 and EXP-CaMV.35S-enh+Zm.DnaK:1:1 driven expression in wheat protoplasts.

TABLE 11

Mean GUS and Luciferase activity in transformed wheat leaf protoplast cells.

| EXP Sequence | SEQ ID NO: | GUS | RLuc |
|---|---|---|---|
| EMPTY | | 20.75 | 187112.50 |
| EXP-Os.Act1:1:9 | 162 | 1234.00 | 176970.50 |
| EXP-CaMV.35S-enh + Ta.Lhcb1 + Os.Act1:1:1 | 161 | 12883.50 | 119439.00 |
| EXP-ARUdo.Ubq1:1:11 | 21 | 30571.50 | 135037.50 |

TABLE 12

GUS/RLuc and GUS/FLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

As can be seen in Table 12 above, GUS expression driven by EXP-ARUdo.Ubq1:1:11 (SEQ ID NO: 21) was higher than both constitutive controls, EXP-Os.Act1:1:9 and EXP-CaMV.35S-enh+Zm.DnaK:1:1.

Example 4

Analysis of Regulatory Elements Driving GUS in Corn and Wheat Protoplasts

Corn and Wheat leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-C1.Ubq10 (SEQ ID NO: 168) was compared with expression from known constitutive promoters. The foregoing EXP sequences were cloned into plant expression vectors as shown in Table 13 below to yield vectors in which an EXP sequence is operably linked 5' to a GUS reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NO: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 13

GUS plant expression plasmid construct and corresponding EXP sequence, GUS coding sequence and 3' UTR used for transformation of corn leaf protoplasts. "SEQ ID NO:" refers to given EXP sequence.

| EXP Sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 162 | 1.00 | 0.06 |
| EXP-CaMV.35S-enh + Ta.Lhcb1 + Os.Act1:1:1 | 161 | 15.47 | 1.00 |
| EXP-ARUdo.Ubq1:1:11 | 21 | 32.47 | 2.10 |

Two plasmids, for use in co-transformation and normalization of data, were also constructed using methods known in the art. Each plasmid contained a specific luciferase coding sequence that was driven by a constitutive EXP sequence. The plant vector pMON19437 comprises an expression cassette with a constitutive promoter operably linked 5' to an intron, (EXP-CaMV.35S-enh+Zm.DnaK:1:1, SEQ ID NO: 163), operably linked 5' to a firefly (*Photinus pyralis*) luciferase coding sequence (LUCIFERASE:1:3, SEQ ID NO: 156), operably linked 5' to a 3' UTR from the *Agrobacterium tumefaciens* nopaline synthase gene (T-AGRtu.nos-1:1:13, SEQ ID NO: 158). The plant vector pMON63934 comprises an expression cassette with a constitutive EXP sequence (EXP-CaMV.35S-enh-Lhcb1, SEQ ID NO: 164), operably linked 5' to a sea pansy (*Renilla reniformis*) luciferase coding sequence (CR-Ren.hRenilla Lucife-0:0:1, SEQ ID NO: 157), operably linked 5' to a 3' UTR from the *Agrobacterium tumefaciens* nopaline synthase gene (T-AGRtu.nos-1:1:13, SEQ ID NO: 158).

Corn leaf protoplasts were transformed using a PEG-based transformation method, which is well known in the art. Protoplast cells were transformed with pMON19437 plasmid DNA, pMON63934 plasmid DNA, and the plasmids presented in Table 13 and incubated overnight in total darkness. Measurements of both GUS and luciferase were conducted in a similar manner as that described in Example 2 above. One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 14. In this table, the firefly luciferase values (e.g., from expression of pMON19437) are provided in the column labeled "FLuc" and the *Renilla* luciferase values are provided as in the column labeled "RLuc."

TABLE 14

Mean GUS and Luciferase activity in transformed corn leaf protoplast cells.

| EXP Sequence | SEQ ID NO: | GUS | FLuc | RLuc |
|---|---|---|---|---|
| EXP-Os.Act1:1:9 | 162 | 83997.3 | 80983 | 61619 |
| EXP-CaMV.35S-enh + Ta.Lhcb1 + Os.Act1:1:1 | 161 | 248832 | 83589.8 | 72064.3 |
| EXP-Cl.Ubq10 | 168 | 30790.8 | 65807.5 | 34846.3 |

Table 15 below shows the GUS/FLuc and GUS/RLuc ratios of expression normalized with respect to EXP-Os-.Act1:1:9 and EXP-CaMV.35S-enh+Zm.DnaK:1:1 driven expression in corn protoplasts.

TABLE 15

GUS/FLuc and GUS/RLuc ratios of expression normalized with respect to EXP-Os.Act1:1:9 (SEQ ID NO: 161) and EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-Os.Act1:1:9 | GUS/Rluc normalized with respect to EXP-Os.Act1:1:9 | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os. Act1:1:1 |
|---|---|---|---|---|---|
| EXP-Os.Act1:1:9 | 162 | 1.00 | 1.00 | 0.35 | 0.39 |
| EXP-CaMV.35S-enh + Ta.Lhcb1 + Os.Act1:1:1 | 161 | 2.87 | 2.53 | 1.00 | 1.00 |
| EXP-Cl.Ubq10 | 168 | 0.45 | 0.65 | 0.16 | 0.26 |

As can be seen in Table 15 above, EXP-C1.Ubq10 (SEQ ID NO: 168) was able to drive expression of GUS, but was at a level lower than that of both constitutive controls.

The plasmids listed in Table 13 above were also used to transform wheat leaf protoplast cells in a similar manner as that for corn leaf protoplasts described above. Mean GUS and luciferase values are shown in Table 16 below. Table 17 below shows the GUS/FLuc and GUS/RLuc ratios of expression normalized with respect to EXP-CaMV.35S-enh+Zm.DnaK:1:1 driven expression in corn protoplasts.

TABLE 16

Mean GUS and Luciferase activity in transformed corn leaf protoplast cells.

| EXP Sequence | SEQ ID NO: | GUS | FLuc | RLuc |
|---|---|---|---|---|
| EXP-CaMV.35S-enh + Ta.Lhcb1 + Os.Act1:1:1 | 161 | 134145 | 1076.67 | 6858.67 |
| EXP-Cl.Ubq10 | 168 | 104669 | 888.67 | 4516 |

TABLE 17

GUS/FLuc and GUS/RLuc ratios of expression normalized with respect to EXP-CaMV.35S-enh + Zm.DnaK:1:1 (SEQ ID NO: 160) in wheat leaf protoplasts.

| EXP Sequence | SEQ ID NO: | GUS/Fluc normalized with respect to EXP-CaMV.35S-enh + Ta.Lhcb1 + Os.Act1:1:1 | GUS/Rluc normalized with respect to EXP-CaMV.35S-enh + Ta.Lhcb1 + Os.Act1:1:1 |
|---|---|---|---|
| EXP-CaMV.35S-enh + Ta.Lhcb1 + Os.Act1:1:1 | 161 | 1.00 | 1.00 |
| EXP-Cl.Ubq10 | 168 | 0.95 | 1.19 |

As can be seen in Table 17 above, EXP-C1.Ubq10 (SEQ ID NO: 168) expressed GUS at a similar level as that of EXP-CaMV.35S-enh+Zm.DnaK:1:1 (SEQ ID NO: 160) in wheat protoplast cells.

Example 5

Analysis of Regulatory Elements Driving GUS in Transgenic Corn

Corn plants were transformed with plant expression vectors containing a EXP sequences driving expression of the GUS transgene, and the resulting plants were analyzed for GUS protein expression. The ubiquitin EXP sequences were cloned into plant binary transformation plasmid constructs using methods known in the art.

The resulting plant expression vectors contain a right border region from *A. tumefaciens*, a first expression cassette to assay the EXP sequence operably linked to a coding sequence for GUS that possesses the processable intron GUS-2, described above, operably linked 5' to the 3' UTR from the rice lipid transfer protein gene (T-Os.LTP-1:1:1, SEQ ID NO: 159); a second transgene selection cassette used for selection of transformed plant cells that confers resistance to the herbicide glyphosate (driven by the rice Actin 1 promoter), and a left border region from *A. tumefaciens*. The resulting plasmids were used to transform corn plants. Table 18 lists the plasmid designations, the EXP sequences and the SEQ ID NOs, which are also described in Table 1.

TABLE 18

| Binary plant transformation plasmids and the associated EXP sequences. | | |
|---|---|---|
| Plasmid Construct | EXP sequence | SEQ ID NO: |
| pMON140869 | EXP-AGRne.Ubq1:1:7 | 1 |
| pMON140870 | EXP-AGRne.Ubq1:1:8 | 5 |
| pMON142650 | EXP-ARUdo.Ubq1:1:8 | 13 |
| pMON142651 | EXP-ARUdo.Ubq1:1:9 | 18 |
| pMON142652 | EXP-ARUdo.Ubq2:1:8 | 27 |
| pMON142653 | EXP-ARUdo.Ubq2:1:9 | 30 |
| pMON140871 | EXP-BOUgr.Ubq1:1:6 | 38 |
| pMON140872 | EXP-BOUgr.Ubq1:1:7 | 41 |
| pMON140873 | EXP-BOUgr.Ubq2:1:14 | 52 |
| pMON140874 | EXP-BOUgr.Ubq2:1:15 | 55 |
| pMON142887 | EXP-MISsi.Ubq1:1:7 | 76 |
| pMON140875 | EXP-SORnu.Ubq1:1:6 | 92 |
| pMON140876 | EXP-SORnu.Ubq1:1:7 | 95 |
| pMON132037 | EXP-SETit.Ubq1:1:10 | 99 |
| pMON131958 | EXP-Sv.Ubq1:1:11 | 114 |
| pMON131959 | EXP-Sv.Ubq1:1:12 | 120 |
| pMON131961 | EXP-Zm.UbqM1:1:10 | 126 |
| pMON131963 | EXP-Zm.UbqM1:1:12 | 132 |
| pMON131962 | EXP-Zm.UbqM1:1:11 | 138 |
| pMON132932 | EXP-Sb.Ubq4:1:2 | 140 |
| pMON132931 | EXP-Sb.Ubq6:1:3 | 148 |
| pMON132974 | EXP-Sb.Ubq7:1:2 | 150 |
| pMON142738 | EXP-Cl.Ubq10 | 168 |

Plants were transformed using *Agrobacterium*-mediated transformations, for instance as described in U.S. Patent Application Publication 2009/0138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves, as well as the anther, silk, and developing seed and embryo, 21 days after pollination (21 DAP).

For quantitative analysis, total protein was extracted from selected tissues of transformed corn plants. One microgram of total protein was used with the fluorogenic substrate 4-methylumbelliferyl-β-D-glucuronide (MUG) in a total reaction volume of 50 μl. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 19 and 20 below.

TABLE 19

Average $R_0$ GUS expression in root and leaf tissue.

| EXP sequence | SEQ ID NO: | V3 Root | V4 Root | V7 Root | VT Root | V3 Leaf | V4 Leaf | V7 Leaf | VT Leaf |
|---|---|---|---|---|---|---|---|---|---|
| EXP-AGRne.Ubq1:1:7 | 1 | 16 | | 25 | 14 | 49 | | 60 | 48 |
| EXP-AGRne.Ubq1:1:8 | 5 | 13 | | 20 | 22 | 38 | | 38 | 52 |
| EXP-ARUdo.Ubq1:1:8 | 13 | 18 | | 34 | 89 | 117 | | 48 | 106 |
| EXP-ARUdo.Ubq1:1:9 | 18 | 19 | | 20 | 68 | 105 | | 33 | 69 |
| EXP-ARUdo.Ubq2:1:8 | 27 | 14 | | 19 | 27 | 58 | | 57 | 47 |
| EXP-ARUdo.Ubq2:1:9 | 30 | 14 | | 15 | 25 | 40 | | 38 | 40 |
| EXP-BOUgr.Ubq1:1:6 | 38 | 12 | | 28 | 16 | 43 | | 46 | 27 |
| EXP-BOUgr.Ubq1:1:7 | 41 | 14 | | 24 | 114 | 51 | | 48 | 48 |
| EXP-BOUgr.Ubq2:1:14 | 52 | 17 | | 13 | 28 | 46 | | 33 | 41 |
| EXP-BOUgr.Ubq2:1:15 | 55 | 11 | | 67 | 36 | 86 | | 72 | 36 |
| EXP-MISsi.Ubq1:1:7 | 76 | 17 | | 28 | 13 | 18 | | 12 | 18 |
| EXP-SORnu.Ubq1:1:6 | 92 | 14 | | 45 | 33 | 44 | | 64 | 55 |
| EXP-SORnu.Ubq1:1:7 | 95 | 11 | | 18 | 20 | 31 | | 36 | 48 |
| EXP-SETit.Ubq1:1:10 | 99 | 0 | | 29 | 57 | 58 | | 37 | 46 |
| EXP-Sv.Ubq1:1:11 | 114 | nd | | nd | 9 | 20 | | 55 | 29 |
| EXP-Sv.Ubq1:1:12 | 120 | 63 | | 0 | 28 | 184 | | 27 | 16 |
| EXP-Zm.UbqM1:1:10 | 126 | 0 | | 237 | 18 | 221 | | 272 | 272 |
| EXP-Zm.UbqM1:1:12 | 132 | 0 | | 21 | 43 | 234 | | 231 | 196 |
| EXP-Zm.UbqM1:1:11 | 138 | 124 | | 103 | 112 | 311 | | 369 | 297 |
| EXP-Sb.Ubq4:1:2 | 140 | 125 | | 0 | 95 | 233 | | 150 | 88 |
| EXP-Sb.Ubq6:1:3 | 148 | 154 | | 13 | 128 | 53 | | 39 | 55 |
| EXP-Sb.Ubq7:1:2 | 150 | 37 | | 22 | 18 | 165 | | 89 | 177 |
| EXP-Cl.Ubq10 | 168 | | 61 | 67 | 32 | | 111 | 58 | 115 |

TABLE 20

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-AGRne.Ubq1:1:7 | 1 | 149 | 36 | 59 | 59 |
| EXP-AGRne.Ubq1:1:8 | 5 | 73 | 66 | 33 | 58 |
| EXP-ARUdo.Ubq1:1:8 | 13 | 321 | 253 | 177 | 355 |
| EXP-ARUdo.Ubq1:1:9 | 18 | 242 | 268 | 97 | 266 |
| EXP-ARUdo.Ubq2:1:8 | 27 | 104 | 99 | 79 | 157 |
| EXP-ARUdo.Ubq2:1:9 | 30 | 78 | 71 | 82 | 139 |
| EXP-BOUgr.Ubq1:1:6 | 38 | 58 | 250 | 43 | 63 |
| EXP-BOUgr.Ubq1:1:7 | 41 | 58 | 77 | 40 | 49 |
| EXP-BOUgr.Ubq2:1:14 | 52 | 236 | 377 | 48 | 137 |
| EXP-BOUgr.Ubq2:1:15 | 55 | 203 | 134 | 47 | 180 |
| EXP-MISsi.Ubq1:1:7 | 76 | 24 | 16 | 29 | 32 |
| EXP-SORnu.Ubq1:1:6 | 92 | 361 | 80 | 37 | 94 |
| EXP-SORnu.Ubq1:1:7 | 95 | 195 | 114 | 20 | 55 |
| EXP-SETit.Ubq1:1:10 | 99 | 132 | 85 | 50 | 63 |
| EXP-Sv.Ubq1:1:11 | 114 | 217 | 3 | 45 | 92 |
| EXP-Sv.Ubq1:1:12 | 120 | 120 | 21 | 49 | 112 |
| EXP-Zm.UbqM1:1:10 | 126 | 261 | 506 | 403 | 376 |
| EXP-Zm.UbqM1:1:12 | 132 | 775 | 362 | 253 | 247 |
| EXP-Zm.UbqM1:1:11 | 138 | 551 | 452 | 234 | 302 |
| EXP-Sb.Ubq4:1:2 | 140 | 213 | 0 | 25 | 79 |
| EXP-Sb.Ubq6:1:3 | 148 | 295 | 87 | 51 | 61 |
| EXP-Sb.Ubq7:1:2 | 150 | 423 | 229 | 274 | 90 |
| EXP-Cl.Ubq10 | 168 | 237 | 82 | 91 | 210 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, the EXP sequences, EXP-AGRne.Ubq1:1:7 (SEQ ID NO: 1), EXP-AGRne.Ubq1:1:8 (SEQ ID NO: 5), EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-ARUdo.Ubq2:1:9 (SEQ ID NO: 30), EXP-BOUgr.Ubq1:1:6 (SEQ ID NO: 38), EXP-BOUgr.Ubq1:1:7 (SEQ ID NO: 41), EXP-BOUgr.Ubq2:1:14 (SEQ ID NO: 52), EXP-BOUgr.Ubq2:1:15 (SEQ ID NO: 55), EXP-MISsi.Ubq1:1:7 (SEQ ID NO: 76), EXP-SORnu.Ubq1:1:6 (SEQ ID NO: 92), EXP-SORnu.Ubq1:1:7 (SEQ ID NO: 95), EXP-SETit.Ubq1:1:10 (SEQ ID NO: 99), EXP-Sv.Ubq1:1:11 (SEQ ID NO: 114), EXP-Zm.UbqM1:1:12 (SEQ ID NO: 132), and EXP-Sb.Ubq7:1:2 (SEQ ID NO: 150) demonstrated lower levels of GUS expression in the root at V3 and V7 stages of development relative to EXP-Sv.Ubq1:1:12 (SEQ ID NO: 120), EXP-Zm.UbqM1:1:10 (SEQ ID NO: 126), EXP-Zm.UbqM1:1:11 (SEQ ID NO: 138), EXP-Sb.Ubq4:1:2 (SEQ ID NO: 140), and EXP-Sb.Ubq6:1:3 (SEQ ID NO: 148). Higher levels of GUS expression were observed in later stages of root development (VT) for EXP-ARUdo.Ubq1:1:8 (SEQ ID NO: 13), EXP-ARUdo.Ubq1:1:9 (SEQ ID NO: 18), EXP-BOUgr.Ubq1:1:7 (SEQ ID NO: 41), EXP-Zm.UbqM1:1:11 (SEQ ID NO: 138), and EXP-Sb.Ubq6:1:3 (SEQ ID NO: 148). Root expression driven by EXP-Zm.UbqM1:1:10 (SEQ ID NO: 140) demonstrated no expression at V3 but was high at V7 and then dropped by VT stage. Root expression driven by EXP-Zm.UbqM1:1:11 (SEQ ID NO: 150) was maintained to a similar level throughout development from stages V3, and V7 through VT. Expression of GUS driven by EXP-C1.Ubq10 (SEQ ID NO: 168) was relatively steady from V4 to V7 stage but dropped to approximately half that of V4 and V7 at VT stage.

GUS expression levels showed dramatic differences in leaf tissue as well. The EXP sequences, EXP-Zm.UbqM1:1:10 (SEQ ID NO: 126), EXP-Zm.UbqM1:1:12 (SEQ ID NO: 132) and EXP-Zm.UbqM1:1:11 (SEQ ID NO: 138) demonstrated the highest level of GUS expression observed across all three stages of development (V3, V7 and VT). The EXP sequence, EXP-Sb.Ubq4:1:2 (SEQ ID NO: 140), showed a decline in expression from V3 to VT stages of development. The EXP sequences, EXP-ARUdo.Ubq1:1:8 (SEQ ID NO: 13) and EXP-Sb.Ubq7:1:2 (SEQ ID NO: 150) demonstrated higher levels of GUS expression in V3 and VT stage of development with a lower level of expression in the middle of growth at V7 stage. The EXP sequence, EXP-ARUdo.Ubq2:1:9 (SEQ ID NO: 30), EXP-BOUgr.Ubq1:1:7 (SEQ ID NO: 41), and EXP-MISsi.Ubq1:1:7 (SEQ ID NO: 76) maintained GUS expression over all three stages, while EXP-ARUdo.Ubq2:1:8 (SEQ ID NO: 27), EXP-BOUgr.Ubq1:1:6 (SEQ ID NO: 38), and EXP-BOUgr.Ubq2:1:15 (SEQ ID NO: 55) showed a slight decrease in expression at VT stage. Expression driven by EXP-C1.Ubq10 (SEQ ID NO: 168) was similar at V4 and VT stage but dropped to about half the level of V4 and VT at V7 stage.

Likewise, with respect to reproductive tissue (anther and silk) different patterns of expression were observed unique to each EXP sequence. For example, high levels of expression were observed in anther and silk for the EXP sequences EXP-ARUdo.Ubq1:1:8 (SEQ ID NO: 13), EXP-ARUdo.Ubq1:1:9 (SEQ ID NO: 18), EXP-BOUgr.Ubq2:1:14 (SEQ ID NO: 52), EXP-BOUgr.Ubq2:1:15 (SEQ ID NO: 55), EXP-SORnu.Ubq1:1:7 (SEQ ID NO: 95), EXP-Zm.UbqM1:1:10 (SEQ ID NO: 126), EXP-Zm.UbqM1:1:12 (SEQ ID NO: 132), EXP-Zm.UbqM1:1:11 (SEQ ID NO: 138), and EXP-Sb.Ubq7:1:2 (SEQ ID NO: 150). Expression driven by the EXP sequences EXP-AGRne.Ubq1:1:7 (SEQ ID NO: 1), EXP-SORnu.Ubq1:1:6 (SEQ ID NO: 92), EXP-Sv.Ubq1:1:11 (SEQ ID NO: 114), EXP-Sv.Ubq1:1:12 (SEQ ID NO: 120), EXP-Sb.Ubq4:1:2 (SEQ ID NO: 140), EXP-Sb.Ubq6:1:3 (SEQ ID NO: 148), and EXP-C1.Ubq10 (SEQ ID NO: 168) was high in the anther but lower in the silk relative to each EXP sequence, while expression driven by EXP-BOUgr.Ubq1:1:6 (SEQ ID NO: 38) was higher in the silk in comparison to expression in the anther.

Expression in the developing seed (21 DAP embryo and endosperm) was different among the EXP sequences. The EXP sequences, EXP-Zm.UbqM1:1:10 (SEQ ID NO: 126), EXP-Zm.UbqM1:1:12 (SEQ ID NO: 132), and EXP-Zm.UbqM1:1:11 (SEQ ID NO: 138) drove high expression of GUS in the developing seed embryo and endosperm tissue. Levels of expression in the endosperm were about two-fold or more higher than in the embryo when GUS was driven by the EXP sequences, EXP-ARUdo.Ubq1:1:8 (SEQ ID NO: 13), EXP-ARUdo.Ubq1:1:9 (SEQ ID NO: 18), EXP-ARUdo.Ubq2:1:8 (SEQ ID NO: 27), EXP-BOUgr.Ubq2:1:14 (SEQ ID NO: 52), EXP-BOUgr.Ubq2:1:15 (SEQ ID NO: 55), EXP-SORnu.Ubq1:1:6 (SEQ ID NO: 92), EXP-SORnu.Ubq1:1:7 (SEQ ID NO: 95), EXP-Sv.Ubq1:1:12 (SEQ ID NO: 120), EXP-Sb.Ubq4:1:2 (SEQ ID NO: 140), and EXP-C1.Ubq10 (SEQ ID NO: 168). Expression of GUS was three-fold higher in the embryo than in the endosperm when driven by EXP-Sb.Ubq7:1:2 (SEQ ID NO: 150). GUS expression levels were relatively equivalent in the embryo and endosperm when driven by the EXP sequences EXP-AGRne.Ubq1:1:7 (SEQ ID NO: 1), EXP-AGRne.Ubq1:1:8 (SEQ ID NO: 5), EXP-BOUgr.Ubq1:1:6 (SEQ ID NO: 38), EXP-BOUgr.Ubq1:1:7 (SEQ ID NO: 41), EXP-MISsi.Ubq1:1:7 (SEQ ID NO: 76), EXP-SETit.Ubq1:1:10 (SEQ ID NO: 99), and EXP-Sb.Ubq6:1:3 (SEQ ID NO: 148).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates that EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 6

Enhancers Derived from the Regulatory Elements

Enhancers are derived from the promoter elements provided herein, such as those presented as SEQ ID NOs: 2, 6, 8, 10, 14, 17, 22, 24, 28, 31, 33, 35, 39, 42, 44, 46, 50, 53, 56, 61, 63, 67, 71, 73, 75, 77, 79, 83, 85, 87, 89, 93, 96, 98 and 169. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream DNA sequence from the promoters that allow transcription to be initiated from the promoters provided herein as described above, including fragments thereof, in which the TATA box or functionally similar elements and DNA sequence downstream of the TATA box are removed.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first expression cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 165) or any of the introns presented herein or any other intron, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158) or the 3' UTR from the rice lipid transfer protein gene (T-Os.LTP-1:1:1, SEQ ID NO: 160); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 7

Analysis of Intron Enhancement of GUS Activity Using Plant Derived Protoplasts An intron is selected based upon experimentation and comparison with an intronless expression vector control to empirically select an intron and configuration within the vector transfer DNA (T-DNA) element arrangement for optimal expression of a transgene. For example, in the expression of an herbicide resistance gene, such as CP4, which confers tolerance to glyphosate, it is desirable to have transgene expression within the reproductive tissues as well as the vegetative tissues, to prevent the loss of yield when applying the herbicide. An intron in this instance would be selected upon its ability, when operably linked to a constitutive promoter, to enhance expression of the herbicide resistance conferring transgene, particularly within the reproductive cells and tissues of the transgenic plant and thus providing both vegetative and reproductive tolerance to the transgenic plant when sprayed with the herbicide. In most ubiquitin genes, the 5' UTR is comprised of a leader, which has an intron sequence embedded within it. The regulatory elements derived from such genes are therefore assayed using the entire 5' UTR comprising the promoter, leader, and intron. To achieve different expression profiles or to modulate the level of transgene expression, the intron from such a regulatory element may be removed or substituted with a heterologous intron.

Figure 9:
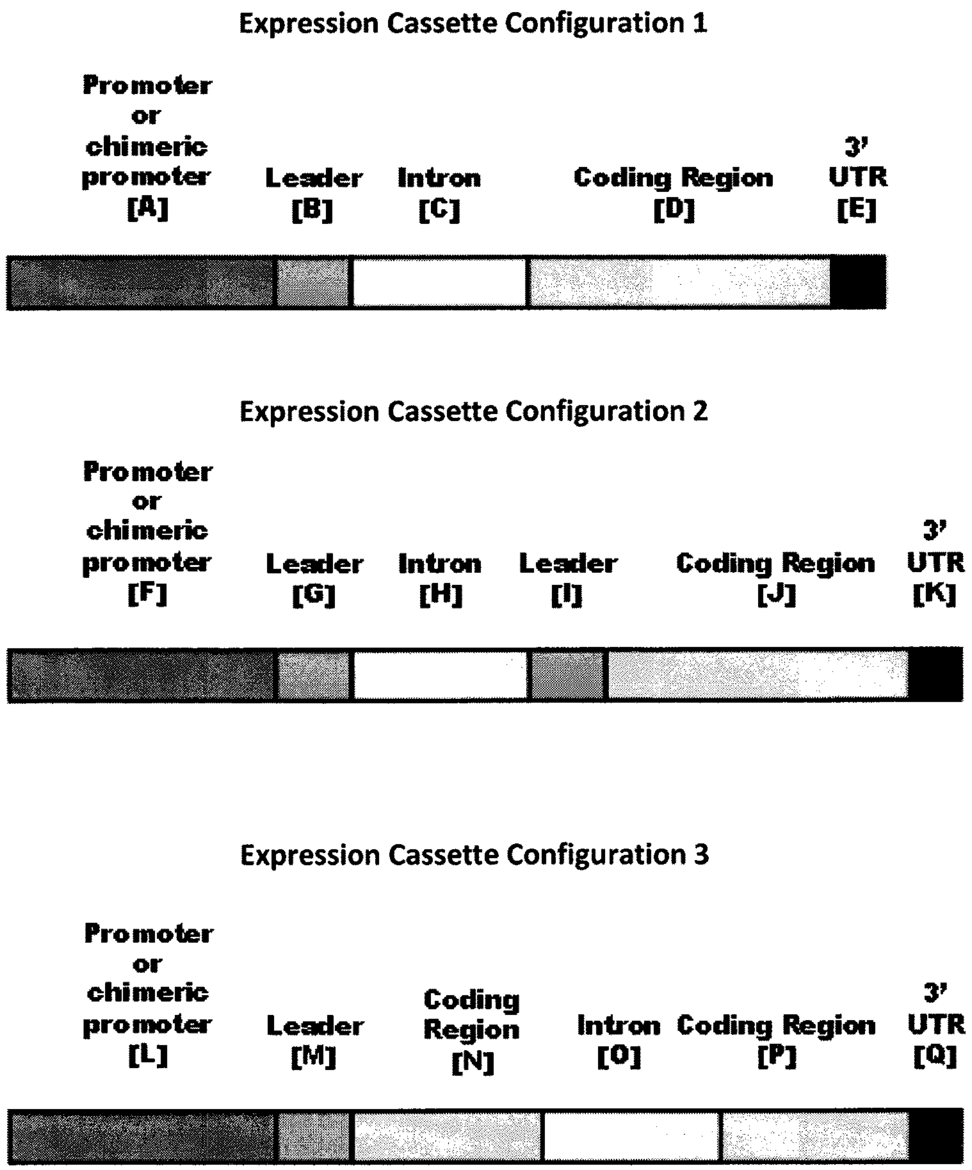
FIG. 9: Shows expression cassette configurations of the invention.

Introns presented herein as SEQ ID NOs: 4, 12, 15, 20, 26, 29, 37, 40, 48, 51, 54, 57, 59, 65, 69, 81, 91, 94 and 171 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a regulatory element and leader fragment and operably linked 5' to either a second leader fragment or to coding sequences, for instance as depicted in the expression cassettes presented in FIG. 9.

Thus, for instance, a first possible expression cassette (Expression Cassette Configuration 1 in FIG. 9) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible expression cassette (Expression Cassette Configuration 2 in FIG. 9) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible expression cassette (Expression Cassette Configuration 3 in FIG. 9) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Expression Cassette Configuration 3 is designed to allow splicing of the intron in such a manner as to produce a complete open reading frame without a frame shift between the first and second fragment of the coding sequence.

As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element (e.g. one of SEQ ID NOs: 4, 12, 15, 20, 26, 29, 37, 40, 48, 51, 54, 57, 59, 65, 69, 81, 91, 94 and 171), operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158). Protoplast cells derived from corn or other genus plant tissue are transformed with the base plant vector and Luciferase control vectors as described previously in Example 2 above, and assayed for activity. To compare the relative ability of the intron to enhance expression, GUS values are expressed as a ratio of GUS to Luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 165), as well as a construct comprising the constitutive promoter, but without an intron operably linked to the promoter.

For stable plant assay of the introns presented as SEQ ID NOs: 4, 12, 15, 20, 26, 29, 37, 40, 48, 51, 54, 57, 59, 65, 69, 81, 91, 94 and 171, a GUS expression plant transformation vector is constructed similar to the constructs described in the previous examples in which the resulting plant expression vectors contains a right border region from *A. tumefaciens*, a first expression cassette to test the intron comprised of a constitutive promoter such as the Cauliflower mosaic virus promoter, P-CaMV.35S-enh-1:1:9 (SEQ ID NO: 166), operably linked 5' to a leader element, L-CaMV.35S-1:1:15 (SEQ ID NO: 167), operably linked 5' to a test intron element provided herein, operably linked to a coding sequence for GUS that either possesses a processable intron (GUS-2, SEQ ID NO: 155) or no intron (GUS-1, SEQ ID NO: 154), operably linked to the Nopaline synthase 3' UTR from *A. tumefaciens* (T-AGRtu.nos-1:1:13, SEQ ID NO: 158); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOs: 4, 12, 15, 20, 26, 29, 37, 40, 48, 51, 54, 57, 59, 65, 69, 81, 91, 94 and 171 can be modified in a number of ways, such as deleting fragments within the intron sequence, which may reduce expression or duplication of fragments with the intron that may enhance expression. In addition, DNA sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi, or animal cells, so long as the intron provides enhancement or attenuation or specificity of expression of the transgene to which it is operably linked.

Having illustrated and described the principles of the invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:

a) a DNA sequence with at least 95 percent sequence identity to SEQ ID NO: 56 and having promoter activity;

b) a DNA sequence comprising SEQ ID NO: 55 or 56; and c) a fragment comprising at least 200 contiguous nucleotides of SEQ ID NO: 56, wherein the fragment has promoter activity;

wherein said DNA sequence is operably linked to a heterologous transcribable DNA molecule.

2. The recombinant DNA molecule of claim 1, wherein said DNA sequence has at least 95 percent sequence identity to the DNA sequence of SEQ ID NO: 56 and has promoter activity.

3. The DNA molecule of claim 1, wherein the heterologous transcribable DNA molecule is a gene of agronomic interest.

4. The recombinant DNA molecule of claim 3, wherein the gene of agronomic interest confers herbicide tolerance in a plant.

5. The recombinant DNA molecule of claim 3, wherein the gene of agronomic interest confers pest resistance in a plant.

6. A construct comprising the recombinant DNA molecule of claim 1.

7. A transgenic plant cell comprising a recombinant DNA molecule comprising a DNA sequence selected from the group consisting of:

a) a DNA sequence with at least 95 percent sequence identity to SEQ ID NO: 56 and having promoter activity;

b) a DNA sequence comprising SEQ ID NO: 55 or 56; and c) a fragment comprising at least 200 contiguous nucleotides of SEQ ID NO: 56, wherein the fragment has promoter activity;

wherein said DNA sequence is operably linked to a heterologous transcribable DNA molecule.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising a recombinant DNA molecule comprising a DNA sequence selected from the group consisting of:

a) a DNA sequence with at least 95 percent sequence identity to SEQ ID NO: 56 and having promoter activity;

b) a DNA sequence comprising SEQ ID NO: 55 or 56; and c) a fragment comprising at least 200 contiguous nucleotides of SEQ ID NO: 56, wherein the fragment has promoter activity;

wherein said DNA sequence is operably linked to a heterologous transcribable DNA molecule.

11. A progeny plant of the transgenic plant of claim 10, wherein the progeny plant comprises said recombinant DNA molecule.

12. A transgenic seed of the transgenic plant of claim 10, wherein the seed comprises said recombinant DNA molecule.

13. A method of expressing a transcribable DNA molecule comprising obtaining a transgenic plant according to claim 10 and cultivating said plant, wherein the transcribable DNA molecule is expressed.

14. A method of producing a transgenic plant comprising:

a) transforming a plant cell with the recombinant DNA molecule of claim 1 to produce a transformed plant cell; and b) regenerating a transgenic plant from the transformed plant cell.

15. The recombinant DNA molecule of claim 1, wherein said DNA sequence is selected from the group consisting of: SEQ ID NOs: 55 and 56.

16. The transgenic plant cell of claim 7, wherein said DNA sequence is selected from the group consisting of: SEQ ID NOs: 55 and 56.

17. The transgenic plant, or part thereof, of claim 10, wherein said DNA sequence is selected from the group consisting of: SEQ ID NOs: 55 and 56.

* * * * *